US011054423B2

(12) United States Patent
Crowe, Jr. et al.

(10) Patent No.: US 11,054,423 B2
(45) Date of Patent: Jul. 6, 2021

(54) ANTIBODY-MEDIATED NEUTRALIZATION OF EBOLAVIRUSES

(71) Applicants: VANDERBILT UNIVERSITY, Nashville, TN (US); THE BOARD OF REGENTS OF THE UNIVERSITY OF TEXAS SYSTEM, Austin, TX (US)

(72) Inventors: James E. Crowe, Jr., Nashville, TN (US); Andrew I. Flyak, Nashville, TN (US); Alexander Bukreyev, Galveston, TX (US); Philipp Ilinykh, Galveston, TX (US)

(73) Assignees: VANDERBILT UNIVERSITY, Nashville, TN (US); BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/790,658

(22) Filed: Feb. 13, 2020

(65) Prior Publication Data
US 2020/0200749 A1    Jun. 25, 2020

Related U.S. Application Data

(62) Division of application No. 15/561,193, filed as application No. PCT/US2016/024296 on Mar. 25, 2016, now Pat. No. 10,620,204.

(60) Provisional application No. 62/138,522, filed on Mar. 26, 2015.

(51) Int. Cl.
| | |
|---|---|
| *G01N 33/569* | (2006.01) |
| *A61K 39/42* | (2006.01) |
| *C07K 16/10* | (2006.01) |
| *G01N 33/577* | (2006.01) |
| *A61K 39/395* | (2006.01) |
| *G01N 33/68* | (2006.01) |
| *A61K 39/00* | (2006.01) |

(52) U.S. Cl.
CPC ..... *G01N 33/56983* (2013.01); *A61K 39/395* (2013.01); *A61K 39/42* (2013.01); *C07K 16/10* (2013.01); *G01N 33/577* (2013.01); *G01N 33/68* (2013.01); *A61K 2039/505* (2013.01); *A61K 2039/507* (2013.01); *A61K 2039/545* (2013.01); *C07K 2317/21* (2013.01); *C07K 2317/33* (2013.01); *C07K 2317/55* (2013.01); *C07K 2317/76* (2013.01); *C07K 2317/92* (2013.01); *G01N 2333/08* (2013.01)

(58) Field of Classification Search
None
See application file for complete search history.

(56) References Cited

U.S. PATENT DOCUMENTS

| | | |
|---|---|---|
| 6,630,144 B1 | 10/2003 | Hart et al. |
| 7,682,618 B2 | 3/2010 | Bavari |
| 2012/0164153 A1 | 6/2012 | Dye et al. |

FOREIGN PATENT DOCUMENTS

| | | |
|---|---|---|
| CN | 104459122 | 3/2015 |
| WO | WO 2011/049836 | 4/2011 |
| WO | WO 2014/170257 | 10/2014 |

OTHER PUBLICATIONS

Dondelinger (Frontiers in Immunology, 2018, p. 1-15).*
Carette, Jan E., et al. "Ebola virus entry requires the cholesterol transporter Niemanno—Pick C1." Nature 477.7364 (2011): 340.
Chandran, Kartik, et al. "Endosomal proteolysis of the Ebola virus glycoprotein is necessary for infection." Science 308.5728 (2005): 1643-1645.
Cook, Jonathan D., and Jeffrey E. Lee. "The secret life of viral entry glycoproteins: moonlighting in immune evasion." PLoS Pathogens 9.5 (2013): e1003258.
Côté, Marceline, et al. "Small molecule inhibitors reveal Niemann—Pick C1 is essential for Ebola virus infection." Nature 477.7364 (2011): 344.
Dias, João M., et al. "A shared structural solution for neutralizing ebolaviruses." Nature Structural and Molecular Biology 18.12 (2011): 1424.
Dube, Derek, et al. "The primed ebolavinis glycoprotein (19-kilodalton GP1, 2): sequence and residues critical for host cell binding." Journal of Virology 83.7 (2009): 2883-2891.
Dye, John M., et al. "Postexposure antibody prophylaxis protects nonhuman primates from filovirus disease." Proceedings of the National Academy of Sciences 109.13 (2012): 5034-5039.
International Preliminary Report on Patentability issued in International Application No. PCT/US2016/024296, dated Oct. 5, 2017.
International Search Report and Written Opinion issued in International Application No. PCT/US2016/024296, dated Sep. 2, 2016.
Invitation to Pay Additional Fees issued in International Application No. PCT/US2016/024296, dated Jun. 6, 2016.

(Continued)

*Primary Examiner* — Agnieszka Boesen
(74) *Attorney, Agent, or Firm* — Parker Highlander PLLC

(57) ABSTRACT

The present disclosure is directed to antibodies binding to and neutralizing ebolavirus and methods for use thereof. The present disclosure is directed to a method of detecting an ebolavirus infection in a subject comprising (a) contacting a sample from said subject with an antibody or antibody fragment having clone-paired heavy and light chain CDR sequences from Table 2, or an antibody fragment thereof; and (b) detecting ebolavirus glycoprotein in said sample by binding of said antibody or antibody fragment to antigen in said sample. In still further embodiments, the present disclosure concerns immunodetection kits for use with the iminunodetection methods described above.

12 Claims, 30 Drawing Sheets

Specification includes a Sequence Listing.

(56) References Cited

OTHER PUBLICATIONS

Keck, Zhen-Yong, et al. "Macaque monoclonal antibodies targeting novel conserved epitopes within filovirus glycoprotein." *Journal of Virology* 90.1 (2016): 279-291.

Lee, Jeffrey E., et al. "Structure of the Ebola virus glycoprotein bound to an antibody from a human survivor." *Nature* 454.7201 (2008): 177.

Lennemann, Nicholas J., et al. "Comprehensive functional analysis of N-linked glycans on Ebola virus GP1." *MBio* 5.1 (2014): e00862-13.

Maruyama, Toshiaki, et al. "Ebola virus can be effectively neutralized by antibody produced in natural human infection." *Journal of Virology* 73.7 (1999): 6024-6030.

Marzi, Andrea, et al. "Protective efficacy of neutralizing monoclonal antibodies in a nonhuman primate model of Ebola hemorrhagic fever." *PloS One* 7.4 (2012): e36192.

Murin, Charles D., et al. "Structures of protective antibodies reveal sites of vulnerability on Ebola virus." *Proceedings of the National Academy of Sciences* 111.48 (2014): 17182-17187.

Nanbo, Asuka, et al. "Ebolavirus is internalized into host cells via macropinocytosis in a viral glycoprotein-dependent manner." *PLoS Pathogens* 6.9 (2010): e1001121.

Niikura, Masahiro, et al. "Detection of Ebola viral antigen by enzyme-linked immunosorbent assay using a novel monoclonal antibody to nucleoprotein." *Journal of clinical microbiology* 39.9 (2001): 3267-3271.

Olinger, Gene Garrard, et al. "Delayed aeatinent of Ebola virus infection with plant-derived monoclonal antibodies provides protection in rhesus macaques." *Proceedings of the National Academy of Sciences* 109.44 (2012): 18030-18035.

Pettitt, James, et al. "Therapeutic intervention of Ebola virus infection in rhesus macaques with the MB-003 monoclonal antibody cocktail." *Science Translational Medicine* 5.199 (2013): 199ra113-199ra113.

Qiu, Xiangguo, et al. "Reversion of advanced Ebola virus disease in nonhuman primates with ZMapp." *Nature* 514.7520 (2014): 47.

Qiu, Xiangguo, et al. "Successful treatment of Ebola virus-infected cynomolgus macaques with monoclonal antibodies." *Science Translational Medicine* 4.138 (2012): 138ra81-138ra81.

Saeed, Mohammad F., et al. "Cellular entry of ebola virus involves uptake by a macropinocytosis-like mechanism and subsequent trafficking through early and late endosomes." *PLoS Pathogens* 6.9 (2010): e1001110.

Saphire, Erica Ollmann. "An update on the use of antibodies against the filoviruses." *Immunotherapy* 5.11 (2013): 1221-1233.

\* cited by examiner

FIG. 1A-C

| Subject | Total number of GP-specific lines | Reactivity of GP-specific B cell lines with diverse GPs (%) | | | | |
|---|---|---|---|---|---|---|
| | | BDBV-specific | BDBV/EBOV cross-reactive | EBOV-specific | BDBV/EBOV/MARV cross-reactive | MARV-specific |
| BDBV | | | | | | |
| Donor 1 | 127 | 65.0 | 24.0 | 8.0 | 2.0 | 1.0 |
| Donor 2 | 158 | 46.2 | 39.2 | 9.5 | 4.4 | 0.6 |
| Donor 3 | 318 | 46.9 | 50.0 | 1.9 | 1.3 | 0 |
| Donor 4 | 208 | 63.0 | 32.2 | 3.4 | 1.0 | 0.5 |
| EBOV | 281 | 0 | 36.3 | 63.3 | 0.4 | 0 |
| MARV | 64 | 1.6 | 1.6 | 4.8 | 1.6 | 90.3 |

FIG. 1D

ELISA binding
($EC_{50}$; ng/mL)

| Group | Donor | mAb | BDBV GP | EBOV GP | SUDV GP | MARV GP | BDBV sGP |
|---|---|---|---|---|---|---|---|
| 1A | 1 | 231 | 120 | > | > | > | 17 |
| | | 241 | 49 | > | > | > | 32 |
| | 2 | 275 | 41 | > | > | > | 25 |
| | 3 | 322 | 20 | > | > | > | 11 |
| | | 327 | 47 | > | > | > | 16 |
| | | 329 | 135 | > | > | > | 21 |
| | | 330 | 58 | > | > | > | 44 |
| | | 335 | 10 | > | > | > | 7 |
| | | 354 | 11 | > | > | > | 8 |
| | | 358 | 2,852 | > | > | > | 441 |
| | | 377 | 56 | > | > | > | 74 |
| | | 378 | 859 | > | > | > | 52 |
| | | 386 | 119 | > | > | > | 17 |
| | | 394 | 4,682 | > | > | > | 284 |
| | | 395 | 4,563 | > | > | > | 436 |
| | | 397 | 519 | > | > | > | 50 |
| | | 399 | 26 | > | > | > | 13 |
| | | 401 | 787 | > | > | > | 61 |
| | | 410 | 212 | > | > | > | 125 |
| | | 415 | 412 | > | > | > | 119 |
| | | 417 | 3,710 | > | > | > | 1,016 |
| | 4 | 315 | 15 | > | > | > | 3,018 |
| | | 318 | 8 | > | > | > | 3 |
| | | 343 | 41 | > | > | > | 12 |
| | | 345 | 300 | > | > | > | 43 |
| | 6 | 75 | 39 | > | > | > | 11 |
| | 7 | 41 | 25 | > | > | > | 5,453 |
| | | 52 | 27 | > | > | > | 15 |
| 1B | 1 | 255 | 7 | > | > | > | > |
| | | 259 | 26 | > | > | > | > |
| | 3 | 328 | 34 | > | > | > | > |
| | | 353 | 18 | > | > | > | > |
| | 4 | 432 | 19 | > | > | > | > |

FROM FIG. 2A-1

ELISA binding
(EC$_{50}$; ng/mL)

| Group | Donor | mAb | BDBV GP | EBOV GP | SUDV GP | MARV GP | BDBV sGP |
|---|---|---|---|---|---|---|---|
| 2A | 3 | 323 | 3,355 | 3,795 | > | > | 160 |
| | | 352 | 112 | 1,477 | > | > | 13 |
| | | 357 | 48 | 641 | > | > | 10 |
| | | 372 | 1,622 | 6,144 | > | > | 276 |
| | | 392 | 200 | 2,686 | > | > | 31 |
| | | 419 | 26 | 2,802 | > | > | 9 |
| | | 425 | 37 | 47 | > | > | 11 |
| | 4 | 316 | 8 | 569 | > | > | 4 |
| | | 342 | 180 | 2,470 | > | > | 16 |
| | | 366 | 150 | 6,538 | > | > | 16 |
| | | 403 | 55 | 4,185 | > | > | 13 |
| | | 406 | 1,399 | 1,915 | > | > | 134 |
| | | 407 | 197 | 413 | > | > | 38 |
| | | 426 | 359 | 591 | > | > | 33 |
| | 6 | 86 | 409 | 1,066 | > | > | 95 |
| | 7 | 26 | 542 | 1,204 | > | > | 105 |
| 2B | 1 | 240 | 91 | 102 | > | > | > |
| | | 252 | 78 | 45 | > | > | > |
| | 2 | 280 | 39 | 137 | > | > | > |
| | 3 | 350 | 14 | 11 | > | > | > |

FROM FIG. 2A-2

ELISA binding
($EC_{50}$; ng/mL)

| Group | Donor | mAb | BDBV GP | EBOV GP | SUDV GP | MARV GP | BDBV sGP |
|---|---|---|---|---|---|---|---|
| 3A | 1 | 220 | 427 | 1,536 | 2,271 | > | 73 |
| | | 238 | 113 | 214 | 238 | > | 17 |
| | | 248 | 448 | 1,795 | 7,175 | > | 109 |
| | 2 | 266 | 38 | 73 | 127 | > | 26 |
| | | 270 | 154 | 173 | 159 | > | 25 |
| | | 272 | 152 | 234 | 177 | > | 177 |
| | | 273 | 1,892 | 1,798 | 3,116 | > | 640 |
| | 3 | 321 | 334 | 1,861 | 5,976 | > | 35 |
| | | 324 | 53 | 131 | 90 | > | 12 |
| | | 373 | 507 | 499 | 1,793 | > | 62 |
| | | 380 | 138 | 191 | 1,810 | > | 19 |
| | | 382 | 1,087 | 1,555 | 9,047 | > | 80 |
| | | 390 | 1,087 | 1,946 | 8,513 | > | 96 |
| | | 396 | 236 | 409 | 2,332 | > | 39 |
| | | 412 | 2,458 | 4,372 | 7,771 | > | 227 |
| | | 413 | 77 | 52 | 1,073 | > | 10 |
| | | 414 | 182 | 217 | 1,865 | > | 45 |
| | | 416 | 111 | 127 | 389 | > | 31 |
| | 6 | 87 | 88 | 597 | 1,083 | > | 11 |
| | | 91 | 13 | 16 | 24 | > | 5 |
| | 7 | 43 | 29 | 22 | 21 | > | 18 |
| | | 47 | 62 | 58 | 226 | > | 10 |
| | | 289 | 20 | 29 | 103 | > | 6 |
| | | 294 | 86 | 255 | 2,572 | > | 37 |
| 3B | 1 | 223 | 22 | 24 | 106 | > | > |
| | 3 | 359 | 24 | 18 | 23 | > | > |
| | | 384 | 14 | 14 | 231 | > | > |
| | | 387 | 44 | 28 | 27 | > | > |
| | | 388 | 105 | 64 | 255 | > | > |
| | | 389 | 9 | 4 | 6 | > | > |
| | | 391 | 21 | 21 | 42 | > | > |
| | | 411 | 356 | 312 | 465 | > | > |
| | | 422 | 26 | 30 | 123 | > | > |
| | 4 | 317 | 9 | 191 | 208 | > | > |
| | | 340 | 69 | 41 | 318 | > | > |
| | | 427 | 508 | 386 | 1,137 | > | > |
| | 5 | 115 | 30 | 39 | 41 | > | > |

FIG. 2A-3

B.Neut
(IC$_{50}$; ng/mL)

| BDBV IC$_{50}$ |
|---|
| 183 |
| > |
| > |
| > |
| > |
| 770 |
| > |
| 0.2 |
| 18 |
| > |
| 8 |
| > |
| 3,276 |
| > |
| > |
| 4,898 |
| 918 |
| > |
| 3,015 |
| 3,546 |
| > |
| 0.3 |
| 4,980 |
| > |
| > |
| 93 |
| > |
| 143 |
| 59 |
| 0.9 |
| <0.1 |
| 59 |

FROM FIG. 2B-1

| BDBV IC$_{50}$ |
|---|
| > |
| > |
| > |
| > |
| 2,159 |
| > |
| 2 |
| > |
| 438 |
| > |
| 876 |
| > |
| 522 |
| 1,659 |
| > |
| > |
| > |
| > |
| > |
| > |
| > |

FROM FIG. 2B-2

| BDBV IC$_{50}$ |
|---|
| > |
| > |
| > |
| > |
| 182 |
| > |
| > |
| 10 |
| > |
| > |
| > |
| > |
| > |
| > |
| > |
| > |
| 139 |
| > |
| 32 |
| > |
| <0.1 |
| > |
| > |
| > |
| > |
| > |
| 6 |
| 1,650 |
| > |
| > |

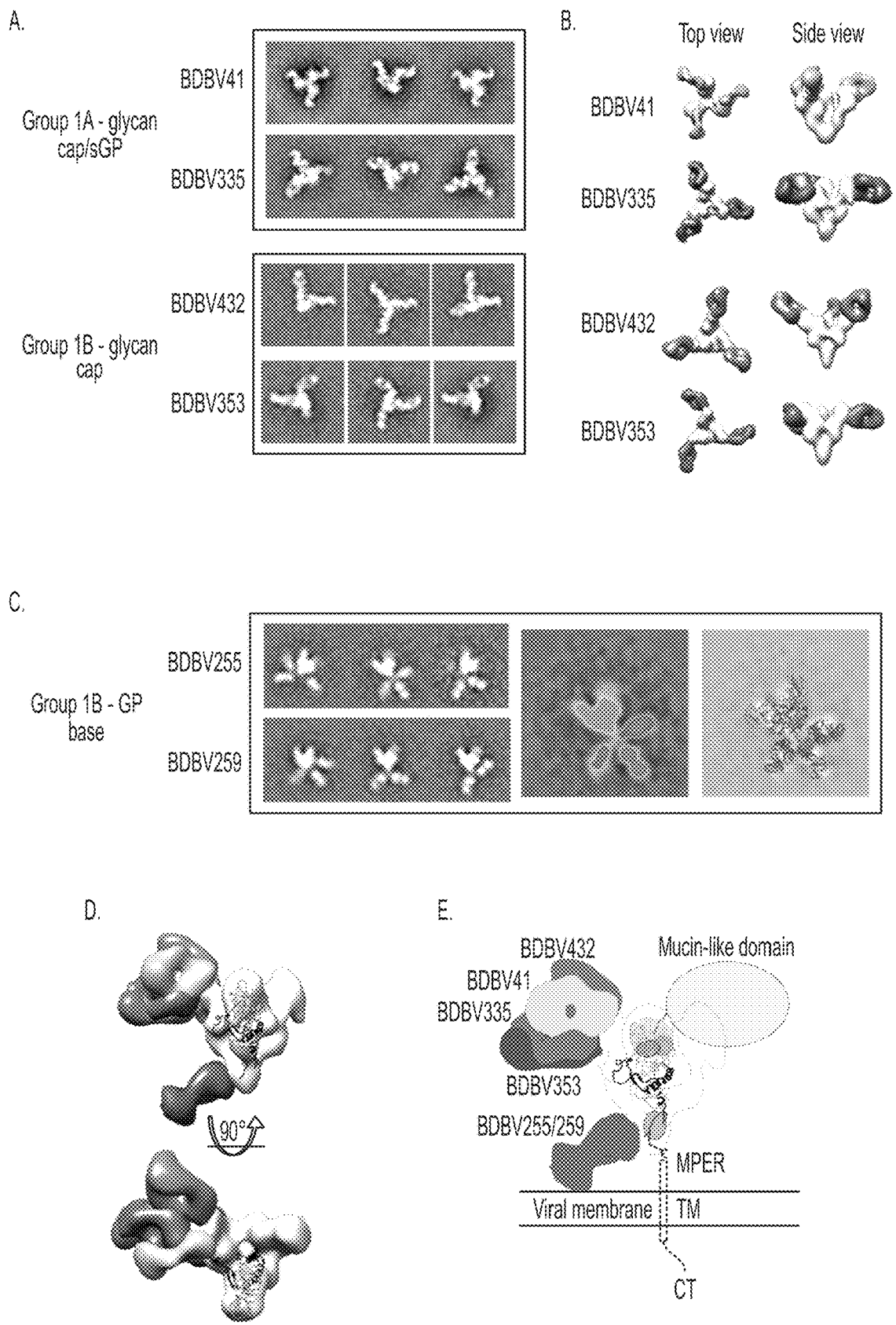
FIG. 4A-E

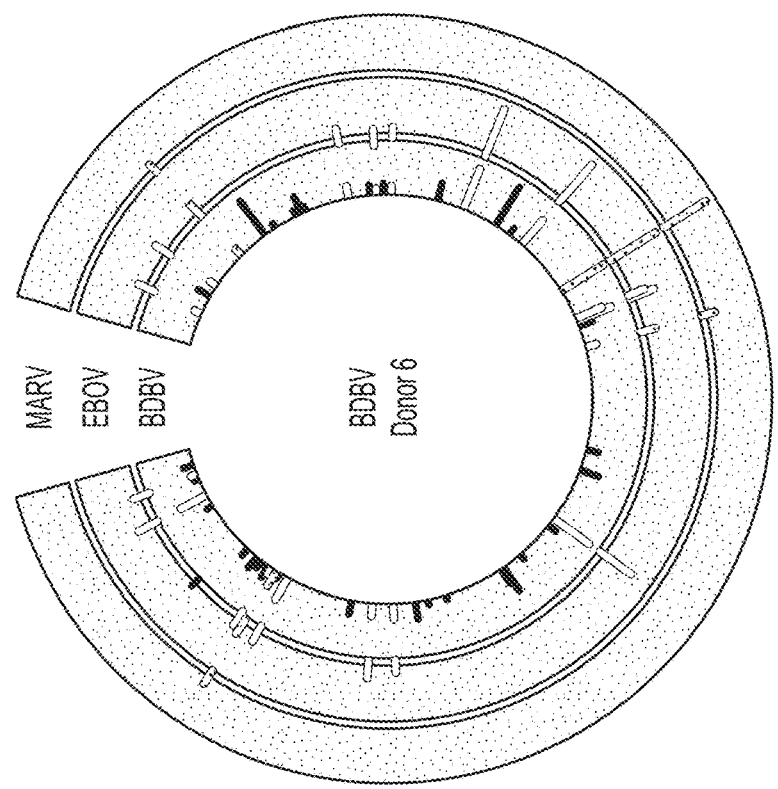
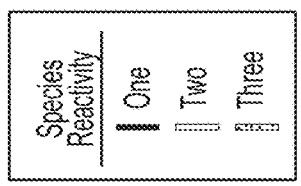
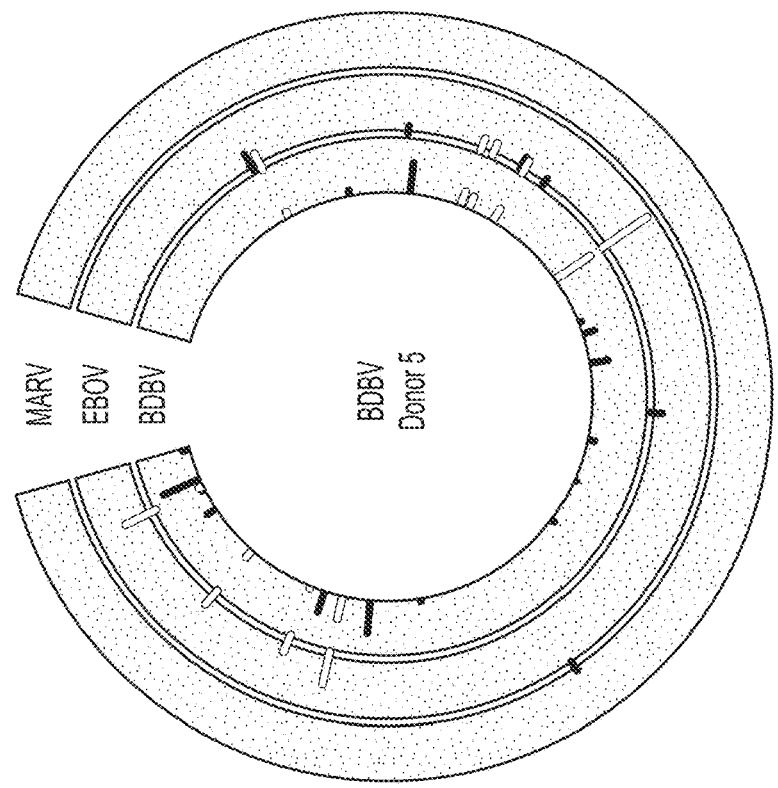
FIG. 8

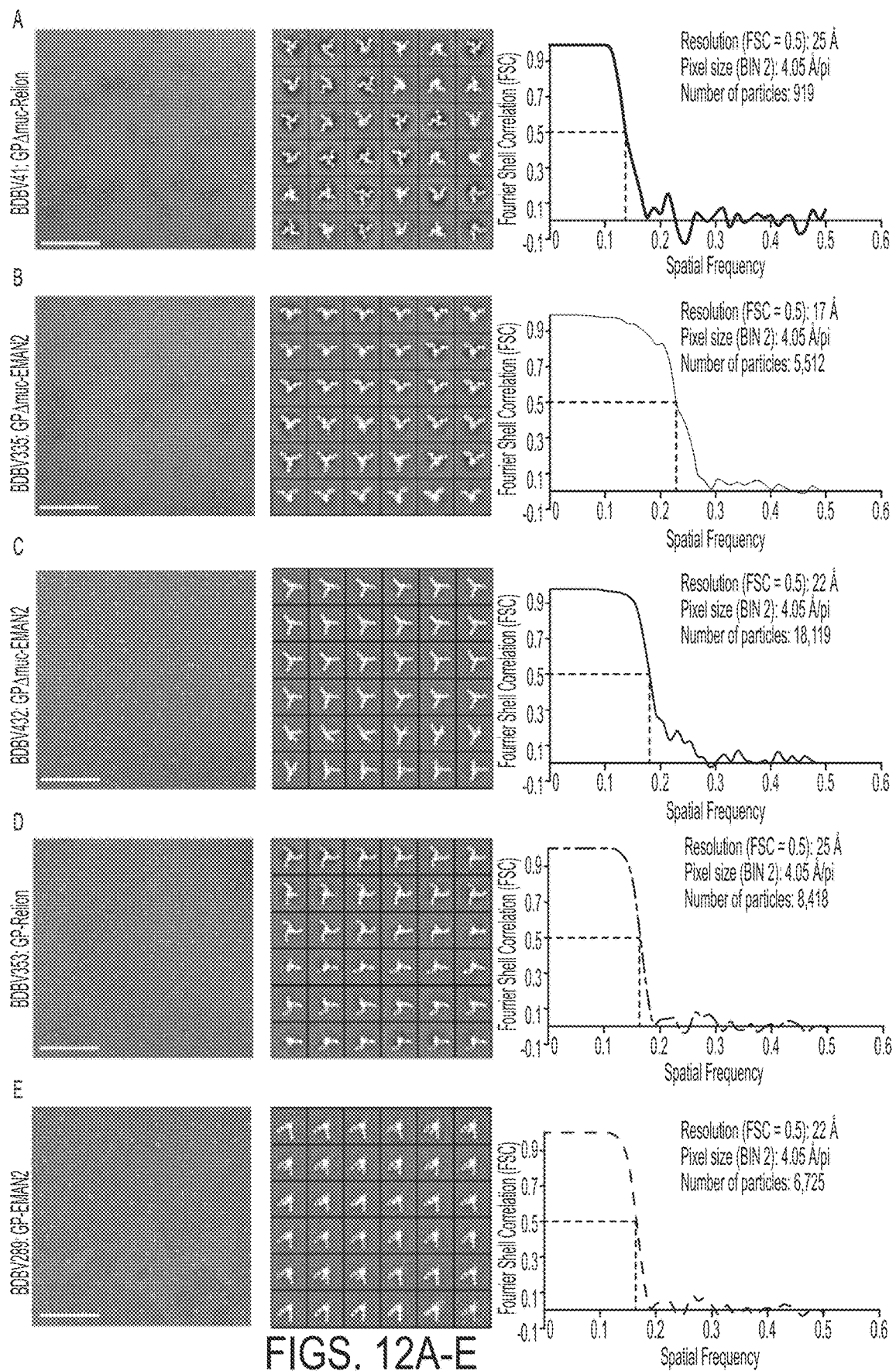
FIGS. 12A-E

| BDBV41 escape mutants | AA changes compared to wt | | Location |
|---|---|---|---|
| VSV/BDBV-GP#7 | 271Gly → Arg | | Glycan Cap |
| | 272Thr → Ser | | Mucin-like Domain |
| | 445His → Arg | | |
| VSV/BDBV-GP#15 | 271Gly → Arg | | Glycan Cap |
| | 272Thr → Ser | | |

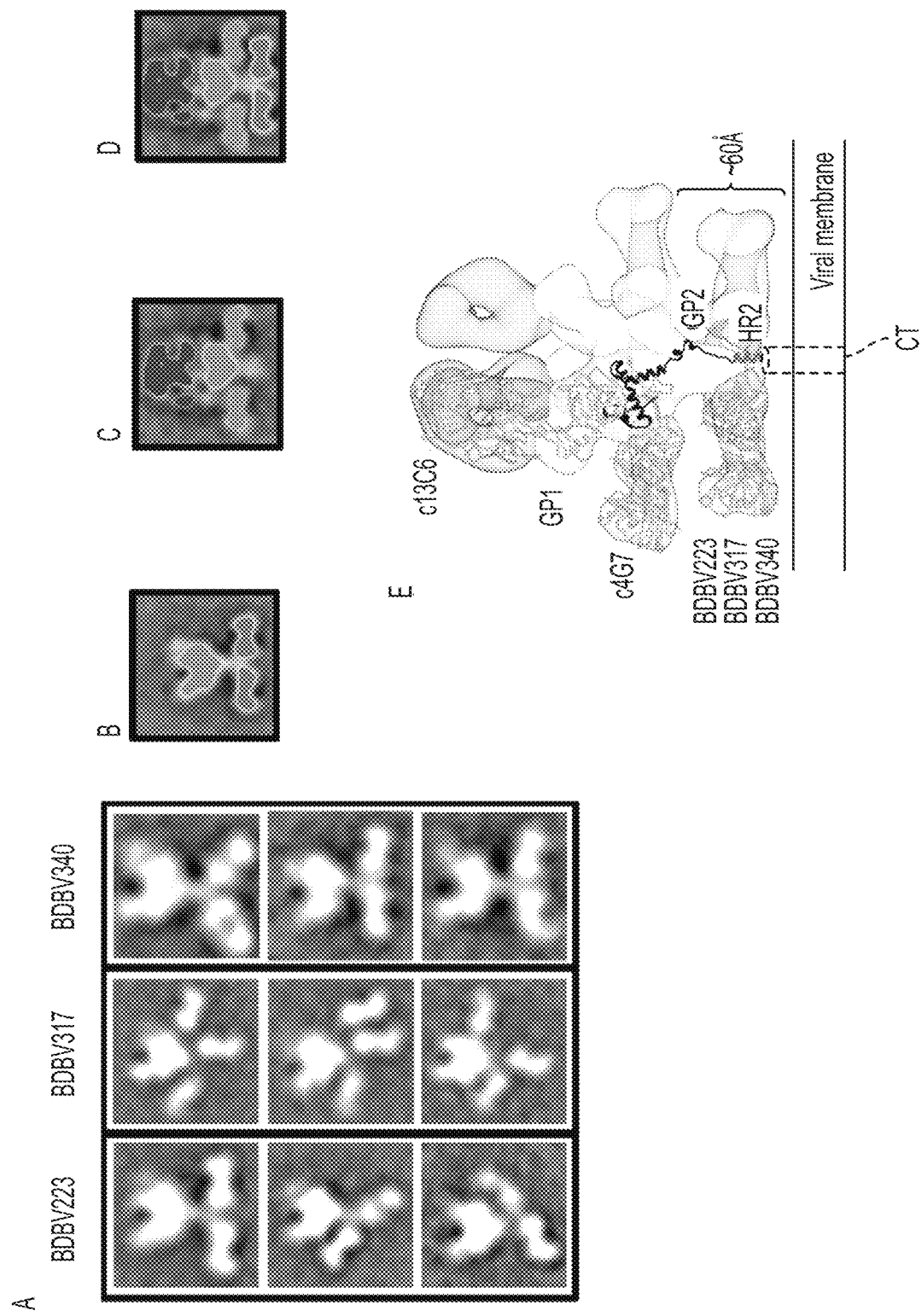
FIGS. 15A-E

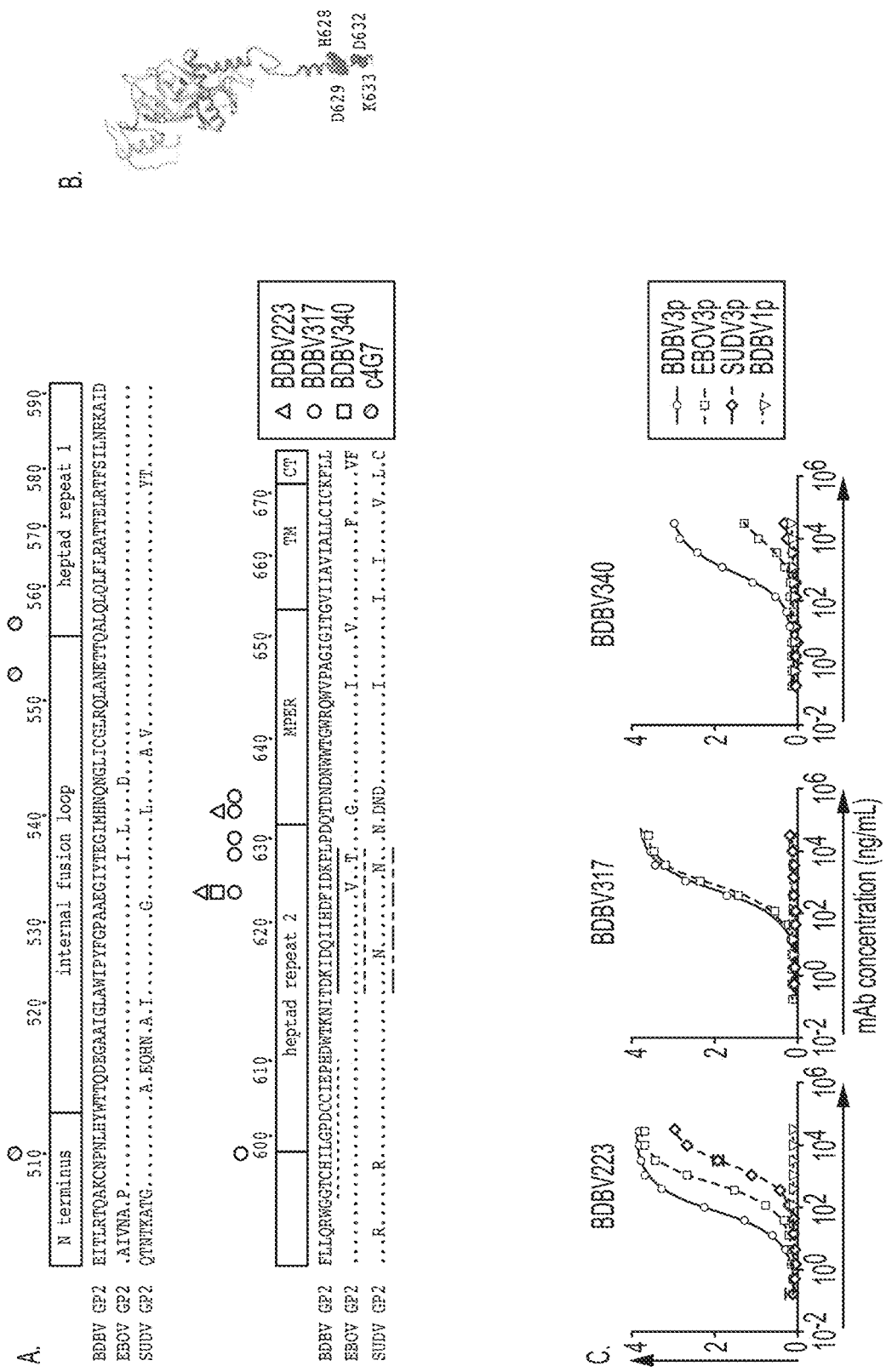
FIG. 16A-C

D.

| Peptide | Sequence | BDBV223, EC$_{50}$, ng/mL | BDBV317, EC$_{50}$, ng/mL | BDBV340, EC$_{50}$, ng/mL |
|---|---|---|---|---|
| BDBV3 | $^{620}$TDKIDQIIHDFIDKPL$^{635}$ | 84.9 | 477.2 | 791.1 |
| EBOV3 | ------V--T-- | 557.5 | 652.9 | 9,668.0 |
| SUDV3 | ---N------N--- | 2,256.0 | > | > |
| BDBV3A | ---------V------- | 125.4 | 886.6 | 4,190.0 |
| BDBV3B | -----------T--- | 812.4 | 15,677.0 | 3,628.0 |
| BDBV3C | ---N------------ | 18,370.0 | > | > |
| BDBV3D | ------------N--- | 72.7 | > | 252.6 |

EBOV NEUTRALIZING ANTIBODIES RECOGNIZE EBOV sGP IN ELISA

NEUTRALIZING mABs ARE HIGHLIGHTED IN RED

| Group | mAb | EBOV GP | BDBV GP | SUDV GP | MARV GP | EBOV sGP |
|---|---|---|---|---|---|---|
| 1A | 49 | 262 | > | > | > | 61 |
| | 53 | 27 | > | > | > | 7 |
| | 63 | 283 | > | > | > | 38 |
| | 66 | 204 | > | > | > | 10 |
| | 82 | 36 | > | > | > | 21 |
| | 90 | 67 | > | > | > | 25 |
| | 95 | 129 | > | > | > | 41 |
| | 129 | 5421 | > | > | > | 641 |
| | 132 | 87 | > | > | > | 13 |
| | 157 | 126 | > | > | > | 1454 |
| | 164 | 139 | > | > | > | 21 |
| | 165 | 100 | > | > | > | 25 |
| 1B | 58 | 294 | > | > | > | > |
| | 94 | 27 | > | > | > | > |
| | 144 | 146 | > | > | > | > |
| | 153 | 142 | > | > | > | > |
| | 168 | 4209 | > | > | > | > |

| Group | mAb | EBOV GP | BDBV GP | SUDV GP | MARV GP | EBOV sGP |
|---|---|---|---|---|---|---|
| 2A | 52 | 712 | 1838 | > | > | 82 |
| | 62 | 228 | 508 | > | > | 51 |
| | 93 | 1747 | 4819 | > | > | 182 |
| | 137 | 907 | 2376 | > | > | 20 |
| 2B | 59 | 59 | 103 | > | > | > |
| | 77 | 29 | 45 | > | > | > |
| | 88 | 46 | 62 | > | > | > |
| | 140 | 49 | 48 | > | > | > |
| | 161 | 88 | 81 | > | > | > |

| Group | mAb | EBOV GP | BDBV GP | SUDV GP | MARV GP | EBOV sGP |
|---|---|---|---|---|---|---|
| 3A | 69 | 19 | 393 | 619 | > | 11 |
| | 87 | 724 | 1389 | 629 | > | 51 |
| | 123 | 418 | 331 | 755 | > | 20 |
| 3B | 68 | 36 | 62 | 29 | > | > |
| | 78 | 83 | 174 | 215 | > | > |
| | 91 | 11 | 14 | 13 | > | > |
| | 155 | 228 | 247 | 301 | > | > |

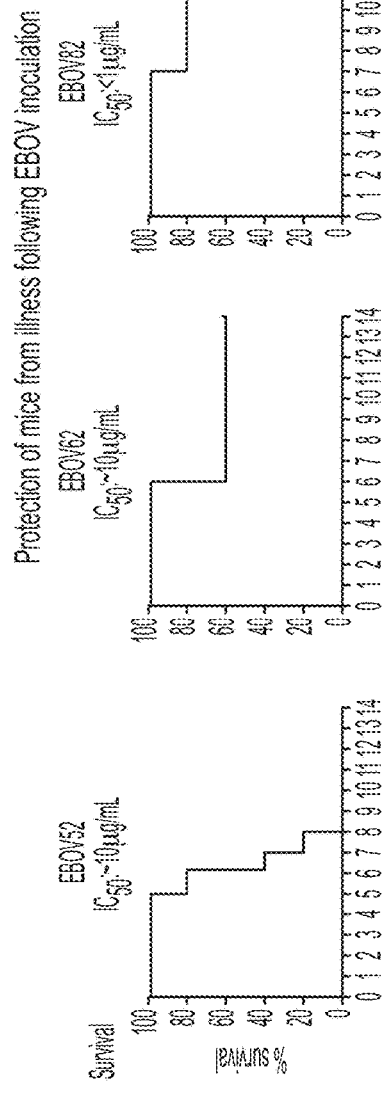
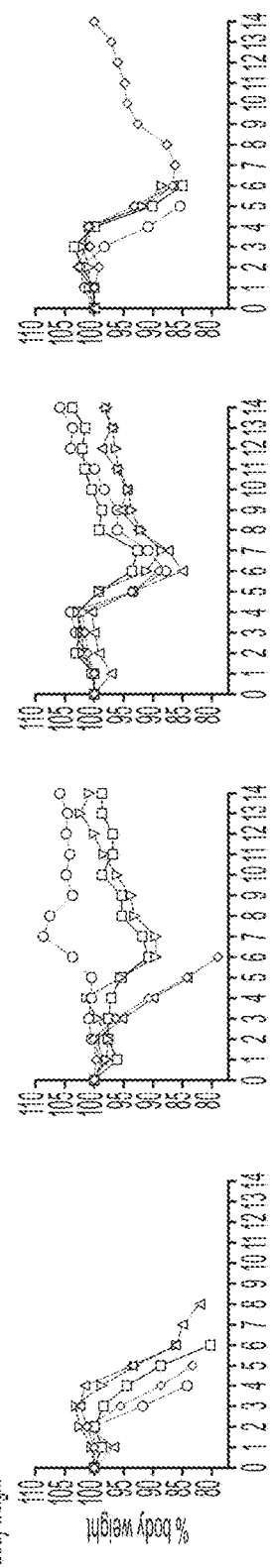
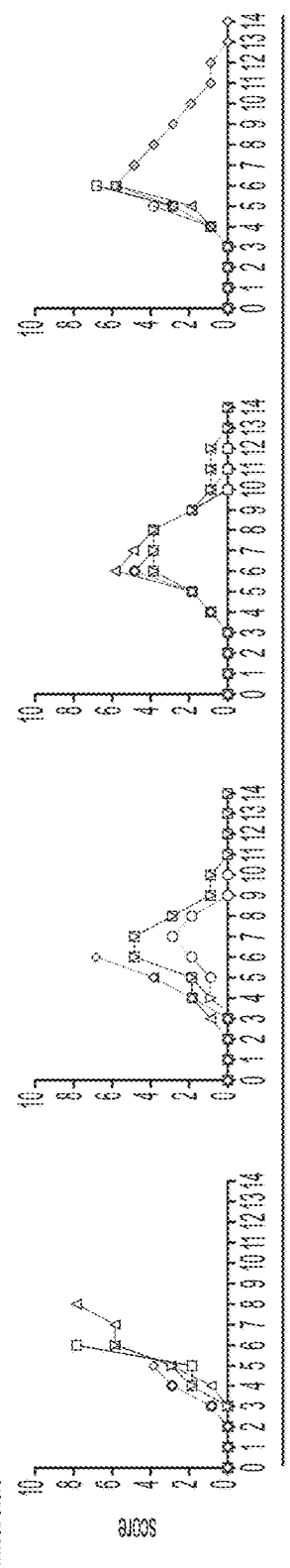
FIG. 18A
FIG. 18B
FIG. 18C

Protection of mice from illness following EBOV inoculation

Days after challenge

FIG. 19C

EBOV 52 binds to a cross-reactive epitope in the glycan cap

EBOV 58 And EBOV 90 bind to a novel epitope in the GP head region

FIG. 20

ANTIBODY-MEDIATED NEUTRALIZATION OF EBOLAVIRUSES

This application is a divisional of U.S. application Ser. No. 15/561,193, filed Sep. 25, 2017, as a national phase application under 35 U.S.C. § 371 of International Application No. PCT/US2016/024296, filed Mar. 25, 2016, which claims benefit of priority to U.S. Provisional Application Ser. No. 62/138,522, filed Mar. 26, 2015, the entire contents of each of which are hereby incorporated by reference.

This invention was made with government support under grant number HDTRA1-13-1-0034 awarded by the Department of Defense and under grant number AI109711 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to antibodies that neutralize ebolavirus.

2. Background

Ebola viruses are members of the family Filoviridae, which infect humans and non-human primates causing a hemorrhagic fever with mortality rates up to 90%. As of Jan. 7, 2015, there have been in excess of 20,000 confirmed, probable, and suspected cases of Ebola virus disease (EVD) in the current EBOV outbreak in nine affected countries (Guinea, Liberia, Mali, Nigeria, Senegal, Sierra Leone, Spain, the United Kingdom and the United States of America) with more than 8,000 deaths (WHO, 2014b).

There is no licensed treatment or vaccine for filovirus infection. Recently, several studies showed that filovirus glycoprotein (GP)-specific neutralizing antibodies (nAbs) can reduce mortality following experimental inoculation of animals with a lethal dose of EBOV (Dye et al., 2012; Marzi et al., 2012; Olinger et al., 2012; Qiu et al., 2012; Pettitt et al., 2013; Qiu et al., 2014) or MARV (Dye et al., 2012). The primary target of these neutralizing mAbs, the filovirus surface GP, is a trimer composed of three heavily glycosylated GP1-GP2 heterodimers. The GP1 subunit can be divided further into base, head, glycan cap and mucin-like domains (Lee et al., 2008). During viral entry, the mucin-like domain and glycan cap mediate binding to multiple host attachment factors present on the cell membrane. After the virus enters the host cell by macropinocytosis (Nanbo et al., 2010; Saeed et al., 2010), the GP is cleaved by host proteases that remove approximately 80% of the mass of the GP1 subunit, including the mucin-like domain and glycan cap (Chandran et al., 2005; Dube et al., 2009). After cleavage of GP in the endosome, the receptor-binding sites on GP become exposed, and the GP1 head then is able to bind to its receptor, Niemann-Pick C1 (NPC1) protein (Carette et al., 2011; Chandran et al., 2005; Côté et al., 2011). Subsequent conformational changes in GP facilitate fusion between viral and endosomal membranes.

The dense clustering of glycans on the glycan cap and mucin-like domain likely shield much of the surface of EBOV GP from humoral immune surveillance, leaving only a few sites on the EBOV GP protein where nAbs could bind without interference by glycans (Cook and Lee, 2013). Most of our knowledge about humoral response against Filovirus infections has come from studies of murine Abs that recognize EBOV GP. From those studies, the inventors learned that mouse neutralizing Abs preferentially target peptides exposed in upper, heavily glycosylated domains or lower areas (the GP1 base) where rearrangements occur that drive fusion of viral and host membranes (Saphire, 2013). Abs have not been identified that target protein features of the membrane proximal external region (MPER) subdomain, which likely rearranges during fusion. Ab KZ52, the only reported human EBOV GP-specific mAb, was obtained from a phage display library that was constructed from bone marrow RNA obtained from a survivor (Maruyama et al., 1999). KZ52 binds a site at the base of the GP and neutralizes EBOV, most likely by inhibiting the conformational changes required for fusion of viral and endosomal membranes (Lee et al., 2008). Some murine Abs also have been reported to bind to the base region of Ebola virus GPs (Dias et al., 2011, Murin et al., 2014).

SUMMARY

Thus, in accordance with the present disclosure, there is provided a method of detecting an ebolavirus infection in a subject comprising (a) contacting a sample from said subject with an antibody or antibody fragment having clone-paired heavy and light chain CDR sequences from Table 2, respectively, or an antibody or antibody fragment thereof as set forth in any figure or Table herein; and (b) detecting ebolavirus glycoprotein in said sample by binding of said antibody or antibody fragment to antigen in said sample. The sample may be a body fluid, such as blood, sputum, tears, saliva, mucous or serum, semen urine or feces. Detection may comprise ELISA, RIA, FACS or Western blot. The method may further comprise performing steps (a) and (b) a second time and determining a change in the glycoprotein levels as compared to the first assay.

The antibody or antibody fragment may be characterized by clone-paired variable sequences as set forth in Table 3, or light and heavy chain variable sequences having 70%, 80%, 90% or 95% identity to clone-paired variable sequences as set forth in Table 3. The antibody or antibody fragment may be encoded by light and heavy chain variable sequences having 70%, 80%, 90% or 95% identity to clone-paired variable sequences as set forth in Table 4. The antibody fragment may be a recombinant ScFv (single chain fragment variable) antibody, Fab fragment, F(ab')$_2$ fragment, or Fv fragment, or incorporated as scFv or Fab in a diabody.

In another embodiment, there is provided a method of treating a subject infected with Ebolavirus, or reducing the likelihood of infection of a subject at risk of contracting Ebolavirus, comprising delivering to said subject an antibody or antibody fragment having clone-paired heavy and light chain CDR sequences from Table 2, respectively, or an antibody or antibody fragment thereof as set forth in any figure or Table herein. The antibody or antibody fragment may be characterized by clone-paired variable sequences as set forth in Table 3, or light and heavy chain variable sequences having 70%, 80%, 90% or 95% identity to clone-paired variable sequences as set forth in Table 3. The antibody or antibody fragment may be encoded by light and heavy chain variable sequences having 70%, 80%, 90% or 95% identity to clone-paired variable sequences as set forth in Table 4. The antibody fragment may be a recombinant ScFv (single chain fragment variable) antibody, Fab fragment, F(ab')$_2$ fragment, or Fv fragment, or incorporated as scFv or Fab in a diabody. The antibody may be a chimeric antibody, or is a bispecific antibody that targets an Ebolavirus antigen other than glycoprotein.

The antibody or fragment thereof may be a bispecific antibody or fragment thereof that (a) targets a structural feature of an Ebola virus particle, and (b) targets receptor binding domain of Ebola virus. The structural feature may be an Ebola virus glycoprotein domain other than the receptor binding domain. The structural feature may be an Ebola virus virion structure other than the glycoprotein. The virion structure is a lipid, carbohydrate or protein. The antibody or fragment thereof may be a bispecific antibody that (a) targets a structural feature of an Ebola virus particle and (b) targets a host cell surface structure cells that is trafficked to endosomes. The host cell surface structure is a virus receptor (the cholesterol transporter Niemann-Pick C1) or glycan. The antibody may be administered prior to infection or after infection. Delivering may comprise antibody or antibody fragment administration, or genetic delivery with an RNA or DNA sequence or vector encoding the antibody or antibody fragment.

In still another embodiment, there is provided a monoclonal antibody, wherein the antibody or antibody fragment thereof is characterized as having clone-paired heavy and light chain CDR sequences from Table 2, respectively, or is an antibody or antibody fragment thereof as set forth in any figure or Table herein. The antibody or antibody fragment may be characterized by clone-paired variable sequences as set forth in Table 3, or light and heavy chain variable sequences having 70%, 80%, 90% or 95% identity to clone-paired variable sequences as set forth in Table 3. The antibody or antibody fragment may be encoded by light and heavy chain variable sequences having 70%, 80%, 90% or 95% identity to clone-paired variable sequences as set forth in Table 4. The antibody fragment may be a recombinant ScFv (single chain fragment variable) antibody, Fab fragment, F(ab')$_2$ fragment, or Fv fragment, or incorporated as scFv or Fab in a diabody. The antibody may be a chimeric antibody, or is a bispecific antibody that targets an Ebolavirus antigen other than glycoprotein.

The antibody or fragment thereof may be a bispecific antibody or fragment thereof that (a) targets a structural feature of an Ebola virus particle, and (b) targets receptor binding domain of Ebola virus. The structural feature may be an Ebola virus glycoprotein domain other than the receptor binding domain. The structural feature may be an Ebola virus virion structure other than the glycoprotein. The virion structure is a lipid, carbohydrate or protein. The antibody or fragment thereof may be a bispecific antibody that (a) targets a structural feature of an Ebola virus particle and (b) targets a host cell surface structure cells that is trafficked to endosomes. The host cell surface structure is a virus receptor (the cholesterol transporter Niemann-Pick C1) or glycan. The antibody may be an IgG. The antibody or antibody fragment may further comprise a cell penetrating peptide or is an intrabody.

In still a further embodiment, there is provided a hybridoma encoding an antibody or antibody fragment, wherein the antibody or antibody fragment has clone-paired heavy and light chain CDR sequences from Table 2, respectively, or is an antibody or antibody fragment thereof as set forth in any figure or Table herein. The antibody or antibody fragment produced by the hybridoma may be characterized by clone-paired variable sequences as set forth in Table 3, or light and heavy chain variable sequences having 70%, 80%, 90% or 95% identity to clone-paired variable sequences as set forth in Table 3. The antibody or antibody fragment produced by the hybridoma may be encoded by light and heavy chain variable sequences having 70%, 80%, 90% or 95% identity to clone-paired variable sequences as set forth in Table 4. The antibody fragment produced by the hybridoma may be a recombinant ScFv (single chain fragment variable) antibody, Fab fragment, F(ab')$_2$ fragment, or Fv fragment, or incorporated as scFv or Fab in a diabody. The antibody may be a chimeric antibody, or is a bispecific antibody that targets an Ebolavirus antigen other than glycoprotein.

The antibody or fragment thereof may be a bispecific antibody or fragment thereof that (a) targets a structural feature of an Ebola virus particle, and (b) targets receptor binding domain of Ebola virus. The structural feature may be an Ebola virus glycoprotein domain other than the receptor binding domain. The structural feature may be an Ebola virus virion structure other than the glycoprotein. The virion structure is a lipid, carbohydrate or protein. The antibody or fragment thereof may be a bispecific antibody that (a) targets a structural feature of an Ebola virus particle and (b) targets a host cell surface structure cells that is trafficked to endosomes. The host cell surface structure is a virus receptor (the cholesterol transporter Niemann-Pick C1) or glycan. The antibody produced by the hybridoma may be an IgG. The antibody or antibody fragment produced by the hybridoma may further comprise a cell penetrating peptide or is an intrabody.

Also provided are:
  a human monoclonal antibody or fragment thereof, or a hybridoma expressing the same, wherein said antibody neutralizes BDBV at 5 ng/ml, and/or neutralizes EBOV at 50 ng/ml;
  a human monoclonal antibody or fragment thereof, or a hybridoma expressing the same, wherein said antibody has in $IC_{50}$ for BDBV and/or EBOV of 1-1,000 ng/ml;
  a human monoclonal antibody or fragment thereof, or a hybridoma expressing the same, wherein said antibody binds to virus strains of at least two of two Ebola virus species selected from BDBV, EBOV and SUDV, such as one that binds to virus strains of all three Ebola virus species BDBV, EBOV and SUDV, and/or that, neutralizes virus strains of at least two of Ebola virus species selected from BDBV, EBOV and SUDV, including one that neutralizes BDBV and EBOV;
  a human monoclonal antibody antibody fragment or hybridoma expressing the same, wherein the antibody, antibody fragment or hybridoma binds to full length Ebolavirus glycoprotein (GP), Ebolavirus GP with a deleted mucin domain, and secreted ebolavirus GP;
  a human monoclonal antibody antibody fragment or hybridoma expressing the same, wherein the antibody, antibody fragment or hybridoma binds to full length Ebolavirus glycoprotein (GP) and Ebolavirus GP with a deleted mucin domain, but not secreted ebolavirus GP;
  a human monoclonal antibody antibody fragment or hybridoma expressing the same, wherein the antibody, antibody fragment or hybridoma binds to secreted Eebolavirus GP, but not to full length Ebolavirus glycoprotein (GP) and ebolavirus GP with a deleted mucin domain;
  a human monoclonal antibody antibody fragment or hybridoma expressing the same, wherein the antibody, antibody fragment or hybridoma binds to the glycan cap domain of Ebolavirus glycoprotein (GP), or to the heptad repeat region 2 and membrane proximal external region of the stem of Ebolavirus GP, but does not bind to the base region of the stem of Ebolavirus GP, such as where the glycan cap domain is defined as amino acids 227-313, and where the heptad repeat region 2 and membrane proximal external region is defined as GP amino acids 599-651 (containing the two components 599-632/heptad repeat region 2 and 633-651 [membrane proximal external region), and where the base region of the stem is defined as the antigenic site at the surface of the GP1/GP2 interface, recognized by the previously reported mAbs c4G7, KZ52, c2G4 and 16F6.

Also provided is a vaccine formulation comprising one or more peptides from the membrane proximal external region of Ebolavirus glycoprotein (GP), and a pharmaceutically acceptable buffer, carrier or diluent. The vaccine formulation may further comprise an adjuvant. The one or more peptides may comprises a sequence selected from the heptad repeat 2 and MPER region of EBOV, BDBV, or SUDV, such as the EBOV peptides ITDKIDQIIHDFVDK (SEQ ID NO: 25) or TDKIDQIIHDFVDKTL (SEQ ID NO: 26) or the SUDV peptides ITDKINQIIHDFIDNPL (SEQ ID NO: 27) or TDKINQIIHDFIDNPL (SEQ ID NO: 28) or the BDBV peptide TDKIDQIIHDFIDKPL (SEQ ID NO: 29). The one or more peptides may be from 15-100 residues, from 15-50 residues or from 15-25. The one or more peptides may be from 15-50 consecutive residues or 15-25 consecutive residues of Ebolavirus. The one or more peptides may consist of a sequence are selected from the heptad repeat 2 and MPER region of EBOV, BDBV, or SUDV, such as the EBOV peptides ITDKIDQIIHDFVDK (SEQ ID NO: 25) or TDKIDQIIHDFVDKTL (SEQ ID NO: 26) or the SUDV peptides ITDKINQIIHDFIDNPL (SEQ ID NO: 27) or TDKINQIIHDFIDNPL (SEQ ID NO: 28) or the BDBV peptide TDKIDQIIHDFIDKPL (SEQ ID NO: 29).

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 1A:
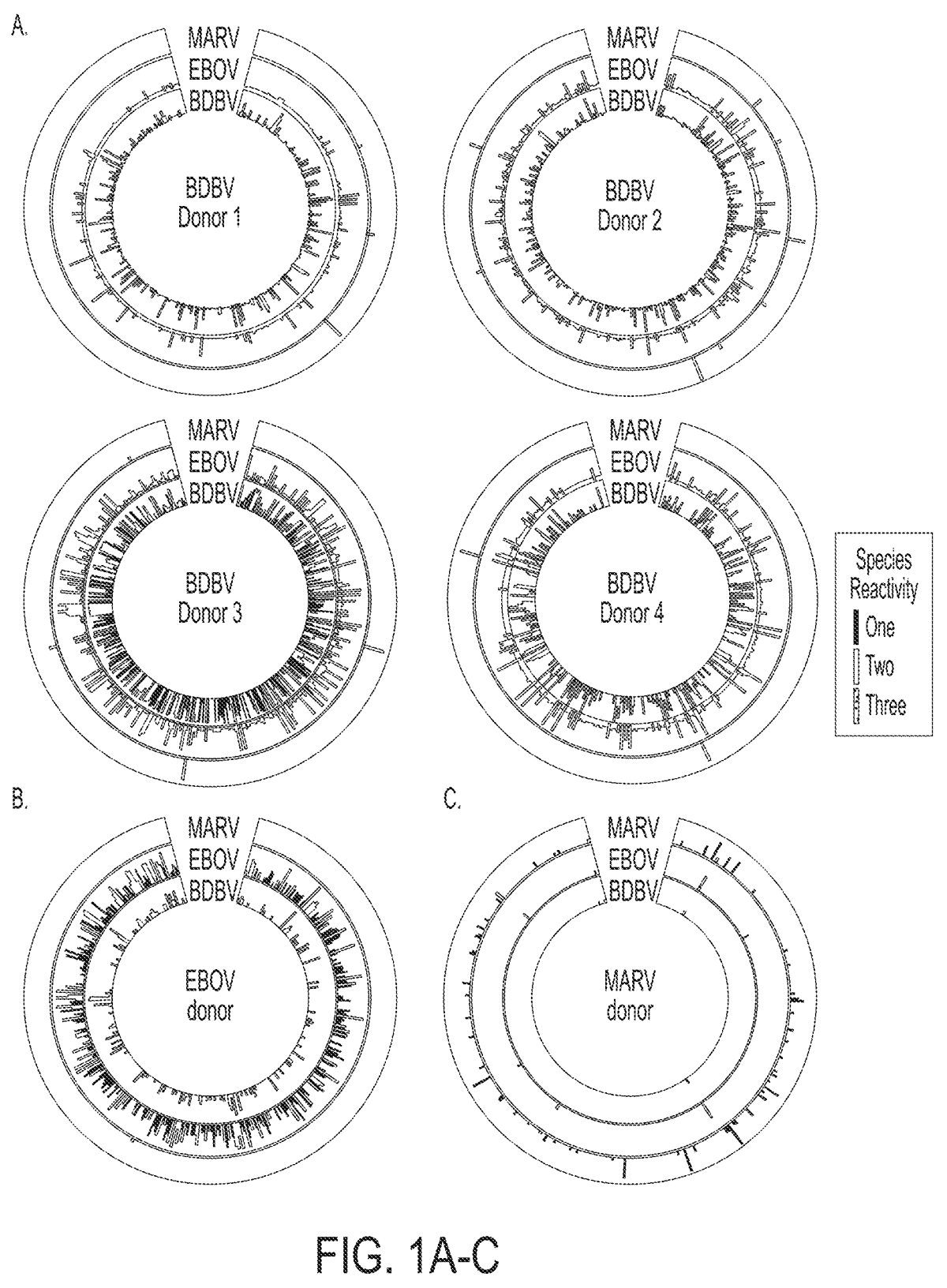

FIGS. 1A-D. Cross-reactive B cell responses in filovirus immune donors. Supernatants from EBV-transformed PBMC samples isolated from survivors were screened in ELISA binding assays using BDBV, EBOV or MARV GPs (FIGS. 1A-C). Results for four BDBV survivors (FIG. 1A), one EBOV survivor (FIG. 1B) or one MARV survivor (FIG. 1C) are shown. Height of the bars indicates $OD_{405\,nm}$ values in ELISA binding to full-length extracellular domain of GP of the indicated virus species. Reactive supernates are color-coded based on the cross-reactivity pattern: species-specific cell lines are highlighted in black; cross-reactive lines to 2 or 3 species are shown in yellow or blue, respectively. Previous work has shown that the amino acid sequence of GP differs between BDBV and EBOV by over 34%, and between BDBV and MARV by over 72%. (FIG. 1D) Percentages of lines secreting antibodies specific to BDBV, EBOV or MARV GPs, or cross-reactive antibodies to BDBV and EBOV (designated BDBV/EBOV) or BDBV, EBOV and MARV (designated BDBV/EBOV/MARV) are shown. Increasing intensity of the pink cell fill color corresponds to increasing reactivity for indicated virus. See also FIG. 8.

Figure 2C:
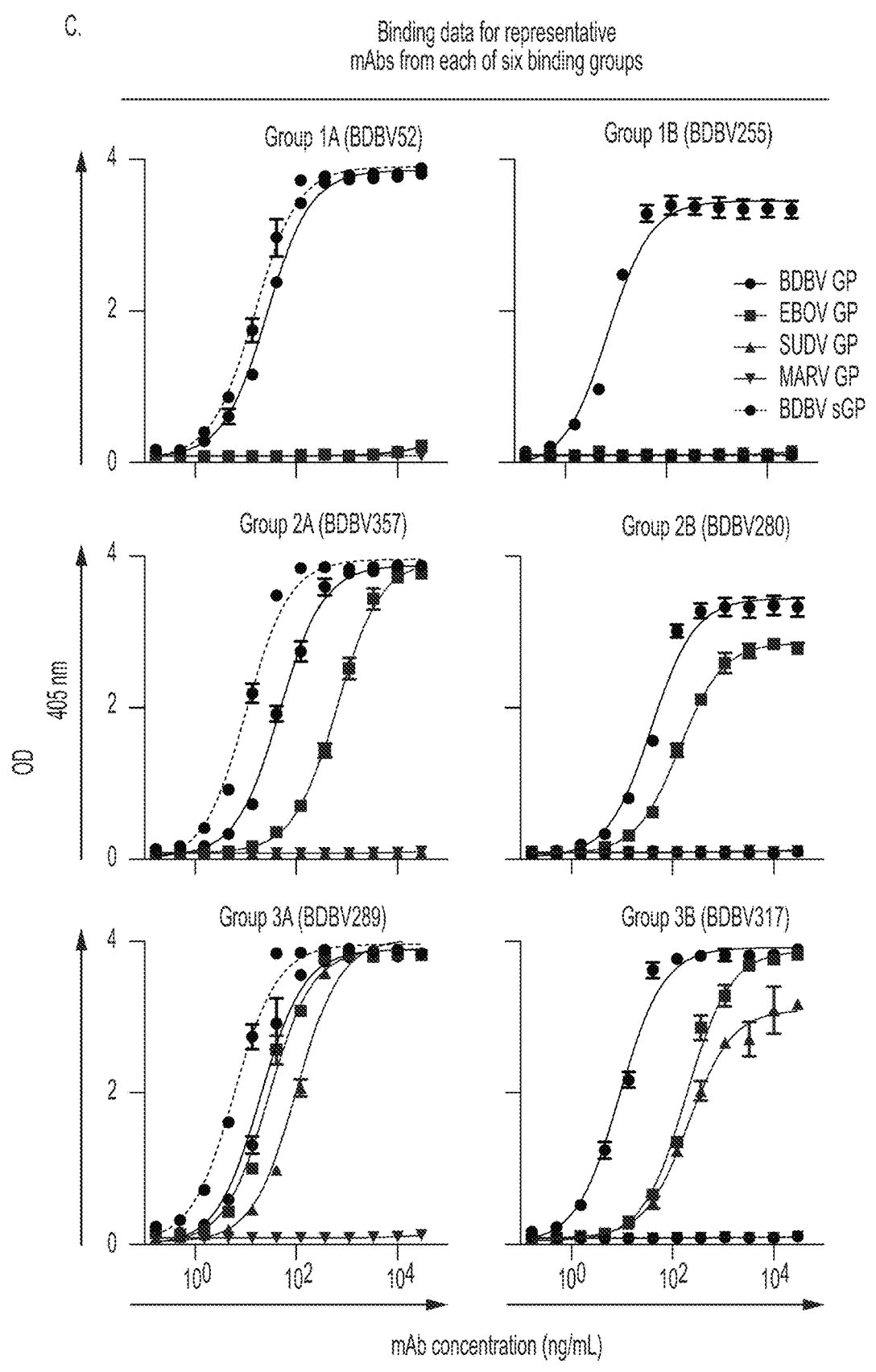

FIGS. 2A-D. Cross-neutralizing antibodies from survivors of natural BDBV infection. (FIG. 2A) Heat map showing the binding of BDBV mAbs to a panel of filovirus GPs. The $EC_{50}$ value for each GP-mAb combination is shown, with dark red, orange, yellow, or white shading indicating high, intermediate, low, or no detectable binding, respectively. $EC_{50}$ values greater than 10,000 ng/mL are indicated by the >symbol. NAb names are highlighted in red. (FIG. 2B) Heat map showing the neutralization potency of BDBV GP-specific mAbs against BDBV. The $IC_{50}$ value for each virus-mAb combination is shown. $IC_{50}$ values greater than 10,000 ng/mL are indicated by the >symbol. Neutralization assays were performed in triplicate. (FIG. 2C) Binding of representative mAbs from six distinct binding groups to the filovirus GP. (FIG. 2D) Neutralization activity of representative neutralizing mAbs from three binding groups against BDBV, EBOV or SUDV. Error bars represent the SE of the experiment, performed in triplicate. See also FIGS. 9-11.

Figure 3:
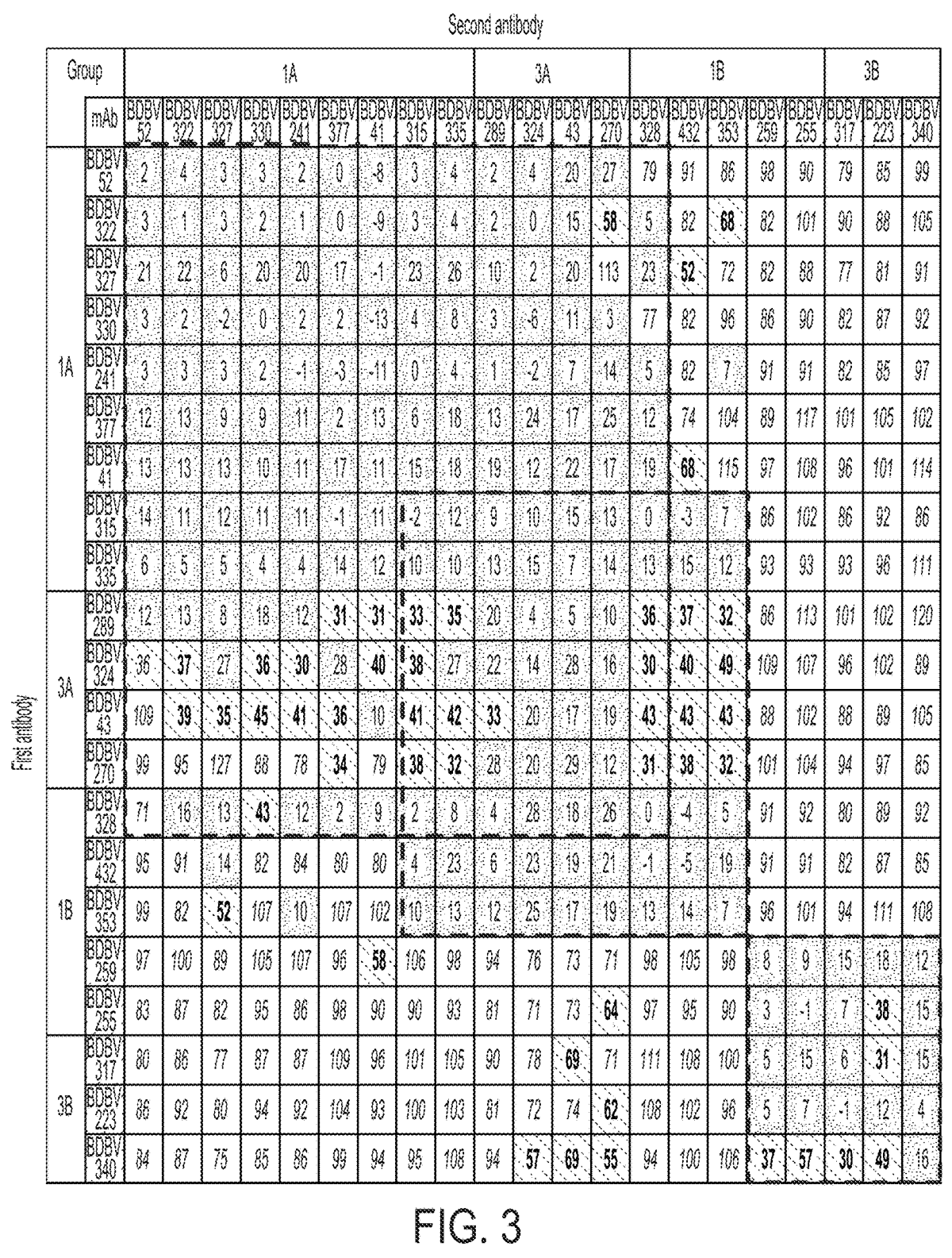

FIG. 3. BDBV-neutralizing antibodies target at least two distinct antigenic regions of the GP surface. Data from competition-binding assays using non-neutralizing mAbs from binding Group 1A (white background) and neutralizing mAbs from binding Groups 1A, 1B, 3A or 3B (pink background). Numbers indicate the percent binding of second mAb in the presence of the first mAb, compared to binding of un-competed second mAb. MAbs were judged to compete for the same site if maximum binding of second mAb was reduced to <30% of its un-competed binding (black boxes with white numbers). MAbs were considered non-competing if maximum binding of second mAb was >70% of its un-competed binding (white boxes with red numbers). Grey boxes with black numbers indicate an intermediate phenotype (competition resulted in between 30 and 70% of un-competed binding). Blue, purple, and green dashed lines indicate what appear to be major competition groups; the blue and purple groups overlap substantially but not completely.

FIGS. 4A-E. BDBV-neutralizing antibodies bind to the glycan cap or base region of GP. (FIG. 4A) Shown are negative-stain electron microscopy reference-free 2D class averages of Group 1A antibodies that bind both the glycan cap of GP and sGP, and Group 1B antibodies that bind the glycan cap of GP but not sGP. BDBV GP or GPΔmuc was used to generate complexes. (FIG. 4B) 3D reconstructions of glycan cap binders from Groups 1A and 1B reveal that these antibodies bind the glycan cap at overlapping but distinct epitopes. Top (left) and side (right) views of the complexes are shown. (FIG. 4C) Reference free 2D class averages of Group 1B antibodies (left) reveals that these antibodies bind an epitope below the base of GP that is flexible. In the middle image, GP is colored yellow and each Fab colored green. The right-hand panel illustrates a superimposition of crystal structures of SUDV GPΔmuc (PDB 3VEO) and Fabs (PDB 3CSY) to demonstrate how Fabs may bind to GP. (FIG. 4D) The composite model delineates the epitopes of the glycan cap mAbs in Group 1A or 1B. Side (above) and top (below) views are shown. (FIG. 4E) Docking a crystal structure of SUDV GPΔmuc (PDB 3VEO) (Bale et al., 2012), which contains a more complete model of the glycan cap region targeted by Group 1A/B mAbs, reveals how Group 1A/B mAbs target a broad region in the GP1 centered on the glycan cap, near the beginning of the mucin-like domains. Group 1B mAbs that target the base likely bind to a loop near the membrane proximal external region (MPER) that is flexible and has not yet been resolved at high resolution. TM=transmembrane region; CT=cytoplasmic tail. See also FIGS. 12A-D.

Figure 5A:
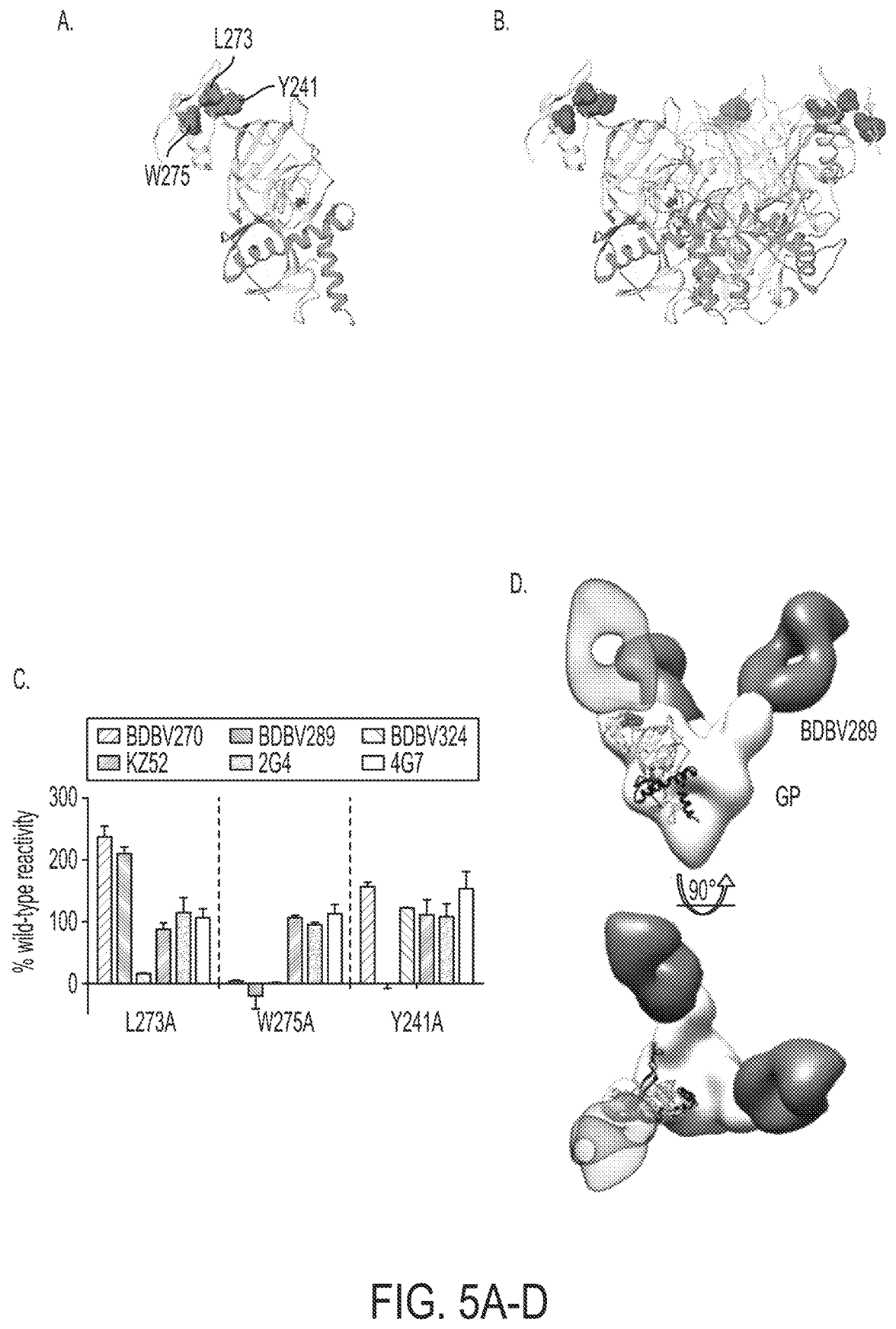

FIGS. 5A-D. Epitope mapping of Group 3A mAbs using saturation mutagenesis and negative stain electron microscopy. Epitope residues for three nAbs from Group 3A (BDBV270, BDBV289 and BDBV324) were identified as those for which mutation to alanine specifically reduced binding of these antibodies (FIGS. 5A-B). GP residue W275 was common to all three nAbs, while L273 was specific for BDBV324, and Y241 was specific for BDBV289. The mutated residues are shown in space filling forms on a ribbon diagram of the EBOV GP structure, based on PDB 3CSY. (FIG. 5C) Binding values for nAbs and previously isolated mAbs KZ52, 2G4 and 4G7 to library clones with mutations at residues L273, W275 and Y241. The Ab reactivities against each mutant EBOV GP clone were calculated relative to reactivity with wild-type EBOV GP. (FIG. 5D) BDBV289 (brown) binds at the top of the viral GP near the glycan cap region. Complexes are of BDBV antibody Fab fragments bound to BDBV GPΔTM with side view (top panel) or top view (bottom panel). A representative Fab crystal structure is fit in the Fab density for each reconstruction (from PDBID 3CSY). A monomer of the GP trimer crystal structure (PDBID 3CSY) is also fit in the GP density, with white corresponding to GP1 and black to GP2. Two critical residues for binding by BDBV289 (W275 and Y241, determined using saturation mutagenesis) are highlighted in green. See also FIGS. 13A-B.

Figure 6A:
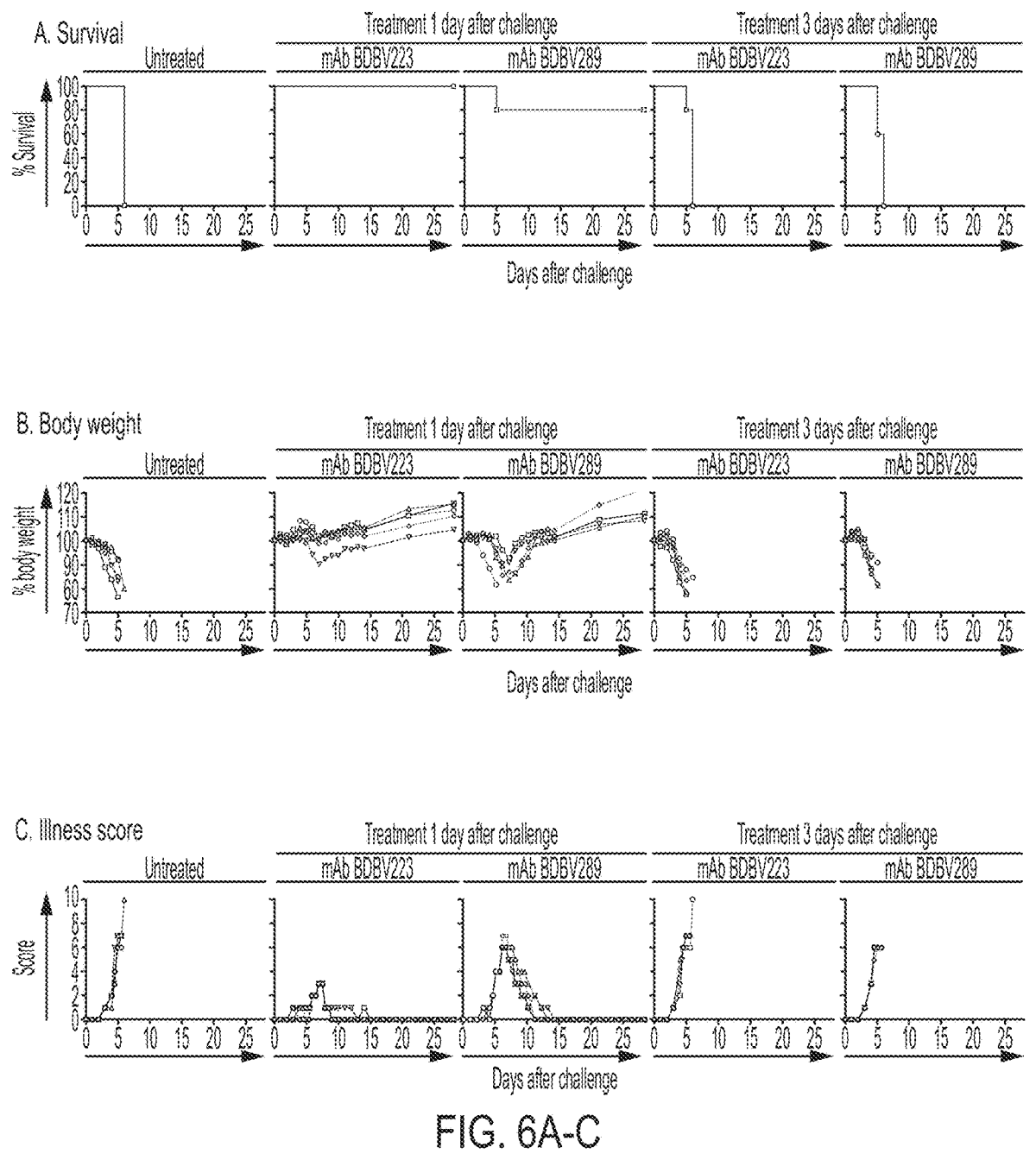

FIGS. 6A-C. Survival and clinical signs of EBOV-inoculated mice treated with BDBV mAbs. Groups of 5 mice in each group were injected with individual mAbs by the intraperitoneal route 1 day after EBOV challenge, using 100 µg of mAb per treatment. Animals treated with dengue virus-specific human mAb 2D22 served as controls. (FIG. 6A) Kaplan-Meier survival curves. (FIG. 6B) Body weight. (FIG. 6C) Illness score.

FIG. 8. Cross-reactive B cell responses in BDBV immune donors 5 and 6. Related to FIG. 1. Supernatants from EBV-transformed PBMC samples isolated from survivors were screened in ELISA binding assays using BDBV, EBOV or MARV GPs. Height of the bars indicates $OD_{405\ nm}$ values in ELISA binding to full-length extracellular domain of GP of the indicated virus species. Reactive supernates are color-coded based on the cross-reactivity pattern: species-specific cell lines are highlighted in black; cross-reactive lines to 2 or 3 species are shown in yellow or blue, respectively.

Figure 10:
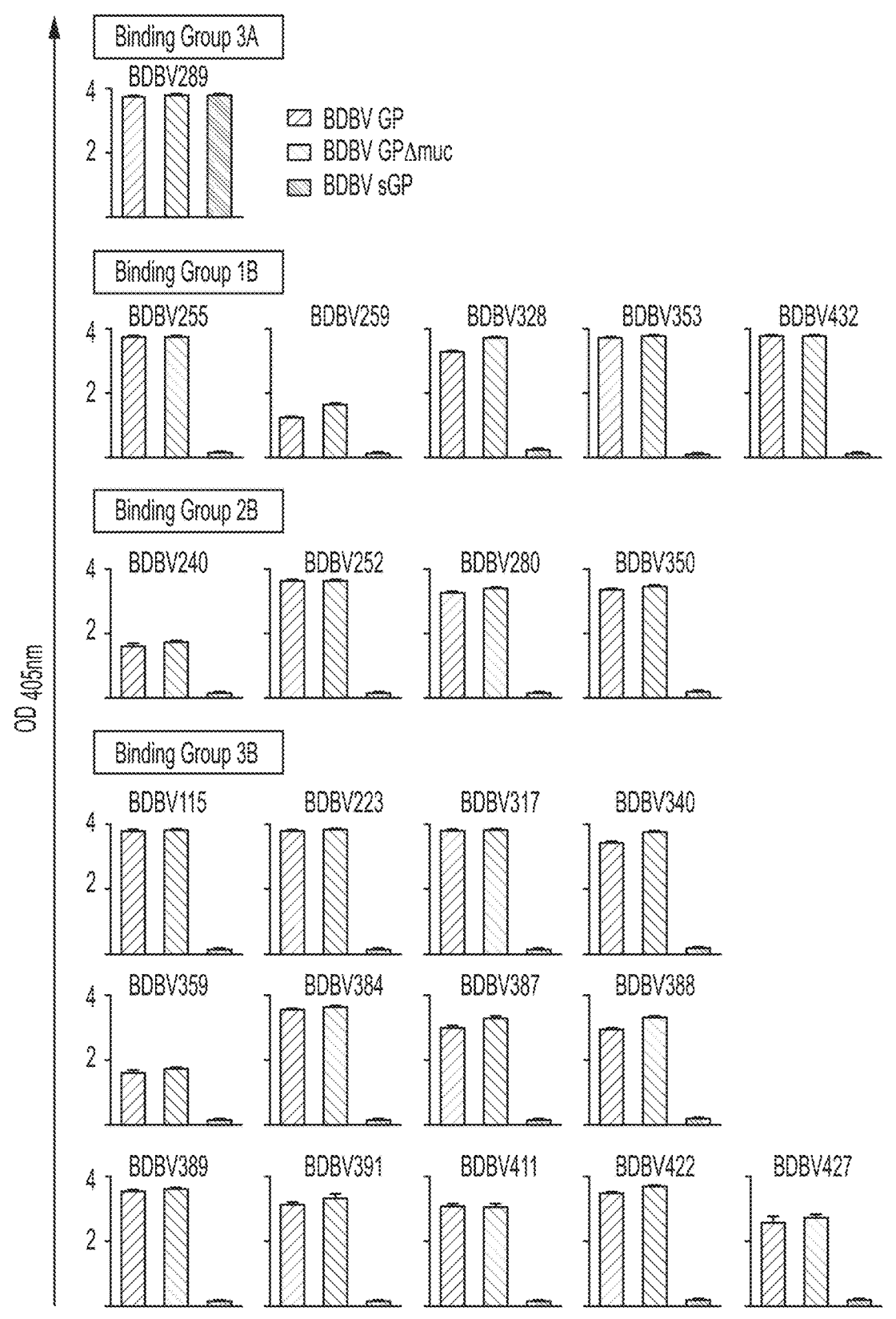

FIG. 10. Antibodies from groups 1B, 2B and 3B recognize BDBV GP and BDBV GPΔmuc but not BDBV sGP in ELISA binding assay (related to FIGS. 2A-B). The binding of selected antibodies to BDBV GP, BDBV GPΔmuc and BDBV sGP proteins was tested at a single mAb concentration 10 µg/mL.

FIGS. 12A-E. Raw data and validation of EM models (related to FIGS. 4A-E). (FIG. 12A) Raw EM micrograph (far left), 2D reference-free class averages (middle left), and an FSC curve with resolution indicated (far right) of BDBV41 in complex with BDBV GPΔmuc. (FIG. 12B) As in FIG. 12A but of BDBV335 in complex with BDBV GPΔmuc. (FIG. 12C) As in FIG. 12A, but of BDBV432 in complex with BDBV GPΔmuc. (FIG. 12D) As in FIG. 12A but of BDBV353 in complex with BDBV GP. (FIG. 12E) As in FIG. 12A, but of BDBV289 in complex with BDBV GP. Refinement package used to generate each reconstruction is indicated on the far left. Scale bar indicates 200 nm.

FIGS. 13A-B. Generation of escape mutant viruses for BDBV41 (related to FIGS. 5A-E). (FIG. 13A) Neutralization activity of BDBV41 against wild-type VSV/BDBV-GP (circles, straight curves), VSV/BDBV-GP #7 (squares, dashed curves), or VSV/BDBV-GP #15 (triangles, dotted curves) escape mutant viruses. (FIG. 13B) Amino acid changes in BDBV41 escape mutant viruses FIGS. 14A-C. Cross-reactive neutralizing antibodies from BDBV survivors bind a unique region on GP surface. (FIG. 14A) Binding of BDBV223, BDBV317 or BDBV340 to BDBV, EBOV, SUDV GP or sGP. (FIG. 14B) Neutralization activity of BDBV223, BDBV317 or BDBV340 against BDBV, EBOV, or SUDV. (FIG. 14C) Data from competition-binding assays using BDBV223, BDBV317 or BDBV340; antibodies from ZMapp™ cocktail (c2G4, c4G7 and 13C6) and previously isolated human antibodies KZ52 and BDBV289. Numbers indicate the percent binding of the second mAb in the presence of the first mAb, compared to binding of second mAb alone. MAbs were judged to compete for the same site if maximum binding of the second mAb was reduced to <30% of its un-competed binding (black boxes with white numbers). MAbs were considered non-competing if maximum binding of the second mAb was >70% of its un-competed binding (white boxes with red numbers). Grey boxes with black numbers indicate an intermediate phenotype (between 30 and 70% of un-competed binding).

FIGS. 15A-E. Cross-reactive neutralizing antibodies from BDBV survivors bind near the membrane proximal region of GP. (FIG. 15A) Representative negative stain class averages of antibodies that bind GP2 exclusively in the HR2/MPER region. Complexes are of BDBV Fabs bound to BDBV GPΔmuc. (FIG. 15B) A class average of BDBV GPΔmuc bound to BDBV223 demonstrates the location of each component, with the core GP colored blue and the Fabs in green. (FIG. 15C) A class average of c13C6 Fab:c4G7 Fab bound to EBOV GPΔTM[7] (with c13C6 in dark blue, c4G7 in yellow and GP core in light blue). (FIG. 15D) Overlaying a class average of c13C6 Fab:c4G7 Fab bound to EBOV GPΔTM[7] (with c13C6 in dark blue, c4G7 in yellow and GP core in light blue) over a class average of BDBV223 Fab bound to BDBV GPΔmuc (with BDBV223 in green and GP core in light blue), demonstrates that BDBV223 binds significantly lower down on GP, well below the epitope of the c4G7 site of vulnerability at the GP1/GP2 interface. (FIG. 15E) A model of the c13C6 Fab:c4G7 Fab bound to EBOV GPΔTM (EMDB ID-6152) is shown with the relative location of BDBV223/317/340 Fabs (segmented c4G7 Fabs from the above map placed in the relative location on GP as indicated by class averages). Measurements of the distance from the bottom of the GP core to the mid-point of the Fab in the class averages showed a distance of ~60A, which corresponds to the length of the HR2 region previously crystalized as post-fusion GP2 (PDBID 1EBO).

FIGS. 16A-D. Structural and functional analysis of GP residues important for mAb cross-reactivity and neutralization. (FIG. 16A) Sequence alignment of GP2 from BDBV (SEQ ID NO: 344), EBOV (SEQ ID NO: 345) and SUDV (SEQ ID NO: 346). The numbers above the sequence correspond to the amino acid position in GP. Amino acids identical to BDBV are indicated by dots. Color-coded shapes indicate the position of residues at which alanine substitutions disrupt mAb binding, as determined by alanine-scanning mutagenesis. BDBV1, BDBV2, EBOV2 or SUDV2 peptide sequences analyzed are indicated by grey, black, blue or purple lines, respectively. (FIG. 16B) Locations of critical residues for BDBV317 and c4G7 binding are displayed on a model of EBOV GP. BDBV317 critical residues are highlighted in green and c4G7 critical residues are highlighted in yellow. (FIG. 16C) Binding of BDBV223, BDBV317 or BDBV340 to BDBV1, BDBV2, EBOV2 or SUDV2 peptides. (FIG. 16D) Binding of BDBV223, BDBV317 or BDBV340 to members of a panel of chimeric BDBV peptides (BDBV3=SEQ ID NO: 107).

FIG. 17. Cross-recognition of antibodies from survivors of natural EBOV infection. Heat map showing the binding of EBOV mAbs to a panel of Filovirus GPs. The $EC_{50}$ value for each GP-mAb combination is shown, with dark red, orange, yellow, or white shading indicating high, intermediate, low, or no detectable binding, respectively. $EC_{50}$ values greater than 10,000 ng/mL are indicated by the >symbol. NAb names are highlighted in red.

FIGS. 18A-C. Survival and clinical signs of EBOV-inoculated mice treated with EBOV mAbs. Groups of 5 mice in each group were injected with individual mAbs by the intraperitoneal route 1 day after EBOV challenge, using 100 μg of mAb per treatment. Animals treated with dengue virus-specific human mAb 2D22 served as controls. (FIG. 18A) Kaplan-Meier survival curves. (FIG. 18B) Body weight. (FIG. 18C) Illness score. $IC_{50}$ values in neut test are shown.

FIGS. 19A-C. Survival and clinical signs of EBOV-inoculated mice treated with EBOV mAbs. Groups of 5 mice in each group were injected with individual mAbs by the intraperitoneal route 1 day after EBOV challenge, using 100 μg of mAb per treatment. (FIG. 19A) Kaplan-Meier survival curves. (FIG. 19B) Body weight. (FIG. 19C) Illness score. $IC_{50}$ values in neut test are shown.

FIG. 20. Epitope mapping for representative EBOV mAbs by alanine scanning mutagenesis of EBOV GP.

DESCRIPTION OF ILLUSTRATIVE EMBODIMENTS

Figure 2D:
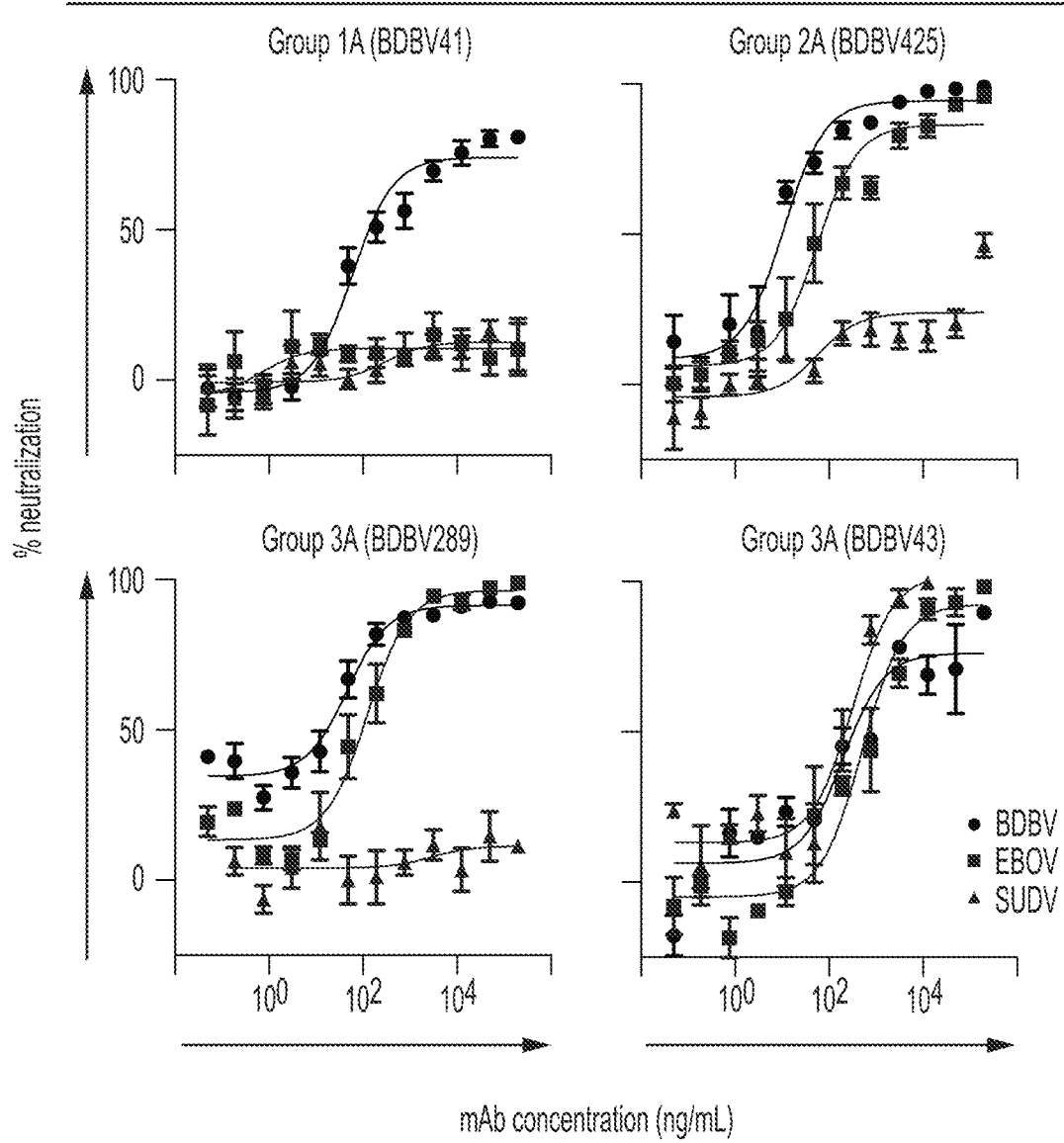
Figure 7A:
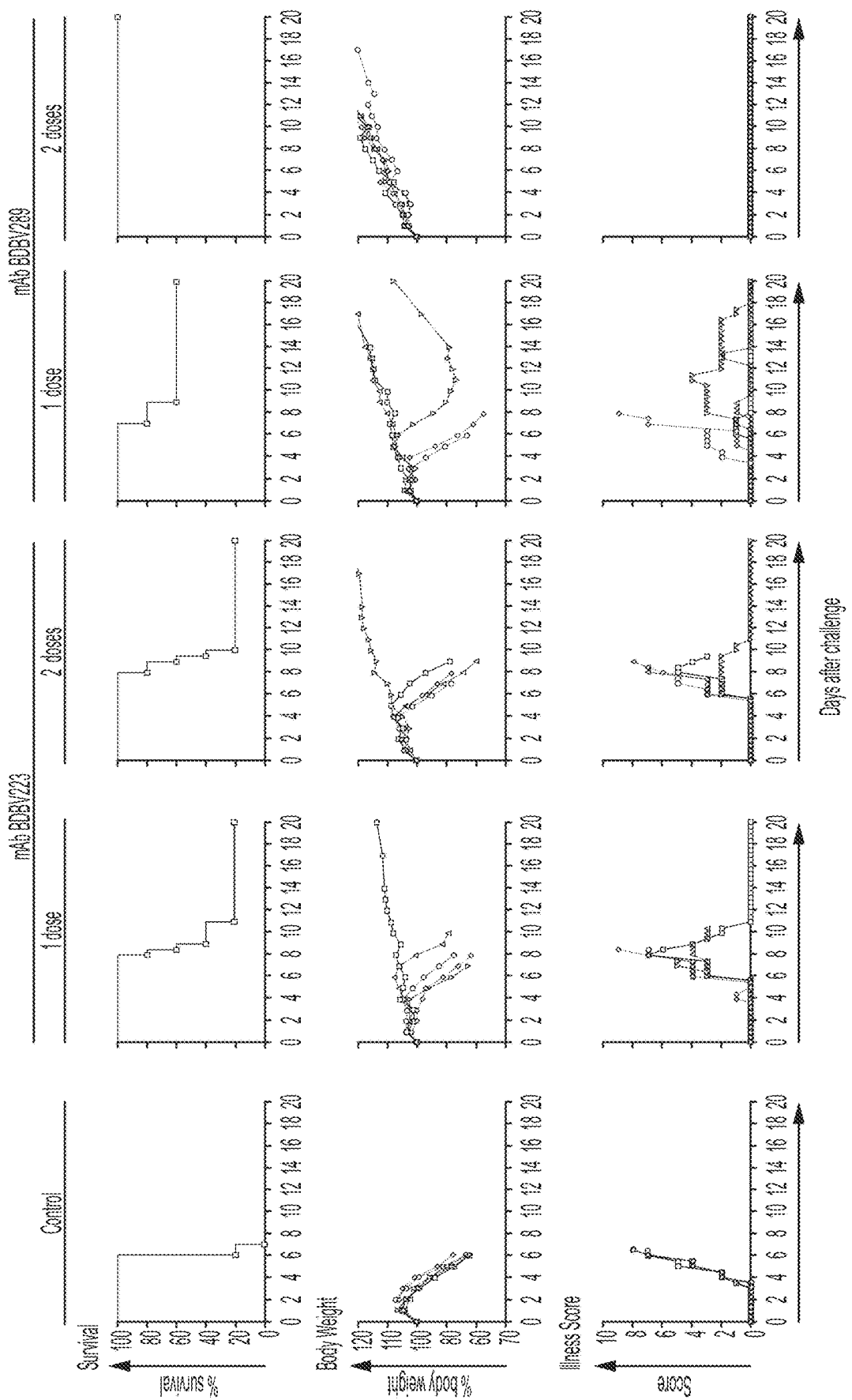
FIGS. 7A-B. Survival and clinical signs of EBOV inoculated guinea pigs treated with BDBV mAbs. Groups of 5 guinea pigs per group were injected with individual mAbs by the intraperitoneal route 1 day or 1 and 3 days after EBOV challenge, using 5 mg of individual mAb (FIG. 7A) or 5 mg of the combination of two mAbs per treatment (FIG. 7B), as indicated. Animals treated with dengue virus-specific human mAb 2D22 served as controls. The survival curves are based on morning and evening observations. Mortality in the morning is shown in whole day numbers, in the evening in ½ day values. The body weight and illness scores are shown with one value per day.
Figure 7B:
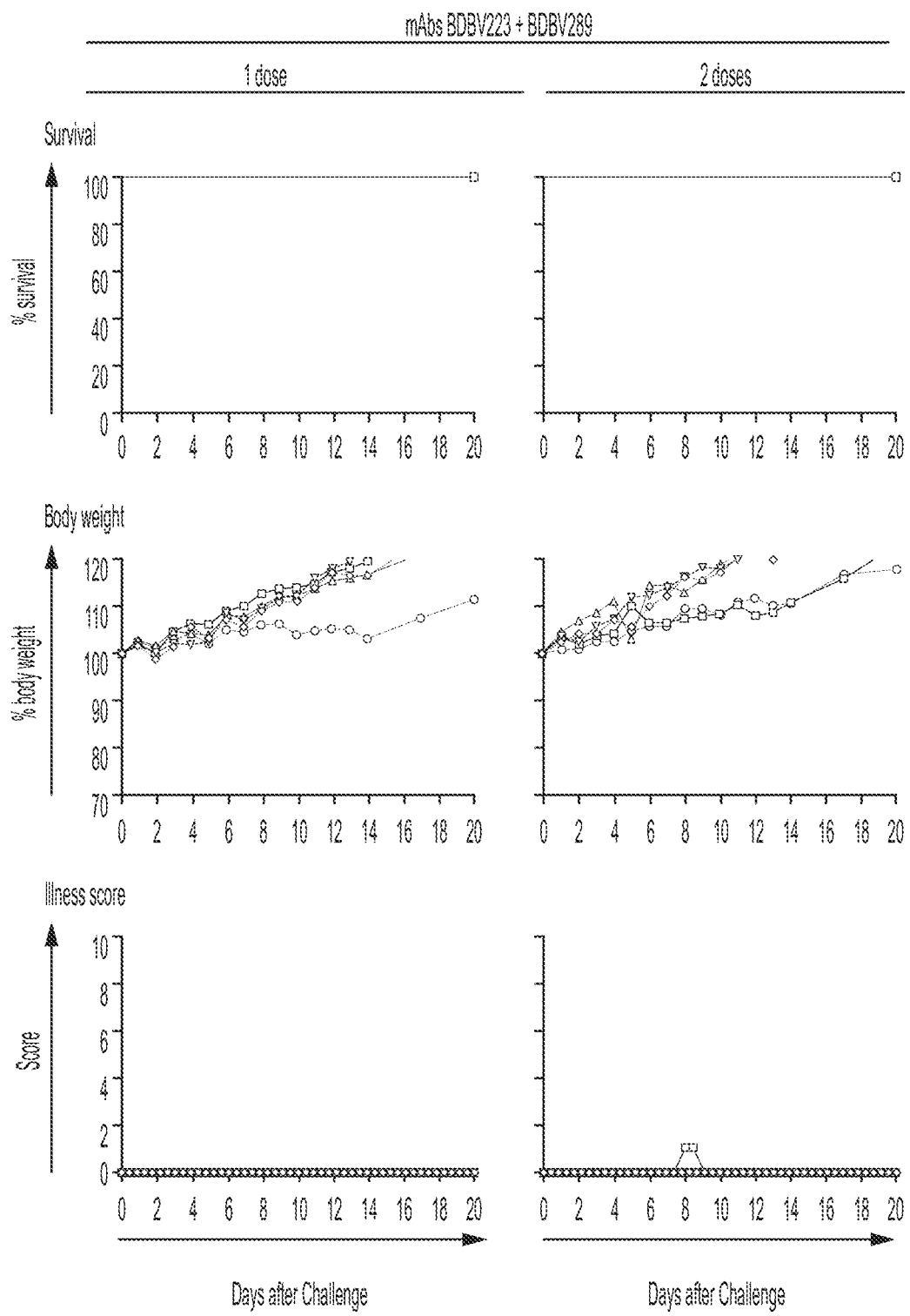
Figure 9:
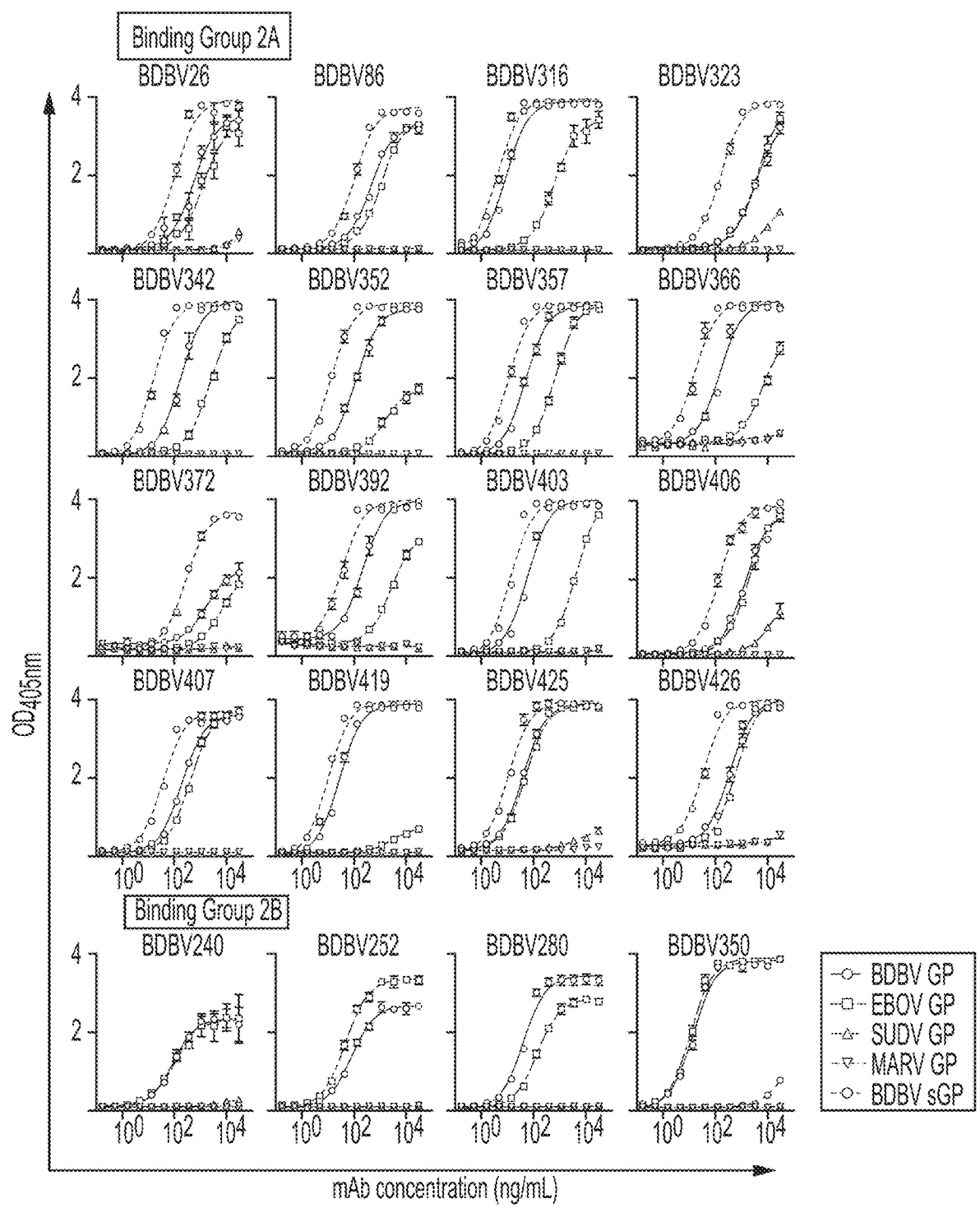
FIG. 9. Binding patterns of BDBV GP-specific antibodies from Binding Group 2. (related to FIGS. 2A-D). Antibodies were segregated into six groups based on the binding to Filovirus GPs. Binding was categorized based on the $OD_{405}$ values at the highest antibody concentration tested ($E_{max}>0.5$) and 50% effective concentration ($EC_{50}<10$ µg/mL).
Figure 11:
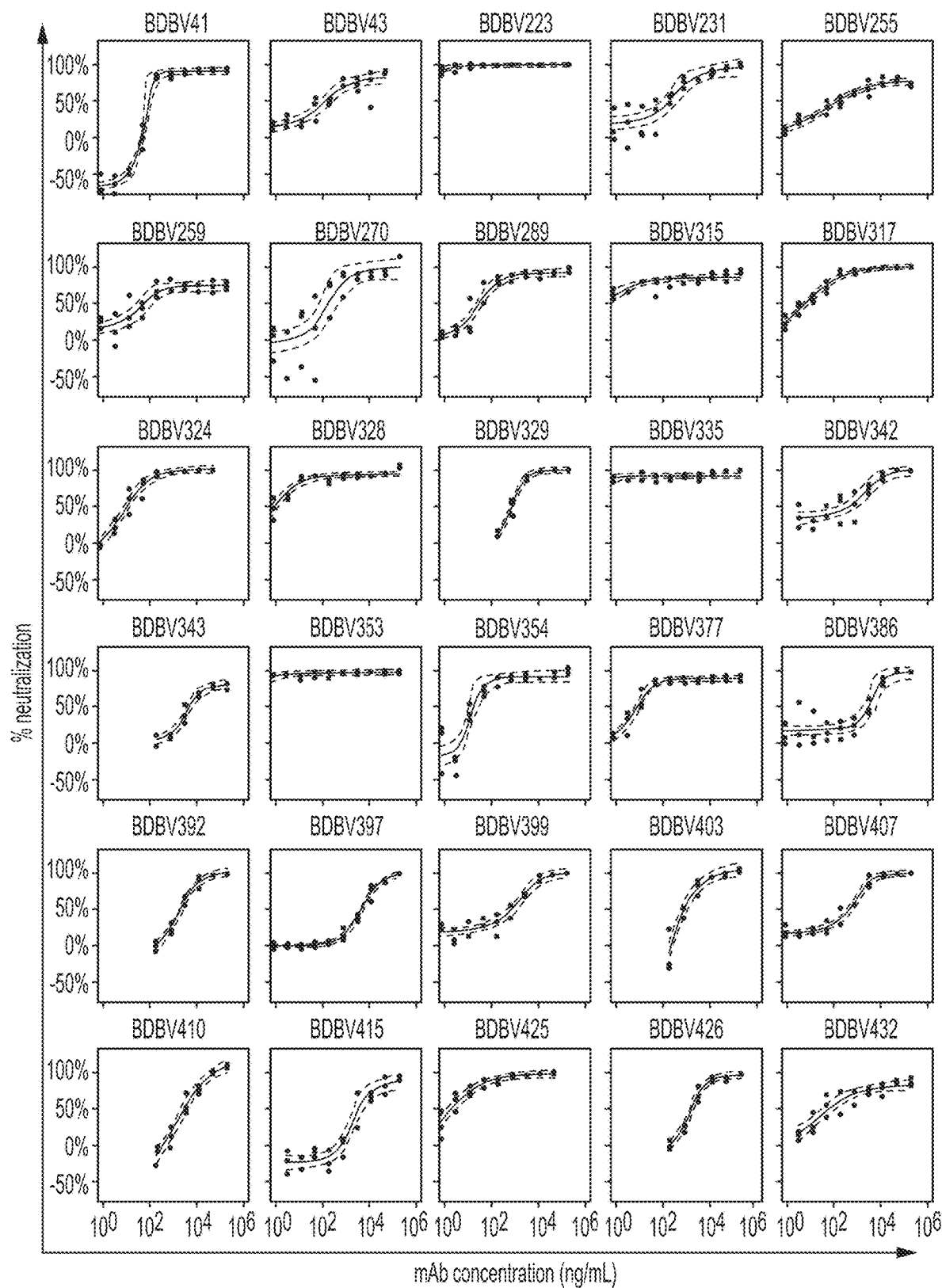
FIG. 11. Neutralization activity of BDBV GP-specific nAbs against BDBV (related to FIGS. 2A-D). Red circles represent percent neutralization relative to control at different antibody concentrations. Logistic curves are indicated by solid lines, and 95% confidence intervals are indicated by dashed lines.

In the work reported here, the inventors isolated a large panel of human binding nAbs from B cells of human survivors of severe infection with Ebola Bundibugyo species or Ebola Zaire (the latter also called 2014 "Makona strain," or "Guinea strain", now properly termed Ebolavirus ebola) and used these Abs to define the molecular basis of MARV neutralization by human Abs. Remarkably, several of the Abs bound to GPs from diverse species of Ebola virus and some neutralized live viruses from diverse species. Single-particle EM structures of Ab-GP complexes revealed that some of the neutralizing Abs bound to EBOV GP near the viral membrane in the membrane proximal external region (MPER). The antibodies reported here are the first human monoclonal antibodies to these regions. Additional antibodies were shown to bind at the top of the glycoprotein, in the glycan cap region. The inventors isolated antibodies that recognize distinct patterns of glycoprotein. Some of the monoclonal antibodies bind to full-length and mucin deleted forms of glycoprotein, while avoiding potential deleterious binding to the secreted form of glycoprotein. They also found monoclonal antibodies that bind to all three forms of glycoprotein, full-length, mucin-deleted, and secreted GP. These and other aspects of the disclosure are described in detail below.

I. EBOLAVIRUS

The genus Ebolavirus is a virological taxon included in the family Filoviridae, order Mononegavirales. The members of this genus are called ebolaviruses. The five known virus species are named for the region where each was originally identified: Bundibugyo ebolavirus, Reston ebolavirus, Sudan ebolavirus, nil Forest ebolavirus (originally Côte d'Ivoire ebolavirus), and Zaire ebolavirus.

The Ebola virus (EBOV) protein VP24 inhibits type I and II interferon (IFN) signaling by binding to NPI-1 subfamily karyopherin α (KPNA) nuclear import proteins, preventing their interaction with tyrosine-phosphorylated STAT1 (phospho-STAT1). This inhibits phospho-STAT1 nuclear import. A biochemical screen now identifies heterogeneous nuclear ribonuclear protein complex C1/C2 (hnRNP C1/C2) nuclear import as an additional target of VP24. Co-immunoprecipitation studies demonstrate that hnRNP C1/C2 interacts with multiple KPNA family members, including KPNA1. Interaction with hnRNP C1/C2 occurs through the same KPNA1 C-terminal region (amino acids 424-457) that binds VP24 and phospho-STAT1. The ability of hnRNP C1/C2 to bind KPNA1 is diminished in the presence of VP24, and cells transiently expressing VP24 redistribute hnRNP C1/C2 from the nucleus to the cytoplasm. These data further define the mechanism of hnRNP C1/C2 nuclear import and demonstrate that the impact of EBOV VP24 on nuclear import extends beyond STAT1.

Ebolaviruses were first described after outbreaks of EVD in southern Sudan in June 1976 and in Zaire in August 1976. The name *Ebolavirus* is derived from the Ebola River in Zaire (now the Democratic Republic of the Congo), the location of the 1976 outbreak, and the taxonomic suffix -virus (denoting a viral genus). This genus was introduced in 1998 as the "Ebola-like viruses." In 2002 the name was changed to *Ebolavirus* and in 2010, the genus was emended. Ebolaviruses are closely related to marburgviruses.

Researchers have now found evidence of Ebola infection in three species of fruit bats. The bats show no symptoms of the disease, indicating that they might be spreading it. Researchers found that bats of three species—*Hypsignathus monstrosus, Epomops franqueti,* and *Myonycteris torquata*—had either genetic material from the Ebola virus, known as RNA sequences, or evidence of an immune response to the disease. The bats showed no symptoms themselves. Other hosts are possible as well.

A. Taxonomy

A virus of the family Filoviridae is a member of the genus *Ebolavirus* if its genome has several gene overlaps, its fourth gene (GP) encodes four proteins (sGP, ssGP, Δ-peptide, and GP1,2) using co-transcriptional editing to express ssGP and GP1,2 and proteolytic cleavage to express sGP and Δ-peptide, peak infectivity of its virions is associated with particles ≈805 nm in length, its genome differs from that of Marburg virus by ≥50% and from that of Ebola virus by <50% at the nucleotide level, its virions show almost no antigenic cross reactivity with Marburg virions.

The genera *Ebolavirus* and *Marburgvirus* were originally classified as the species of the now-obsolete Filovirus genus. In March 1998, the Vertebrate Virus Subcommittee proposed in the International Committee on Taxonomy of Viruses (ICTV) to change the Filovirus genus to the Filoviridae family with two specific genera: Ebola-like viruses and Marburg-like viruses. This proposal was implemented in Washington, D.C., as of April 2001 and in Paris as of July 2002. In 2000, another proposal was made in Washington, D.C., to change the "-like viruses" to "-virus" resulting in today's *Ebolavirus* and *Marburgvirus*.

Each species of the genus *Ebolavirus* has one member virus, and four of these cause Ebola virus disease (EVD) in humans, a type of hemorrhagic fever having a very high case fatality rate; the fifth, Reston virus, has caused EVD in other primates. Zaire ebolavirus is the type species (reference or example species) for *Ebolavirus*, and has the highest mortality rate of the ebolaviruses, and is also responsible for the largest number of outbreaks of the five known members of the genus, including the 1976 Zaire outbreak and the outbreak with the most deaths (2014). The five characterized species of the *Ebolavirus* genus are:

Zaire Ebolavirus (ZEBOV).

Also known simply as the Zaire virus, ZEBOV has the highest case-fatality rate, up to 90% in some epidemics, with an average case fatality rate of approximately 83% over 27 years. There have been more outbreaks of Zaire ebolavirus than of any other species. The first outbreak took place on 26 Aug. 1976 in Yambuku. Mabalo Lokela, a 44-year-old schoolteacher, became the first recorded case. The symptoms resembled malaria, and subsequent patients received quinine. Transmission has been attributed to reuse of unsterilized needles and close personal contact. The virus is responsible for the 2014 West Africa Ebola virus outbreak, with the largest number of deaths to date.

Sudan Ebolavirus (SUDV).

Like ZEBOV, SUDV emerged in 1976; it was at first assumed to be identical with ZEBOV. SUDV is believed to have broken out first amongst cotton factory workers in Nzara, Sudan (now in South Sudan), in June 1976, with the first case reported as a worker exposed to a potential natural reservoir. Scientists tested local animals and insects in response to this; however, none tested positive for the virus. The carrier is still unknown. The lack of barrier nursing (or "bedside isolation") facilitated the spread of the disease. The average fatality rates for SUDV were 54% in 1976, 68% in 1979, and 53% in 2000 and 2001.

Reston Ebolavirus (RESTV).

This virus was discovered during an outbreak of simian hemorrhagic fever virus (SHFV) in crab-eating macaques from Hazleton Laboratories (now Covance) in 1989. Since the initial outbreak in Reston, Va., it has since been found in nonhuman primates in Pennsylvania, Texas, and Siena, Italy. In each case, the affected animals had been imported from a facility in the Philippines, where the virus has also infected pigs. Despite its status as a Level-4 organism and its apparent pathogenicity in monkeys, RESTV did not cause disease in exposed human laboratory workers.

Taï Forest Ebolavirus (TAFV).

Formerly known as "Côte d'Ivoire ebolavirus," it was first discovered among chimpanzees from the Tai Forest in Côte d'Ivoire, Africa, in 1994. Necropsies showed blood within the heart to be brown; no obvious marks were seen on the organs; and one necropsy displayed lungs filled with blood. Studies of tissues taken from the chimpanzees showed results similar to human cases during the 1976 Ebola outbreaks in Zaire and Sudan. As more dead chimpanzees were discovered, many tested positive for Ebola using molecular techniques. The source of the virus was believed to be the meat of infected western red colobus monkeys (*Procolubus badius*) upon which the chimpanzees preyed. One of the scientists performing the necropsies on the infected chimpanzees contracted Ebola. She developed symptoms similar to those of dengue fever approximately a week after the necropsy, and was transported to Switzerland for treatment. She was discharged from hospital after two weeks and had fully recovered six weeks after the infection.

Bundibugyo Ebolavirus (BDBV).

On Nov. 24, 2007, the Uganda Ministry of Health confirmed an outbreak of Ebola in the Bundibugyo District. After confirmation of samples tested by the United States National Reference Laboratories and the CDC, the World Health Organization confirmed the presence of the new species. On 20 Feb. 2008, the Uganda Ministry officially announced the end of the epidemic in Bundibugyo, with the last infected person discharged on 8 Jan. 2008. An epidemiological study conducted by WHO and Uganda Ministry of Health scientists determined there were 116 confirmed and probable cases the new Ebola species, and that the outbreak had a mortality rate of 34% (39 deaths).

B. Ebola Virus Disease

Symptoms of Ebola Virus Disease.

The incubation period from infection with the virus to onset of symptoms is 2 to 21 days. Humans are not infectious until they develop symptoms. First symptoms are the sudden onset of fever fatigue, muscle pain, headache and sore throat. This is followed by vomiting, diarrhea, rash, symptoms of impaired kidney and liver function, and in some cases, both internal and external bleeding (e.g., oozing from the gums, blood in the stools). Laboratory findings include low white blood cell and platelet counts and elevated liver enzymes.

Diagnosis.

It can be difficult to distinguish ebolavirus from other infectious diseases such as malaria, typhoid fever and meningitis. Confirmation that symptoms are caused by ebolavirus infection are made using antibody-capture ELISA, antigen-capture detection tests, serum neutralization test, RT-PCR assay, electron microscopy, and virus isolation by cell culture. Samples from patients are an extreme biohazard risk; laboratory testing on non-inactivated samples should be conducted under maximum biological containment conditions.

Treatment and Vaccines.

Supportive care-rehydration with oral or intravenous fluids—and treatment of specific symptoms, improves survival. There is as yet no proven treatment available for ebolavirus. However, a range of potential treatments including blood products, immune therapies and drug therapies are currently being evaluated. No licensed vaccines are available yet, but 2 potential vaccines are undergoing human safety testing.

Prevention and Control.

Good outbreak control relies on applying a package of interventions, namely case management, surveillance and contact tracing, a good laboratory service, safe burials and social mobilization. Community engagement is key to successfully controlling outbreaks. Raising awareness of risk factors for Ebola infection and protective measures that individuals can take is an effective way to reduce human transmission. Risk reduction messaging should focus on several factors:

reducing the risk of wildlife-to-human transmission from contact with infected fruit bats or monkeys/apes and the consumption of their raw meat;

reducing the risk of human-to-human transmission from direct or close contact with people with Ebola symptoms, particularly with their bodily fluids;

outbreak containment measures including prompt and safe burial of the dead;

identifying people who may have been in contact with someone infected with Ebola and monitoring the health of contacts for 21 days;

the importance of separating the healthy from the sick to prevent further spread; and the importance of good hygiene and maintaining a clean environment.

In terms of controlling infection in health-care settings, health-care workers should always take standard precautions when caring for patients, regardless of their presumed diagnosis. These include basic hand hygiene, respiratory hygiene, use of personal protective equipment (to block splashes or other contact with infected materials), safe injection practices and safe burial practices. Health-care workers caring for patients with suspected or confirmed Ebola virus should apply extra infection control measures to prevent contact with the patient's blood and body fluids and contaminated surfaces or materials such as clothing and bedding. When in close contact (within 1 meter) of patients with EBV, health-care workers should wear face protection (a face shield or a medical mask and goggles), a clean, non-sterile long-sleeved gown, and gloves (sterile gloves for some procedures). Laboratory workers are also at risk. Samples taken from humans and animals for investigation of Ebola infection should be handled by trained staff and processed in suitably equipped laboratories.

II. MONOCLONAL ANTIBODIES AND PRODUCTION THEREOF

A. General Methods

It will be understood that monoclonal antibodies binding to *Ebolavirus* will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host, or as described below, the identification of subjects who are immune due to prior natural infection. Antibody-producing cells may be induced to expand by priming with immunogens. A variety of routes can be used to administer such immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the animal can be bled and the serum isolated and stored, and/or the animal can be used to generate mAbs.

Somatic cells with the potential for producing antibodies, specifically B lymphocytes (B cells), are selected for use in the mAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

mAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods that include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, which in this case is for *Ebolavirus* glycoprotein (GP). Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDRs from the heavy and light chains as illustrated in Table 2. Such antibodies may be produced by the clones discussed below in the Examples section using methods described herein.

In a second aspect, the antibodies may be defined by their variable sequence, which include additional "framework" regions. These are provided in Tables 3-4 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing apply to the nucleic acid sequences set forth as Table 3 and the amino acid sequences of Table 4.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF EBOLA VIRUS INFECTION

The present disclosure provides pharmaceutical compositions comprising anti-ebolavirus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines of the present disclosure, as described herein, can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting *Ebolavirus* and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (MA), immunoradiometric assay, fluoroimmunoassay, chemiluminescent assay, bioluminescent assay, and Western blot to mention a few. In particular, a competitive assay for the detection and quantitation of *Ebolavirus* antibodies directed to specific parasite epitopes in samples also is provided. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample suspected of containing *Ebolavirus*, and contacting the sample with a first antibody in accordance with the present disclosure, as the case may be, under conditions effective to allow the formation of immunocomplexes.

These methods include methods for purifying *Ebolavirus* or related antigens from a sample. The antibody will preferably be linked to a solid support, such as in the form of a column matrix, and the sample suspected of containing the *Ebolavirus* or antigenic component will be applied to the immobilized antibody. The unwanted components will be washed from the column, leaving the *Ebolavirus* antigen immunocomplexed to the immobilized antibody, which is then collected by removing the organism or antigen from the column.

The immunobinding methods also include methods for detecting and quantifying the amount of *Ebolavirus* or related components in a sample and the detection and quantification of any immune complexes formed during the binding process. Here, one would obtain a sample suspected of containing *Ebolavirus* or its antigens, and contact the sample with an antibody that binds *Ebolavirus* or components thereof, followed by detecting and quantifying the amount of immune complexes formed under the specific conditions. In terms of antigen detection, the biological sample analyzed may be any sample that is suspected of containing *Ebolavirus* or *Ebolavirus* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *Ebolavirus* or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the *Ebolavirus* or *Ebolavirus* antigen is added to the wells. After binding and washing to remove non-specifically bound immune complexes, the bound antigen may be detected. Detection may be achieved by the addition of another anti-*Ebolavirus* antibody that is linked to a detectable label. This type of ELISA is a simple "sandwich ELISA." Detection may also be achieved by the addition of a second anti-*Ebolavirus* antibody, followed by the addition of a third antibody that has binding affinity for the second antibody, with the third antibody being linked to a detectable label.

In another exemplary ELISA, the samples suspected of containing the *Ebolavirus* or *Ebolavirus* antigen are immobilized onto the well surface and then contacted with the anti-*Ebolavirus* antibodies of the disclosure. After binding and washing to remove non-specifically bound immune complexes, the bound anti-*Ebolavirus* antibodies are detected. Where the initial anti-*Ebolavirus* antibodies are linked to a detectable label, the immune complexes may be detected directly. Again, the immune complexes may be detected using a second antibody that has binding affinity for the first anti-*Ebolavirus* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of *Ebolavirus* antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled *Ebolavirus* monoclonal antibodies to determine the amount of *Ebolavirus* antibodies in a sample. The basic format would include contacting a known amount of *Ebolavirus* monoclonal antibody (linked to a detectable label) with *Ebolavirus* antigen or particle. The *Ebolavirus* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect *Ebolavirus* or *Ebolavirus* antigens, the antibodies may be included in the kit. The immunodetection kits will thus comprise, in suitable container means, a first antibody that binds to *Ebolavirus* or *Ebolavirus* antigen, and optionally an immunodetection reagent.

In certain embodiments, the *Ebolavirus* antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the *Ebolavirus* or *Ebolavirus* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Donors.

The donors were human subjects previously naturally infected with Ebola Bundibugyo in Uganda in 2007 or U.S. citizens infected with Ebola 2014 strain in 2014 in West Africa. Peripheral blood from the donors was obtained months or years after the illness, when viral clearance had been demonstrated, following informed consent. The study was approved by the Vanderbilt University Institutional Review Board.

Viruses.

The recombinant Ebola Zaire strain Mayinga (EBOV) expressing eGFP was generated in our laboratory by reverse genetics (Lubaki et al., 2013; Towner et al., 2005) from plasmids provided by the Special Pathogens Branch at CDC and passaged 3 times in Vero E6 cells. For analysis of antibody binding by ELISA, viruses were gamma-irradiated with the dose of $5 \times 10^6$ rad. All work with Ebola virus was performed within the Galveston National Laboratory BSL-4 laboratories.

Generation of Human Hybridomas Secreting Monoclonal Antibodies (mAbs).

Peripheral blood mononuclear cells (PBMCs) from the donors were isolated with Ficoll-Histopaque by density gradient centrifugation. The cells were cryopreserved immediately and stored in the vapor phase of liquid nitrogen until use. Previously cryopreserved samples were thawed, and 10 million PBMCs were plated into 384-well plates (Nunc #164688) using: 17 mL of cell culture medium (ClonaCell-HY Medium A, Stemcell Technologies #03801), 8 µg/mL of the TLR agonist CpG (phosphorothioate-modified oligodeoxynucleotide ZOEZOEZZZZZOEEZOEZZZT (SEQ ID NO: 81), Invitrogen), 3 µg/mL Chk2 inhibitor (Sigma #C3742), 1 µg/mL cyclosporine A (Sigma #C1832) and 4.5 mL of clarified supernate from cultures of B95.8 cells (ATCC VR-1492) containing Epstein-Barr virus (EBV). After 7 days, cells from each 384-well culture plate were expanded into four 96-well culture plates (Falcon #353072) using cell culture medium containing 8 µg/mL CpG, 3 µg/mL Chk2i and 10 million irradiated heterologous human PBMCs (Nashville Red Cross) and incubated for an additional four days. Plates were screened for Ebola virus antigen-specific antibody-secreting cell lines using enzyme-linked immunosorbent assays (ELISAs). Cells from wells with supernates reacting in an Ebola virus antigen ELISA were fused with HMMA2.5 myeloma cells using an established electrofusion technique (Yu et al., 2008). After fusion, hybridomas were resuspended in medium containing 100 µM hypoxanthine, 0.4 µM aminopterin, 16 µM thymidine (HAT Media Supplement, Sigma #H0262) and 7 µg/mL ouabain (Sigma #03125) and incubated for 18 days before screening hybridomas for antibody production by ELISA.

Human mAb and Fab Production and Purification.

After fusion with HMMA2.5 myeloma cells, hybridomas producing Ebola-specific antibodies were cloned biologically by two rounds of limiting dilution and by single-cell fluorescence-activated cell sorting. After cloning, hybridomas were expanded in post-fusion medium (ClonaCell-HY Medium E, STEMCELL Technologies #03805) until 50% confluent in 75-cm² flasks (Corning #430641). For antibody production, cells from one 75-cm² flask were collected with a cell scraper and expanded to four 225-cm² flasks (Corning #431082) in serum-free medium (Hybridoma-SFM, Gibco #12045-076). After 21 days, supernates were clarified by centrifugation and sterile filtered using 0.2-µm pore size filter devices. HiTrap Protein G or HiTrap MabSelectSure columns (GE Healthcare Life Sciences #17040501 and #11003494 respectively) were used to purify antibodies from filtered supernates. Fab fragments were generated by papain digestion (Pierce Fab Preparation Kit, Thermo Scientific #44985) and purified by chromatography using a two-column system where the first column contained protein G resin (GE Healthcare Life Sciences #29048581) and the second column contained either anti-kappa or anti-lambda antibody light chain resins (GE Healthcare Life Sciences #17545811 and #17548211 respectively).

Screening ELISA.

ELISA plates were coated with recombinant Ebola virus proteins (20 μg in 10 mL DPBS per plate) and incubated at 4° C. overnight. Plates were blocked with 100 μL of blocking solution/well for 1 h. Blocking solution consisted of 10 g powdered milk, 10 mL of goat serum, 100 mL of 10×DPBS, and 0.5 mL of Tween-20 mixed to a 1 L final volume with distilled water. The presence of antibodies bound to the GP was determined using goat anti-human IgG horseradish peroxidase conjugated secondary antibodies (Southern Biotech #2040-05, 1:4,000 dilution) and 1-Step Ultra TMB-ELISA substrate (Thermo Scientific #34029), with optical density read at 450 nM after stopping the reaction with 1M HCl.

Half Maximal Effective Concentration ($EC_{50}$) Binding Analysis.

Ebola virus GPs were coated onto 384-well plates (Thermo Scientific Nunc #265203) in DPBS at 2 μg/mL overnight, then antigen was removed and plates were blocked with blocking solution made as above. Antibodies were applied to the plates using serial dilutions. The presence of antibodies bound to the GP was determined using goat anti-human IgG alkaline phosphatase conjugate (Meridian Life Science #W99008A, 1:4,000 dilution) and p-nitrophenol phosphate substrate tablets (Sigma #S0942), with optical density read at 405 nM after 120 minutes. A non-linear regression analysis was performed on the resulting curves using Prism version 5 (GraphPad) to calculate $EC_{50}$ values.

Ebola Virus Neutralization Experiments.

Dilutions of mAbs in triplicate were mixed with Ebola virus or Ebola virus expressing eGFP in MEM containing 10% FBS (HyClone), 50 μg/mL gentamicin (Cellgro #30-005-CR) with or without 5% guinea pig complement (MP Biomedicals #642836) in a total volume of 0.1 mL, and incubated for 1 hour at 37° C. for virus neutralization. Following neutralization, virus-antibody mixtures were placed on monolayers of Vero E6 cells in 24-well plates, incubated for 1 hour at 37° C. for virus adsorption, and overlayed with MEM containing 2% FBS and 0.8% methylcellulose (Sigma-Aldrich #M0512-1KG). After incubation for 5 days, medium was removed, cells were fixed with 10% formalin (Fisher Scientific #245-684), plates were sealed in plastic bags and incubated for 24 hours at room temperature. Sealed plates were taken out of the BSL-4 laboratory according to approved SOPs, and monolayers were washed three times with phosphate buffered saline. Viral plaques were immunostained with a mAb against EBOV, clone 15H10 (BEI Resources #NR-12184). Alternatively, following virus adsorption, monolayers were covered with MEM containing 10% FBS and 1.6% tragacanth (Sigma-Aldrich #G1128). After incubation for 14 days, medium was removed, cells were fixed with 10% formalin, plates were sealed in plastic bags, incubated for 24 hours at room temperature, and taken out of the BSL-4 laboratory as above. Fixed monolayers were stained with 10% formalin containing 0.25% crystal violet (Fisher Scientific #C581-100), and plaques were counted. In some cases, when Ebola virus expressing eGFP, neutralization was scored using reduction of fluorescence.

Biolayer Interferometry Competition Binding Assay.

Biotinylated GP or GPΔmuc (EZ-Link® Micro NHS-PEG4-Biotinylation Kit, Thermo Scientific #21955) (1 μg/mL) was immobilized onto streptavidin-coated biosensor tips (ForteBio #18-5019) for 2 minutes. After measuring the baseline signal in kinetics buffer (KB: 1×PBS, 0.01% BSA and 0.002% Tween 20) for two minutes, biosensor tips were immersed into the wells containing primary antibody at a concentration of 100 μg/mL for 10 minutes. Biosensors then were immersed into wells containing competing mAbs at a concentration of 100 μg/mL for 5 minutes. The percent binding of the competing mAb in the presence of the first mAb was determined by comparing the maximal signal of competing mAb applied after the first mAb complex to the maximal signal of competing mAb alone. MAbs were judged to compete for binding to the same site if maximum binding of the competing mAb was reduced to <30% of its un-competed binding. MAbs were considered non-competing if maximum binding of the competing mAb was >70% of its un-competed binding. A level of 30-70% of its un-competed binding was considered intermediate competition.

Sequence Analysis of Antibody Variable Region Genes.

Total cellular RNA was extracted from clonal hybridomas that produced Ebola virus antibodies, and RT-PCR reaction was performed using mixtures of primers designed to amplify all heavy chain or light chain antibody variable regions. The generated PCR products were purified and cloned into the pJet 1.2 plasmid vector (Thermo Scientific, #K1231) for sequence analysis. The nucleotide sequences of plasmid DNAs were determined using an ABI3700 automated DNA sequencer. Heavy chain or light chain antibody variable region sequences were analyzed using the IMGT/V-Quest program (Brochet et al., 2008; Giudicelli et al., 2011). The analysis involved the identification of germline genes that were used for antibody production, location of complementary determining regions (CDRs) and framework regions (FRs) as well as the number and location of somatic mutations that occurred during affinity maturation.

Statistical Analysis.

$EC_{50}$ values for neutralization were determined by finding the concentration of mAb at which a 50% reduction in plaque counts occurred after incubation of virus with neutralizing antibody. A logistic curve was fit to the data using the count as the outcome and the log-concentration as the predictor variable. The results of the model then were transformed back to the concentration scale. Results are presented as the concentration at the dilution that achieve a 50% reduction from challenge control with accompanying 95% confidence intervals. Each antibody was treated as a distinct analysis in a Bayesian non-linear regression model.

In Vivo Testing.

The animal protocol for testing of mAbs in mice was approved by the Institutional Animal Care and Use Committee of the University of Texas Medical Branch at Galveston. BALB/c mice (Harlan) were placed in the AB SL-4 facility of the Galveston National Laboratory. Groups of mice at 5 animals per group were injected with individual mAbs by the intraperitoneal route. Untreated animals served as controls. For the challenge, mice were injected with 1,000 PFU of the mouse-adapted Ebola virus Mayinga strain by the intraperitoneal route. Animals were weighed and monitored daily over the three-week period after challenge. Once animals were symptomatic, they were examined twice per day. The disease was scored using the following parameters: dyspnea (possible scores 0-5), recumbency (0-9), unresponsiveness (0-5), and bleeding/hemorrhage (0-5); the individual scores for each animal were summarized. Guinea pig studies were conducted in a similar fashion.

Example 2—Results

Isolation of Monoclonal Antibodies (mAbs).

To generate human hybridoma cell lines secreting mAbs to Ebola virus GP, the inventors screened supernatants from EBV-transformed B cell lines derived from survivors of Ebola Bundibugyo virus (BDBV) in Uganda in 2007 or of *Ebolavirus* ebola (EBOV) in the 2014 West African outbreak, for binding to several recombinant forms of Ebola GP or to irradiated cell lysates prepared from Ebola virus-infected cell cultures. The inventors fused transformed cells from B cell lines producing Ebola GP-reactive Abs to the Ebola GP antigens with myeloma cells and generated 90 cloned hybridomas secreting BDBV-reactive human mAbs from BDBV survivors, and 119 cloned hybridomas secreting EBOV-reactive human mAbs from EBOV survivors. The inventors screened for binding phenotype against three types of glycoprotein, specifically, full-length glycoprotein, mucin deleted glycoprotein, and secreted glycoprotein. They found antibodies that bound with diverse patterns recognizing the various forms of glycoprotein, including clones that down to full-length and mucin delete a glycoprotein but did not have the potential deleterious property of binding to secreted like protein. The inventors also found antibodies that bound all three forms of glycoprotein.

Neutralization Activity.

To evaluate the inhibitory activity of the mAbs, the inventors first performed in vitro neutralization studies using a chimeric vesicular stomatitis virus with Ebola GP from on its surface (VSV/GP-Ebola) and later they tested each of the antibodies for activity against live Ebola virus strains. For the monoclonal antibodies isolated from BDBV survivors, 34 of the 90 BDBV mAb clones exhibited neutralizing activity in vitro. The inventors have found a similar proportion of neutralizing clones in the monoclonal antibodies isolated from survivors of the 2014 *Ebolavirus* outbreak. Within clones isolated from the 2007 or 2014 outbreak survivors, several of the antibodies isolated exhibit a higher potency for neutralization then any monoclonal antibody of any species ever reported for Ebola virus. The designated BDBV223 clone neutralizes BDBV with an $IC_{50}$ of 5 ng/mL remarkably, it also has the property of cross-reactivity, and it neutralizes EBOV with an $IC_{50}$ of 50 ng/mL. Antibodies with this level of activity for neutralization have not been reported previously. The inventors also found neutralizing clones from survivors of the 2014 Ebola virus outbreak, including two clones that neutralize with $IC_{50}$ of <1 µg/mL. The neutralization activity of neutralizing Abs was in many cases enhanced by the presence of complement.

Recognition of Varying Forms of GP.

To characterize the binding of isolated Abs to recombinant Ebola virus GPs, the inventors performed binding assays using either a recombinant MARV GP ectodomain containing the mucin-like domain (designated "full length GP" of just "GP") or a recombinant GP lacking residues of the mucin-like domain (GPΔmuc, from EBOV or BDBV or SUDV). Based on $OD_{405}$ values at the highest Ab concentration tested ($E_{max}$) and 50% effective concentration ($EC_{50}$), the inventors divided the GP-specific Abs into different major phenotypic binding groups, based on binding phenotype (designated Patterns 1, 2, 3 and 4). These distinctions are important, because they show some of the antibodies are more cross-reactive for diverse Ebola virus species than any antibodies ever reported. They also showed that different antibodies recognize different forms of glycoprotein, which may be useful. For example in some cases, one may find it desirable to have prophylactic or therapeutic antibodies that bind to full-length or mucin deleted glycoprotein, but avoid binding to secreted glycoprotein. Alternatively, if one is seeking to prevent pathogenic effects mediated by the secreted glycoprotein, one would seek antibodies that retained binding to the secreted form of glycoprotein. The inventors have isolated antibodies with both types of binding patterns, and with differing levels of cross-reactivity for diverse Ebola virus species.

Competition-Binding Studies.

To determine whether mAbs from distinct binding groups targeted different antigenic regions on the Ebola virus GP surface, the inventors performed competition-binding assays using a real-time biosensor. They tested diverse nAbs from our panel of Ebola virus antibodies in a tandem blocking assay in which biotinylated GP was attached to a streptavidin biosensor. The inventors identified several major competition binding groups within their antibodies, and subsequent electron microscopy studies of antigen antibody complexes show that one group binds to the glycan cap region on the glycoprotein, and another 2 groups bind lower on the glycoprotein, one at the base and one group lower down at the heptad repeat 2 region. These data suggested that these neutralizing Abs target at least three major antigenic regions on the Ebola virus GP surface.

Electron Microscopy Studies of Antigen-Antibody Complexes.

To determine the location of the antigenic region targeted by Ebola virus neutralizing Abs, the inventors performed with collaborators negative stain single-particle electron microscopy (EM) studies using complexes of GP with Fab fragments of neutralizing Abs. The EM reconstructions showed that Fab fragments for one competition binding pattern group of neutralizing Abs bind at the top of the GP in or near the glycan cap site. A second competition binding pattern group of neutralizing Abs bind at the bottom of the GP in or near what would be a putative MPER or heptad repeat 2 region.

Cross-Reactive Binding of Ebola Virus Antibodies with Diverse Species of GP.

It is surprising that human MARV neutralizing Abs recognize GP from diverse species of Ebola, since previously reported murine mAbs and one human phage display library derived antibody (KZ52) exhibited a binding pattern that was restricted to a single species of Ebola virus, To determine whether the isolated Ebola virus neutralizing Abs could bind in a cross-reactive manner to diverse Ebola virus species, the inventors performed ELISA binding assays using recombinant forms of BDBV, EBOV, and SUDV GPs. Several of the Ebola virus antibodies neutralizing Abs recognized two or even three species Ebola GP. They tested the breadth of neutralization of MARV neutralizing Abs for filoviruses using a panel of different Ebola virus isolates. Some of the neutralizing Abs neutralized diverse Ebola virus species, which is a newly discovered and desirable property.

In Vivo Testing.

The inventors tested the in vivo protective activity of the mAbs in murine and guinea pig models of infection using mouse- or guinea-pig adapted Ebola Zaire Mayinga strain. Inoculation of mice or guinea pigs with live Ebola virus caused clinical disease, and in a proportion or all of animals caused lethal disease. They selected five of the BDBV survivor mAbs among those with in vitro neutralization IC$_{50}$ values and diverse properties: BDBV223, BDBV270, and BDBV289, BDBV317, BDBV324. When used as monotherapy and given at 24 hours after lethal inoculation, each exhibited a marked therapeutic effect. The inventors also tested combinations BDBV223+BDBV270, or BDBV223+BDBV289, since BDBV223 recognizes the MPER region and the other two (BDBV270 and BDBV289) recognize the glycan. Each of the combinations exhibited increased therapeutic effect. They also tested the most potent antibody (BDBV223) as monotherapy but given as a two-dose treatment (at 1 day and 3 day after lethal inoculation). This two-dose regimen appeared more effective than single dose therapy.

Example 3—Discussion

There is an obvious urgent need for prophylactic and therapeutic interventions for Filovirus infections given the massive outbreak of EBOV infections in West Africa in 2014. There is very little information about the structural determinants of neutralization on which to base the rational selection of antibodies, and for Ebola virus there have been no reported human neutralizing Abs with naturally paired heavy and light antibody chains.

For the three most important species, EBOV and BDBV and SUDV, the inventors studied survivors of the first two species, EBOV and BDBV and obtained human monoclonal antibodies from survivors of each of those two infections. Ninety human monoclonal antibodies that obtained from eight survivors of BDBV infection in Uganda in 2007. They have also obtained cells from U.S. survivors who were infected while working in West Africa in 2014. From one of those individuals, they obtained about 93 new human monoclonal antibodies that were induced by the current strain, EBOV, historically called the Zaire strain. Additional donors have yielded 26 more clones from EBOV immune donors. Data show that some of these antibodies have neutralizing activity against the EBOV (20 of the ~50 mAbs tested from the one individual so far for neutralizing activity). Thus, in summary, the inventors have two sets of antibodies, one set of 90 mAbs induced by BDBV infection and one set of 119 mAbs induced by EBOV infection.

In conclusion, this study reveals that naturally-occurring human Ebola neutralizing Abs isolated from the B cells of recovered donors target several antigenic sites on Ebola virus GP, suggesting that at least two major mechanisms of Ebola virus neutralization. Remarkably, some of the isolated antibodies bound not only to the inducing virus (BDBV or EBOV) but also exhibited cross-reactive binding to other GPs, including BDBV, EBOV and SUDV GP. This information can be used to inform development of new therapeutics and structure-based vaccine designs against filoviruses. Furthermore, as these neutralizing mAbs are fully human and exhibit inhibitory activity, they could be formulated as components of a prophylactic or therapeutic approach for filovirus infection and disease. Indeed, challenge studies using murine and guinea pig modeled here show clear evidence of in vivo activity. Their ability to bind a broad range of Ebola virus isolates indicates they may offer detection of or efficacy against new viral strains yet to emerge. Since these mAbs bind to diverse forms of Ebola virus GP, these antibodies could be selected for preferred activity in vivo, for instance avoiding binding to secreted GP or including binding to secreted GP.

TABLE 1A

Biological properties of human mAbs isolated from a 2014 survivor of West African outbreak: in vivo protection, binding to GP of various filovirus species, and epitope mapping

| | EBOV49 | EBOV52 | EBOV62 | EBOV63 | EBOV82 | EBOV87 | EBOV90 | EBOV95 |
|---|---|---|---|---|---|---|---|---|
| Mice protection | 80% | 0% | 60% | 0% | 80% | 20% | 100% | 0% |
| EBOV GP binding (EC50, µg/ml) | 262 | 712 | 228 | 283 | 36 | 724 | 67 | 129 |
| BDBV GP binding (EC50, µg/ml) | — | 1838 | 508 | — | — | 1389 | — | — |
| SUDV GP binding (EC50, µg/ml) | — | — | — | — | — | 629 | — | — |
| EBOV sGP binding (EC50, µg/ml) | 61 | 82 | 51 | 38 | 21 | 51 | 25 | 41 |
| Location of escape mutations | 252Phe→Cys, glycan cap | 275Trp→Gly, glycan cap | 234Phe→Val, 273Leu→Pro, 308Phe→Leu, glycan cap; 365Leu→Pro, 368Leu→Pro, 394Tyr→His, mucin-like domain | 155Lys→Arg, receptor-binding domain; 280Gln→Lys, glycan cap | 224Gly→Asp, glycan cap | 267Ser→Asn, 271Gly→Glu, glycan cap | 227Thr→Ile, glycan cap | 280Glu→Lys, glycan cap |

TABLE 1B

Heatmap showing the neutralization potency of EBOV GP-specific mAbs against EBOV*

| Mab | IC$_{50}$, μg/mL |
|---|---|
| EBOV49 | 6.5 |
| EBOV52 | 4.0 |
| EBOV62 | 8.5 |
| EBOV63 | 6.4 |
| EBOV82 | <0.2 |
| EBOV87 | 3.3 |
| EBOV90 | 5.1 |
| EBOV95 | 15.9 |
| EBOV137 | 4.9 |
| EBOV141 | 48.1 |
| EBOV157 | 29.9 |
| EBOV293 | 1.7 |
| EBOV311 | 4.3 |
| EBOV317 | 0.7 |
| EBOV329 | 0.4 |
| EBOV333 | 0.7 |
| EBOV416 | 11.3 |
| EBOV427 | 1.0 |

*The IC$_{50}$ value for each virus-mAb combination is shown. Neutralization assays were performed in triplicate in the absence of complement.

TABLE 2

CDR sequences

| Antibody | CDRH1 | CDRH2 | CDRH3 |
|---|---|---|---|
| BDBV43 | DSFSRKYG (SEQ ID NO: 33) | IMPIVGLT (SEQ ID NO: 34) | ARDEIIGARPHWFDS (SEQ ID NO: 35) |
| BDBV223 | GGSFTTTY (SEQ ID NO: 36) | VNYSGNA (SEQ ID NO: 37) | TSRIRSHIAYSWKGDV (SEQ ID NO: 38) |
| EBOV9 | GGTFSSYT (SEQ ID NO: 39) | IIPKLGIA (SEQ ID NO: 40) | LYYCARVLLSSRDAFDIW (SEQ ID NO: 41) |
| EBOV49 | GFTFSSYE (SEQ ID NO: 42) | ISSSGRTI (SEQ ID NO: 43) | AREPYVDGILYGAGDSYFDY (SEQ ID NO: 44) |
| EBOV52 | GGSISSYY (SEQ ID NO: 45) | IYDSGRT (SEQ ID NO: 46) | ASLGPFDKLWFGELLPGWFDP (SEQ ID NO: 47) |
| EBOV63 | GFTLNFYN (SEQ ID NO: 48) | ISSSSNYI (SEQ ID NO: 49) | ARDFVQLLIPQRDEWQGVHDYYGMDV (SEQ ID NO: 50) |
| EBOV82 | GFTFTNAW (SEQ ID NO: 51) | IKSNTDGGTT (SEQ ID NO: 52) | TTGKSDCSGGNCYVVDY (SEQ ID NO: 53) |
| EBOV90 | GFTFSNAW (SEQ ID NO: 54) | IKSKNDGGTA (SEQ ID NO: 55) | ITFLRPDH (SEQ ID NO: 56) |
| EBOV109 | GYTFTGYY (SEQ ID NO: 57) | INPNSGGT (SEQ ID NO: 58) | CATNKGTNGRYYYYGMDVW (SEQ ID NO: 59) |
| EBOV62 | GFTFSSYW (SEQ ID NO: 82) | IKQDGSAK (SEQ ID NO: 83) | ARDGLLGISDLLYPIYYFDY (SEQ ID NO: 84) |
| EBOV87 | GYTFTSYA (SEQ ID NO: 85) | ISGNNGNT (SEQ ID NO: 86) | ARDADIVVVGATGTYYYGMDV (SEQ ID NO: 87) |
| EBOV157 | GFTVSNNY (SEQ ID NO: 88) | FYSDGTT (SEQ ID NO: 89) | ARQASGYDAYYMDV (SEQ ID NO: 90) |
| BDBV289 | GATFGSDT (SEQ ID NO: 91) | IIPFFGEA (SEQ ID NO: 92) | ARQINEMATFGEIHYYTYMDV (SEQ ID NO: 93) |
| BDBV231 | SDSIRSYS (SEQ ID NO: 94) | IYYSGNI (SEQ ID NO: 95) | ARDWITIFGRYFDV (SEQ ID NO: 96) |
| BDBV275 | GFNFGDYV (SEQ ID NO: 97) | IRGKTFGATT (SEQ ID NO: 98) | TRRATSTWYEDY (SEQ ID NO: 99) |

TABLE 2-continued

CDR sequences

| | | | |
|---|---|---|---|
| BDBV315 | GDSISSGSYY (SEQ ID NO: 100) | IYTSGST (SEQ ID NO: 101) | ARDPITIFGGVIFGWG MDV (SEQ ID NO: 102) |
| BDBV329 | GGTFDTYA (SEQ ID NO: 103) | IIPVLGIV (SEQ ID NO: 104) | ARGLRSLSPRGQEGPT PAPGWRRAQYHYYYMD V (SEQ ID NO: 105) |
| BDBV335 | GGSINSDSYY (SEQ ID NO: 106) | VYTSGST (SEQ ID NO: 108) | ARVVWGSYRSYHYSYG MDV (SEQ ID NO: 109) |
| BDBV354 | GYAFTTYA (SEQ ID NO: 110) | ISTYYGTT (SEQ ID NO: 111) | VRDRSWLATSRPYDAF DI (SEQ ID NO: 112) |
| BDBV386 | GGSISSGRFY (SEQ ID NO: 113) | IYTSGST (SEQ ID NO: 114) | ATELYYYGSGSYDPLW S (SEQ ID NO: 115) |
| BDBV397 | GGSISSGSYF (SEQ ID NO: 116) | IYTSGTT (SEQ ID NO: 117) | ATSPYYYDSSHYYDY (SEQ ID NO: 118) |
| BDBV399 | GGSISNGGYH (SEQ ID NO: 119) | IYYSGST (SEQ ID NO: 120) | ARDRIRGGPIDY (SEQ ID NO: 121) |
| BDBV353 | GYTFSDYY (SEQ ID NO: 122) | INPYSGGT (SEQ ID NO: 123) | ARLYGAGSHYNHYNGM DV (SEQ ID NO: 124) |
| BDBV410 | GGSVSSGRYF (SEQ ID NO: 125) | IHSSGRT (SEQ ID NO: 126) | <Not yet available> |
| BDBV270 | GASISRGLYY (SEQ ID NO: 127) | IYTSGSI (SEQ ID NO: 128) | VRDAPWGDFLTGYFGF YGMDV (SEQ ID NO: 129) |
| BDBV324 | GYTFTSFE (SEQ ID NO: 130) | MNPKSGDT (SEQ ID NO: 131) | ARGPHVGEVVPGLMAG TYYFPLDV (SEQ ID NO: 132) |
| BDBV403 | GGTFSNSI (SEQ ID NO: 133) | IIPIVGLV (SEQ ID NO: 134) | AINGVNIPDTLT (SEQ ID NO: 135) |
| BDBV407 | GGSIRSYF (SEQ ID NO: 136) | IYYSGRP (SEQ ID NO: 137) | ARDERLLVEVGTDHFY YGLDV (SEQ ID NO: 138) |
| BDBV425 | GYTFTSFG (SEQ ID NO: 139) | INTYNGDT (SEQ ID NO: 140) | ARDSHLISIAVANTPN DF (SEQ ID NO: 141) |
| BDBV426 | GGSISSDDRY (SEQ ID NO: 142) | IYYSGST (SEQ ID NO: 143) | ATVTAYSPATMIVVGT EHGFDY (SEQ ID NO: 144) |
| BDBV317 | GLTFSNFG (SEQ ID NO: 145) | IRFDGSNK (SEQ ID NO: 146) | GRVLYGAAADF (SEQ ID NO: 147) |
| BDBV342 | GGTFSSYA (SEQ ID NO: 148) | IIPIFGKP (SEQ ID NO: 149) | ARGQGEIVVMVGHDDG GDYLGY (SEQ ID NO: 150) |
| BDBV357 | GGSISGSI (SEQ ID NO: 151) | ISLSGST (SEQ ID NO: 152) | ARHRKSSKMVRGIEVF YYYYMDV (SEQ ID NO: 153) |
| BDBV340 | GGSISSGSFY (SEQ ID NO: 154) | FYTTGST (SEQ ID NO: 155) | ARGPVSYYSGNLYYFD Y (SEQ ID NO: 156) |
| BDBV392 | GFTFSSFG (SEQ ID NO: 157) | IRYDGSDK (SEQ ID NO: 158) | AKRGGHDYGYYDNNRY IDL (SEQ ID NO: 159) |

TABLE 2-continued

| | CDR sequences | | |
|---|---|---|---|
| BDBV415 | GGTFSSYG (SEQ ID NO: 160) | IIPKFATA (SEQ ID NO: 161) | AGHFPQRKPITTIVVI TYWSLDL (SEQ ID NO: 162) |
| BDBV343 | GVTFSRYT (SEQ ID NO: 163) | ISPILGTA (SEQ ID NO: 164) | ARDAPIILVEGPETGM DV (SEQ ID NO: 165) |
| BDBV377 | GFTFNSYG (SEQ ID NO: 166) | IWFDGSKK (SEQ ID NO: 167) | AKDLLYGSGMVPNYYY YGLDV (SEQ ID NO: 168) |
| Antibody | CDRL1 | CDRL2 | CDRL3 |
| BDBV43 | QSVSSN (SEQ ID NO: 60) | GSS | LQYYNWPRT (SEQ ID NO: 61) |
| BDBV223 | QSVPRNY (SEQ ID NO: 62) | GAS | HQYDRLPYT (SEQ ID NO: 63) |
| EBOV49 | QSISNY (SEQ ID NO: 64) | AAS | QQSYNTPPVT (SEQ ID NO: 65) |
| EBOV52 | QSVHNY (SEQ ID NO: 66) | DAS | QHRSNWLT (SEQ ID NO: 67) |
| EBOV63 | QSVSNY (SEQ ID NO: 68) | GAS | QHYGSSQLT (SEQ ID NO: 69) |
| EBOV109 | QSLLHSNGYNY (SEQ ID NO: 70) | LGS | CMQALQTITF (SEQ ID NO: 71) |
| EBOV62 | QNIGSY (SEQ ID NO: 169) | AAS | QQSYSIPRT (SEQ ID NO: 170) |
| EBOV87 | QSISSW (SEQ ID NO: 171) | DAS | QQYKSSLRT (SEQ ID NO: 172) |
| EBOV157 | QSINSW (SEQ ID NO: 173) | QAS | QQYSSFPLT (SEQ ID NO: 174) |
| BDBV41 | QSITSTY (SEQ ID NO: 175) | GAS | QQYHSSL (SEQ ID NO: 176) |
| BDBV231 | QNLLYSSNNKNF (SEQ ID NO: 177) | WAS | QQYYTIPPT (SEQ ID NO: 178) |
| BDBV275 | QSVLYTPNNHNY (SEQ ID NO: 179) | WAS | QQYHIPPYS (SEQ ID NO: 180) |
| BDBV315 | QTLLHSNGYNY (SEQ ID NO: 181) | LGS | MQALQTPVT (SEQ ID NO: 182) |
| BDBV329 | QSVSSNY (SEQ ID NO: 183) | GAS | QQYGSSPGT (SEQ ID NO: 184) |
| BDBV335 | QSVGSSY (SEQ ID NO: 185) | GAS | QQSGSSPET (SEQ ID NO: 186) |
| BDBV354 | QDISST (SEQ ID NO: 187) | GAS | QHFYYFPRT (SEQ ID NO: 188) |
| BDBV386 | QGINNN (SEQ ID NO: 189) | DAS | QQNANLPHT (SEQ ID NO: 190) |
| BDBV397 | QDITNY (SEQ ID NO: 191) | DAS | QQSADLPLT (SEQ ID NO: 192) |
| BDBV399 | QGIDNY (SEQ ID NO: 193) | AAS | QRYNLAPSA (SEQ ID NO: 194) |
| BDBV353 | QSIGSL (SEQ ID NO: 195) | RAS | QQFNSY (SEQ ID NO: 196) |
| BDBV410 | QSLLHSNGETY (SEQ ID NO: 197) | EVS | MQSVLLPYT (SEQ ID NO: 198) |

TABLE 2-continued

| CDR sequences | | | |
|---|---|---|---|
| BDBV270 | QSINTY (SEQ ID NO: 199) | AAS | QQSFTTPYT (SEQ ID NO: 200) |
| BDBV324 | QSISRW (SEQ ID NO: 201) | KVS | QQYDTYPWT (SEQ ID NO: 202) |
| BDBV403 | QSVSSSY (SEQ ID NO: 203) | DAS | QQYGSSAIT (SEQ ID NO: 204) |
| BDBV407 | QSLLHSNGYNF (SEQ ID NO: 205) | LGS | MQA |
| BDBV425 | QSVYSYY (SEQ ID NO: 206) | DAS | QYYGNSHQGAA (SEQ ID NO: 207) |
| BDBV317 | HSLLYSSDNKNY (SEQ ID NO: 208) | WAS | QQYYTKSFT (SEQ ID NO: 209) |
| BDBV342 | SSNVGAYNY (SEQ ID NO: 210) | DVT | YSYAGSYTWI (SEQ ID NO: 211) |
| BDBV357 | ISDIGGYDY (SEQ ID NO: 212) | DVS | SSYTRTYTPHVV (SEQ ID NO: 213) |
| BDBV340 | SSDIGNNNY (SEQ ID NO: 214) | DVN | SSYTNNRTFS (SEQ ID NO: 215) |
| BDBV259 | KLGDRY (SEQ ID NO: 216) | QDT | QAWDTS (SEQ ID NO: 217) |
| BDBV343 | NSDVGGYDY (SEQ ID NO: 218) | DVN | CSYAGSYTFV (SEQ ID NO: 219) |

TABLE 3

Variable Region Protein Sequences

BDBV43 VH (SEQ ID NO: 1)

QVQLVQSGAEVKKPGSSVKVSCRASGDSFSRKYGISWVRQAPGQGFEWM

GTIMPIVGLTTSAQKFQGRVTITADKSTSTAHMELNSLTSEDTAIYYCA

RDEIIGARPHWFDSWGQGTLVTVSS

BDBV43 VL (SEQ ID NO: 2)

EIVMTQSPAIMSVSPGKRATLSCRASQSVSSNLAWYQRKPGQAPRLLIY

GSSTRATGIPARFSGSGSGTEFTLTISSLQSEDFAVYYCLQYYNWPRTF

GQGTKVEIK

BDBV223 VH (SEQ ID NO: 3)

QVQLQQWGAGLLKPSETLSLTCAVYGGSFTTTYWNWIRQPPGKGLEWIG

EVNYSGNANYNPSLKGRVAISVDTSKNQFSLRLNSVTAADTAIYYCTSR

IRSHIAYSWKGDVWGKGTTVTVSS

BDBV223 VL (SEQ ID NO: 4)

EIVMTQSPGTLSLSPGERATLSCRASQSVPRNYIGWFQQKPGQAPRLLI

YGASSRAAGFPDRFSGSGSGTDFTLTITRLEPEDFAMYYCHQYDRLPYT

FGQGTKLEIK

TABLE 3-continued

Variable Region Protein Sequences

EBOV49 VH (SEQ ID NO: 5)

EVQLVESGGGLVQPGGSLRLSCAASGFTFSSYEINWVRQAPGRGLEWVS

YISSSGRTIYYADSVKGRFTISRDNAKNSLYLQMNSLRAEDTAVYYCAR

EPYVDGILYGAGDSYFDYWGQGTLVTVSS

EBOV49 VL (SEQ ID NO: 6)

DIQMTQSPSSLSASVGDRVTITCRASQSISNYLNWYQQKPGKAPKVLIY

AASSLQSGVSSRFSGSGSGTDFTLTISSLQPEDFATYFCQQSYNTPPVT

FGQGTRLEIK

EBOV52 VH (SEQ ID NO: 7)

QVQLQESGPGLVKPSETLSLNCTVSGGSISSYYWSWIRQPPGKGLEWIG

YIYDSGRTKYNPSLKSRVTISLDTSKNQFSLKLSSVTAADTAVYYCASL

GPFDKLWFGELLPGWFDPWGQGTLVTVSS

EBOV52 VL (SEQ ID NO: 8)

EIVLTQSPATLSLSPGGRATLSCRASQSVHNYLAWYQQKSGQAPRLLIY

DASNRATGIPARFSGSGSGTDFTLTISSLEPDDFAVYYCQHRSNWLTFG

GGTKVEIK

TABLE 3-continued

Variable Region Protein Sequences

EBOV63 VH
(SEQ ID NO: 9)
EVQLVESGGGLVKPGGSLRLSCAASGFTLNFYNMNWVRQAPGKGLEWVS

SISSSSNYIYYADSVKGRFTISRDNARKSLYLQMNSLRAEDTAVYYCAR

DFVQLLIPQRDEWQGVHDYYGMDVWGQGTLVTVSS

EBOV63 VL
(SEQ ID NO: 10)
EIVLTQSPGTLSLSPGGRATLSCRASQSVSNSYLAWYQQKPGQAPRLLI

YGASSRATGIPDRFSGSGSGTDFILTISRLEPEDFAVYYCQHYGSSQLT

FGGGTKVEIK

EBOV82 VH
(SEQ ID NO: 11)
EVQLVESGGGLVKPGGSLRLSCAASGFTFTNAWMNWVRQAPGKGLEWVG

RIKSNTDGGTTDYAAPVKGRFTISRDDSKKTLYLQMNSLKTEDTAVYYC

TTGKSDCSGGNCYVVDYWGQGTLVTVSS

EBOV82 VL
<Not Yet Available>

EBOV90 VH
(SEQ ID NO: 12)
EVQLVESGGGLVKPGGALRLSCAASGFTFSNAWMSWVRQAPGKGLEWVG

RIKSKNDGGTADYAAPVKGRFSISRDDSKNTLYLQMNSLKIEDTAVYYC

ITFLRPDHWGQGTLVTVSS

EBOV90 VL
<Not Yet Available>

EBOV9 VH
(SEQ ID NO: 72)
QVQLVQSGVEVKKPGSSVKVSCKASGGTFSSYTISWVRQAPGQGLEWMG

RIIPKLGIANYAQNAQKFQGRVTITADKSTSTAYMELSRLRSEDTALYY

CARVLLSSRDAFDIWGQGTLVTVSS

EBOV9 VL
<Not Yet Available>

EBOV109 VH
(SEQ ID NO: 73)
QVQLVQSGAEVKKPGASVKVSCKASGYTFTGYYMHWVRQAPGQGLEWMG

WINPNSGGTNYAQKFQGWVTMTRDTSISTAYMELRRLRSDDTAVYYCAT

NKGTNGRYYYYGMDVWGQGTLVTVSS

EBOV109 VL
(SEQ ID NO: 74)
DIVMTQSPLSLPVTPGEPASISCRSSQSLLHSNGYNYLDWYLQKPGQSP

QLLIYLGSNRASGVPDRFSGSGSGTDFTLKISRVEAEDVGVYYCMQALQ

TITFGQGTRLEIK

EBOV119 VH
(SEQ ID NO: 75)
QVQLVQSGVEVKKPGSSVKVSCKASGGTFSSYTISWVRQAPGQGLEWMG

RIIPKLGIANYAQNAQKFQGRVTITADKSTSTAYMELSRLRSEDTALYY

CARVLLSSRDAFDIWGQGTLVT

EBOV119 VL
<Not Yet Available>

EBOV62_VH
(SEQ ID NO: 220)
EVQLVESGGGLVQPGGSLRLSCAASGFTFSSYWMSWVRQAPGKGLEWVA

NIKQDGSAKYYVDSVKGRFTISRDNAKNSLYLQMNSLRAEDTAVYYCAR

DGLLGISDLLYPIYYFDYWGQGTLVTVSS

EBOV62_VL
(SEQ ID NO: 221)
DIVMTQSPSSLSASVGDRVTITCRASQNIGSYLNWYQQKPGKAPNLLMY

AASSLQSGVPSRFSGSGSGTDFTLTITSLQPEDFATYYCQQSYSIPRTF

GQGTQLEIK

>EBOV87_VH
(SEQ ID NO: 222)
QVQLVQSGAEVKRPGASVKVSCKASGYTFTSYAISWVRQAPGQGLEWMG

WISGNNGNTNYAQKLQGRLTMTTDTSTSTAYMELRSLRSDDTAVYYCAR

DADIVVVVGATGTYYYGMDVWGQGTLVTVSS

>EBOV87_VL
(SEQ ID NO: 223)
DIVMTQSPSTLSASVGDRVTITCRASQSISSWLAWYQQKPGKAPKLLIY

DASSLESGVPSRFSGSGSGTEFTLTISSLQPDDFATYYCQQYKSSLRTF

GQGTQLEIK

EBOV157_VH
(SEQ ID NO: 224)
QVQLVQSGGGLVQPGGSLRLSCAASGFTVSNNYMSWVRQAPGKGLEWVS

IFYSDGTTYNADSVKGRFTISRDNSKNTLYLQMNSLRAEDTAVYYCARQ

ASGYDAYYMDVWGQGTLVTVSS

EBOV157_VL
(SEQ ID NO: 225)
DIVMTQSPSTLSASVGDRVTITCRASQSINSWLAWYQQKPGKAPKLLIY

QASTLERGVPSRFSGSGAGTEFTLTISSLQPDDFATYYCQQYSSFPLTF

GGGTKVELK

BDBV289_VH
(SEQ ID NO: 226)
QVQLVQSGAEVKKPGSSVKVSCKASGATFGSDTVTWVRQAPGQGLEWMG

GIIPFFGEANYAQRFQGRVTITADKSTNTAYMELSSLRSEDTAVYFCAR

QINEMATFGEIHYYTYMDVWGQGTLVTVSS

BDBV289_VL
(SEQ ID NO: 227)
GSELTQDPAVSVALGQTVRITCQGDSLRNYYASWYQQKPRQAPVLVFYG

KNNRPSGIPDRFSGSSSGNTASLTISGAQAEDEADYYCNSRDSSSNHLV

FGGGTKLTVLS

BDBV41
<Not Yet Available>

BDBV41_VL
(SEQ ID NO: 228)
EIVMTQSPGTLSLSPGERATLSCRASQSITSTYLAWYQQKPGQAPRLLI

YGASNRATGIPDRFSGSGSGTDFTLTISRLEPEDFAVYYCQQYHSSLFG

GGTKVEIK

TABLE 3-continued

Variable Region Protein Sequences

BDBV231_VH
(SEQ ID NO: 229)
QVQLVQSGPGLVKPSETLSLTCTVSSDSIRSYSWSWLRQPPGKGLEWIG
FIYYSGNINYNPSLKSRVTISVDTSKNQLSLNLSSVTAADTAVYYCARD
WITIFGRYFDVWGRGTLVTVSS

BDBV231_VL
(SEQ ID NO: 230)
DIVMTQSPDSLAVSLGERATINCKSSQNLLYSSNNKNFLTWYQHKPGQP
PKLLISWASTRESGVPDRFSGSGSGTDFTLTISSLQAEDVALYYCQQYY
TIPPTFGQGTKVEIK

BDBV275_VH
(SEQ ID NO: 231)
QVQLVQSGGGFVQPGRSLRLSCTASGFNFGDYVMSWVRQAPGKGLEWVG
FIRGKTFGATTEYAASVKGRFTISRDDSKSIAYLQIKSLKTEDTAVYYC
TRRATSTWYEDYWGQGTLVTVSS

BDBV275_VL
(SEQ ID NO: 232)
DIVMTQSPDSLAVSLGERATINCKSSQSVLYTPNNHNYLAWYQQKPGQP
PKLLIYWASAREPGVPDRFSGSGSGTDFTLTISSLQAEDVAVYYCQQYH
IPPYSFGQGTKLEIK

BDBV315_VH
(SEQ ID NO: 233)
QVQLVQSGPGLVKPSQTLSLTCTVSGDSISSGSYYWSWIRQPAGKGLEW
IGRIYTSGSTNYNPSLKSRVTISVDTSKNQFSLNLSSVTAADTAVYYCA
RDPITIFGGVIFGWGMDVWGQGTLVTVSS

BDBV315_VL
(SEQ ID NO: 234)
DIVMTQSPLSLPVTPGEPASISCRSSQTLLHSNGYNYLYWYLQKPGQSP
QLLIYLGSNRASGVPDRFSGSGSGTDFTLKISRVEAEDVGVYYCMQALQ
TPVTFGPGTKVDIK

BDBV329_VH
(SEQ ID NO: 235)
QVQLVQSGAEVKKPGSSVKVSCKASGGTFDTYAISWVRQAPGQGLEWMG
GIIPVLGIVDYAQKFQGRVTITAAKFTNIAYMELSSLRSEDAAVYYCAR
GLRSLSPRGQEGPTPAPGWRRAQYHYYYMDVWGTGTLVTVSS

BDBV329_VL
(SEQ ID NO: 236)
EIVMTQSPGTLSLSPGERATLSCRASQSVSSNYLAWYQQKPGQAPRLLI
YGASSRATGIPDRFSGSGSGPDFTLTISRLEPEDFAVYYCQQYGSSPGT
FGGGTKVEIK

BDBV335_VH
(SEQ ID NO: 237)
QVQLQESGPGLVRPSQTLSLTCTVSGGSINSDSYYWNWIRQPAGKGLEW
LGRVYTSGSTNYNPSLKSRVTISVDTSKNQVSLRLNSVTAADTGVYYCA
RVVWGSYRSYHYSYGMDVWGQGTLVTVSS

BDBV335_VL
(SEQ ID NO: 238)
EIVMTQSPGTLSLSPGERATLSCRASQSVGSSYLAWYQQRPGQAPRLLF
YGASYRATGIPDRFSASGSGTDFSLTINRLEPEDFAVYYCQQSGSSPET
FGQGTKLEIK

BDBV354_VH
(SEQ ID NO: 239)
QVQLVQSGVEVKKPGASVKVSCKASGYAFTTYAISWVRQAPGQGLEWMG
WISTYYGTTYYAQNLQGRVTMTTDTSTSTSYLELRSLRSDDTAVYYCVR
DRSWLATSRPYDAFDIWGQGTLVTVSS

BDBV354_VL
(SEQ ID NO: 240)
AIQMTQSPSSLSASVGDRVTITCRASQDISSTLAWYQQKPGKAPKLLIY
GASSLESGVPSRFNGSGSGTDFTLTISSLQPEDFATYYCQHFYYFPRTF
GQGTRLEIR

BDBV386_VH
(SEQ ID NO: 241)
QVQLVQSGPGLVKPSQTLSLTCTVSGGSISSGRFYWSWVRQPAGRGLEW
IGRIYTSGSTNYNPSLKSRVSISVDTSKNQFSLKLSSVTAADTAVYYCA
TELYYYGSGSYDPLWSWGQGTLVTVSS

BDBV386_VL
(SEQ ID NO: 242)
DIVMTQSPSSLSASVGDRVTITCQASQGINNNLNWHQQKPGKAPKLLIY
DASNLERGVPSRFSGSGSGTDFTFTISSLQPEDIATYYCQQNANLPHTF
GQGTKLEIK

BDBV397_VH
(SEQ ID NO: 243)
QVQLVQSGPGLVKPSQTLSLTCTVSGGSISSGSYFWNWIRQPAGKGLEW
IGRIYTSGTTNYNPSLKSRLTISVDTSKNQFSLKLNSVTAADTAVYYCA
TSPYYYDSSHYYDYWGQGTLVTVSS

BDBV397_VL
(SEQ ID NO: 244)
DIQMTQSPSSLSASVGDRVTITCQASQDITNYLNWYQQKPGKAPKLLIF
DASNLEKGVPSRFSATGSATDFTFTISSLQPEDTATYYCQQSADLPLTF
GQGTRLDIK

BDBV399_VH
(SEQ ID NO: 245)
QVQLVQSGPGLVKPSQTLSLTCNVSGGSISNGGYHWSWIRQVPGKGLEW
IGHIYYSGSTSYTPSLKSRLTISVDTSKNQFSLKLSSVTAADTAVYYCA
RDRIRGGPIDYWGQGTLVTVSS

BDBV399_VL
(SEQ ID NO: 246)
DIQMTQSPSSLSASVGERVTITCRASQGIDNYLAWYQQKPGKVPKLLIY
AASTLHSGVPSRFSGSGSGTDFTLTISSLQPEDVATYYCQRYNLAPSAF
GQGTKVEIR

TABLE 3-continued

Variable Region Protein Sequences

BDBV353_VH
(SEQ ID NO: 247)
QVQLVQSGAEMRKPGASVKVSCKASGYTFSDYYIHWVRQAPGQGLEWLG
WINPYSGGTNYAQKFQGRVTMTRDTSISTAHMELSGLRSDDTALYFCAR
LYGAGSHYNHYNGMDVWGQGTLVTVSS

BDBV353_VL
(SEQ ID NO: 248)
DIQMTQSPSTLSASVGDRVTITCRASQSIGSLLAWYQQKPGKAPKLLIY
RASTLQGGVPSRFSGSGSGTEFTLTISSLQPDDVATYYCQQFNSYFGGG
TKVEIK

BDBV410_VH
(SEQ ID NO: 249)
QVQLQQSGPGLVRPSQTLSLTCSVSGGSVSSGRYFWNWIRQSAGKGLEW
IGRIHSSGRTNSNPSLKSRVTISVDTSKNQFSLHLGSVTAADTAVYYCA
R

BDBV410_VL
(SEQ ID NO: 250)
DIVMTQTPLSLSVTPGQPASISCKSSQSLLHSNGETYLFWYLQKPGQPP
QLLIYEVSNRFSGVPDRFSGSGSGTDFTLKISRVEAEDVGVYYCMQSVL
LPYTFGQGTKLEIK

BDBV270_VH
(SEQ ID NO: 251)
QVQLQESGPGLVKPSQTLSLTCTVSGASISRGLYYWSWIRQPAGKGLEW
IGRIYTSGSINYNPSLKSRVTISVDTSKNQFSLRLSSVIATDTAVYYCV
RDAPWGDFLTGYFGFYGMDVWGQGTLVTVSS

BDBV270_VL
(SEQ ID NO: 252)
DIVMTQSPSSLSASVGDRVTITCRASQSINTYLNWYQQKPGKAPKFLIY
AASSLHSGVPSRFSGSGSGTDFTLTINSLQPDDFATYYCQQSFTTPYTF
GQGTKLEIK

BDBV324_VH
(SEQ ID NO: 253)
QVQLVQSGAEVKKPGASVKVSCKTSGYTFTSFEIHWVRQGSGQGLEWMG
RMNPKSGDTVSAQKFQGRVTLTRDTSINAAYMELGSLSSEDTAVYYCAR
GPHVGEVVPGLMAGTYYFPLDVWGQGTLVTVSS

BDBV324_VL
(SEQ ID NO: 254)
DIQMTQSPSTLSASIGDRVTITCRASQSISRWLAWYQQKPGKAPKLLIY
KVSDLQGSVPSRFSGSGYGTEFTLTIGSLQPDDLATYYCQQYDTYPWTF
GQGTKLEIK

BDBV403_VH
(SEQ ID NO: 255)
QVQLVQSGAEVKKPGSSVKVSCNASGGTFSNSILNWVRQAPGQGLEWMG
RIIPIVGLVNFAQKFEGRVTFTADKFTNTAYMELNSLRFEDTAVYYCAI
NGGKYPGYFDYWGQGTLVTVSS

TABLE 3-continued

Variable Region Protein Sequences

BDBV403_VL
(SEQ ID NO: 256)
DIVMTQSPGTLSLSPGERATLSCRASQSVSSSYLAWYQHPGQAPRLLI
YDASSRATGIPDRFSGSGSGTDFTLIISRLEPEDFAVYYCQQYGSSAIT
FGQGTRLEIK

BDB407_VH
(SEQ ID NO: 257)
QVQLQESGPGLVKPSETLSLTCAVSGGSIRSYFWSWIRQAPGKGLEWIG
NIYYSGRPNYNPSLKNRVTISADTSNNEVSLELSAVTAADTAVYFCARD
ERLLVEVGTDHFYYGLDVWGQGTLVTVSS

BDBV407_VL
(SEQ ID NO: 258)
EIVMTQSPLSLSVTPGEPASISCRSSQSLLHSNGYNFLDWYLQKPGQSP
QLLIYLGSNRASGVPDRFSGSGSGADFTLKISRVEAEDVGVXYCMQA

BDBV425_VH
(SEQ ID NO: 259)
QVQLVQSGAEVKKPGASVKVSCKASGYTFTSFGISWVRQAPGQGLEWLG
WINTYNGDTNYAQKFQGRVTMTTDTSTSTGFMELRSLRSDDTAVYYCAR
DSHLISIAVANTPNDFWGQGTLVTVSS

BDBV425_VL
(SEQ ID NO: 260)
EIVMTQSPGTLSLSPGDRVTLSCRASQSVYSYYLAWYQQKPGQAPRLLM
YDASIRATGIPDRFSGSGSGTDFTLTISSLEPEDFAVYYCQYYGNSHQG
AAFGQGTKVEVK

BDBV426_VH
(SEQ ID NO: 261)
QVQLQESGPGLVKPSQTLSLTCNVSGGSISSDDRYWSWIRQPPGKGLEW
LGFIYYSGSTDYNPSLKSRVTMSLDTSKNQFSLKLNSVTAADTAMYYCA
TVTAYSPATMIVVGTEHGFDYWGQGTLVTVSS

BDBV426_VL
(SEQ ID NO: 262)
DIVMTQSPSSLSASVGDRVTIFCRATQSIRSFLNWYQQKPGKAPNLLIY
AASSLQSGVPSRFSGSGSGTDFTLTISSLQPEDFATYYCQQSYSTPWTF
GQGTKVEIK

BDBV317_VH
(SEQ ID NO: 263)
QVQLVESGGGVVQPGGSLRLSCEVSGLTFSNFGMQWVRQAPGKGLEWVA
FIRFDGSNKYYADSVKGRFTISRDNSKNTVYLQMGSLRAEDTAVYFCGR
VLYGAAADFWGQGTLVTVSS

BDBV317_VL
(SEQ ID NO: 264)
DIVMTQSPDSLAVSLGERATINCTSSHSLLYSSDNKNYLTWYQQKAGQP
PKLLIYWASTRQSGVPDRFSGSGSGTEFTLTISSLQAEDVAVYYCQQYY
TKSFTFGQGTKVEIK

BDBV342_VH
(SEQ ID NO: 265)
QVQLVQSGAEVKKPGSSVKVSCKASGGTFSSYAINWVRQAPGQGLEWMG
GIIPIFGKPNYAQKFQGRVTITADKSTSTAYMELRSLRSEDTAVYYCAR
GQGEIVVMVGHDDGGDYLGYWGQGTLVTVSS

TABLE 3-continued

Variable Region Protein Sequences

BDBV342_VL
(SEQ ID NO: 266)
QSALTQPRSVSGSPGXSVTISCTGTSSNVGAYNYVSWYQQHPGKAPKLM

IFDVTKRPSGVPDRFSGSKSGNTASLTISGLQAEDEADFYCYSYAGSYT

WIFGGGTKLTVLG

BDBV357_VH
(SEQ ID NO: 267)
QVQLVQSGPGLVKPSETLSLTCSVSGGSISGSIWTWIRQSPGKGLEWIG

YISLSGSTNFNPSLKSRVTISVDTSKNQFSLKLSSVTAADTAVYYCARH

RKSSKMVRGIEVFYYYYMDVWGKGTLVTVSS

BDBV357_VL
(SEQ ID NO: 268)
QSALTQPASVSGSPGQSITISCTGTISDIGGYDYVSWYQQHPGKAPKLM

IYDVSDRPSGVSNRFSGSKSGNTASLTISGLQSEDEADYYCSSYTRTYT

PHVVFGGGTKLTVLG

BDBV340_VH
(SEQ ID NO: 269)
QVQLVQSGPGLVKPSQTLSLTCTVSGGSISSGSFYWSWIRQPAGKGLEW

IGRFYTTGSTHYNPSLKSRVTISADTSKNHFSLNLTSLTAADTAVYYCA

RGPVSYYSGNLYYFDYWGLGTLVTVSS

BDBV340_VL
(SEQ ID NO: 270)
QSALTQPASVSGSPGQSITITCTGTSSDIGNNNYVSWYQQHPGKAPKLI

IFDVNKRPSGVSNRFSGSKSDNTASLTISGLQAEDEADYYCSSYTNNRT

FSFGGGTKVTVL

BDBV392_VH
(SEQ ID NO: 271)
QVQLVQSGGGVVQPGGSLRLSCAASGFTFSSFGIHWVRQAPGKGLEWVA

FIRYDGSDKFYLDSVKGRFTISRDNSKNTLFLQMSSLRVEDTAVYYCAK

RGGHDYGYYDNNRYIDLWGRGTLVTVSS

BDBV259_VH
<Not Yet Available>

BDBV259_VL
(SEQ ID NO: 272)
SYVLTQPPSVSVSPGQTASITCSGDKLGDRYTCWYQQKPGQSPVLVIYQ

DTKRPSGIPERFSGSNSGNTATLTISETQAIDEADYYCQAWDTS

BDBV328_VH
<Not Yet Available>

BDBV328_VL
(SEQ ID NO: 273)
DIQMTQSPSTLSASVGDRVTITCRASQSISTYLAWYQQKPGKAPNLLIY

KASSLQSGVPPRFSGSGSGTEFTLTISSLQPDDFATYYCQQYHSYWWTF

GQGTKVEII

BDBV415_VH
(SEQ ID NO: 274)
QVQLVQSGAEVKKPGSSVKVSCKASGGTFSSYGVSWVRQAPGQGLEWMG

GIIPKFATAKYAQKFQGRVTITADESTSTAYMELSSLRSEDTAVYYCAG

HFPQRKPITTIVVITYWSLDLWGRGTLVTVSS

BDBV415_VL
<Not Yet Available>

BDBV343_VH
(SEQ ID NO: 275)
QVQLVESGAEGKKPGSSVKVSCKAPGVTFSRYTISWVRQAPGQGLEWMG

RISPILGTANYAQKFQGRVTITADKSSSTVYMELNRLKSDDTAVYYCAR

DAPIILVEGPETGMDVWGQGTLVTVSS

BDBV343_VL
(SEQ ID NO: 276)
QSALTQPRSVSASPGQSVTISCTGTNSDVGGYDYVSWYQQHPGKAPKLM

ISDVNMRPSGVPDRFSGSKSGNTASLTISGLQSEDEADYYCCSYAGSYT

FVFGSGTKVTVLG

BDBV377_VH
(SEQ ID NO: 277)
QVQLVQSGGGVVQPGRSLRLSCAASGFTFNSYGMHWVRQAPGKGLEWVA

VIWFDGSKKYYADSVKGRFTISRDNSKNSLYLQMNSLRAEDTAVYYCAK

DLLYGSGMVPNYYYYGLDVWGQGTLVTVSS

BDBV377_VL
<Not Yet Available>

BDBV255_VH
(SEQ ID NO: 278)
QVQLVQSGGGLVRPGGSLRLSCTASGFTLSTYSMTWVRQAPGKGLEWVS

SISSSSTYKYYVDSIKGRFTISRDNAKNSLYLQMESLGVEDTAVYYCSR

ADWDSGKGDLDSWGQGTLVTVSS

BDBV255_VL
(SEQ ID NO: 279)
QPVVTQSPSASASLGASVRLTCTLNSGRSKYAIAWHQQQPGKGPRYLMT

LNHDGSHSKGDGIPFRFSGSSSGTERYLTISSLQSEDEADYYCQTWGKG

IVVFGGGTKLTVLG

BDBV432_VH
(SEQ ID NO: 280)
QVQLVQSGPRLVKPSETLSLTCTVSGDSSGRYYWSWIRQTPGKGLEWIG

YISYTGSTNYNPSLKSRVTISSDMSKSHFSLNLTSVTAADTAVYYCARG

GWNLLVSYFDFWGLGTLVTVSS

BDBV432_VL
<Not Yet Available>

BDBV91_VH
(SEQ ID NO: 281)
QVQLVQSGAELKPPGASVKVSCKPSGYTFTDYYIHWVRQAPGQGLEWMG

WINPKSGETHYAQKFRGWVTLTRDTSISTTYMDLTRLKSDDTAVYFCAR

GDLETTIFFYNAVDVWGQGTLVTVSS

BDBV91_VL
(SEQ ID NO: 282)
DIQMTQSPSSLSASVGDRVTITCRATESIGIYLNWYQRKPGKAPNLLIF

ATSSLQSGVPSRFSGSGSGTEFTLTISSLQPEDFATYFCQQGFSSPFSF

GQGTRLEIK

TABLE 4

Variable Region Nucleic Acid Sequences

BDBV43 VH
(SEQ ID NO: 13)
caggtgcagctggtgcagtctggggctgaggtgaagaagcctgggtcctcggtgaaggtc tcctgcagggcttctggagactccttcagccgcaagtatggcatcagctgggtgcgacag gcccctggacaaggatttgagtggatgggaacgatcatgccaatcgttggtttgaccacc tccgcccagaaattccagggcagagtcacaattaccgcggacaagtccacgagcacagcc cacatggaactgaacagcctgacatctgaggacacggccatttattactgtgcgagagat gaaattattggggctcgaccccactggttcgactcttggggccagggaaccctggtcacc gtctcctca BDBV43 VL
(SEQ ID NO: 14)
gaaattgtgatgacccagtctccagccatcatgtctgtgtctccagggaaaagagccacc ctctcctgcagggccagtcagagtgtcagtagcaacttagcctggtaccagcggaaacct ggccaggctcccaggctcctcatctatggttcttccaccagggccactggtatcccagcc aggttcagtggcagtgggtctgggacagagttcactctcaccatcagcagcctgcagtct gaggattttgcagtttattactgtctgcaatattataactggcctcggacgttcggccaa gggaccaaggtggaaatcaaa BDBV223 VH
(SEQ ID NO: 15)
caggtgcagctacagcagtggggcgcaggactgttgaagccttcggagaccctgtccctc acctgcgctgtctatggtgggtccttcacgactacctactggaattggatccgccagccc ccagggaaggggctggaatggataggggaagtcaattatagtggaaacgccaactacaac ccgtccctcaagggtcgagtcgccatatcagtggacacatccaagaaccagttctccctg aggttgaactctgtgaccgccgcggacacggctatatattactgtacgagtcgcatacgt tcgcacattgcctactcgtggaaggggggacgtctggggcaaagggaccacggtcaccgtc tcctca BDBV223 VL
(SEQ ID NO: 16)
gaaattgtgatgacccagtctccaggcaccctgtctttgtctccaggggaaagagccacc ctctcctgcagggccagtcagagtgttcccaggaattatataggttggttccagcagaaa cctggccaggctcccaggctcctcatctatggtgcatccagcagggccgctggcttccca gacagattcagtggcagtgggtctgggacagacttcactctcaccatcaccagactggag cctgaagattttgcaatgtattactgtcaccagtatgataggttaccgtacacttttggc caggggaccaagctggagatcaaa EBOV49 VH
(SEQ ID NO: 17)
gaggtgcagctggtggagtctgggggaggcttggtacagcctggagggtccctgagactc tcctgtgcagcctctggattcaccttcagtagttatgaaatcaactgggtccgccaggct ccagggaggggctggagtgggtttcatacattagtagtagtggtagaaccatatactac gcagactctgtgaagggccgattcaccatctccagagacaacgccaagaactcactgtat ctgcaaatgaacagcctgagagccgaggacacggctgtttattactgtgcgagagaacca tatgttgacggaatattatatggggccggggatagctactttgactactggggccaggga accctggtcaccgtctcctca TABLE 4-continued Variable Region Nucleic Acid Sequences EBOV49 VL
(SEQ ID NO: 18)
gacatccagatgacccagtctccatcctccctgtctgcatctgtaggagacagagtcacc
atcacttgccgggcaagtcagagcattagcaactatttaaattggtatcagcagaaacca
gggaaagcccctaaggtcctgatctatgctgcatccagtttgcaaagtggggtctcatca
aggttcagtggcagtggatctgggacagacttcactctcaccatcagcagtctgcaacct
gaagattttgcaacttacttctgtcaacagagttacaataccccctccggtcaccttcggc
caagggacacgactggagattaaa EBOV52 VH
(SEQ ID NO: 19)
caggtgcagctgcaggagtcgggcccaggactggtgaagccttcggagaccctgtccctc
aactgcactgtctctggtggctccatcagtagttactactggagctggatccggcagccc
ccagggaagggactggagtggattgggtatatctatgacagtgggagaaccaagtacaac
ccctcccctcaagagtcgagtcaccatatcattagacacgtccaagaaccagttctccctg
aagctgagctctgtgaccgccgcagacacggccgtgtattactgtgcgagtctgggccat
tcgacaaattatggttcggggagttgttgccgggatggttcgacccctggggccagggaa
ccctggtcaccgtctcctca EBOV52 VL
(SEQ ID NO: 20)
gaaattgtgttgacacagtctccagccaccctgtctttgtctccaggggaagagccacc
ctctcctgcagggccagtcagagtgttcacaactacttagcctggtaccaacagaagtct
ggccaggctcccaggctcctcatctatgatgcatccaacagggccactggcatcccagcc
aggttcagtggcagtgggtctgggacagacttcactctcaccatcagcagcctggagcct
gacgattttgcagtttattactgtcagcaccgtagcaactggctcactttcggcggaggg
accaaggtggagatcaaa EBOV63 VH
(SEQ ID NO: 21)
gaggtgcagctggtggagtctgggggaggcctggtcaagcctggggggtccctgagactc
tcctgtgcggcctctggattcaccttaaatttctataacatgaactgggtccgccaggct
ccagggaaggggctggagtgggtctcatccattagtagtagtagtaattacatatactac
gcagactcagtgaagggccgattcaccatctccagagacaacgccaggaagtcactgtat
ctgcaaatgaacagcctgagagccgaggacacggctgtgtattactgtgcgagagatttt
gtccagctattaattccgcaaagggacgagtggcagggtgtccacgactactacggtatg
gacgtctggggccaagggaccctggtcaccgtctcctca EBOV63 VL
(SEQ ID NO: 22)
gaaattgtgttgacgcagtctccaggcaccctgtctttgtctccaggggaagagccacc
ctctcctgcagggccagtcagagtgttagcaacagctacttagcctggtaccagcagaaa
cctggccaggctcccaggctcctcatctatggtgcatccagcagggccactggcatccca
gacaggttcagtggcagtgggtctgggacagacttcattctcaccatcagcagactggag
cctgaagattttgcagtgtattactgtcagcactatggtagctctcagctcactttcggc
ggagggaccaaggtggagatcaaa TABLE 4-continued Variable Region Nucleic Acid Sequences EBOV82 VH
(SEQ ID NO: 23)
gaggtgcagctggtggagtctgggggaggcttggtaaagcctgggggtcccttagactc tcctgtgcagcctctggattcacttttactaacgcctggatgaactgggtccgccaggct ccagggaaggggctggagtgggttggccgtattaaaagcaacactgatggtgggacaaca gactacgctgcacccgtgaaaggcagattcaccatctcaagagatgattcaaaaaagacg ctgtatctgcaaatgaacagcctgaaaaccgaggacacagccgtgtattactgtaccaca gggaaaagtgactgtagtggtggtaactgctacgtggttgactactggggccagggaacc ctggtcaccgtctcctca EBOV82 VL
<Not Yet Available>

EBOV90 VH
(SEQ ID NO: 24)
gaggtgcagctggtggagtctgggggaggcttggtaaagcctggggggcccttagactc agctgtgcagcctctggattcactttcagtaacgcctggatgagctgggtccgccaggct ccagggaaggggctggagtgggttggccgtattaaaagcaaaaatgatggtgggacagca gactacgctgcacccgtgaaaggcagattcagcatctcaagagatgattcaaaaaacacg ctttatctgcaaatgaacagcctgaaaatcgaggacacagccgtgtattactgtatcacg tttttacgccccgaccactggggccagggaaccctggtcaccgtctcctca EBOV90 VL
<Not Yet Available>

EBOV9 VH
(SEQ ID NO: 76)
CAGGTGCAGCTGGTGCAGTCTGGGGTTGAGGTGAAGAAGCCTGGGTCCTCGGTGAAGGTC

TCCTGCAAGGCTTCTGGAGGCACCTTCAGCAGCTATACTATCAGCTGGGTGCGACAGGCC

CCTGGACAAGGGCTTGAGTGGATGGGAAGGATCATCCCTAAGCTTGGTATAGCAAACTAC

GCACAGAACGCACAGAAGTTCCAGGGCAGAGTCACGATTACCGCGGACAAATCCACGAGC

ACAGCCTACATGGAGCTGAGCAGGCTGAGATCTGAGGACACGGCCCTGTATTACTGTGCG

AGAGTATTACTGAGTAGCAGGGATGCTTTTGATATCTGGGGCCAAGGGACCCTGGTCACC

GTCTCCTCA

EBOV9 VL
(SEQ ID NO: 77)
QVQLVQSGVEVKKPGSSVKVSCKASGGTFSSYTISWVRQAPGQGLEWMGRIIPKLGIANY

AQNAQKFQGRVTITADKSTSTAYMELSRLRSEDTALYYCARVLLSSRDAFDIWGQGTLVT

VSS

EBOV109 VH
(SEQ ID NO: 78)
CAGGTGCAGCTGGTGCAGTCTGGGGCTGAGGTGAAGAAGCCTGGGGCCTCAGTGAAGGTC

TCCTGCAAGGCTTCTGGATACACCTTCACCGGCTACTATATGCACTGGGTGCGACAGGCC

CCTGGACAAGGGCTTGAATGGATGGGATGGATCAACCCTAACAGTGGTGGCACAAACTAT

GCACAGAAGTTTCAGGGCTGGGTCACCATGACCAGGGACACGTCCATCAGCACAGCCTAC

ATGGAGCTGAGAAGGCTGAGATCTGACGACACGGCCGTGTATTACTGTGCGACCAACAAA

GGAACTAACGGTCGCTACTACTACTACGGTATGGACGTCTGGGGCCAAGGGACCCTGGTC

ACCGTCTCCTCA

TABLE 4-continued

Variable Region Nucleic Acid Sequences

EBOV109 VL (SEQ ID NO: 79)
GACATTGTGATGACCCAGTCTCCACTCTCCCTGCCCGTCACCCCTGGAGAGCCGGCCTCC

ATCTCCTGCAGGTCTAGTCAGAGCCTCCTGCATAGTAATGGATACAACTATTTGGATTGG

TACCTGCAGAAGCCAGGGCAGTCTCCACAGCTCCTGATCTATTTGGGTTCTAATCGGGCC

TCCGGGGTCCCTGACAGGTTCAGTGGCAGTGGATCAGGCACAGATTTTACACTGAAAATC

AGCAGAGTGGAGGCTGAGGATGTTGGGGTTTATTACTGCATGCAAGCTCTACAAACTATC

ACCTTCGGCCAAGGGACACGACTGGAGATTAAA

EBOV119 VH (SEQ ID NO: 80)
CAGGTGCAGCTGGTGCAGTCTGGGGTTGAGGTGAAGAAGCCTGGGTCCTCGGTGAAGGTC

TCCTGCAAGGCTTCTGGAGGCACCTTCAGCAGCTATACTATCAGCTGGGTGCGACAGGCC

CCTGGACAAGGGCTTGAGTGGATGGGAAGGATCATCCCTAAGCTTGGTATAGCAAACTAC

GCACAGAACGCACAGAAGTTCCAGGGCAGAGTCACGATTACCGCGGACAAATCCACGAGC

ACAGCCTACATGGAGCTGAGCAGGCTGAGATCTGAGGACACGGCCCTGTATTACTGTGCG

AGAGTATTACTGAGTAGCAGGGATGCTTTTGATATCTGGGGCCAAGGGACCCTGGTCACC

EBOV119 VL
<Not Yet Available>

EBOV62 VH (SEQ ID NO: 283)
gaggtgcagctggtggagtctgggggaggcttggtccagcctggggggtccctgagactc tcctgtgcagcctctggattcacctttagtagctattggatgagctgggtccggcaggct ccagggaaggggctggagtgggtggccaacataaagcaagatggaagtgcgaaatactat gtggactctgtgaagggccgattcaccatctccagagacaacgccaagaactcgctgtat ctgcaaatgaacagcctgagagccgaggacacggccgtctattactgtgcgagagatgga ttactcgggatcagtgatttattataccccatatactactttgactactggggccaggga accctggtcaccgtctcctca

EBOV62 VL (SEQ ID NO: 284)
gacattgtgatgacccagtctccatcctccctgtctgcatctgtaggagacagagtcacc atcacttgccgggcaagtcagaacattgggagctatttaaattggtatcagcagaaacca gggaaagcccctaacctcctgatgtatgctgcatccagtttgcaaagtggggtcccatca aggttcagtggcagtggatctgggacagatttcactctcaccatcaccagtctgcaacct gaagattttgcaacttactactgtcaacagagttacagtatccctcgaacttttggccag gggacccagctggagattaaa

EBOV87_VH (SEQ ID NO: 285)
caggttcagctggtgcagtctggagctgaggtgaagaggcctggggcctcagtgaaggtc tcctgcaaggcttctggttacacctttaccagctacgctatcagctgggtgcgacaggcc cctggacaagggcttgagtggatgggatggatcagcggtaacaatggtaacacaaactat gcacagaagctccagggcagactcaccatgaccacagacacatccacgagcacagcctac atggagctgaggagcctgagatctgacgacacggccgtttattactgtgcgagagatgcc gatattgtcgtggtggtaggtgctacgggggacctactactacggtatggacgtctgggc caagggaccctggtcaccgtctcctca TABLE 4-continued Variable Region Nucleic Acid Sequences EBOV87_VL
(SEQ ID NO: 286)
gacatcgtgatgacccagtctccttccaccctgtctgcatctgtaggagacagagtcacc atcacttgccgggccagtcagagtattagtagctggttggcctggtatcagcagaaacca gggaaagcccctaagctcctgatctatgatgcctccagtttggaaagtggggtcccatca aggttcagcggcagtggatctgggacagaattcactctcaccatcagcagcctgcagcct gatgattttgcaacttattactgcaacagtataaaagttctctgaggacgttcggccag gggacccagctggagattaaa EBOV157 VH
(SEQ ID NO: 287)
caggtgcagctggtgcagtctggggggaggcttggtccagcctggggggtccctgagactc tcctgtgcagcctctggattcaccgtcagtaacaactacatgagctgggtccgccaggct ccagggaaggggctggagtgggtctcaattttttatagcgatggtaccacatacaacgca gactccgtgaagggcagattcaccatctccagagacaattccaagaacacgctgtatctt caaatgaacagcctgagagccgaggacacggctgtgtattactgtgcgagacaagcaagt ggctacgacgcctactacatggacgtctggggccagggaaccctggtcaccgtctcctca EBOV157 VL
(SEQ ID NO: 288)
gacatygtgatgacccagtctccttccaccctgtctgcatctgtaggagacagagtcacc atcacttgccgggccagtcagagtattaatagctggttggcctggtatcagcagaaacca gggaaagcccctaagctcctgatctatcaggcgtctactttagaaagaggggtcccatca aggttcagcggcagtggagctgggacagaattcactctcaccattagcagcctgcagcct gatgattttgcaacttattactgccaacaatatagtagtttcccgctcactttcggcgga gggaccaaggtggagctcaaa BDBV289 VH
(SEQ ID NO: 289)
caggtgcagctggtgcagtctggggctgaagtgaagaagcctgggtcctcggtgaaggtc tcctgcaaggcttctggagccaccttcggcagcgatactgtcacctgggtgcgacaggcc cctggacaagggcttgagtggatgggagggatcatcccttttttggtgaagcaaactac gcacagagggtttcagggcagagtcacgataaccgcggacaagtccacgaacacagcctac atggaactgagcagcctgagatctgaggacacggccgtgtacttctgtgcgagacaaata aacgagatggctacatttggggagatacattattatacgtacatggatgtctggggccaa gggaccctggtcaccgtctcctca BDBV289 VL
<Not Yet Available>

BDBV41 VH
<Not Yet Available>

BDBV41 VL
(SEQ ID NO: 290)
gaaattgtgatgacccagtctccaggcaccctgtctttgtctccaggggaaagagccacc ctctcctgcagggccagtcagagtattaccagcacctacttagcctggtaccagcagaaa cctggccaggctcccaggctcctcatctatggtgcatccaacagggccactggcatccca gacaggttcagtggcagtgggtctgggacagacttcactctcaccatcagcagactggag cctgaagattttgcagtgtattactgtcagcagtatcatagctcacttttcggcggaggg accaaggtggagatcaaa TABLE 4-continued Variable Region Nucleic Acid Sequences BDBV231 VH
(SEQ ID NO: 291)
caggtgcagctggtgcagtcgggcccaggtctggtgaagccttcggagaccctgtccctc acctgcactgtctctagtgactccatcaggagttactcctggagctggctccggcagccc ccagggaagggcctggagtggattgggtttatctattacagtgggaacatcaattacaac ccgtccctcaagagtcgagtcaccatatcagtagacacgtccaagaaccagttgtccctg aacctgagctctgtgaccgctgcggacacggccgtgtattattgtgcgagagattggatt acgattttttggaggtacttcgatgtctggggccgtggcaccctggtcaccgtctcctca BDBV231VL
(SEQ ID NO: 292)
gacatcgtgatgacccagtctccagactcctggctgtttctctgggcgagagggccacc atcaactgcaagtccagccagaatctttatacagctccaacaataagaacttcttaact tggtaccaacacaaaccaggacagcctcctaagctgctcatttcctgggcatctactcgg gaatccggggtccctgaccgattcagtggcagcgggtctgggacagatttcactctcacc atcagcagcctgcaggctgaagatgtggcactttattactgtcagcaatattatactatt cctccaacgttcggccaagggaccaaggtggaaatcaaa BDBV275_VH
(SEQ ID NO: 293)
caggtgcagctggtgcagtctggggaggcttcgtacagccagggcggtccctgagactg tcctgtacagcctctggattcaactttggtgattatgttatgagctgggtccgccaggct ccagggaaggggctggagtgggtaggtttcattaggggcaaaacttttggtgcgacaaca gagtacgccgcgtctgtgaaaggcagatttaccatctcaagggatgattccaaaagcatc gcctacctgcaaattaaatccctgaaaaccgaggacacagccgtctactattgtactaga agggccaccagcacctggtacgaggactattggggccagggaaccctggtcaccgtctcc tca BDBV275_VL
(SEQ ID NO: 294)
gacatcgtgatgacccagtctccggactcctggctgtgtctctgggcgagagggccacc atcaactgcaagtccagccagagtgttttatacaccccaacaatcataattacttagct tggtaccagcagaaaccaggacagcctcctaagctgctcatttactgggcatctgcccgg gaacccggggtccctgaccgattcagtggcagcgggtctgggacagatttcactctcacc ataagcagcctgcaggctgaggatgtggcagtttattactgtcagcaatatcatattcct ccgtacagttttggccaggggaccaagctggagatcaaa BDBV315_VH
(SEQ ID NO: 295)
caggtgcagctggtgcagtcgggcccaggactggtgaagccttcacagaccctgtccctc acctgcactgtctctggtgactccatcagcagtggtagttactactggagctggatccgg cagcccgccgggaagggactggagtggattgggcgtatctataccagtgggagcaccaac tacaatccctccctcaagagtcgagtcaccatttcagtagacacgtccaagaaccagttc tccctgaacctgagctctgtgaccgccgcagacacggccgtgtattactgtgcgagagat ccgattacgattttttggaggggttattttcggctggggaatggacgtctggggccaaggg accctggtcaccgtctcctca TABLE 4-continued Variable Region Nucleic Acid Sequences BDBV315_VL (SEQ ID NO: 296)
gacattgtgatgacccagtctccactctccctgcccgtcaccctggagagccggcctcc atctcctgcaggtctagtcagaccctcctgcatagtaatggatacaactatttgtattgg tacctgcagaagccagggcagtctccacagctcctgatctatttgggttctaatcgggcc tccggggtccctgacaggttcagtggcagtggatccggcacagattttacactgaaaatc agcagagtggaggctgaggatgttggggtttattactgcatgcaagctctacaaactccc gtcactttcggccctgggaccaaagtggatatcaaa BDBV329_VH (SEQ ID NO: 297)
caggtccagctggtgcagtctggggctgaagtgaagaagcctgggtcctcagtgaaggtc tcctgcaaggcttctggaggcaccttcgacacctatgctatcagctgggtgcgacaggcc cctggacaagggcttgagtggatgggagggattatcccctgttcttggtatagtagattat gcacagaagttccagggcagagtcacaattactgcggccaaattcacgaacatagcctac atggagctgagcagcctgagatctgaggacgcggccgtgtattactgtgcgagaggcctg cggagcctttctccccggggacaagagggacctactccagcgcccgggtggagaagggct cataccactactactacatggacgtctggggcacagggaccctggtcaccgtctcctca BDBV329_VL (SEQ ID NO: 298)
gaaattgtgatgacccagtctccaggcaccctgtctttgtctccaggggaaagagccacc ctctcctgcagggccagtcagagtgttagtagcaactatttagcctggtaccagcaaaaa cctggccaggctcccaggctcctcatctatggtgcatccagcagggccactggcatccca gacaggttcagtggcagtgggtctgggccagacttcactctcaccatcagcagactggag cctgaagattttgcagtgtattattgtcagcagtatggtagttcacccggcacttttcggc ggagggaccaaggtggagatcaaa BDBV335_VH (SEQ ID NO: 299)
caggtgcagctgcaggagtcgggcccaggactggtgaggccttcacagaccctgtccctc acctgcactgtgtctggtggctccatcaacagtgatagttactactggaactggatccgg cagcccgccgggaagggactggagtggcttgggcgtgtctataccagtgggagcaccaac tacaacccctccctcaagagtcgagtcaccatatcagtagacacgtccaagaaccaggtc tccctgaggctgaactccgtgaccgccgcagacacggccgtatattactgtgcgagagtg gtttggggggagttatcgttcctaccactactcctacggtatggacgtctggggccaaggg accctggtcaccgtctcctca BDBV335_VL (SEQ ID NO: 300)
gaaattgtgatgacccagtctccaggcaccctgtctttgtctccaggggaaagagccacc ctctcctgcagggccagtcagagtgttggcagcagctacttagcctggtaccagcagaga cctggccaggctcccaggctcctcttctatggtgcatcctacagggccactggcatccca gacaggttcagtgccagtgggtctggaacagacttcagtctcaccatcaacagactggag cctgaagattttgcagtctattactgtcagcagtctggtagctcgccggagacttttggc caggggaccaagctggagatcaaa TABLE 4-continued Variable Region Nucleic Acid Sequences BDBV354_VH
(SEQ ID NO: 301)
caggtgcagctggtgcagtctggagttgaggtgaagaagcctggggcctcagtgaaggtc tcctgcaaggcgtctggttacgcctttaccacctatgctatcagctgggtgcgacaggcc cctggacaagggcttgagtggatgggttggatcagcacttactatggtaccacatactat gcacagaacctccagggcagagtcaccatgaccacagacacatccacgagcacatcctac ttggaactgaggagcctaagatctgacgacacggccgtctattactgtgtgagagatcgg tcgtggctggccacttcccgaccatatgatgcttttgatatctggggccaagggaccctg gtcaccgtctcctca BDBV354_VL
(SEQ ID NO: 302)
gccatccagatgacccagtctccatcctccctgtctgcatctgtaggagacagagtcacc atcacttgccgggcaagtcaggacattagcagtactttagcctggtatcagcagaaaccg ggaaaagctcctaaactcctgatctatggtgcctccagtttggaaagtggggtcccatcc aggttcaacggcagtggatctgggacagatttcactctcaccatcagcagcctgcagcct gaagatttcgcaacttattactgtcagcacttttactatttcccccgcaccttcggccaa gggacacgactggagattaga BDBV386_VH
(SEQ ID NO: 303)
caggtgcagctggtgcagtcgggcccaggactggtgaagccttcacagaccctgtccctc acctgcactgtctctggtggctccatcagcagtggtcgtttctactggagctgggtccgg cagcccgccgggaggggactggagtggattgggcgcatctataccagtgggagcaccaac tacaacccctccctcaagagtcgagtcagcatatcagtagacacgtccaagaaccagttc tccctgaagctgagctctgtgaccgccgcagatacggccgtgtattactgtgcgactgaa ctgtactactatggttcggggagttatgacccgctttggtcctggggccagggaaccctg gtcaccgtctcctca BDBV386_VL
(SEQ ID NO: 304)
gacattgtgatgacccagtctccatcctccctgtctgcatctgtaggagacagagtcacc atcacttgccaggcgagtcagggcattaacaacaatttaaattggcatcagcaaaaacca ggtaaagcccctaagctcctgatctacgatgcatccaatttggaaagaggggtcccatca aggttcagtggaagtggatctgggacagattttactttcaccatcagcagcctgcagcct gaagatattgctacatattactgtcaacagaatgccaatctcccgcacacttttggccag gggaccaagctggagatcaaa BDBV397_VH
(SEQ ID NO: 305)
caggtgcagctggtgcagtcgggcccaggactggtgaagccttcacagaccctgtccctc acctgcactgtctctggtggctccatcagcagtgggagttacttctggaactggatccgg cagcccgccgggaagggactggagtggattgggcgtatctataccagcgggaccaccaac tacaatccctccctcaagagtcgcctcaccatttcagtagacacgtccaagaaccaattc tccctgaagctgaactctgtgaccgccgcagacacggccgtgtattactgtgcgacaagc ccgtattactatgatagttctcattattacgactactggggccagggaaccctggtcacc gtctcctca TABLE 4-continued Variable Region Nucleic Acid Sequences BDBV397_VL
(SEQ ID NO: 306)
gacatccagatgacccagtctccatcctccctgtctgcatctgtaggagacagagtcacc atcacttgccaggcgagtcaggacattaccaactatttaaattggtatcagcagaagcca gggaaagcccctaagctcctgatcttcgatgcttccaatttggaaaaggggtcccatca aggttcagtgctactggatctgcgacagattttactttcaccatcagcagcctgcagcct gaagatactgcgacatattactgtcaacagtctgctgatctccccctccaccttcggccaa gggacacgactggacattaaa BDBV399_VH
(SEQ ID NO: 307)
caggtgcagctggtgcagtcgggcccaggactggtgaagccttcacagaccctgtccctc acctgcaatgtctctggtggctccatcagcaatggtggttaccactggagttggatccgc caggtcccagggaagggcctggagtggattggacacatttattacagtgggagcacctcc tacaccccgtccctcaagagtcgacttaccatatcagtggacacctctaagaaccagttc tccctgaagctgagctctgtgactgccgcggacacggccgtatattactgtgcgagagat aggatacggggcgggcccattgactactggggccagggaaccctggtcaccgtctcctca BDBV399_VL
(SEQ ID NO: 308)
gacatccagatgacccagtctccatcctccctgtctgcatctgttggagaaagagtcacc atcacttgccgggcgagtcagggcatcgacaattatttagcctggtatcaacaaaaacca gggaaagttcctaaactcctgatctatgctgcatccactttgcactcaggggtcccatct cggttcagtggcagtggatctgggacagatttcactctcaccatcagcagcctgcagcct gaagatgttgcaacttattactgtcaaaggtataaccttgccccgagcgcttttggccag gggaccaaggtggagatcaga BDBV353_VH
(SEQ ID NO: 309)
caggtgcagctggtgcagtctggggctgagatgaggaagcctggggcctcagtgaaggtc tcctgcaaggcttctggatacaccttcagtgactactatatacactgggtgcgccaggcc cctggacaagggcttgagtggctgggatggatcaacccttatagtggaggcacaaattat gcacagaagtttcagggcagggtcaccatgaccagggacacgtccatcagcacagcccac atggagctgagcgggctcagatctgacgacacggccctatatttctgtgcgagactatat ggtgcggggagtcattataatcactacaacggcatggacgtctggggtcaagggaccctg gtcaccgtctcctca BDBV353_VL
(SEQ ID NO: 310)
gacatccagatgacccagtctccttccaccctgtctgcatctgtaggagacagagtcacc atcacttgccgggccagtcagagtattggtagtttattggcctggtatcagcagaaaccg gggaaagcccctaagctcctgatctatagggcgtctactttacaaggtggggtcccatca aggttcagcggcagtggatctgggacagaattcactctcaccatcagcagcctgcagcct gatgatgttgctacttattactgccaacaatttaatagttatttcggcggagggaccaag gtggagatcaaa BDBV410_VH
(SEQ ID NO: 311)
caggtgcagctgcagcagtcgggcccaggactggtgaggccgtcacagaccctgtccctc acctgctctgtctctggtggctccgtcagtagtggtcgttacttctggaactggatccgg TABLE 4-continued Variable Region Nucleic Acid Sequences cagtccgccgggaagggactggagtggattgggcgtatccattccagtgggagaaccaac tccaaccccctccctcaagagtcgagtcaccatatcagtcgacacgtccaagaaccagttc tccctgcacctgggctctgtgaccgccgcagacacggccgtctattactgtgcgagaga BDBV410_VL
    (SEQ ID NO: 312)
gatattgtgatgacccagactccactctctctgtccgtcacccctggacagccggcctcc atctcctgcaagtctagtcagagcctcctgcatagtaatggagagacctatttattttgg tacctgcagaagccaggccagccgccacaactcctgatctatgaagtttccaaccggttc tctggagtgccagataggttcagtggcagcgggtcagggacagatttcacactgaagatc agccgggtggaggctgaggatgttggagtttattactgcatgcaaagtgtactccttccg tacacttttggccaggggaccaagctggagatcaag BDBV270_VH
    (SEQ ID NO: 313)
caggtgcagctgcaggagtcgggcccaggactggtgaagccttcacagaccctgtccctc acctgcactgtctctggtgcctccatcagcaggggtctttactactggagctggatccgg cagcccgccgggaagggactggagtggattgggcgcatctataccagtgggagcatcaac tacaatccttccctcaagagtcgagtcaccatatcagtagacacgtccaagaatcagttc tccctgaggctgagctctgtaatcgccacagacacggccgtgtattattgtgtgagagat gctccctggggagattttttgactggttattttggcttctacggtatggacgtctggggc caagggaccctggtcaccgtctcctca BDBV270_VL
    (SEQ ID NO: 314)
gacattgtgatgacccagtctccatcctccctgtctgcatctgtaggagacagagtcacc atcacttgccgggcaagtcagagcattaacacctatttaaattggtatcagcagaaacca gggaaagcccctaagttcctgatctatgctgcatccagtttgcacagtggggtcccatca aggttcagtggtagtggatctgggacagatttcactctcaccatcaacagtctacaacct gatgattttgcaacttactactgtcaacagagtttcactaccccgtacacttttggccag gggaccaagctggagatcaag BDBV324_VH
    (SEQ ID NO: 315)
caggtgcagctggtgcagtctggggctgaggtgaagaagcctggggcctcagtgaaggtc tcctgtaagacttctggatacaccttcaccagctttgaaatccactgggtgcgacagggc agtggacaagggcttgagtggatgggacgtatgaatcctaaaagtggtgacacagtctct gcacagaagttccagggcagagtcaccccttaccagggacacgtccataaatgcagcctac atggagctgggcagcctgagttctgaggacacggccgtgtactactgtgcgagaggccca cacgttggcgaagttgttccaggtcttatggcgggcacctactattttcctttggacgtc tggggccaagggaccctggtcaccgtctcctca BDBV324_VL
    (SEQ ID NO: 316)
gacatccagatgacccagtctccctccaccctgtctgcatctataggagacagagtcacc atcacttgccgggccagtcagagcattagtcgctggttggcctggtatcagcagaaacca gggaaagcccctaaactcctgatctataaggtgtctgatttacaaagtggggtcccatca TABLE 4-continued Variable Region Nucleic Acid Sequences aggttcagcggcagtggatatgggacagaattcactctcaccatcggcagcctgcagcct gatgatttggcaacttattattgccaacaatatgatacatatccgtggacgttcggccag gggaccaagctggagatcaag BDBV403_VH
(SEQ ID NO: 317)
caggtccagctggtgcaatctggggctgaggtgaagaagcctgggtcctcggtgaaggtc tcctgcaacgcttctggaggcaccttcagcaactccattcttaactgggtgcgacaggcc cctggacaagggcttgagtggatgggaaggatcatccctatcgttggtctagtaaacttc gcacaaaagttcgagggcagagtcacatttaccgcggacaaattcacgaacacagcctac atggagctgaacagtctgagatttgaggacacggccgtgtactactgtgcgataaatggg gtaaatatcccggatactttgactactggggccagggaaccctggtcaccgtctcctca BDBV403_VL
(SEQ ID NO: 318)
gacattgtgatgacccagtctccaggcaccctgtctttgtctccaggggaaagagccacc ctctcctgcagggccagtcagagtgtgagcagcagctacttagcctggtaccagcaccaa cctggccaggctcccaggctcctcatctatgatgcatccagcagggccactggcatccca gacaggttcagtggcagtgggtctgggacagacttcactctcatcatcagcagactggag cctgaagattttgcagtgtattactgtcagcagtatggaagctcagcgatcaccttcggc caagggacacgactggagatcaag BDBV407_VH
(SEQ ID NO: 319)
caggtgcagctgcaggagtcgggcccaggactggtgaagccttcggagaccctgtccctc acctgcgctgtctctggtggctccatcaggagttatttctggagctggatccggcaggcc ccagggaagggactggaatggattgggaatatctattacagtgggcgccccaattacaac ccctccctcaagaatcgagtcaccatatcagcagacacgtccaacaatgaggtctcactg gagctgagcgctgtgaccgctgcggacacggccgtgtatttctgtgcgagagatgagaga ctactggtggaggtcggaaccgaccacttctactacggttttggacgtctggggccaaggg accctggtcaccgtctcctca BDBV407_VL
(SEQ ID NO: 320)
gaaattgtgatgacccagtctccactctccctgtctgtcacccctggagagccggcctcc atctcctgcaggtctagtcagagcctcctacatagtaatggatacaactttttggattgg tatttgcagaagccagggcagtctccacagctcctgatttatttgggttctaatcgggcc tccggggtccctgacaggttcagtggcagtggatccggcgcagattttacactgaaaatc agcagagtggaggctgaggatgttggggtnnattactgcatgcaagct BDBV425_VH
(SEQ ID NO: 321)
caggttcagctggtgcagtctggagctgaggtgaagaagcctggggcctcagtgaaggtc tcctgcaaggcctcgggctacacctttaccagttttggtatcagctgggtgcgacaggcc ccgggacaagggctagagtggctgggatggatcaacacttacaatggtgacacaaactat gcacagaagttccagggcagagtcaccatgacaacagatacatccacgagtacaggcttc atggagctgaggagcctgagatctgacgacacggccgtctattactgtgcgagagactcc TABLE 4-continued Variable Region Nucleic Acid Sequences cacttaataagtatagcagtggctaatacgcccaatgacttctggggccagggaaccctg gtcaccgtctcctca BDBV425_VL (SEQ ID NO: 322)
gaaattgtgatgacccagtcgccaggcaccctgtctttgtctccaggggacagagtcacc ctctcctgcagggccagtcagagtgtttacagctactacttagcctggtaccagcagaaa cctggccaggctcccaggctcctcatgtatgatgcatccatcagggccactggcatccca gacaggttcagtggcagtgggtctgggacagacttcactctcaccatcagcagtctggag cctgaagattttgcagtgtactactgtcagtactatggtaactcacaccaggggcggcg ttcggccaagggactaaggtggaagtcaaa BDBV426_VH (SEQ ID NO: 323)
caggtgcagctgcaggagtcgggcccaggactggtgaagccttcacagaccctgtccctc acctgcaatgtctctggtggctccatcagcagtgatgatagatactggagctggatccgc cagcccccagggaagggcctggagtggcttgggttcatctattacagtgggagcaccgac tacaacccgtccctcaagagtcgagttaccatgtcactagacacctccaagaaccagttc tccctgaagctgaactctgtgactgccgcagacacggccatgtattactgtgccacagta acagcttactctcctgctactatgatagtagtgggtaccgaacatgggtttgactactgg ggccagggaaccctggtcaccgtctcctca BDBV426_VL (SEQ ID NO: 324)
gacattgtgatgacccagtctccatcctccctgtctgcatctgtaggagacagagtcacc atcttttgccgggcaactcagagcattcgcagctttttaaattggtatcagcagaaacca gggaaagcccctaacctcctgatctatgctgcatccagtttgcaaagtggggtcccatcc aggttcagtggcagtggatctgggacagatttcactctcaccatcagcagtctacaacct gaagattttgcaacttactactgtcaacagagttacagtaccccatggacgttcggccaa gggaccaaggtggagatcaag BDBV317_VH (SEQ ID NO: 325)
aggtgcagctggtggagtctggggaggcgtggtccagcctggggggtccctgagactct cctgtgaagtgtccggactcaccttcagtaactttggcatgcagtgggtccgccaggctc caggcaagggtctggagtgggtggcctttatacggtttgatggaagtaataagtattatg cagactccgtgaagggccgattcaccatatccagagacaactccaagaacacggtttatc tccaaatgggcagcctgagagccgaggacacggcagtgtattttgtgggagagttctat acggagccgcagctgacttttggggccagggaaccctggtcaccgtctcctca BDBV317_VL (SEQ ID NO: 326)
gacatcgtgatgacccagtctccagactccctggctgtgtctctgggcgagagggccacc atcaactgcacgtccagtcacagtcttttatacagctccgacaataagaactatttaact tggtaccagcagaaagcaggacagcctcctaagctgctcatctactgggcttctacccgg caatccggggtccctgaccgattcagtggcagcgggtctgggacagagttcactctcacc atcagcagcctgcaggctgaagatgtggcagtctattactgtcagcagtattatactaag tctttcacttttcggccaagggaccaaggtggagatcaag TABLE 4-continued Variable Region Nucleic Acid Sequences BDBV342_VH (SEQ ID NO: 327)
caggtgcagctggtgcagtctggggctgaggtgaagaagcctgggtcgtcggtgaaggtc
tcctgcaaggcctctggaggcaccttcagcagctatgctatcaactgggtgcgacaggcc
cctggacaagggcttgagtggatgggagggatcatccctatctttggtaaaccaaactac
gcacagaagttccagggcagagtcacgattaccgcggacaaatccacgagcacagcctac
atggaactgagaagcctgagatctgaggacacggccgtatattactgtgcgcggggacag
ggagagattgtggtgatggttggtcatgacgacgggggggactaccttggctactggggc
cagggaaccctggtcaccgtctcctca BDBV342_VL (SEQ ID NO: 328)
cagtctgccctgactcagcctcgctcggtgtccgggtctcctggacwgtcagtcaccatc
tcctgcactggaaccagcagtaatgttggtgcttataactatgtctcctggtaccaacaa
cacccaggcaaagccccaaactcatgattttgatgtcactaagcggccctcaggggtc
cctgatcgcttctctggctccaagtctggcaacacggcctccctgaccatctctggactc
caggctgaggatgaggctgattttactgctactcatatgcaggcagctacacttggatt
ttcggcggagggaccaagctgaccgtcctaggt BDBV357_VH (SEQ ID NO: 329)
caggtgcagctggtgcagtcgggcccaggactggtgaagccttcggagaccctgtccctc
acctgcagtgtctctggtggctccatcagtggttccatctggacctggatccggcagtcc
ccagggaagggactggagtggattggatatatctctttaagtgggagcaccaacttcaac
ccctccctcaagagtcgagtcaccatttcagtagacacgtccaagaaccagttctccctg
aagctgagctctgtgaccgccgcagacactgccgtgtattactgtgcgagacatcggaaa
tcgtcgaagatggttcgaggaattgaagttttctactactacatggacgtctggggc
aaagggaccctggtcaccgtctcctca BDBV357_VL (SEQ ID NO: 330)
cagtctgccctgactcagcctgcctccgtgtctgggtctcctggacagtcgatcaccatc
tcctgcactggaaccatcagtgacattggtggttatgactatgtctcctggtaccaacaa
cacccaggcaaagccccaaactcatgatttatgatgtcagtgatcggccctcaggggtt
tctaatcgcttctctggctccaagtctggcaacacggcctccctgaccatctctgggctc
cagtctgaggacgaggctgattattactgcagttcatatacaagaacttacactccccac
gtggtattcggcggagggaccaagctgaccgtcctaggt BDBV340_VH (SEQ ID NO: 331)
caggtgcagctggtgcagtcgggcccaggactggtgaagccttcacagaccctgtccctc
acctgcactgtctctggtggctccatcagcagtggaagtttctactggagctggatccgg
cagcccgccgggaagggactggagtggattgggcgtttctataccactggaagcacccac
tacaatccctccctcaagagtcgagtcaccatatcggcggacacgtcgaagaaccacttc
tccctgaacctcacttcttgaccgccgcagacacggccgtttattactgtgcgagaggg
ccggtctcctattatagtggcaacctctactactttgactactggggcctggggaaccctg
gtcaccgtctcctca TABLE 4-continued Variable Region Nucleic Acid Sequences BDBV340_VL
(SEQ ID NO: 332)
cagtctgccctgactcagcctgcctccgtgtctgggtctcctggacagtcgatcaccatc acctgcactggaaccagcagtgacattggtaataataactatgtctcctggtaccaacag cacccaggcaaggcccccaaactcatcattttgatgtcaataagcgaccctcaggggtt tctaaccgcttctctggctccaagtctgacaacacggcctccctgaccatctctgggctc caggctgaggacgaggctgattattactgcagctcatatacaaacaacaggactttctcc ttcggaggtgggaccaaggtcaccgtccta BDBV392_VH
(SEQ ID NO: 333)
caggtgcagctggtgcagtctgggggaggcgtggtccagcctggggggtccctgagactc tcctgtgcagcgtctggattcaccttcagtagctttggcatccactgggtccgccaggct ccgggcaaggggctggagtgggtggcatttatacgatatgatggaagtgataagttctat ttagactccgtgaagggccgattcaccatctctagagacaattccaagaatacgctgttt ctgcaaatgagcagccttagagttgaagacacggctgtgtattactgtgcgaagagaggg gggcatgattatggttactacgacaacaatcgctacatcgatctctggggccgtggcacc ctggtcaccgtctcctca BDBV259_VL
(SEQ ID NO: 334)
tcctatgtgctgactcagccaccctcagtgtccgtgtccccgggacagacagccagcatc acctgctctggagataaattgggggatagatatacttgctggtatcaacagaagccaggc cagtcccctgtattggtcatctatcaagatactaagcggccctcagggatccctgagcga ttctctggctccaactctgggaacacagccactctgaccatcagcgagacccaggctata gatgaggctgactattactgtcaggcgtgggacaccagca BDBV415_VH
(SEQ ID NO: 335)
caggtgcagctggtgcagtctggggctgaggtgaagaagcctgggtcctcggtgaaggtc tcctgcaaggcttctggaggcaccttcagcagttatggtgttagctgggtgcgacaggcc cctggacaagggcttgagtggatgggagggatcatccctaagtttgctacagcaaaatac gcacagaagttccagggcagagtcacgattaccgcggacgaatccacgagcacagcctac atggagctgagcagcctgagatctgaggacacggccgtgtattactgtgcgggacacttc ccccagaggaaaccgattactacgatagtagtgattacttactggtccctcgatctctgg ggccgtggcaccctggtcaccgtctcctca BDBV343_VH
(SEQ ID NO: 336)
caggtgcagctggtggagtctggggctgaggggaagaagcctgggtcctcggtgaaggtc tcctgcaaggctccaggagtcaccttcagcagatataccatcagctgggtgcgacaggcc cctggacaggggcttgagtggatgggaaggatcagcccaatccttggcacagcaaactac gcacagaagttccagggcagagtcacgattaccgcggacaaatcctcgagcacagtctac atggaactgaacagactgaaatctgacgacacggctgtatattactgtgcgagagatgca ccgattattctggttgagggaccggagaccggtatggacgtctggggccaagggaccctg gtcaccgtctcctca TABLE 4-continued Variable Region Nucleic Acid Sequences BDBV343_VL (SEQ ID NO: 337)
cagtctgccctgactcagcctcgctcagtgtccgcgtctcctggacagtcagtcaccatc tcctgcactggcaccaacagtgatgttggtggttatgactatgtctcctggtaccagcaa cacccaggcaaagcccccaaactcatgatttctgatgtcaatatgcggccctcaggggtc cctgatcgcttctctggctccaagtctggcaacacggcctccctgaccatctctgggctc caatctgaggatgaggctgattattactgctgctcatatgcaggcagctacacttttgtc ttcggaagtgggaccaaggtcaccgtcctaggt BDBV377_VH (SEQ ID NO: 338)
caggtgcagctggtgcagtctgggggaggcgtggtccagcctgggaggtccctgagactc tcctgtgcagcgtctggattcaccttcaatagctatggcatgcactgggtccgccaggct ccaggcaaggggctggagtgggtggcagttatatggtttgatggaagtaaaaaatactat gcagactccgtgaagggccgattcaccatctccagagacaattccaagaactcactgtac ttgcaaatgaacagcctgagagccgaggacacggccgtgtattactgtgcgaaagacctc ctgtatggttcggggatggtcccaaattactactactacggtttggacgtctggggccaa gggaccctggtcaccgtctcctca BDBV377_VL
<Not Yet Available>

BDBV255_VH (SEQ ID NO: 339)
caggtgcagctggtgcagtctggggggaggcctggtcaggcctggggggtccctgagactc tcctgtacggcctctggattcaccctcagtacttatagcatgacctgggtccgccaggct ccagggaagggcctggagtgggtctcatccatcagtagttcgtctacctacaagtactac gtggactcgattaagggccgattcaccatctccagagacaacgccaagaactcactgtat ctgcaaatggagagcctgggagtcgaggacacggctgtgtattactgttcgagagcggac tgggactccgggaaaggagaccttgactcctggggccagggaaccctggtcaccgtctcc tca BDBV255_VL (SEQ ID NO: 340)
cagcctgtggtgactcagtcgccctctgcctctgcctccctgggagcctcggtcagactc acctgcactctcaacagcgggcgcagtaaatacgccatcgcatggcaccagcaacagcca gggaagggcccctcgctacttgatgacacttaatcatgatggcagtcacagcaagggagac gggatccctttttcgcttctcaggctccagctctgggactgagcgctacctcaccatctcc agcctccagtctgaggatgaggctgactattactgtcagacttggggcaagggcatcgtg gtattcggcggagggaccaagctgaccgtcctaggt BDBV432_VH (SEQ ID NO: 341)
caggtgcagctggtgcagtcgggcccacgactggtgaagccttcggagaccctgtccctc acctgcactgtctctggtgactccagcggtcgttactactggagctggatccggcagacc ccagggaagggactagaatggattgggtatatctcttacactgggagcaccaactacaac ccctccctcaagagtcgagtcaccatatcttcagacatgtccaagagccacttctccctg aacttgacctctgtgaccgctgcggacacggccgtgtattattgtgcgagaggggatgg aacctcctagtaagctactttgacttctggggcctgggaaccctggtcaccgtctcctca TABLE 4-continued Variable Region Nucleic Acid Sequences BDBV432_VL
<Not Yet Available>

BDBV91_VH
(SEQ ID NO: 342)
caggtgcagctggtgcagtctggggctgagttgaagccgcctggggcctcagtgaaggtc tcctgcaagccttctggatacacgttcaccgactactatatacactgggtgcgacaggcc cctggacaagggcttgagtggatgggatggatcaaccctaaaagtggagaaacacactat gcacagaagtttcggggctgggtcaccttgaccagggacacgtccatcagcacaacctac atggacctgaccaggctgaaatctgacgacacggccgtgtatttctgtgcgagaggggat ctagagactacgatcttcttctacaacgctgtggacgtctggggccaagggaccctggtc accgtctcctca BDBV91_VL
(SEQ ID NO: 343)
gacatccagatgacccagtctccatcttccctgtctgcatctgtaggagacagagtcacc atcacttgccgggcaactgagagtattggcatctatttaaattggtatcagcggaaacca gggaaggcccctaacctcctgatctttgctacatccagtttgcagagtggggtcccgtca aggttcagtggcagtggatctgggacagaattcactctcaccatcagcagtctgcaacct gaagattttgcaacttactttgtcaacagggtttcagttctcctttcagttttggccag gggaccaggctggagatcaag All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," Cold Spring Harbor Press, Cold Spring Harbor, N.Y., 1988.
Abbondanzo et al., *Am. J. Pediatr. Hematol. Oncol.,* 12(4), 480-489, 1990.
Allred et al., *Arch. Surg.,* 125(1), 107-113, 1990.
Atherton et al., *Biol. of Reproduction,* 32, 155-171, 1985.
Brown et al., *J. Immunol. Meth.,* 12; 130(1), 111-121, 1990.
Campbell, In: *Monoclonal Antibody Technology, Laboratory Techniques in Biochemistry and Molecular Biology,* Vol. 13, Burden and Von Knippenberg, Eds. pp. 75-83, Amsterdam, Elsevier, 1984.
Capaldi et al., *Biochem. Biophys. Res. Comm.,* 74(2):425-433, 1977.
De Jager et al., *Semin. Nucl. Med.* 23(2), 165-179, 1993.
Dholakia et al., *J. Biol. Chem.,* 264, 20638-20642, 1989.
Doolittle and Ben-Zeev, *Methods Mol. Biol.,* 109, 215-237, 1999.
Gefter et al., *Somatic Cell Genet.,* 3:231-236, 1977.
Goding, In: *Monoclonal Antibodies: Principles and Practice,* 2d ed., Orlando, Fla., Academic Press, 60-61, 65-66, 71-74, 1986.
Gulbis and Galand, *Hum. Pathol.* 24(12), 1271-1285, 1993.
Khatoon et al., *Ann. of Neurology,* 26, 210-219, 1989.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.

Kyte and Doolittle, *J. Mol. Biol.,* 157(1):105-132, 1982.

Nakamura et al., In: *Enzyme Immunoassays: Heterogeneous and Homogeneous Systems,* Chapter 27, 1987.

O'Shannessy et al., *J. Immun. Meth.,* 99, 153-161, 1987.

Owens and Haley, *J. Biol. Chem.,* 259, 14843-14848, 1987.

Persic et al., *Gene* 187:1, 1997

Potter and Haley, *Meth. Enzymol.,* 91, 613-633, 1983.

*Remington's Pharmaceutical Sciences,* 15th Ed., 3:624-652, 1990.

Tang et al., *J. Biol. Chem.,* 271:28324-28330, 1996.

Wawrzynczak & Thorpe, In: *Immunoconjugates, Antibody Conjugates In Radioimaging And Therapy Of Cancer,* Vogel (Ed.), NY, Oxford University Press, 28, 1987.

Beniac et al., (2012). The organisation of Ebola virus reveals a capacity for extensive, modular polyploidy. PloS One 7, e29608.

Brauburger et al., (2012). Forty-five years of Marburg virus research. Viruses 4, 1878-1927.

Brochet et al., (2008). IMGT/V-QUEST: the highly customized and integrated system for IG and TR standardized V-J and V-D-J sequence analysis. Nucleic Acids Res. 36, W503-508.

Carette et al., (2011). Ebola virus entry requires the cholesterol transporter Niemann-Pick C1. Nature 477, 340-343.

Carragher et al., (2000). Leginon: An automated system for acquisition of images from vitreous ice specimens. J. Struct. Biol. 132, 33-45.

CDC (2009). Imported case of Marburg hemorrhagic fever—Colorado, 2008. MMWR 58, 1377-1381.

Chandran et al., (2005). Endosomal proteolysis of the Ebola virus glycoprotein is necessary for infection. Science (New York, N.Y.) 308, 1643-1645.

Cook, J. D., and Lee, J. E. (2013). The secret life of viral entry glycoproteins: moonlighting in immune evasion. PLoS Path. 9, e1003258.

Côté et al., (2011). Small molecule inhibitors reveal Niemann-Pick C1 is essential for Ebola virus infection. Nature 477, 344-348.

Dias et al., (2011). A shared structural solution for neutralizing ebolaviruses. Nat. Struct. Mol. Biol. 18, 1424-7.

Dube et al., (2009). The primed ebolavirus glycoprotein (19-kilodalton GP1,2): sequence and residues critical for host cell binding. J. Virol. 83, 2883-2891.

Dye et al., (2012). Postexposure antibody prophylaxis protects nonhuman primates from Filovirus disease. Proc. Natl. Acad. Sci U.S.A. 109, 5034-5039.

Garbutt et al., (2004). Properties of replication-competent vesicular stomatitis virus vectors expressing glycoproteins of filoviruses and arenaviruses. J. Virol. 78, 5458-5465.

Giudicelli et al., (2011). IMGT/V-QUEST: IMGT standardized analysis of the immunoglobulin (IG) and T cell receptor (TR) nucleotide sequences. Cold Spring Harb. Protoc. 2011, 695-715.

Hashiguchi et al., Cell 2015, in press.

Johnson et al., (1996). Characterization of a new Marburg virus isolated from a 1987 fatal case in Kenya. Arch. Virol. Suppl. 11, 101-114.

Kajihara et al., (2012). Inhibition of Marburg virus budding by nonneutralizing antibodies to the envelope glycoprotein. J. Virol. 86, 13467-13474.

Ksiazek et al., (1999). ELISA for the detection of antibodies to Ebola viruses. J. Infect. Dis. 179 Suppl 1, S192-198.

Lander et al., (2009). Appion: an integrated, database-driven pipeline to facilitate EM image processing. J. Struct. Bio. 166, 95-102.

Lee et al., (2008). Structure of the Ebola virus glycoprotein bound to an antibody from a human survivor. Nature 454,177-182.

Lubaki et al., (2013). The lack of maturation of Ebola virus-infected dendritic cells results from the cooperative effect of at least two viral domains. J. Virol. 87, 7471-7485.

Maruyama et al., (1999). Ebola virus can be effectively neutralized by antibody produced in natural human infection. J. Virol. 73, 6024-6030.

Marzi et al., (2012). Protective efficacy of neutralizing monoclonal antibodies in a nonhuman primate model of Ebola hemorrhagic fever. PloS One 7, e36192.

Murin et al., (2014). Structures of protective antibodies reveal sites of vulnerability on Ebola virus. Proc. Natl. Acad. Sci. U.S.A 111, 17182-17187.

Nanbo et al., (2010). Ebolavirus is internalized into host cells via macropinocytosis in a viral glycoprotein-dependent manner. PLoS Pathog. 6, e1001121.

Olinger et al., (2012). Delayed treatment of Ebola virus infection with plant-derived monoclonal antibodies provides protection in rhesus macaques. Proc. Natl. Acad. Sci U.S.A. 109, 18030-18035.

Pettersen et al., (2004). UCSF Chimera—A visualization system for exploratory research and analysis. J. Comput. Chem. 25, 1605-1612.

Pettitt et al., (2103). Therapeutic intervention of Ebola virus infection in rhesus macaques with the MB-003 monoclonal antibody cocktail. Sci. Transl. Med. 5, 199ra113.

Potter et al., (1999). Leginon: A system for fully automated acquisition of 1000 electron micrographs a day. Ultramicroscopy 77, 153-161.

Qiu et al., (2012). Successful treatment of Ebola virus-infected cynomolgus macaques with monoclonal antibodies. Sci. Trans. Med. 4, 138ra181-138ra181.

Qiu et al., (2014). Reversion of advanced Ebola virus disease in nonhuman primates with ZMapp. Nature 514, 47-53.

Saeed et al., (2010). Cellular entry of ebola virus involves uptake by a macropinocytosis-like mechanism and subsequent trafficking through early and late endosomes. PLoS Pathog. 6, e1001110.

Saphire, E. O. (2013). An update on the use of antibodies against the filoviruses. Immunotherapy 5, 1221-1233.

Smith et al., (1982). Marburg-virus disease in Kenya. Lancet 1, 816-820.

Suloway et al., (2005). Automated molecular microscopy: the new Leginon system. J. Struct. Bio. 151, 41-60.

Tang et al., (2007). EMAN2: an extensible image processing suite for electron microscopy. J. Struct. Bio. 157, 38-46.

Thomas et al., (1985). Mass and molecular composition of vesicular stomatitis virus: a scanning transmission electron microscopy analysis. J. Virol. 54, 598-607.

Towner et al., (2009). Isolation of genetically diverse Marburg viruses from Egyptian fruit bats. PLoS Path. 5, e1000536.

Towner et al., (2006). Marburgvirus genomics and association with a large hemorrhagic fever outbreak in Angola. J. Virol. 80, 6497-6516.

Towner et al., (2005). Generation of eGFP expressing recombinant Zaire ebolavirus for analysis of early pathogenesis events and high-throughput antiviral drug screening. Virology 332, 20-27.

van Heel et al., (1996). A new generation of the IMAGIC image processing system. J. Struct. Bio. 116, 17-24.

Warfield et al., (2007). Development of a model for marburgvirus based on severe-combined immunodeficiency mice. Virol. J. 4, 108.

Warfield et al., (2009). Development and characterization of a mouse model for Marburg hemorrhagic fever. J. Virol. 83, 6404-6415.

Warren et al., (2014). Protection against Filovirus diseases by a novel broad-spectrum nucleoside analogue BCX4430. Nature 508, 402-405.

World Health Organization (2014a). Ebola Situation Report, in W.H.O. Global Alert and Response. 7 Jan. 2015.

World Health Organization (2014b). Marburg virus disease—Uganda, 10 Oct. 2014, in W.H.O. Global Alert and Response.

Yu et al., (2008). An optimized electrofusion-based protocol for generating virus-specific human monoclonal antibodies. J. Immunol. Met. 336, 142-151.

What is claimed is:

1. A method of treating a subject infected with Ebolavirus, or reducing the likelihood of infection of a subject at risk of contracting Ebolavirus, comprising delivering to said subject an antibody specifically binding ebolavirus glycoprotein or an antigen binding fragment thereof having heavy chain CDR1, CDR2 and CDR3 sequences of SEQ ID NOS: 91, 92 and 93, and light chain CDR1, CDR2 and CDR3 sequences of SEQ ID NO: 347, 348 and 349.

2. The method of claim 1, wherein said antibody or antibody fragment is encoded by light chain variable sequence encoding SEQ ID NO: 227 and heavy chain variable sequence encoding SEQ ID NO: 226.

3. The method of claim 1, wherein said antibody or antibody fragment comprises light chain variable sequence of SEQ ID NO: 227 and heavy chain variable sequence encoding SEQ ID NO: 226.

4. The method of claim 1, wherein said antibody or antibody fragment comprises (a) heavy chain CDR1, CDR2, and CDR3 sequences of SEQ ID NOS: 91, 92 and 93, and light chain CDR1, CDR2, and CDR3 sequences of SEQ ID NO: 347, 348 and 349 and (b) light chain variable sequence having 70%, 80%, 90% or 95% identity to SEQ ID NO: 227 and having 70%, 80%, 90%, or 95% identity to heavy chain variable sequence encoding SEQ ID NO: 226.

5. A hybridoma or engineered cell encoding an antibody specifically binding ebolavirus glycoprotein or an antigen binding fragment thereof, wherein the antibody or antibody fragment comprises heavy chain CDR1, CDR2, and CDR3 sequences of SEQ ID NOS: 91, 92 and 93, and light chain CDR1, CDR2 and CDR3 sequences of SEQ ID NO: 347, 348, and 349.

6. The hybridoma or engineered cell of claim 5, wherein said antibody or antibody fragment is encoded by light chain variable sequence encoding SEQ ID NO: 227 and heavy chain variable sequence encoding SEQ ID NO: 226.

7. The hybridoma or engineered cell of claim 5, wherein said antibody or antibody fragment comprises light chain variable sequence of SEQ ID NO: 227 and heavy chain variable sequence encoding SEQ ID NO: 226.

8. The hybridoma or engineered cell of claim 5, wherein said antibody or antibody fragment comprises (a) heavy chain CDR sequences of SEQ ID NOS: 91, 92 and 93, and light chain CDR sequences of SEQ ID NO: 347, 348, and 349 and (b) light chain variable sequence having 70%, 80%, 90%, or 95% identity to SEQ ID NO: 227 and having 70%, 80%, 90%, or 95% identity to heavy chain variable sequence encoding SEQ ID NO: 226.

9. The hybridoma or engineered cell of claim 5, wherein the antibody fragment is a recombinant ScFv (single chain fragment variable) antibody, Fab fragment, F(ab')$_2$ fragment, or Fv fragment, or incorporated as scFv or Fab in a diabody.

10. The hybridoma or engineered cell of claim 5, wherein said antibody is a chimeric antibody.

11. The hybridoma or engineered cell of claim 5, wherein said antibody is an IgG.

12. The hybridoma or engineered cell of claim 5, wherein said antibody or antibody fragment further comprises a cell penetrating peptide or is an intrabody.

* * * * *

SEQUENCE LISTING

```
<160> NUMBER OF SEQ ID NOS: 349

<210> SEQ ID NO 1
<211> LENGTH: 123
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Arg Ala Ser Gly Asp Ser Phe Ser Arg Lys
            20                  25                  30

Tyr Gly Ile Ser Trp Val Arg Gln Ala Pro Gly Gln Gly Phe Glu Trp
        35                  40                  45

Met Gly Thr Ile Met Pro Ile Val Gly Leu Thr Thr Ser Ala Gln Lys
    50                  55                  60

Phe Gln Gly Arg Val Thr Ile Thr Ala Asp Lys Ser Thr Ser Thr Ala
65                  70                  75                  80

His Met Glu Leu Asn Ser Leu Thr Ser Glu Asp Thr Ala Ile Tyr Tyr
                85                  90                  95

Cys Ala Arg Asp Glu Ile Ile Gly Ala Arg Pro His Trp Phe Asp Ser
            100                 105                 110

Trp Gly Gln Gly Thr Leu Val Thr Val Ser Ser
        115                 120

<210> SEQ ID NO 2
<211> LENGTH: 107
<212> TYPE: PRT
<213> ORGANISM: Homo sapiens

<400> SEQUENCE: 2

Glu Ile Val Met Thr Gln Ser Pro Ala Ile Met Ser Val Ser Pro Gly
1               5                   10                  15

Lys Arg Ala Thr Leu Ser Cys Arg Ala Ser Gln Ser Val Ser Ser Asn
            20                  25                  30

Leu Ala Trp Tyr Gln Arg Lys Pro Gly Gln Ala Pro Arg Leu Leu Ile
        35                  40                  45

Tyr Gly Ser Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Leu Gln Tyr Tyr Asn Trp Pro Arg
                85                  90                  95

Thr Phe Gly Gln Gly Thr Lys Val Glu Ile Lys
            100                 105

<210> SEQ ID NO 3
<211> LENGTH: 122
<212> TYPE: PRT
```

<213> ORGANISM: Homo sapiens

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Thr Thr Thr
            20                  25                  30

Tyr Trp Asn Trp Ile Arg Gln Pro Pro Gly Lys Gly Leu Glu Trp Ile
        35                  40                  45

Gly Glu Val Asn Tyr Ser Gly Asn Ala Asn Tyr Asn Pro Ser Leu Lys
    50                  55                  60

Gly Arg Val Ala Ile Ser Val Asp Thr Ser Lys Asn Gln Phe Ser Leu
65                  70                  75                  80

Arg Leu Asn Ser Val Thr Ala Ala Asp Thr Ala Ile Tyr Tyr Cys Thr
                85                  90                  95

Ser Arg Ile Arg Ser His Ile Ala Tyr Ser Trp Lys Gly Asp Val Trp
            100                 105                 110

Gly Lys Gly Thr Thr Val Thr Val Ser Ser
        115                 120

<210> SEQ ID NO 4
<211> LENGTH: 108
<212> TYPE: PRT
<213> ORGANISM: Homo sapiens

<400> SEQUENCE: 4

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Pro Arg Asn
            20                  25                  30

Tyr Ile Gly Trp Phe Gln Gln Lys Pro Gly Gln Ala Pro Arg Leu Leu
        35                  40                  45

Ile Tyr Gly Ala Ser Ser Arg Ala Ala Gly Phe Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Met Tyr Tyr Cys His Gln Tyr Asp Arg Leu Pro
                85                  90                  95

Tyr Thr Phe Gly Gln Gly Thr Lys Leu Glu Ile Lys
            100                 105

<210> SEQ ID NO 5
<211> LENGTH: 127
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Ile Asn Trp Val Arg Gln Ala Pro Gly Arg Gly Leu Glu Trp Val
        35                  40                  45

Ser Tyr Ile Ser Ser Ser Gly Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Glu Pro Tyr Val Asp Gly Ile Leu Tyr Gly Ala Gly Asp Ser
            100                 105                 110

Tyr Phe Asp Tyr Trp Gly Gln Gly Thr Leu Val Thr Val Ser Ser
        115                 120                 125

<210> SEQ ID NO 6
<211> LENGTH: 108
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Asn Thr Pro Pro
                85                  90                  95

Val Thr Phe Gly Gln Gly Thr Arg Leu Glu Ile Lys
            100                 105

<210> SEQ ID NO 7
<211> LENGTH: 127
<212> TYPE: PRT
<213> ORGANISM: Homo sapiens

<400> SEQUENCE: 7

Gln Val Gln Leu Gln Glu Ser Gly Pro Gly Leu Val Lys Pro Ser Glu
1               5                   10                  15

Thr Leu Ser Leu Asn Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Asp Ser Gly Arg Thr Lys Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Leu Gly Pro Phe Asp Lys Leu Trp Phe Gly Glu Leu Leu Pro Gly
            100                 105                 110

Trp Phe Asp Pro Trp Gly Gln Gly Thr Leu Val Thr Val Ser Ser
        115                 120                 125

<210> SEQ ID NO 8
<211> LENGTH: 106
<212> TYPE: PRT
<213> ORGANISM: Homo sapiens

<400> SEQUENCE: 8
```

Glu Ile Val Leu Thr Gln Ser Pro Ala Thr Leu Ser Leu Ser Pro Gly
1               5                   10                  15

Gly Arg Ala Thr Leu Ser Cys Arg Ala Ser Gln Ser Val His Asn Tyr
            20                  25                  30

Leu Ala Trp Tyr Gln Gln Lys Ser Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Asp Asp Phe Ala Val Tyr Tyr Cys Gln His Arg Ser Asn Trp Leu Thr
                85                  90                  95

Phe Gly Gly Gly Thr Lys Val Glu Ile Lys
                100                 105

<210> SEQ ID NO 9
<211> LENGTH: 133
<212> TYPE: PRT
<213> ORGANISM: Homo sapiens

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Leu Asn Phe Tyr
            20                  25                  30

Asn Met Asn Trp Val Arg Gln Ala Pro Gly Lys Gly Leu Glu Trp Val
            35                  40                  45

Ser Ser Ile Ser Ser Ser Ser Asn Tyr Ile Tyr Tyr Ala Asp Ser Val
    50                  55                  60

Lys Gly Arg Phe Thr Ile Ser Arg Asp Asn Ala Arg Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Val Gln Leu Leu Ile Pro Gln Arg Asp Glu Trp Gln
                100                 105                 110

Gly Val His Asp Tyr Tyr Gly Met Asp Val Trp Gly Gln Gly Thr Leu
            115                 120                 125

Val Thr Val Ser Ser
        130

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
1               5                   10                  15

Gly Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln His Tyr Gly Ser Ser Gln
            85                  90                  95

Leu Thr Phe Gly Gly Gly Thr Lys Val Glu Ile Lys
        100                 105
```

<210> SEQ ID NO 11
<211> LENGTH: 126
<212> TYPE: PRT
<213> ORGANISM: Homo sapiens

<400> SEQUENCE: 11

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Asn Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Lys Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Lys Ser Asp Cys Ser Gly Gly Asn Cys Tyr Val
            100                 105                 110

Val Asp Tyr Trp Gly Gln Gly Thr Leu Val Thr Val Ser Ser
        115                 120                 125
```

<210> SEQ ID NO 12
<211> LENGTH: 117
<212> TYPE: PRT
<213> ORGANISM: Homo sapiens

<400> SEQUENCE: 12

```
Glu Val Gln Leu Val Glu Ser Gly Gly Gly Leu Val Lys Pro Gly Gly
1               5                   10                  15

Ala Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Asn Asp Gly Gly Thr Ala Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Ile Glu Asp Thr Ala Val Tyr
                85                  90                  95

Tyr Cys Ile Thr Phe Leu Arg Pro Asp His Trp Gly Gln Gly Thr Leu
            100                 105                 110

Val Thr Val Ser Ser
        115
```

<210> SEQ ID NO 13
<211> LENGTH: 369
<212> TYPE: DNA
<213> ORGANISM: Homo sapiens

<400> SEQUENCE: 13

```
caggtgcagc tggtgcagtc tggggctgag gtgaagaagc ctgggtcctc ggtgaaggtc    60
```

```
tcctgcaggg cttctggaga ctccttcagc cgcaagtatg gcatcagctg ggtgcgacag    120
gcccctggac aaggatttga gtggatggga acgatcatgc caatcgttgg tttgaccacc    180
tccgcccaga aattccaggg cagagtcaca attaccgcgg acaagtccac gagcacagcc    240
cacatggaac tgaacagcct gacatctgag gacacggcca tttattactg tgcgagagat    300
gaaattattg gggctcgacc ccactggttc gactcttggg gccagggaac cctggtcacc    360
gtctcctca                                                            369
```

<210> SEQ ID NO 14
<211> LENGTH: 321
<212> TYPE: DNA
<213> ORGANISM: Homo sapiens

<400> SEQUENCE: 14

```
gaaattgtga tgacccagtc tccagccatc atgtctgtgt ctccagggaa aagagccacc     60
ctctcctgca gggccagtca gagtgtcagt agcaacttag cctggtacca gcggaaacct    120
ggccaggctc ccaggctcct catctatggt tcttccacca gggccactgg tatcccagcc    180
aggttcagtg gcagtgggtc tgggacagag ttcactctca ccatcagcag cctgcagtct    240
gaggattttg cagtttatta ctgtctgcaa tattataact ggcctcggac gttcggccaa    300
gggaccaagg tggaaatcaa a                                              321
```

<210> SEQ ID NO 15
<211> LENGTH: 366
<212> TYPE: DNA
<213> ORGANISM: Homo sapiens

<400> SEQUENCE: 15

```
caggtgcagc tacagcagtg gggcgcagga ctgttgaagc cttcggagac cctgtccctc     60
acctgcgctg tctatggtgg gtccttcacg actacctact ggaattggat ccgccagccc    120
ccagggaagg ggctggaatg gataggggaa gtcaattata gtggaaacgc caactacaac    180
ccgtccctca gggtcgagt cgccatatca gtggacacat ccaagaacca gttctccctg    240
aggttgaact ctgtgaccgc cgcggacacg gctatatatt actgtacgag tcgcatacgt    300
tcgcacattg cctactcgtg gaagggggac gtctggggca aagggaccac ggtcaccgtc    360
tcctca                                                               366
```

<210> SEQ ID NO 16
<211> LENGTH: 324
<212> TYPE: DNA
<213> ORGANISM: Homo sapiens

<400> SEQUENCE: 16

```
gaaattgtga tgacccagtc tccaggcacc ctgtctttgt ctccagggga aagagccacc     60
ctctcctgca gggccagtca gagtgttccc aggaattata taggttggtt ccagcagaaa    120
cctggccagg ctcccaggct cctcatctat ggtgcatcca gcagggccgc tggcttccca    180
gacagattca gtggcagtgg gtctgggaca gacttcactc tcaccatcac cagactggag    240
cctgaagatt ttgcaatgta ttactgtcac cagtatgata ggttaccgta cacttttggc    300
caggggacca agctggagat caaa                                           324
```

<210> SEQ ID NO 17
<211> LENGTH: 381
<212> TYPE: DNA

<213> ORGANISM: Homo sapiens

<400> SEQUENCE: 17

| | |
|---|---|
| gaggtgcagc tggtggagtc tgggggaggc ttggtacagc ctggagggtc cctgagactc | 60 |
| tcctgtgcag cctctggatt caccttcagt agttatgaaa tcaactgggt ccgccaggct | 120 |
| ccagggaggg gctggagtg ggtttcatac attagtagta gtggtagaac catatactac | 180 |
| gcagactctg tgaagggccg attcaccatc tccagagaca acgccaagaa ctcactgtat | 240 |
| ctgcaaatga acagcctgag agccgaggac acggctgttt attactgtgc gagagaacca | 300 |
| tatgttgacg gaatattata tggggccggg gatagctact ttgactactg gggccaggga | 360 |
| accctggtca ccgtctcctc a | 381 |

<210> SEQ ID NO 18
<211> LENGTH: 324
<212> TYPE: DNA
<213> ORGANISM: Homo sapiens

<400> SEQUENCE: 18

| | |
|---|---|
| gacatccaga tgacccagtc tccatcctcc ctgtctgcat ctgtaggaga cagagtcacc | 60 |
| atcacttgcc gggcaagtca gagcattagc aactatttaa attggtatca gcagaaacca | 120 |
| gggaaagccc ctaaggtcct gatctatgct gcatccagtt tgcaaagtgg ggtctcatca | 180 |
| aggttcagtg gcagtggatc tgggacagac ttcactctca ccatcagcag tctgcaacct | 240 |
| gaagattttg caacttactt ctgtcaacag agttacaata cccctccggt caccttcggc | 300 |
| caagggacac gactggagat taaa | 324 |

<210> SEQ ID NO 19
<211> LENGTH: 381
<212> TYPE: DNA
<213> ORGANISM: Homo sapiens

<400> SEQUENCE: 19

| | |
|---|---|
| caggtgcagc tgcaggagtc gggcccagga ctggtgaagc cttcggagac cctgtccctc | 60 |
| aactgcactg tctctggtgg ctccatcagt agttactact ggagctggat ccggcagccc | 120 |
| ccagggaagg gactggagtg gattgggtat atctatgaca gtgggagaac caagtacaac | 180 |
| ccctccctca agagtcgagt caccatatca ttagacacgt ccaagaacca gttctccctg | 240 |
| aagctgagct ctgtgaccgc cgcagacacg gccgtgtatt actgtgcgag tctgggccct | 300 |
| ttcgacaaat tatggttcgg ggagttgttg ccgggatggt tcgaccctg gggccaggga | 360 |
| accctggtca ccgtctcctc a | 381 |

<210> SEQ ID NO 20
<211> LENGTH: 318
<212> TYPE: DNA
<213> ORGANISM: Homo sapiens

<400> SEQUENCE: 20

| | |
|---|---|
| gaaattgtgt tgacacagtc tccagccacc ctgtctttgt ctccagggg aagagccacc | 60 |
| ctctcctgca gggccagtca gagtgttcac aactacttag cctggtacca acagaagtct | 120 |
| ggccaggctc ccaggctcct catctatgat gcatccaaca gggccactgg catcccagcc | 180 |
| aggttcagtg gcagtgggtc tgggacagac ttcactctca ccatcagcag cctggagcct | 240 |
| gacgattttg cagtttatta ctgtcagcac cgtagcaact ggctcacttt cggcggaggg | 300 |
| accaaggtgg agatcaaa | 318 |

<210> SEQ ID NO 21
<211> LENGTH: 399
<212> TYPE: DNA
<213> ORGANISM: Homo sapiens -continued

```
<400> SEQUENCE: 21
gaggtgcagc tggtggagtc tgggggaggc ctggtcaagc ctgggggtc cctgagactc    60 tcctgtgcgg cctctggatt caccttaaat ttctataaca tgaactgggt ccgccaggct   120
ccagggaagg gctggagtg gtctcatcc attagtagta gtagtaatta catatactac    180
gcagactcag tgaagggccg attcaccatc tccagagaca acgccaggaa gtcactgtat   240
ctgcaaatga acagcctgag agccgaggac acggctgtgt attactgtgc gagagatttt   300
gtccagctat taattccgca aagggacgag tggcagggtg tccacgacta ctacggtatg   360
gacgtctggg gccaagggac cctggtcacc gtctcctca                          399

<210> SEQ ID NO 22
<211> LENGTH: 324
<212> TYPE: DNA
<213> ORGANISM: Homo sapiens

<400> SEQUENCE: 22
gaaattgtgt tgacgcagtc tccaggcacc ctgtctttgt ctccagggg aagagccacc    60 ctctcctgca gggccagtca gagtgttagc aacagctact tagcctggta ccagcagaaa   120
cctggccagg ctcccaggct cctcatctat ggtgcatcca gcagggccac tggcatccca   180
gacaggttca gtggcagtgg gtctgggaca gacttcattc tcaccatcag cagactggag   240
cctgaagatt ttgcagtgta ttactgtcag cactatggta gctctcagct cactttcggc   300
ggagggacca aggtggagat caaa                                          324

<210> SEQ ID NO 23
<211> LENGTH: 378
<212> TYPE: DNA
<213> ORGANISM: Homo sapiens

<400> SEQUENCE: 23
gaggtgcagc tggtggagtc tgggggaggc ttggtaaagc ctgggggtc ccttagactc    60 tcctgtgcag cctctggatt cactttact aacgcctgga tgaactgggt ccgccaggct   120
ccagggaagg gctggagtg gttggccgt attaaaagca acactgatgg tgggacaaca    180
gactacgctg cacccgtgaa aggcagattc accatctcaa gagatgattc aaaaaagacg   240
ctgtatctgc aaatgaacag cctgaaaacc gaggacacag ccgtgtatta ctgtaccaca   300
gggaaaagtg actgtagtgg tggtaactgc tacgtggttg actactgggg ccagggaacc   360
ctggtcaccg tctcctca                                                 378

<210> SEQ ID NO 24
<211> LENGTH: 351
<212> TYPE: DNA
<213> ORGANISM: Homo sapiens

<400> SEQUENCE: 24
gaggtgcagc tggtggagtc tgggggaggc ttggtaaagc ctgggggggc ccttagactc    60
agctgtgcag cctctggatt cactttcagt aacgcctgga tgagctgggt ccgccaggct   120
ccagggaagg gctggagtg gttggccgt attaaaagca aaaatgatgg tgggacagca    180
gactacgctg cacccgtgaa aggcagattc agcatctcaa gagatgattc aaaaaacacg   240
ctttatctgc aaatgaacag cctgaaaatc gaggacacag ccgtgtatta ctgtatcacg   300
tttttacgcc ccgaccactg gggccaggga accctggtca ccgtctcctc a            351
```

```
<210> SEQ ID NO 25
<211> LENGTH: 15
<212> TYPE: PRT
<213> ORGANISM: Ebolavirus

<400> SEQUENCE: 25

Ile Thr Asp Lys Ile Asp Gln Ile Ile His Asp Phe Val Asp Lys
1               5                   10                  15

<210> SEQ ID NO 26
<211> LENGTH: 16
<212> TYPE: PRT
<213> ORGANISM: Ebolavirus

<400> SEQUENCE: 26

Thr Asp Lys Ile Asp Gln Ile Ile His Asp Phe Val Asp Lys Thr Leu
1               5                   10                  15

<210> SEQ ID NO 27
<211> LENGTH: 17
<212> TYPE: PRT
<213> ORGANISM: Sudan virus

<400> SEQUENCE: 27

Ile Thr Asp Lys Ile Asn Gln Ile Ile His Asp Phe Ile Asp Asn Pro
1               5                   10                  15

Leu

<210> SEQ ID NO 28
<211> LENGTH: 16
<212> TYPE: PRT
<213> ORGANISM: Sudan virus

<400> SEQUENCE: 28

Thr Asp Lys Ile Asn Gln Ile Ile His Asp Phe Ile Asp Asn Pro Leu
1               5                   10                  15

<210> SEQ ID NO 29
<211> LENGTH: 16
<212> TYPE: PRT
<213> ORGANISM: Bundibugyo virus

<400> SEQUENCE: 29

Thr Asp Lys Ile Asp Gln Ile Ile His Asp Phe Ile Asp Lys Pro Leu
1               5                   10                  15

<210> SEQ ID NO 30
<211> LENGTH: 53
<212> TYPE: PRT
<213> ORGANISM: Ebolavirus

<400> SEQUENCE: 30

Gly Thr Cys His Ile Leu Gly Pro Asp Cys Cys Ile Glu Pro His Asp
1               5                   10                  15

Trp Thr Lys Asn Ile Thr Asp Lys Ile Asp Gln Ile Ile His Asp Phe
            20                  25                  30

Val Asp Lys Thr Leu Pro Asp Gln Gly Asp Asn Asp Asn Trp Trp Thr
        35                  40                  45

Gly Trp Arg Gln Trp
    50

<210> SEQ ID NO 31
<211> LENGTH: 15
```

```
<212> TYPE: PRT
<213> ORGANISM: Ebolavirus

<400> SEQUENCE: 31

Gly Thr Cys His Ile Leu Gly Pro Asp Cys Cys Ile Glu Pro His
1               5                   10                  15

<210> SEQ ID NO 32
<211> LENGTH: 15
<212> TYPE: PRT
<213> ORGANISM: Ebolavirus

<400> SEQUENCE: 32

Cys Ile Glu Pro His Asp Trp Thr Lys Asn Ile Thr Asp Lys Ile
1               5                   10                  15

<210> SEQ ID NO 33
<211> LENGTH: 8
<212> TYPE: PRT
<213> ORGANISM: Artificial sequence
<220> FEATURE:
<223> OTHER INFORMATION: Synthetic peptide

<400> SEQUENCE: 33

Asp Ser Phe Ser Arg Lys Tyr Gly
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic peptide

<400> SEQUENCE: 34

Ile Met Pro Ile Val Gly Leu Thr
1               5

<210> SEQ ID NO 35
<211> LENGTH: 15
<212> TYPE: PRT
<213> ORGANISM: Artificial sequence
<220> FEATURE:
<223> OTHER INFORMATION: Synthetic peptide

<400> SEQUENCE: 35

Ala Arg Asp Glu Ile Ile Gly Ala Arg Pro His Trp Phe Asp Ser
1               5                   10                  15

<210> SEQ ID NO 36
<211> LENGTH: 8
<212> TYPE: PRT
<213> ORGANISM: Artificial sequence
<220> FEATURE:
<223> OTHER INFORMATION: Synthetic peptide

<400> SEQUENCE: 36

Gly Gly Ser Phe Thr Thr Thr Tyr
1               5

<210> SEQ ID NO 37
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 37

Val Asn Tyr Ser Gly Asn Ala
1               5

<210> SEQ ID NO 38
<211> LENGTH: 16
<212> TYPE: PRT
<213> ORGANISM: Artificial sequence
<220> FEATURE:
<223> OTHER INFORMATION: Synthetic peptide

<400> SEQUENCE: 38

Thr Ser Arg Ile Arg Ser His Ile Ala Tyr Ser Trp Lys Gly Asp Val
1               5                   10                  15

<210> SEQ ID NO 39
<211> LENGTH: 8
<212> TYPE: PRT
<213> ORGANISM: Artificial sequence
<220> FEATURE:
<223> OTHER INFORMATION: Synthetic peptide

<400> SEQUENCE: 39

Gly Gly Thr Phe Ser Ser Tyr Thr
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic peptide

<400> SEQUENCE: 40

Ile Ile Pro Lys Leu Gly Ile Ala
1               5

<210> SEQ ID NO 41
<211> LENGTH: 18
<212> TYPE: PRT
<213> ORGANISM: Artificial sequence
<220> FEATURE:
<223> OTHER INFORMATION: Synthetic peptide

<400> SEQUENCE: 41

Leu Tyr Tyr Cys Ala Arg Val Leu Leu Ser Ser Arg Asp Ala Phe Asp
1               5                   10                  15

Ile Trp

<210> SEQ ID NO 42
<211> LENGTH: 8
<212> TYPE: PRT
<213> ORGANISM: Artificial sequence
<220> FEATURE:
<223> OTHER INFORMATION: Synthetic peptide

<400> SEQUENCE: 42

Gly Phe Thr Phe Ser Ser Tyr Glu
1               5

<210> SEQ ID NO 43
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 43

Ile Ser Ser Ser Gly Arg Thr Ile
1               5

<210> SEQ ID NO 44
<211> LENGTH: 20
<212> TYPE: PRT
<213> ORGANISM: Artificial sequence
<220> FEATURE:
<223> OTHER INFORMATION: Synthetic peptide

<400> SEQUENCE: 44

Ala Arg Glu Pro Tyr Val Asp Gly Ile Leu Tyr Gly Ala Gly Asp Ser
1               5                   10                  15

Tyr Phe Asp Tyr
            20

<210> SEQ ID NO 45
<211> LENGTH: 8
<212> TYPE: PRT
<213> ORGANISM: Artificial sequence
<220> FEATURE:
<223> OTHER INFORMATION: Synthetic peptide

<400> SEQUENCE: 45

Gly Gly Ser Ile Ser Ser Tyr Tyr
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic peptide

<400> SEQUENCE: 46

Ile Tyr Asp Ser Gly Arg Thr
1               5

<210> SEQ ID NO 47
<211> LENGTH: 21
<212> TYPE: PRT
<213> ORGANISM: Artificial sequence
<220> FEATURE:
<223> OTHER INFORMATION: Synthetic peptide

<400> SEQUENCE: 47

Ala Ser Leu Gly Pro Phe Asp Lys Leu Trp Phe Gly Glu Leu Leu Pro
1               5                   10                  15

Gly Trp Phe Asp Pro
            20

<210> SEQ ID NO 48
<211> LENGTH: 8
<212> TYPE: PRT
<213> ORGANISM: Artificial sequence
<220> FEATURE:
<223> OTHER INFORMATION: Synthetic peptide

<400> SEQUENCE: 48

Gly Phe Thr Leu Asn Phe Tyr Asn
1               5

<210> SEQ ID NO 49
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 49

Ile Ser Ser Ser Ser Asn Tyr Ile
1               5

<210> SEQ ID NO 50
<211> LENGTH: 26
<212> TYPE: PRT
<213> ORGANISM: Artificial sequence
<220> FEATURE:
<223> OTHER INFORMATION: Synthetic peptide

<400> SEQUENCE: 50

Ala Arg Asp Phe Val Gln Leu Leu Ile Pro Gln Arg Asp Glu Trp Gln
1               5                   10                  15

Gly Val His Asp Tyr Tyr Gly Met Asp Val
            20                  25

<210> SEQ ID NO 51
<211> LENGTH: 8
<212> TYPE: PRT
<213> ORGANISM: Artificial sequence
<220> FEATURE:
<223> OTHER INFORMATION: Synthetic peptide

<400> SEQUENCE: 51

Gly Phe Thr Phe Thr Asn Ala Trp
1               5

<210> SEQ ID NO 52
<211> LENGTH: 10
<212> TYPE: PRT
<213> ORGANISM: Artificial sequence
<220> FEATURE:
<223> OTHER INFORMATION: Synthetic peptide

<400> SEQUENCE: 52

Ile Lys Ser Asn Thr Asp Gly Gly Thr Thr
1               5                   10

<210> SEQ ID NO 53
<211> LENGTH: 17
<212> TYPE: PRT
<213> ORGANISM: Artificial sequence
<220> FEATURE:
<223> OTHER INFORMATION: Synthetic peptide

<400> SEQUENCE: 53

Thr Thr Gly Lys Ser Asp Cys Ser Gly Gly Asn Cys Tyr Val Val Asp
1               5                   10                  15

Tyr

<210> SEQ ID NO 54
<211> LENGTH: 8
<212> TYPE: PRT
<213> ORGANISM: Artificial sequence
<220> FEATURE:
<223> OTHER INFORMATION: Synthetic peptide

<400> SEQUENCE: 54

Gly Phe Thr Phe Ser Asn Ala Trp
1               5
```

```
1               5
```

<210> SEQ ID NO 55
<211> LENGTH: 10
<212> TYPE: PRT
<213> ORGANISM: Artificial sequence
<220> FEATURE:
<223> OTHER INFORMATION: Synthetic peptide

<400> SEQUENCE: 55

```
Ile Lys Ser Lys Asn Asp Gly Gly Thr Ala
1               5                   10
```

<210> SEQ ID NO 56
<211> LENGTH: 8
<212> TYPE: PRT
<213> ORGANISM: Artificial sequence
<220> FEATURE:
<223> OTHER INFORMATION: Synthetic peptide

<400> SEQUENCE: 56

```
Ile Thr Phe Leu Arg Pro Asp His
1               5
```

<210> SEQ ID NO 57
<211> LENGTH: 8
<212> TYPE: PRT
<213> ORGANISM: Artificial sequence
<220> FEATURE:
<223> OTHER INFORMATION: Synthetic peptide

<400> SEQUENCE: 57

```
Gly Tyr Thr Phe Thr Gly Tyr Tyr
1               5
```

<210> SEQ ID NO 58
<211> LENGTH: 8
<212> TYPE: PRT
<213> ORGANISM: Artificial sequence
<220> FEATURE:
<223> OTHER INFORMATION: Synthetic peptide

<400> SEQUENCE: 58

```
Ile Asn Pro Asn Ser Gly Gly Thr
1               5
```

<210> SEQ ID NO 59
<211> LENGTH: 19
<212> TYPE: PRT
<213> ORGANISM: Artificial sequence
<220> FEATURE:
<223> OTHER INFORMATION: Synthetic peptide

<400> SEQUENCE: 59

```
Cys Ala Thr Asn Lys Gly Thr Asn Gly Arg Tyr Tyr Tyr Gly Met
1               5                   10                  15

Asp Val Trp
```

<210> SEQ ID NO 60
<211> LENGTH: 6
<212> TYPE: PRT
<213> ORGANISM: Artificial sequence
<220> FEATURE:
<223> OTHER INFORMATION: Synthetic peptide

<400> SEQUENCE: 60

```
Gln Ser Val Ser Ser Asn
1               5

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Leu Gln Tyr Tyr Asn Trp Pro Arg Thr
1               5

<210> SEQ ID NO 62
<211> LENGTH: 7
<212> TYPE: PRT
<213> ORGANISM: Artificial sequence
<220> FEATURE:
<223> OTHER INFORMATION: Synthetic peptide

<400> SEQUENCE: 62

Gln Ser Val Pro Arg Asn Tyr
1               5

<210> SEQ ID NO 63
<211> LENGTH: 9
<212> TYPE: PRT
<213> ORGANISM: Artificial sequence
<220> FEATURE:
<223> OTHER INFORMATION: Synthetic peptide

<400> SEQUENCE: 63

His Gln Tyr Asp Arg Leu Pro Tyr Thr
1               5

<210> SEQ ID NO 64
<211> LENGTH: 6
<212> TYPE: PRT
<213> ORGANISM: Artificial sequence
<220> FEATURE:
<223> OTHER INFORMATION: Synthetic peptide

<400> SEQUENCE: 64

Gln Ser Ile Ser Asn Tyr
1               5

<210> SEQ ID NO 65
<211> LENGTH: 10
<212> TYPE: PRT
<213> ORGANISM: Artificial sequence
<220> FEATURE:
<223> OTHER INFORMATION: Synthetic peptide

<400> SEQUENCE: 65

Gln Gln Ser Tyr Asn Thr Pro Pro Val Thr
1               5                   10

<210> SEQ ID NO 66
<211> LENGTH: 6
<212> TYPE: PRT
<213> ORGANISM: Artificial sequence
<220> FEATURE:
<223> OTHER INFORMATION: Synthetic peptide

<400> SEQUENCE: 66

Gln Ser Val His Asn Tyr
```

```
1               5
```

<210> SEQ ID NO 67
<211> LENGTH: 8
<212> TYPE: PRT
<213> ORGANISM: Artificial sequence
<220> FEATURE:
<223> OTHER INFORMATION: Synthetic peptide

<400> SEQUENCE: 67

```
Gln His Arg Ser Asn Trp Leu Thr
1               5
```

<210> SEQ ID NO 68
<211> LENGTH: 7
<212> TYPE: PRT
<213> ORGANISM: Artificial sequence
<220> FEATURE:
<223> OTHER INFORMATION: Synthetic peptide

<400> SEQUENCE: 68

```
Gln Ser Val Ser Asn Ser Tyr
1               5
```

<210> SEQ ID NO 69
<211> LENGTH: 9
<212> TYPE: PRT
<213> ORGANISM: Artificial sequence
<220> FEATURE:
<223> OTHER INFORMATION: Synthetic peptide

<400> SEQUENCE: 69

```
Gln His Tyr Gly Ser Ser Gln Leu Thr
1               5
```

<210> SEQ ID NO 70
<211> LENGTH: 11
<212> TYPE: PRT
<213> ORGANISM: Artificial sequence
<220> FEATURE:
<223> OTHER INFORMATION: Synthetic peptide

<400> SEQUENCE: 70

```
Gln Ser Leu Leu His Ser Asn Gly Tyr Asn Tyr
1               5                   10
```

<210> SEQ ID NO 71
<211> LENGTH: 10
<212> TYPE: PRT
<213> ORGANISM: Artificial sequence
<220> FEATURE:
<223> OTHER INFORMATION: Synthetic peptide

<400> SEQUENCE: 71

```
Cys Met Gln Ala Leu Gln Thr Ile Thr Phe
1               5                   10
```

<210> SEQ ID NO 72
<211> LENGTH: 123
<212> TYPE: PRT
<213> ORGANISM: Homo sapiens

<400> SEQUENCE: 72

```
Gln Val Gln Leu Val Gln Ser Gly Val Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30
Thr Ile Ser Trp Val Arg Gln Ala Pro Gly Gln Gly Leu Glu Trp Met
        35                  40                  45
Gly Arg Ile Ile Pro Lys Leu Gly Ile Ala Asn Tyr Ala Gln Asn Ala
    50                  55                  60
Gln Lys Phe Gln Gly Arg Val Thr Ile Thr Ala Asp Lys Ser Thr Ser
65                  70                  75                  80
Thr Ala Tyr Met Glu Leu Ser Arg Leu Arg Ser Glu Asp Thr Ala Leu
                85                  90                  95
Tyr Tyr Cys Ala Arg Val Leu Leu Ser Ser Arg Asp Ala Phe Asp Ile
            100                 105                 110
Trp Gly Gln Gly Thr Leu Val Thr Val Ser Ser
            115                 120

<210> SEQ ID NO 73
<211> LENGTH: 124
<212> TYPE: PRT
<213> ORGANISM: Homo sapiens

<400> SEQUENCE: 73

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Trp Val Thr Met Thr Arg Asp Thr Ser Ile Ser Thr Ala Tyr
65                  70                  75                  80
Met Glu Leu Arg Arg Leu Arg Ser Asp Asp Thr Ala Val Tyr Tyr Cys
                85                  90                  95
Ala Thr Asn Lys Gly Thr Asn Gly Arg Tyr Tyr Tyr Gly Met Asp
            100                 105                 110
Val Trp Gly Gln Gly Thr Leu Val Thr Val Ser Ser
            115                 120

<210> SEQ ID NO 74
<211> LENGTH: 111
<212> TYPE: PRT
<213> ORGANISM: Homo sapiens

<400> SEQUENCE: 74

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Ile Thr Phe Gly Gln Gly Thr Arg Leu Glu Ile Lys
```

<210> SEQ ID NO 75
<211> LENGTH: 120
<212> TYPE: PRT
<213> ORGANISM: Homo sapiens

<400> SEQUENCE: 75

Gln Val Gln Leu Val Gln Ser Gly Val Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Lys Leu Gly Ile Ala Asn Tyr Ala Gln Asn Ala
    50                  55                  60

Gln Lys Phe Gln Gly Arg Val Thr Ile Thr Ala Asp Lys Ser Thr Ser
65                  70                  75                  80

Thr Ala Tyr Met Glu Leu Ser Arg Leu Arg Ser Glu Asp Thr Ala Leu
                85                  90                  95

Tyr Tyr Cys Ala Arg Val Leu Leu Ser Ser Arg Asp Ala Phe Asp Ile
            100                 105                 110

Trp Gly Gln Gly Thr Leu Val Thr
        115                 120

<210> SEQ ID NO 76
<211> LENGTH: 369
<212> TYPE: DNA
<213> ORGANISM: Homo sapiens

<400> SEQUENCE: 76
caggtgcagc tggtgcagtc tggggttgag gtgaagaagc ctgggtcctc ggtgaaggtc      60
tcctgcaagg cttctggagg cacctteagc agctatacta tcagctgggt gcgacaggcc     120
cctggacaag ggcttgagtg gatgggaagg atcatcccta agcttggtat agcaaactac     180
gcacagaacg cacagaagtt ccagggcaga gtcacgatta ccgcggacaa atccacgagc     240
acagcctaca tggagctgag caggctgaga tctgaggaca cggccctgta ttactgtgcg     300
agagtattac tgagtagcag ggatgctttt gatatctggg gccaagggac cctggtcacc     360
gtctcctca                                                             369

<210> SEQ ID NO 77
<211> LENGTH: 123
<212> TYPE: PRT
<213> ORGANISM: Homo sapiens

<400> SEQUENCE: 77

Gln Val Gln Leu Val Gln Ser Gly Val Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Lys Leu Gly Ile Ala Asn Tyr Ala Gln Asn Ala
    50                  55                  60

Gln Lys Phe Gln Gly Arg Val Thr Ile Thr Ala Asp Lys Ser Thr Ser
65                  70                  75                  80

```
Thr Ala Tyr Met Glu Leu Ser Arg Leu Arg Ser Glu Asp Thr Ala Leu
             85                  90                  95

Tyr Tyr Cys Ala Arg Val Leu Leu Ser Ser Arg Asp Ala Phe Asp Ile
        100                 105                 110

Trp Gly Gln Gly Thr Leu Val Thr Val Ser Ser
        115                 120

<210> SEQ ID NO 78
<211> LENGTH: 372
<212> TYPE: DNA
<213> ORGANISM: Homo sapiens

<400> SEQUENCE: 78
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgaatg atgggatgg atcaaccta acagtggtgg cacaaactat        180
gcacagaagt tccagggctg gtcaccatg accaggaca cgtccatcag cacagcctac       240
atggagctga aaggctgag atctgacgac acggccgtgt attactgtgc gaccaacaaa      300
ggaactaacg tcgctacta ctactacggt atggacgtct ggggccaagg gaccctggtc      360
accgtctcct ca                                                         372

<210> SEQ ID NO 79
<211> LENGTH: 333
<212> TYPE: DNA
<213> ORGANISM: Homo sapiens

<400> SEQUENCE: 79
gacattgtga tgacccagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactatc     300
accttcggcc aagggacacg actggagatt aaa                                  333

<210> SEQ ID NO 80
<211> LENGTH: 360
<212> TYPE: DNA
<213> ORGANISM: Homo sapiens

<400> SEQUENCE: 80
caggtgcagc tggtgcagtc tggggttgag gtgaagaagc ctgggtcctc ggtgaaggtc      60
tcctgcaagg cttctggagg caccttcagc agctatacta tcagctgggt gcgacaggcc     120
cctggacaag gcttgagtg atgggaagg atcatcccta agcttggtat agcaaactac       180
gcacagaacg cacagaagtt ccagggcaga gtcacgatta ccgcggacaa atccacgagc     240
acagcctaca tggagctgag caggctgaga tctgaggaca cggccctgta ttactgtgcg     300
agagtattac tgagtagcag ggatgctttt gatatctggg gccaagggac cctggtcacc     360

<210> SEQ ID NO 81
<211> LENGTH: 21
<212> TYPE: DNA
<213> ORGANISM: Artificial sequence
<220> FEATURE:
<223> OTHER INFORMATION: Synthetic phosphorothioate-modified
      oligodeoxynucleotide
```

<220> FEATURE:
<221> NAME/KEY: modified_base
<222> LOCATION: (1)..(20)
<223> OTHER INFORMATION: phosphorothioate base

<400> SEQUENCE: 81
tcgtcgtttt tcggtcgttt t                      21

<210> SEQ ID NO 82
<211> LENGTH: 8
<212> TYPE: PRT
<213> ORGANISM: Artificial sequence
<220> FEATURE:
<223> OTHER INFORMATION: Synthetic peptide

<400> SEQUENCE: 82

Gly Phe Thr Phe Ser Ser Tyr Trp
1               5

<210> SEQ ID NO 83
<211> LENGTH: 8
<212> TYPE: PRT
<213> ORGANISM: Artificial sequence
<220> FEATURE:
<223> OTHER INFORMATION: Synthetic peptide

<400> SEQUENCE: 83

Ile Lys Gln Asp Gly Ser Ala Lys
1               5

<210> SEQ ID NO 84
<211> LENGTH: 20
<212> TYPE: PRT
<213> ORGANISM: Artificial sequence
<220> FEATURE:
<223> OTHER INFORMATION: Synthetic peptide

<400> SEQUENCE: 84

Ala Arg Asp Gly Leu Leu Gly Ile Ser Asp Leu Leu Tyr Pro Ile Tyr
1               5                   10                  15

Tyr Phe Asp Tyr
            20

<210> SEQ ID NO 85
<211> LENGTH: 8
<212> TYPE: PRT
<213> ORGANISM: Artificial sequence
<220> FEATURE:
<223> OTHER INFORMATION: Synthetic peptide

<400> SEQUENCE: 85

Gly Tyr Thr Phe Thr Ser Tyr Ala
1               5

<210> SEQ ID NO 86
<211> LENGTH: 8
<212> TYPE: PRT
<213> ORGANISM: Artificial sequence
<220> FEATURE:
<223> OTHER INFORMATION: Synthetic peptide

<400> SEQUENCE: 86

Ile Ser Gly Asn Asn Gly Asn Thr
1               5

<210> SEQ ID NO 87

```
<211> LENGTH: 22
<212> TYPE: PRT
<213> ORGANISM: Artificial sequence
<220> FEATURE:
<223> OTHER INFORMATION: Synthetic peptide

<400> SEQUENCE: 87

Ala Arg Asp Ala Asp Ile Val Val Val Val Gly Ala Thr Gly Thr Tyr
1               5                   10                  15

Tyr Tyr Gly Met Asp Val
            20

<210> SEQ ID NO 88
<211> LENGTH: 8
<212> TYPE: PRT
<213> ORGANISM: Artificial sequence
<220> FEATURE:
<223> OTHER INFORMATION: Synthetic peptide

<400> SEQUENCE: 88

Gly Phe Thr Val Ser Asn Asn Tyr
1               5

<210> SEQ ID NO 89
<211> LENGTH: 7
<212> TYPE: PRT
<213> ORGANISM: Artificial sequence
<220> FEATURE:
<223> OTHER INFORMATION: Synthetic peptide

<400> SEQUENCE: 89

Phe Tyr Ser Asp Gly Thr Thr
1               5

<210> SEQ ID NO 90
<211> LENGTH: 14
<212> TYPE: PRT
<213> ORGANISM: Artificial sequence
<220> FEATURE:
<223> OTHER INFORMATION: Synthetic peptide

<400> SEQUENCE: 90

Ala Arg Gln Ala Ser Gly Tyr Asp Ala Tyr Tyr Met Asp Val
1               5                   10

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Gly Ala Thr Phe Gly Ser Asp Thr
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic peptide

<400> SEQUENCE: 92

Ile Ile Pro Phe Phe Gly Glu Ala
1               5
```

<210> SEQ ID NO 93
<211> LENGTH: 21
<212> TYPE: PRT
<213> ORGANISM: Artificial sequence
<220> FEATURE:
<223> OTHER INFORMATION: Synthetic peptide

<400> SEQUENCE: 93

Ala Arg Gln Ile Asn Glu Met Ala Thr Phe Gly Glu Ile His Tyr Tyr
1               5                   10                  15

Thr Tyr Met Asp Val
            20

<210> SEQ ID NO 94
<211> LENGTH: 8
<212> TYPE: PRT
<213> ORGANISM: Artificial sequence
<220> FEATURE:
<223> OTHER INFORMATION: Synthetic peptide

<400> SEQUENCE: 94

Ser Asp Ser Ile Arg Ser Tyr Ser
1               5

<210> SEQ ID NO 95
<211> LENGTH: 7
<212> TYPE: PRT
<213> ORGANISM: Artificial sequence
<220> FEATURE:
<223> OTHER INFORMATION: Synthetic peptide

<400> SEQUENCE: 95

Ile Tyr Tyr Ser Gly Asn Ile
1               5

<210> SEQ ID NO 96
<211> LENGTH: 14
<212> TYPE: PRT
<213> ORGANISM: Artificial sequence
<220> FEATURE:
<223> OTHER INFORMATION: Synthetic peptide

<400> SEQUENCE: 96

Ala Arg Asp Trp Ile Thr Ile Phe Gly Arg Tyr Phe Asp Val
1               5                   10

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Gly Phe Asn Phe Gly Asp Tyr Val
1               5

<210> SEQ ID NO 98
<211> LENGTH: 10
<212> TYPE: PRT
<213> ORGANISM: Artificial sequence
<220> FEATURE:
<223> OTHER INFORMATION: Synthetic peptide

<400> SEQUENCE: 98

Ile Arg Gly Lys Thr Phe Gly Ala Thr Thr

```
1               5                  10
```

<210> SEQ ID NO 99
<211> LENGTH: 12
<212> TYPE: PRT
<213> ORGANISM: Artificial sequence
<220> FEATURE:
<223> OTHER INFORMATION: Synthetic peptide

<400> SEQUENCE: 99

```
Thr Arg Arg Ala Thr Ser Thr Trp Tyr Glu Asp Tyr
1               5                  10
```

<210> SEQ ID NO 100
<211> LENGTH: 10
<212> TYPE: PRT
<213> ORGANISM: Artificial sequence
<220> FEATURE:
<223> OTHER INFORMATION: Synthetic peptide

<400> SEQUENCE: 100

```
Gly Asp Ser Ile Ser Ser Gly Ser Tyr Tyr
1               5                  10
```

<210> SEQ ID NO 101
<211> LENGTH: 7
<212> TYPE: PRT
<213> ORGANISM: Artificial sequence
<220> FEATURE:
<223> OTHER INFORMATION: Synthetic peptide

<400> SEQUENCE: 101

```
Ile Tyr Thr Ser Gly Ser Thr
1               5
```

<210> SEQ ID NO 102
<211> LENGTH: 19
<212> TYPE: PRT
<213> ORGANISM: Artificial sequence
<220> FEATURE:
<223> OTHER INFORMATION: Synthetic peptide

<400> SEQUENCE: 102

```
Ala Arg Asp Pro Ile Thr Ile Phe Gly Gly Val Ile Phe Gly Trp Gly
1               5                  10                 15

Met Asp Val
```

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

```
Gly Gly Thr Phe Asp Thr Tyr Ala
1               5
```

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

```
Ile Ile Pro Val Leu Gly Ile Val
1               5
```

<210> SEQ ID NO 105
<211> LENGTH: 33
<212> TYPE: PRT
<213> ORGANISM: Artificial sequence
<220> FEATURE:
<223> OTHER INFORMATION: Synthetic peptide

<400> SEQUENCE: 105

```
Ala Arg Gly Leu Arg Ser Leu Ser Pro Arg Gly Gln Glu Gly Pro Thr
1               5                   10                  15

Pro Ala Pro Gly Trp Arg Arg Ala Gln Tyr His Tyr Tyr Tyr Met Asp
            20                  25                  30

Val
```

<210> SEQ ID NO 106
<211> LENGTH: 10
<212> TYPE: PRT
<213> ORGANISM: Artificial sequence
<220> FEATURE:
<223> OTHER INFORMATION: Synthetic peptide

<400> SEQUENCE: 106

```
Gly Gly Ser Ile Asn Ser Asp Ser Tyr Tyr
1               5                   10
```

<210> SEQ ID NO 107
<211> LENGTH: 16
<212> TYPE: PRT
<213> ORGANISM: Artificial sequence
<220> FEATURE:
<223> OTHER INFORMATION: Synthetic peptide

<400> SEQUENCE: 107

```
Thr Asp Lys Ile Asp Gln Ile Ile His Asp Phe Ile Asp Lys Pro Leu
1               5                   10                  15
```

<210> SEQ ID NO 108
<211> LENGTH: 7
<212> TYPE: PRT
<213> ORGANISM: Artificial sequence
<220> FEATURE:
<223> OTHER INFORMATION: Synthetic peptide

<400> SEQUENCE: 108

```
Val Tyr Thr Ser Gly Ser Thr
1               5
```

<210> SEQ ID NO 109
<211> LENGTH: 19
<212> TYPE: PRT
<213> ORGANISM: Artificial sequence
<220> FEATURE:
<223> OTHER INFORMATION: Synthetic peptide

<400> SEQUENCE: 109

```
Ala Arg Val Val Trp Gly Ser Tyr Arg Ser Tyr His Tyr Ser Tyr Gly
1               5                   10                  15

Met Asp Val
```

<210> SEQ ID NO 110
<211> LENGTH: 8
<212> TYPE: PRT

```
<213> ORGANISM: Artificial sequence
<220> FEATURE:
<223> OTHER INFORMATION: Synthetic peptide

<400> SEQUENCE: 110

Gly Tyr Ala Phe Thr Thr Tyr Ala
1               5

<210> SEQ ID NO 111
<211> LENGTH: 8
<212> TYPE: PRT
<213> ORGANISM: Artificial sequence
<220> FEATURE:
<223> OTHER INFORMATION: Synthetic peptide

<400> SEQUENCE: 111

Ile Ser Thr Tyr Tyr Gly Thr Thr
1               5

<210> SEQ ID NO 112
<211> LENGTH: 18
<212> TYPE: PRT
<213> ORGANISM: Artificial sequence
<220> FEATURE:
<223> OTHER INFORMATION: Synthetic peptide

<400> SEQUENCE: 112

Val Arg Asp Arg Ser Trp Leu Ala Thr Ser Arg Pro Tyr Asp Ala Phe
1               5                   10                  15

Asp Ile

<210> SEQ ID NO 113
<211> LENGTH: 10
<212> TYPE: PRT
<213> ORGANISM: Artificial sequence
<220> FEATURE:
<223> OTHER INFORMATION: Synthetic peptide

<400> SEQUENCE: 113

Gly Gly Ser Ile Ser Ser Gly Arg Phe Tyr
1               5                   10

<210> SEQ ID NO 114
<211> LENGTH: 7
<212> TYPE: PRT
<213> ORGANISM: Artificial sequence
<220> FEATURE:
<223> OTHER INFORMATION: Synthetic peptide

<400> SEQUENCE: 114

Ile Tyr Thr Ser Gly Ser Thr
1               5

<210> SEQ ID NO 115
<211> LENGTH: 17
<212> TYPE: PRT
<213> ORGANISM: Artificial sequence
<220> FEATURE:
<223> OTHER INFORMATION: Synthetic peptide

<400> SEQUENCE: 115

Ala Thr Glu Leu Tyr Tyr Tyr Gly Ser Gly Ser Tyr Asp Pro Leu Trp
1               5                   10                  15

Ser
```

```
<210> SEQ ID NO 116
<211> LENGTH: 10
<212> TYPE: PRT
<213> ORGANISM: Artificial sequence
<220> FEATURE:
<223> OTHER INFORMATION: Synthetic peptide

<400> SEQUENCE: 116

Gly Gly Ser Ile Ser Ser Gly Ser Tyr Phe
1               5                   10

<210> SEQ ID NO 117
<211> LENGTH: 7
<212> TYPE: PRT
<213> ORGANISM: Artificial sequence
<220> FEATURE:
<223> OTHER INFORMATION: Synthetic peptide

<400> SEQUENCE: 117

Ile Tyr Thr Ser Gly Thr Thr
1               5

<210> SEQ ID NO 118
<211> LENGTH: 15
<212> TYPE: PRT
<213> ORGANISM: Artificial sequence
<220> FEATURE:
<223> OTHER INFORMATION: Synthetic peptide

<400> SEQUENCE: 118

Ala Thr Ser Pro Tyr Tyr Tyr Asp Ser Ser His Tyr Tyr Asp Tyr
1               5                   10                  15

<210> SEQ ID NO 119
<211> LENGTH: 10
<212> TYPE: PRT
<213> ORGANISM: Artificial sequence
<220> FEATURE:
<223> OTHER INFORMATION: Synthetic peptide

<400> SEQUENCE: 119

Gly Gly Ser Ile Ser Asn Gly Gly Tyr His
1               5                   10

<210> SEQ ID NO 120
<211> LENGTH: 7
<212> TYPE: PRT
<213> ORGANISM: Artificial sequence
<220> FEATURE:
<223> OTHER INFORMATION: Synthetic peptide

<400> SEQUENCE: 120

Ile Tyr Tyr Ser Gly Ser Thr
1               5

<210> SEQ ID NO 121
<211> LENGTH: 12
<212> TYPE: PRT
<213> ORGANISM: Artificial sequence
<220> FEATURE:
<223> OTHER INFORMATION: Synthetic peptide

<400> SEQUENCE: 121

Ala Arg Asp Arg Ile Arg Gly Gly Pro Ile Asp Tyr
1               5                   10

<210> SEQ ID NO 122
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 122

Gly Tyr Thr Phe Ser Asp Tyr Tyr
1               5

<210> SEQ ID NO 123
<211> LENGTH: 8
<212> TYPE: PRT
<213> ORGANISM: Artificial sequence
<220> FEATURE:
<223> OTHER INFORMATION: Synthetic peptide

<400> SEQUENCE: 123

Ile Asn Pro Tyr Ser Gly Gly Thr
1               5

<210> SEQ ID NO 124
<211> LENGTH: 18
<212> TYPE: PRT
<213> ORGANISM: Artificial sequence
<220> FEATURE:
<223> OTHER INFORMATION: Synthetic peptide

<400> SEQUENCE: 124

Ala Arg Leu Tyr Gly Ala Gly Ser His Tyr Asn His Tyr Asn Gly Met
1               5                   10                  15

Asp Val

<210> SEQ ID NO 125
<211> LENGTH: 10
<212> TYPE: PRT
<213> ORGANISM: Artificial sequence
<220> FEATURE:
<223> OTHER INFORMATION: Synthetic peptide

<400> SEQUENCE: 125

Gly Gly Ser Val Ser Ser Gly Arg Tyr Phe
1               5                   10

<210> SEQ ID NO 126
<211> LENGTH: 7
<212> TYPE: PRT
<213> ORGANISM: Artificial sequence
<220> FEATURE:
<223> OTHER INFORMATION: Synthetic peptide

<400> SEQUENCE: 126

Ile His Ser Ser Gly Arg Thr
1               5

<210> SEQ ID NO 127
<211> LENGTH: 10
<212> TYPE: PRT
<213> ORGANISM: Artificial sequence
<220> FEATURE:
<223> OTHER INFORMATION: Synthetic peptide

<400> SEQUENCE: 127

Gly Ala Ser Ile Ser Arg Gly Leu Tyr Tyr
1               5                   10
```

-continued

```
<210> SEQ ID NO 128
<211> LENGTH: 7
<212> TYPE: PRT
<213> ORGANISM: Artificial sequence
<220> FEATURE:
<223> OTHER INFORMATION: Synthetic peptide

<400> SEQUENCE: 128

Ile Tyr Thr Ser Gly Ser Ile
1               5

<210> SEQ ID NO 129
<211> LENGTH: 21
<212> TYPE: PRT
<213> ORGANISM: Artificial sequence
<220> FEATURE:
<223> OTHER INFORMATION: Synthetic peptide

<400> SEQUENCE: 129

Val Arg Asp Ala Pro Trp Gly Asp Phe Leu Thr Gly Tyr Phe Gly Phe
1               5                   10                  15

Tyr Gly Met Asp Val
            20

<210> SEQ ID NO 130
<211> LENGTH: 8
<212> TYPE: PRT
<213> ORGANISM: Artificial sequence
<220> FEATURE:
<223> OTHER INFORMATION: Synthetic peptide

<400> SEQUENCE: 130

Gly Tyr Thr Phe Thr Ser Phe Glu
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic peptide

<400> SEQUENCE: 131

Met Asn Pro Lys Ser Gly Asp Thr
1               5

<210> SEQ ID NO 132
<211> LENGTH: 24
<212> TYPE: PRT
<213> ORGANISM: Artificial sequence
<220> FEATURE:
<223> OTHER INFORMATION: Synthetic peptide

<400> SEQUENCE: 132

Ala Arg Gly Pro His Val Gly Glu Val Val Pro Gly Leu Met Ala Gly
1               5                   10                  15

Thr Tyr Tyr Phe Pro Leu Asp Val
            20

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133
```

```
Gly Gly Thr Phe Ser Asn Ser Ile
1               5
```

<210> SEQ ID NO 134
<211> LENGTH: 8
<212> TYPE: PRT
<213> ORGANISM: Artificial sequence
<220> FEATURE:
<223> OTHER INFORMATION: Synthetic peptide

<400> SEQUENCE: 134

```
Ile Ile Pro Ile Val Gly Leu Val
1               5
```

<210> SEQ ID NO 135
<211> LENGTH: 12
<212> TYPE: PRT
<213> ORGANISM: Artificial sequence
<220> FEATURE:
<223> OTHER INFORMATION: Synthetic peptide

<400> SEQUENCE: 135

```
Ala Ile Asn Gly Val Asn Ile Pro Asp Thr Leu Thr
1               5                   10
```

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

```
Gly Gly Ser Ile Arg Ser Tyr Phe
1               5
```

<210> SEQ ID NO 137
<211> LENGTH: 7
<212> TYPE: PRT
<213> ORGANISM: Artificial sequence
<220> FEATURE:
<223> OTHER INFORMATION: Synthetic peptide

<400> SEQUENCE: 137

```
Ile Tyr Tyr Ser Gly Arg Pro
1               5
```

<210> SEQ ID NO 138
<211> LENGTH: 21
<212> TYPE: PRT
<213> ORGANISM: Artificial sequence
<220> FEATURE:
<223> OTHER INFORMATION: Synthetic peptide

<400> SEQUENCE: 138

```
Ala Arg Asp Glu Arg Leu Leu Val Glu Val Gly Thr Asp His Phe Tyr
1               5                   10                  15

Tyr Gly Leu Asp Val
            20
```

<210> SEQ ID NO 139
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 139

Gly Tyr Thr Phe Thr Ser Phe Gly
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic peptide

<400> SEQUENCE: 140

Ile Asn Thr Tyr Asn Gly Asp Thr
1               5

<210> SEQ ID NO 141
<211> LENGTH: 18
<212> TYPE: PRT
<213> ORGANISM: Artificial sequence
<220> FEATURE:
<223> OTHER INFORMATION: Synthetic peptide

<400> SEQUENCE: 141

Ala Arg Asp Ser His Leu Ile Ser Ile Ala Val Ala Asn Thr Pro Asn
1               5                   10                  15

Asp Phe

<210> SEQ ID NO 142
<211> LENGTH: 10
<212> TYPE: PRT
<213> ORGANISM: Artificial sequence
<220> FEATURE:
<223> OTHER INFORMATION: Synthetic peptide

<400> SEQUENCE: 142

Gly Gly Ser Ile Ser Ser Asp Asp Arg Tyr
1               5                   10

<210> SEQ ID NO 143
<211> LENGTH: 7
<212> TYPE: PRT
<213> ORGANISM: Artificial sequence
<220> FEATURE:
<223> OTHER INFORMATION: Synthetic peptide

<400> SEQUENCE: 143

Ile Tyr Tyr Ser Gly Ser Thr
1               5

<210> SEQ ID NO 144
<211> LENGTH: 22
<212> TYPE: PRT
<213> ORGANISM: Artificial sequence
<220> FEATURE:
<223> OTHER INFORMATION: Synthetic peptide

<400> SEQUENCE: 144

Ala Thr Val Thr Ala Tyr Ser Pro Ala Thr Met Ile Val Val Gly Thr
1               5                   10                  15

Glu His Gly Phe Asp Tyr
            20

<210> SEQ ID NO 145
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 145

Gly Leu Thr Phe Ser Asn Phe Gly
1               5

<210> SEQ ID NO 146
<211> LENGTH: 8
<212> TYPE: PRT
<213> ORGANISM: Artificial sequence
<220> FEATURE:
<223> OTHER INFORMATION: Synthetic peptide

<400> SEQUENCE: 146

Ile Arg Phe Asp Gly Ser Asn Lys
1               5

<210> SEQ ID NO 147
<211> LENGTH: 11
<212> TYPE: PRT
<213> ORGANISM: Artificial sequence
<220> FEATURE:
<223> OTHER INFORMATION: Synthetic peptide

<400> SEQUENCE: 147

Gly Arg Val Leu Tyr Gly Ala Ala Ala Asp Phe
1               5                   10

<210> SEQ ID NO 148
<211> LENGTH: 8
<212> TYPE: PRT
<213> ORGANISM: Artificial sequence
<220> FEATURE:
<223> OTHER INFORMATION: Synthetic peptide

<400> SEQUENCE: 148

Gly Gly Thr Phe Ser Ser Tyr Ala
1               5

<210> SEQ ID NO 149
<211> LENGTH: 8
<212> TYPE: PRT
<213> ORGANISM: Artificial sequence
<220> FEATURE:
<223> OTHER INFORMATION: Synthetic peptide

<400> SEQUENCE: 149

Ile Ile Pro Ile Phe Gly Lys Pro
1               5

<210> SEQ ID NO 150
<211> LENGTH: 22
<212> TYPE: PRT
<213> ORGANISM: Artificial sequence
<220> FEATURE:
<223> OTHER INFORMATION: Synthetic peptide

<400> SEQUENCE: 150

Ala Arg Gly Gln Gly Glu Ile Val Val Met Val Gly His Asp Asp Gly
1               5                   10                  15

Gly Asp Tyr Leu Gly Tyr
            20
```

```
<210> SEQ ID NO 151
<211> LENGTH: 8
<212> TYPE: PRT
<213> ORGANISM: Artificial sequence
<220> FEATURE:
<223> OTHER INFORMATION: Synthetic peptide

<400> SEQUENCE: 151

Gly Gly Ser Ile Ser Gly Ser Ile
1               5

<210> SEQ ID NO 152
<211> LENGTH: 7
<212> TYPE: PRT
<213> ORGANISM: Artificial sequence
<220> FEATURE:
<223> OTHER INFORMATION: Synthetic peptide

<400> SEQUENCE: 152

Ile Ser Leu Ser Gly Ser Thr
1               5

<210> SEQ ID NO 153
<211> LENGTH: 23
<212> TYPE: PRT
<213> ORGANISM: Artificial sequence
<220> FEATURE:
<223> OTHER INFORMATION: Synthetic peptide

<400> SEQUENCE: 153

Ala Arg His Arg Lys Ser Ser Lys Met Val Arg Gly Ile Glu Val Phe
1               5                   10                  15

Tyr Tyr Tyr Tyr Met Asp Val
            20

<210> SEQ ID NO 154
<211> LENGTH: 10
<212> TYPE: PRT
<213> ORGANISM: Artificial sequence
<220> FEATURE:
<223> OTHER INFORMATION: Synthetic peptide

<400> SEQUENCE: 154

Gly Gly Ser Ile Ser Ser Gly Ser Phe Tyr
1               5                   10

<210> SEQ ID NO 155
<211> LENGTH: 7
<212> TYPE: PRT
<213> ORGANISM: Artificial sequence
<220> FEATURE:
<223> OTHER INFORMATION: Synthetic peptide

<400> SEQUENCE: 155

Phe Tyr Thr Thr Gly Ser Thr
1               5

<210> SEQ ID NO 156
<211> LENGTH: 17
<212> TYPE: PRT
<213> ORGANISM: Artificial sequence
<220> FEATURE:
<223> OTHER INFORMATION: Synthetic peptide

<400> SEQUENCE: 156

Ala Arg Gly Pro Val Ser Tyr Tyr Ser Gly Asn Leu Tyr Tyr Phe Asp
1               5                   10                  15
```

Tyr

<210> SEQ ID NO 157
<211> LENGTH: 8
<212> TYPE: PRT
<213> ORGANISM: Artificial sequence
<220> FEATURE:
<223> OTHER INFORMATION: Synthetic peptide

<400> SEQUENCE: 157

Gly Phe Thr Phe Ser Ser Phe Gly
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158

Ile Arg Tyr Asp Gly Ser Asp Lys
1               5

<210> SEQ ID NO 159
<211> LENGTH: 19
<212> TYPE: PRT
<213> ORGANISM: Artificial sequence
<220> FEATURE:
<223> OTHER INFORMATION: Synthetic peptide

<400> SEQUENCE: 159

Ala Lys Arg Gly Gly His Asp Tyr Gly Tyr Tyr Asp Asn Asn Arg Tyr
1               5                   10                  15

Ile Asp Leu

<210> SEQ ID NO 160
<211> LENGTH: 8
<212> TYPE: PRT
<213> ORGANISM: Artificial sequence
<220> FEATURE:
<223> OTHER INFORMATION: Synthetic peptide

<400> SEQUENCE: 160

Gly Gly Thr Phe Ser Ser Tyr Gly
1               5

<210> SEQ ID NO 161
<211> LENGTH: 8
<212> TYPE: PRT
<213> ORGANISM: Artificial sequence
<220> FEATURE:
<223> OTHER INFORMATION: Synthetic peptide

<400> SEQUENCE: 161

Ile Ile Pro Lys Phe Ala Thr Ala
1               5

<210> SEQ ID NO 162
<211> LENGTH: 23
<212> TYPE: PRT
<213> ORGANISM: Artificial sequence
<220> FEATURE:
<223> OTHER INFORMATION: Synthetic peptide

<400> SEQUENCE: 162

```
Ala Gly His Phe Pro Gln Arg Lys Pro Ile Thr Thr Ile Val Val Ile
1               5                   10                  15

Thr Tyr Trp Ser Leu Asp Leu
            20

<210> SEQ ID NO 163
<211> LENGTH: 8
<212> TYPE: PRT
<213> ORGANISM: Artificial sequence
<220> FEATURE:
<223> OTHER INFORMATION: Synthetic peptide

<400> SEQUENCE: 163

Gly Val Thr Phe Ser Arg Tyr Thr
1               5

<210> SEQ ID NO 164
<211> LENGTH: 8
<212> TYPE: PRT
<213> ORGANISM: Artificial sequence
<220> FEATURE:
<223> OTHER INFORMATION: Synthetic peptide

<400> SEQUENCE: 164

Ile Ser Pro Ile Leu Gly Thr Ala
1               5

<210> SEQ ID NO 165
<211> LENGTH: 18
<212> TYPE: PRT
<213> ORGANISM: Artificial sequence
<220> FEATURE:
<223> OTHER INFORMATION: Synthetic peptide

<400> SEQUENCE: 165

Ala Arg Asp Ala Pro Ile Ile Leu Val Glu Gly Pro Glu Thr Gly Met
1               5                   10                  15

Asp Val

<210> SEQ ID NO 166
<211> LENGTH: 8
<212> TYPE: PRT
<213> ORGANISM: Artificial sequence
<220> FEATURE:
<223> OTHER INFORMATION: Synthetic peptide

<400> SEQUENCE: 166

Gly Phe Thr Phe Asn Ser Tyr Gly
1               5

<210> SEQ ID NO 167
<211> LENGTH: 8
<212> TYPE: PRT
<213> ORGANISM: Artificial sequence
<220> FEATURE:
<223> OTHER INFORMATION: Synthetic peptide

<400> SEQUENCE: 167

Ile Trp Phe Asp Gly Ser Lys Lys
1               5

<210> SEQ ID NO 168
<211> LENGTH: 21
<212> TYPE: PRT
<213> ORGANISM: Artificial sequence
```

```
<220> FEATURE:
<223> OTHER INFORMATION: Synthetic peptide

<400> SEQUENCE: 168

Ala Lys Asp Leu Leu Tyr Gly Ser Gly Met Val Pro Asn Tyr Tyr Tyr
1               5                   10                  15

Tyr Gly Leu Asp Val
            20

<210> SEQ ID NO 169
<211> LENGTH: 6
<212> TYPE: PRT
<213> ORGANISM: Artificial sequence
<220> FEATURE:
<223> OTHER INFORMATION: Synthetic peptide

<400> SEQUENCE: 169

Gln Asn Ile Gly Ser Tyr
1               5

<210> SEQ ID NO 170
<211> LENGTH: 9
<212> TYPE: PRT
<213> ORGANISM: Artificial sequence
<220> FEATURE:
<223> OTHER INFORMATION: Synthetic peptide

<400> SEQUENCE: 170

Gln Gln Ser Tyr Ser Ile Pro Arg Thr
1               5

<210> SEQ ID NO 171
<211> LENGTH: 6
<212> TYPE: PRT
<213> ORGANISM: Artificial sequence
<220> FEATURE:
<223> OTHER INFORMATION: Synthetic peptide

<400> SEQUENCE: 171

Gln Ser Ile Ser Ser Trp
1               5

<210> SEQ ID NO 172
<211> LENGTH: 9
<212> TYPE: PRT
<213> ORGANISM: Artificial sequence
<220> FEATURE:
<223> OTHER INFORMATION: Synthetic peptide

<400> SEQUENCE: 172

Gln Gln Tyr Lys Ser Ser Leu Arg Thr
1               5

<210> SEQ ID NO 173
<211> LENGTH: 6
<212> TYPE: PRT
<213> ORGANISM: Artificial sequence
<220> FEATURE:
<223> OTHER INFORMATION: Synthetic peptide

<400> SEQUENCE: 173

Gln Ser Ile Asn Ser Trp
1               5

<210> SEQ ID NO 174
<211> LENGTH: 9
```

<212> TYPE: PRT
<213> ORGANISM: Artificial sequence
<220> FEATURE:
<223> OTHER INFORMATION: Synthetic peptide

<400> SEQUENCE: 174

Gln Gln Tyr Ser Ser Phe Pro Leu Thr
1               5

<210> SEQ ID NO 175
<211> LENGTH: 7
<212> TYPE: PRT
<213> ORGANISM: Artificial sequence
<220> FEATURE:
<223> OTHER INFORMATION: Synthetic peptide

<400> SEQUENCE: 175

Gln Ser Ile Thr Ser Thr Tyr
1               5

<210> SEQ ID NO 176
<211> LENGTH: 7
<212> TYPE: PRT
<213> ORGANISM: Artificial sequence
<220> FEATURE:
<223> OTHER INFORMATION: Synthetic peptide

<400> SEQUENCE: 176

Gln Gln Tyr His Ser Ser Leu
1               5

<210> SEQ ID NO 177
<211> LENGTH: 12
<212> TYPE: PRT
<213> ORGANISM: Artificial sequence
<220> FEATURE:
<223> OTHER INFORMATION: Synthetic peptide

<400> SEQUENCE: 177

Gln Asn Leu Leu Tyr Ser Ser Asn Asn Lys Asn Phe
1               5                   10

<210> SEQ ID NO 178
<211> LENGTH: 9
<212> TYPE: PRT
<213> ORGANISM: Artificial sequence
<220> FEATURE:
<223> OTHER INFORMATION: Synthetic peptide

<400> SEQUENCE: 178

Gln Gln Tyr Tyr Thr Ile Pro Pro Thr
1               5

<210> SEQ ID NO 179
<211> LENGTH: 12
<212> TYPE: PRT
<213> ORGANISM: Artificial sequence
<220> FEATURE:
<223> OTHER INFORMATION: Synthetic peptide

<400> SEQUENCE: 179

Gln Ser Val Leu Tyr Thr Pro Asn Asn His Asn Tyr
1               5                   10

<210> SEQ ID NO 180
<211> LENGTH: 9
<212> TYPE: PRT

```
<213> ORGANISM: Artificial sequence
<220> FEATURE:
<223> OTHER INFORMATION: Synthetic peptide

<400> SEQUENCE: 180

Gln Gln Tyr His Ile Pro Pro Tyr Ser
1               5

<210> SEQ ID NO 181
<211> LENGTH: 11
<212> TYPE: PRT
<213> ORGANISM: Artificial sequence
<220> FEATURE:
<223> OTHER INFORMATION: Synthetic peptide

<400> SEQUENCE: 181

Gln Thr Leu Leu His Ser Asn Gly Tyr Asn Tyr
1               5                   10

<210> SEQ ID NO 182
<211> LENGTH: 9
<212> TYPE: PRT
<213> ORGANISM: Artificial sequence
<220> FEATURE:
<223> OTHER INFORMATION: Synthetic peptide

<400> SEQUENCE: 182

Met Gln Ala Leu Gln Thr Pro Val Thr
1               5

<210> SEQ ID NO 183
<211> LENGTH: 7
<212> TYPE: PRT
<213> ORGANISM: Artificial sequence
<220> FEATURE:
<223> OTHER INFORMATION: Synthetic peptide

<400> SEQUENCE: 183

Gln Ser Val Ser Ser Asn Tyr
1               5

<210> SEQ ID NO 184
<211> LENGTH: 9
<212> TYPE: PRT
<213> ORGANISM: Artificial sequence
<220> FEATURE:
<223> OTHER INFORMATION: Synthetic peptide

<400> SEQUENCE: 184

Gln Gln Tyr Gly Ser Ser Pro Gly Thr
1               5

<210> SEQ ID NO 185
<211> LENGTH: 7
<212> TYPE: PRT
<213> ORGANISM: Artificial sequence
<220> FEATURE:
<223> OTHER INFORMATION: Synthetic peptide

<400> SEQUENCE: 185

Gln Ser Val Gly Ser Ser Tyr
1               5

<210> SEQ ID NO 186
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 186

Gln Gln Ser Gly Ser Ser Pro Glu Thr
1               5

<210> SEQ ID NO 187
<211> LENGTH: 6
<212> TYPE: PRT
<213> ORGANISM: Artificial sequence
<220> FEATURE:
<223> OTHER INFORMATION: Synthetic peptide

<400> SEQUENCE: 187

Gln Asp Ile Ser Ser Thr
1               5

<210> SEQ ID NO 188
<211> LENGTH: 9
<212> TYPE: PRT
<213> ORGANISM: Artificial sequence
<220> FEATURE:
<223> OTHER INFORMATION: Synthetic peptide

<400> SEQUENCE: 188

Gln His Phe Tyr Tyr Phe Pro Arg Thr
1               5

<210> SEQ ID NO 189
<211> LENGTH: 6
<212> TYPE: PRT
<213> ORGANISM: Artificial sequence
<220> FEATURE:
<223> OTHER INFORMATION: Synthetic peptide

<400> SEQUENCE: 189

Gln Gly Ile Asn Asn Asn
1               5

<210> SEQ ID NO 190
<211> LENGTH: 9
<212> TYPE: PRT
<213> ORGANISM: Artificial sequence
<220> FEATURE:
<223> OTHER INFORMATION: Synthetic peptide

<400> SEQUENCE: 190

Gln Gln Asn Ala Asn Leu Pro His Thr
1               5

<210> SEQ ID NO 191
<211> LENGTH: 6
<212> TYPE: PRT
<213> ORGANISM: Artificial sequence
<220> FEATURE:
<223> OTHER INFORMATION: Synthetic peptide

<400> SEQUENCE: 191

Gln Asp Ile Thr Asn Tyr
1               5

<210> SEQ ID NO 192
<211> LENGTH: 9
<212> TYPE: PRT
<213> ORGANISM: Artificial sequence
<220> FEATURE:
```

<223> OTHER INFORMATION: Synthetic peptide

<400> SEQUENCE: 192

Gln Gln Ser Ala Asp Leu Pro Leu Thr
1               5

<210> SEQ ID NO 193
<211> LENGTH: 6
<212> TYPE: PRT
<213> ORGANISM: Artificial sequence
<220> FEATURE:
<223> OTHER INFORMATION: Synthetic peptide

<400> SEQUENCE: 193

Gln Gly Ile Asp Asn Tyr
1               5

<210> SEQ ID NO 194
<211> LENGTH: 9
<212> TYPE: PRT
<213> ORGANISM: Artificial sequence
<220> FEATURE:
<223> OTHER INFORMATION: Synthetic peptide

<400> SEQUENCE: 194

Gln Arg Tyr Asn Leu Ala Pro Ser Ala
1               5

<210> SEQ ID NO 195
<211> LENGTH: 6
<212> TYPE: PRT
<213> ORGANISM: Artificial sequence
<220> FEATURE:
<223> OTHER INFORMATION: Synthetic peptide

<400> SEQUENCE: 195

Gln Ser Ile Gly Ser Leu
1               5

<210> SEQ ID NO 196
<211> LENGTH: 6
<212> TYPE: PRT
<213> ORGANISM: Artificial sequence
<220> FEATURE:
<223> OTHER INFORMATION: Synthetic peptide

<400> SEQUENCE: 196

Gln Gln Phe Asn Ser Tyr
1               5

<210> SEQ ID NO 197
<211> LENGTH: 11
<212> TYPE: PRT
<213> ORGANISM: Artificial sequence
<220> FEATURE:
<223> OTHER INFORMATION: Synthetic peptide

<400> SEQUENCE: 197

Gln Ser Leu Leu His Ser Asn Gly Glu Thr Tyr
1               5                   10

<210> SEQ ID NO 198
<211> LENGTH: 9
<212> TYPE: PRT
<213> ORGANISM: Artificial sequence
<220> FEATURE:
<223> OTHER INFORMATION: Synthetic peptide

<400> SEQUENCE: 198

Met Gln Ser Val Leu Leu Pro Tyr Thr
1               5

<210> SEQ ID NO 199
<211> LENGTH: 6
<212> TYPE: PRT
<213> ORGANISM: Artificial sequence
<220> FEATURE:
<223> OTHER INFORMATION: Synthetic peptide

<400> SEQUENCE: 199

Gln Ser Ile Asn Thr Tyr
1               5

<210> SEQ ID NO 200
<211> LENGTH: 9
<212> TYPE: PRT
<213> ORGANISM: Artificial sequence
<220> FEATURE:
<223> OTHER INFORMATION: Synthetic peptide

<400> SEQUENCE: 200

Gln Gln Ser Phe Thr Thr Pro Tyr Thr
1               5

<210> SEQ ID NO 201
<211> LENGTH: 6
<212> TYPE: PRT
<213> ORGANISM: Artificial sequence
<220> FEATURE:
<223> OTHER INFORMATION: Synthetic peptide

<400> SEQUENCE: 201

Gln Ser Ile Ser Arg Trp
1               5

<210> SEQ ID NO 202
<211> LENGTH: 9
<212> TYPE: PRT
<213> ORGANISM: Artificial sequence
<220> FEATURE:
<223> OTHER INFORMATION: Synthetic peptide

<400> SEQUENCE: 202

Gln Gln Tyr Asp Thr Tyr Pro Trp Thr
1               5

<210> SEQ ID NO 203
<211> LENGTH: 7
<212> TYPE: PRT
<213> ORGANISM: Artificial sequence
<220> FEATURE:
<223> OTHER INFORMATION: Synthetic peptide

<400> SEQUENCE: 203

Gln Ser Val Ser Ser Ser Tyr
1               5

<210> SEQ ID NO 204
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 204

Gln Gln Tyr Gly Ser Ser Ala Ile Thr
1               5

<210> SEQ ID NO 205
<211> LENGTH: 11
<212> TYPE: PRT
<213> ORGANISM: Artificial sequence
<220> FEATURE:
<223> OTHER INFORMATION: Synthetic peptide

<400> SEQUENCE: 205

Gln Ser Leu Leu His Ser Asn Gly Tyr Asn Phe
1               5                   10

<210> SEQ ID NO 206
<211> LENGTH: 7
<212> TYPE: PRT
<213> ORGANISM: Artificial sequence
<220> FEATURE:
<223> OTHER INFORMATION: Synthetic peptide

<400> SEQUENCE: 206

Gln Ser Val Tyr Ser Tyr Tyr
1               5

<210> SEQ ID NO 207
<211> LENGTH: 11
<212> TYPE: PRT
<213> ORGANISM: Artificial sequence
<220> FEATURE:
<223> OTHER INFORMATION: Synthetic peptide

<400> SEQUENCE: 207

Gln Tyr Tyr Gly Asn Ser His Gln Gly Ala Ala
1               5                   10

<210> SEQ ID NO 208
<211> LENGTH: 12
<212> TYPE: PRT
<213> ORGANISM: Artificial sequence
<220> FEATURE:
<223> OTHER INFORMATION: Synthetic peptide

<400> SEQUENCE: 208

His Ser Leu Leu Tyr Ser Ser Asp Asn Lys Asn Tyr
1               5                   10

<210> SEQ ID NO 209
<211> LENGTH: 9
<212> TYPE: PRT
<213> ORGANISM: Artificial sequence
<220> FEATURE:
<223> OTHER INFORMATION: Synthetic peptide

<400> SEQUENCE: 209

Gln Gln Tyr Tyr Thr Lys Ser Phe Thr
1               5

<210> SEQ ID NO 210
<211> LENGTH: 9
<212> TYPE: PRT
<213> ORGANISM: Artificial sequence
<220> FEATURE:
<223> OTHER INFORMATION: Synthetic peptide

<400> SEQUENCE: 210
```

```
Ser Ser Asn Val Gly Ala Tyr Asn Tyr
1               5

<210> SEQ ID NO 211
<211> LENGTH: 10
<212> TYPE: PRT
<213> ORGANISM: Artificial sequence
<220> FEATURE:
<223> OTHER INFORMATION: Synthetic peptide

<400> SEQUENCE: 211

Tyr Ser Tyr Ala Gly Ser Tyr Thr Trp Ile
1               5                   10

<210> SEQ ID NO 212
<211> LENGTH: 9
<212> TYPE: PRT
<213> ORGANISM: Artificial sequence
<220> FEATURE:
<223> OTHER INFORMATION: Synthetic peptide

<400> SEQUENCE: 212

Ile Ser Asp Ile Gly Gly Tyr Asp Tyr
1               5

<210> SEQ ID NO 213
<211> LENGTH: 12
<212> TYPE: PRT
<213> ORGANISM: Artificial sequence
<220> FEATURE:
<223> OTHER INFORMATION: Synthetic peptide

<400> SEQUENCE: 213

Ser Ser Tyr Thr Arg Thr Tyr Thr Pro His Val Val
1               5                   10

<210> SEQ ID NO 214
<211> LENGTH: 9
<212> TYPE: PRT
<213> ORGANISM: Artificial sequence
<220> FEATURE:
<223> OTHER INFORMATION: Synthetic peptide

<400> SEQUENCE: 214

Ser Ser Asp Ile Gly Asn Asn Asn Tyr
1               5

<210> SEQ ID NO 215
<211> LENGTH: 10
<212> TYPE: PRT
<213> ORGANISM: Artificial sequence
<220> FEATURE:
<223> OTHER INFORMATION: Synthetic peptide

<400> SEQUENCE: 215

Ser Ser Tyr Thr Asn Asn Arg Thr Phe Ser
1               5                   10

<210> SEQ ID NO 216
<211> LENGTH: 6
<212> TYPE: PRT
<213> ORGANISM: Artificial sequence
<220> FEATURE:
<223> OTHER INFORMATION: Synthetic peptide

<400> SEQUENCE: 216
```

```
Lys Leu Gly Asp Arg Tyr
1               5

<210> SEQ ID NO 217
<211> LENGTH: 6
<212> TYPE: PRT
<213> ORGANISM: Artificial sequence
<220> FEATURE:
<223> OTHER INFORMATION: Synthetic peptide

<400> SEQUENCE: 217

Gln Ala Trp Asp Thr Ser
1               5

<210> SEQ ID NO 218
<211> LENGTH: 9
<212> TYPE: PRT
<213> ORGANISM: Artificial sequence
<220> FEATURE:
<223> OTHER INFORMATION: Synthetic peptide

<400> SEQUENCE: 218

Asn Ser Asp Val Gly Gly Tyr Asp Tyr
1               5

<210> SEQ ID NO 219
<211> LENGTH: 10
<212> TYPE: PRT
<213> ORGANISM: Artificial sequence
<220> FEATURE:
<223> OTHER INFORMATION: Synthetic peptide

<400> SEQUENCE: 219

Cys Ser Tyr Ala Gly Ser Tyr Thr Phe Val
1               5                   10

<210> SEQ ID NO 220
<211> LENGTH: 127
<212> TYPE: PRT
<213> ORGANISM: Artificial sequence
<220> FEATURE:
<223> OTHER INFORMATION: Synthetic peptide

<400> SEQUENCE: 220

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Ala Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Leu Gly Ile Ser Asp Leu Leu Tyr Pro Ile Tyr
            100                 105                 110

Tyr Phe Asp Tyr Trp Gly Gln Gly Thr Leu Val Thr Val Ser Ser
        115                 120                 125

<210> SEQ ID NO 221
<211> LENGTH: 107
```

<212> TYPE: PRT
<213> ORGANISM: Artificial sequence
<220> FEATURE:
<223> OTHER INFORMATION: Synthetic peptide

<400> SEQUENCE: 221

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Ser Tyr
            20                  25                  30

Leu Asn Trp Tyr Gln Gln Lys Pro Gly Lys Ala Pro Asn Leu Leu Met
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Ile Pro Arg
                85                  90                  95

Thr Phe Gly Gln Gly Thr Gln Leu Glu Ile Lys
            100                 105

<210> SEQ ID NO 222
<211> LENGTH: 129
<212> TYPE: PRT
<213> ORGANISM: Artificial sequence
<220> FEATURE:
<223> OTHER INFORMATION: Synthetic peptide

<400> SEQUENCE: 222

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Ser Gly Asn Asn Gly Asn Thr Asn Tyr Ala Gln Lys Leu
    50                  55                  60

Gln Gly Arg Leu Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Asp Ile Val Val Val Gly Ala Thr Gly Thr Tyr
            100                 105                 110

Tyr Tyr Gly Met Asp Val Trp Gly Gln Gly Thr Leu Val Thr Val Ser
        115                 120                 125

Ser

<210> SEQ ID NO 223
<211> LENGTH: 107
<212> TYPE: PRT
<213> ORGANISM: Artificial sequence
<220> FEATURE:
<223> OTHER INFORMATION: Synthetic peptide

<400> SEQUENCE: 223

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Ser Leu Arg
                85                  90                  95

Thr Phe Gly Gln Gly Thr Gln Leu Glu Ile Lys
                100                 105

<210> SEQ ID NO 224
<211> LENGTH: 120
<212> TYPE: PRT
<213> ORGANISM: Artificial sequence
<220> FEATURE:
<223> OTHER INFORMATION: Synthetic peptide

<400> SEQUENCE: 224

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30

Tyr Met Ser Trp Val Arg Gln Ala Pro Gly Lys Gly Leu Glu Trp Val
        35                  40                  45

Ser Ile Phe Tyr Ser Asp Gly Thr Thr Tyr Asn Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Ser Gly Tyr Asp Ala Tyr Tyr Met Asp Val Trp Gly Gln
                100                 105                 110

Gly Thr Leu Val Thr Val Ser Ser
        115                 120

<210> SEQ ID NO 225
<211> LENGTH: 107
<212> TYPE: PRT
<213> ORGANISM: Artificial sequence
<220> FEATURE:
<223> OTHER INFORMATION: Synthetic peptide

<400> SEQUENCE: 225

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
            35                  40                  45

Tyr Gln Ala Ser Thr Leu Glu Arg Gly Val Pro Ser Arg Phe Ser Gly
        50                  55                  60

Ser Gly Ala Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Pro Leu
                85                  90                  95

Thr Phe Gly Gly Gly Thr Lys Val Glu Leu Lys

<210> SEQ ID NO 226
<211> LENGTH: 128
<212> TYPE: PRT
<213> ORGANISM: Artificial sequence
<220> FEATURE:
<223> OTHER INFORMATION: Synthetic peptide

<400> SEQUENCE: 226

Gln Val Gln Leu Val Gln Ser Gly Ala Glu Val Lys Lys Pro Gly Ser
1               5                   10                  15
Ser Val Lys Val Ser Cys Lys Ala Ser Gly Ala Thr Phe Gly Ser Asp
            20                  25                  30
Thr Val Thr Trp Val Arg Gln Ala Pro Gly Gln Gly Leu Glu Trp Met
        35                  40                  45
Gly Gly Ile Ile Pro Phe Phe Gly Glu Ala Asn Tyr Ala Gln Arg Phe
    50                  55                  60
Gln Gly Arg Val Thr Ile Thr Ala Asp Lys Ser Thr Asn Thr Ala Tyr
65                  70                  75                  80
Met Glu Leu Ser Ser Leu Arg Ser Glu Asp Thr Ala Val Tyr Phe Cys
                85                  90                  95
Ala Arg Gln Ile Asn Glu Met Ala Thr Phe Gly Glu Ile His Tyr Tyr
            100                 105                 110
Thr Tyr Met Asp Val Trp Gly Gln Gly Thr Leu Val Thr Val Ser Ser
        115                 120                 125

<210> SEQ ID NO 227
<211> LENGTH: 109
<212> TYPE: PRT
<213> ORGANISM: Artificial sequence
<220> FEATURE:
<223> OTHER INFORMATION: Synthetic peptide

<400> SEQUENCE: 227

Gly Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Asn Tyr Tyr Ala
            20                  25                  30
Ser Trp Tyr Gln Gln Lys Pro Arg Gln Ala Pro Val Leu Val Phe Tyr
        35                  40                  45
Gly Lys Asn Asn Arg Pro Ser Gly Ile Pro Asp Arg Phe Ser Gly Ser
    50                  55                  60
Ser Ser Gly Asn Thr Ala Ser Leu Thr Ile Ser Gly Ala Gln Ala Glu
65                  70                  75                  80
Asp Glu Ala Asp Tyr Tyr Cys Asn Ser Arg Asp Ser Ser Ser Asn His
                85                  90                  95
Leu Val Phe Gly Gly Gly Thr Lys Leu Thr Val Leu Ser
            100                 105

<210> SEQ ID NO 228
<211> LENGTH: 106
<212> TYPE: PRT
<213> ORGANISM: Artificial sequence
<220> FEATURE:
<223> OTHER INFORMATION: Synthetic peptide

<400> SEQUENCE: 228

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Ser Thr
            20                  25                  30

Tyr Leu Ala Trp Tyr Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr His Ser Ser Leu
                85                  90                  95

Phe Gly Gly Gly Thr Lys Val Glu Ile Lys
            100                 105

<210> SEQ ID NO 229
<211> LENGTH: 120
<212> TYPE: PRT
<213> ORGANISM: Artificial sequence
<220> FEATURE:
<223> OTHER INFORMATION: Synthetic peptide

<400> SEQUENCE: 229

Gln Val Gln Leu Val Gln Ser Gly Pro Gly Leu Val Lys Pro Ser Glu
1               5                   10                  15

Thr Leu Ser Leu Thr Cys Thr Val Ser Ser Asp Ser Ile Arg Ser Tyr
            20                  25                  30

Ser Trp Ser Trp Leu Arg Gln Pro Pro Gly Lys Gly Leu Glu Trp Ile
        35                  40                  45

Gly Phe Ile Tyr Tyr Ser Gly Asn Ile Asn Tyr Asn Pro Ser Leu Lys
 50                  55                  60

Ser Arg Val Thr Ile Ser Val Asp Thr Ser Lys Asn Gln Leu Ser Leu
 65                  70                  75                  80

Asn Leu Ser Ser Val Thr Ala Ala Asp Thr Ala Val Tyr Tyr Cys Ala
                85                  90                  95

Arg Asp Trp Ile Thr Ile Phe Gly Arg Tyr Phe Asp Val Trp Gly Arg
            100                 105                 110

Gly Thr Leu Val Thr Val Ser Ser
        115                 120

<210> SEQ ID NO 230
<211> LENGTH: 113
<212> TYPE: PRT
<213> ORGANISM: Artificial sequence
<220> FEATURE:
<223> OTHER INFORMATION: Synthetic peptide

<400> SEQUENCE: 230

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Leu Leu Tyr Ser
            20                  25                  30

Ser Asn Asn Lys Asn Phe Leu Thr Trp Tyr Gln His Lys Pro Gly Gln
        35                  40                  45

Pro Pro Lys Leu Leu Ile Ser Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Leu Tyr Tyr Cys Gln Gln

```
                    85                  90                  95

Tyr Tyr Thr Ile Pro Pro Thr Phe Gly Gln Gly Thr Lys Val Glu Ile
                100                 105                 110

Lys

<210> SEQ ID NO 231
<211> LENGTH: 121
<212> TYPE: PRT
<213> ORGANISM: Artificial sequence
<220> FEATURE:
<223> OTHER INFORMATION: Synthetic peptide

<400> SEQUENCE: 231

Gln Val Gln Leu Val Gln Ser Gly Gly Gly Phe Val Gln Pro Gly Arg
1               5                   10                  15

Ser Leu Arg Leu Ser Cys Thr Ala Ser Gly Phe Asn Phe Gly Asp Tyr
                20                  25                  30

Val Met Ser Trp Val Arg Gln Ala Pro Gly Lys Gly Leu Glu Trp Val
            35                  40                  45

Gly Phe Ile Arg Gly Lys Thr Phe Gly Ala Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Ile Lys Ser Leu Lys Thr Glu Asp Thr Ala Val Tyr
                85                  90                  95

Tyr Cys Thr Arg Arg Ala Thr Ser Thr Trp Tyr Glu Asp Tyr Trp Gly
                100                 105                 110

Gln Gly Thr Leu Val Thr Val Ser Ser
            115                 120

<210> SEQ ID NO 232
<211> LENGTH: 113
<212> TYPE: PRT
<213> ORGANISM: Artificial sequence
<220> FEATURE:
<223> OTHER INFORMATION: Synthetic peptide

<400> SEQUENCE: 232

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
                20                  25                  30

Pro Asn Asn His Asn Tyr Leu Ala Trp Tyr Gln Gln Lys Pro Gly Gln
            35                  40                  45

Pro Pro Lys Leu Leu Ile Tyr Trp Ala Ser Ala Arg Glu Pro Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr His Ile Pro Pro Tyr Ser Phe Gly Gln Gly Thr Lys Leu Glu Ile
                100                 105                 110

Lys

<210> SEQ ID NO 233
<211> LENGTH: 127
<212> TYPE: PRT
<213> ORGANISM: Artificial sequence
```

```
<220> FEATURE:
<223> OTHER INFORMATION: Synthetic peptide

<400> SEQUENCE: 233

Gln Val Gln Leu Val Gln Ser Gly Pro Gly Leu Val Lys Pro Ser Gln
1               5                   10                  15

Thr Leu Ser Leu Thr Cys Thr Val Ser Gly Asp Ser Ile Ser Ser Gly
            20                  25                  30

Ser Tyr Tyr Trp Ser Trp Ile Arg Gln Pro Ala Gly Lys Gly Leu Glu
        35                  40                  45

Trp Ile Gly Arg Ile Tyr Thr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Asn Leu Ser Ser Val Thr Ala Ala Asp Thr Ala Val Tyr Tyr
                85                  90                  95

Cys Ala Arg Asp Pro Ile Thr Ile Phe Gly Val Ile Phe Gly Trp
            100                 105                 110

Gly Met Asp Val Trp Gly Gln Gly Thr Leu Val Thr Val Ser Ser
        115                 120                 125

<210> SEQ ID NO 234
<211> LENGTH: 112
<212> TYPE: PRT
<213> ORGANISM: Artificial sequence
<220> FEATURE:
<223> OTHER INFORMATION: Synthetic peptide

<400> SEQUENCE: 234

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Tyr Asn Tyr Leu Tyr Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Val Thr Phe Gly Pro Gly Thr Lys Val Asp Ile Lys
            100                 105                 110

<210> SEQ ID NO 235
<211> LENGTH: 140
<212> TYPE: PRT
<213> ORGANISM: Artificial sequence
<220> FEATURE:
<223> OTHER INFORMATION: Synthetic peptide

<400> SEQUENCE: 235

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asp Thr Tyr
            20                  25                  30

Ala Ile Ser Trp Val Arg Gln Ala Pro Gly Gln Gly Leu Glu Trp Met
        35                  40                  45
```

Gly Gly Ile Ile Pro Val Leu Gly Ile Val Asp Tyr Ala Gln Lys Phe
            50                  55                  60

Gln Gly Arg Val Thr Ile Thr Ala Ala Lys Phe Thr Asn Ile Ala Tyr
 65                  70                  75                  80

Met Glu Leu Ser Ser Leu Arg Ser Glu Asp Ala Ala Val Tyr Tyr Cys
                    85                  90                  95

Ala Arg Gly Leu Arg Ser Leu Ser Pro Arg Gly Gln Glu Gly Pro Thr
                100                 105                 110

Pro Ala Pro Gly Trp Arg Arg Ala Gln Tyr His Tyr Tyr Tyr Met Asp
            115                 120                 125

Val Trp Gly Thr Gly Thr Leu Val Thr Val Ser Ser
            130                 135                 140

<210> SEQ ID NO 236
<211> LENGTH: 108
<212> TYPE: PRT
<213> ORGANISM: Artificial sequence
<220> FEATURE:
<223> OTHER INFORMATION: Synthetic peptide

<400> SEQUENCE: 236

Glu Ile Val Met Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Pro Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Gly Thr Phe Gly Gly Gly Thr Lys Val Glu Ile Lys
            100                 105

<210> SEQ ID NO 237
<211> LENGTH: 127
<212> TYPE: PRT
<213> ORGANISM: Artificial sequence
<220> FEATURE:
<223> OTHER INFORMATION: Synthetic peptide

<400> SEQUENCE: 237

Gln Val Gln Leu Gln Glu Ser Gly Pro Gly Leu Val Arg Pro Ser Gln
 1               5                   10                  15

Thr Leu Ser Leu Thr Cys Thr Val Ser Gly Gly Ser Ile Asn Ser Asp
                20                  25                  30

Ser Tyr Tyr Trp Asn Trp Ile Arg Gln Pro Ala Gly Lys Gly Leu Glu
            35                  40                  45

Trp Leu Gly Arg Val Tyr Thr Ser Gly Ser Thr Asn Tyr Asn Pro Ser
 50                  55                  60

Leu Lys Ser Arg Val Thr Ile Ser Val Asp Thr Ser Lys Asn Gln Val
 65                  70                  75                  80

Ser Leu Arg Leu Asn Ser Val Thr Ala Ala Asp Thr Gly Val Tyr Tyr
                85                  90                  95

Cys Ala Arg Val Val Trp Gly Ser Tyr Arg Ser Tyr His Tyr Ser Tyr
                100                 105                 110

Gly Met Asp Val Trp Gly Gln Gly Thr Leu Val Thr Val Ser Ser
            115                 120                 125

<210> SEQ ID NO 238
<211> LENGTH: 108
<212> TYPE: PRT
<213> ORGANISM: Artificial sequence
<220> FEATURE:
<223> OTHER INFORMATION: Synthetic peptide

<400> SEQUENCE: 238

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Arg Pro Gly Gln Ala Pro Arg Leu Leu
        35                  40                  45

Phe Tyr Gly Ala Ser Tyr Arg Ala Thr Gly Ile Pro Asp Arg Phe Ser
    50                  55                  60

Ala Ser Gly Ser Gly Thr Asp Phe Ser Leu Thr Ile Asn Arg Leu Glu
65                  70                  75                  80

Pro Glu Asp Phe Ala Val Tyr Tyr Cys Gln Gln Ser Gly Ser Ser Pro
                85                  90                  95

Glu Thr Phe Gly Gln Gly Thr Lys Leu Glu Ile Lys
            100                 105

<210> SEQ ID NO 239
<211> LENGTH: 125
<212> TYPE: PRT
<213> ORGANISM: Artificial sequence
<220> FEATURE:
<223> OTHER INFORMATION: Synthetic peptide

<400> SEQUENCE: 239

Gln Val Gln Leu Val Gln Ser Gly Val Glu Val Lys Lys Pro Gly Ala
1               5                   10                  15

Ser Val Lys Val Ser Cys Lys Ala Ser Gly Tyr Ala Phe Thr Thr Tyr
            20                  25                  30

Ala Ile Ser Trp Val Arg Gln Ala Pro Gly Gln Gly Leu Glu Trp Met
        35                  40                  45

Gly Trp Ile Ser Thr Tyr Tyr Gly Thr Thr Tyr Tyr Ala Gln Asn Leu
    50                  55                  60

Gln Gly Arg Val Thr Met Thr Thr Asp Thr Ser Thr Ser Thr Ser Tyr
65                  70                  75                  80

Leu Glu Leu Arg Ser Leu Arg Ser Asp Asp Thr Ala Val Tyr Tyr Cys
                85                  90                  95

Val Arg Asp Arg Ser Trp Leu Ala Thr Ser Arg Pro Tyr Asp Ala Phe
            100                 105                 110

Asp Ile Trp Gly Gln Gly Thr Leu Val Thr Val Ser Ser
            115                 120                 125

<210> SEQ ID NO 240
<211> LENGTH: 107
<212> TYPE: PRT
<213> ORGANISM: Artificial sequence
<220> FEATURE:
<223> OTHER INFORMATION: Synthetic peptide

<400> SEQUENCE: 240

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Thr
            20                  25                  30

Leu Ala Trp Tyr Gln Gln Lys Pro Gly Lys Ala Pro Lys Leu Leu Ile
            35                  40                  45

Tyr Gly Ala Ser Ser Leu Glu Ser Gly Val Pro Ser Arg Phe Asn Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Pro Tyr Tyr Phe Pro Arg
                85                  90                  95

Thr Phe Gly Gln Gly Thr Arg Leu Glu Ile Arg
            100                 105
```

<210> SEQ ID NO 241
<211> LENGTH: 125
<212> TYPE: PRT
<213> ORGANISM: Artificial sequence
<220> FEATURE:
<223> OTHER INFORMATION: Synthetic peptide

<400> SEQUENCE: 241

```
Gln Val Gln Leu Val Gln Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Arg Phe Tyr Trp Ser Trp Val Arg Gln Pro Ala Gly Arg Gly Leu Glu
            35                  40                  45

Trp Ile Gly Arg Ile Tyr Thr Ser Gly Ser Thr Asn Tyr Asn Pro Ser
50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Thr Glu Leu Tyr Tyr Gly Ser Gly Ser Tyr Asp Pro Leu
            100                 105                 110

Trp Ser Trp Gly Gln Gly Thr Leu Val Thr Val Ser Ser
        115                 120                 125
```

<210> SEQ ID NO 242
<211> LENGTH: 107
<212> TYPE: PRT
<213> ORGANISM: Artificial sequence
<220> FEATURE:
<223> OTHER INFORMATION: Synthetic peptide

<400> SEQUENCE: 242

```
Asp Ile Val Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Asn
            20                  25                  30

Leu Asn Trp His Gln Gln Lys Pro Gly Lys Ala Pro Lys Leu Leu Ile
            35                  40                  45

Tyr Asp Ala Ser Asn Leu Glu Arg Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Gln Gln Asn Ala Asn Leu Pro His
                85                  90                  95

Thr Phe Gly Gln Gly Thr Lys Leu Glu Ile Lys
            100                 105

<210> SEQ ID NO 243
<211> LENGTH: 123
<212> TYPE: PRT
<213> ORGANISM: Artificial sequence
<220> FEATURE:
<223> OTHER INFORMATION: Synthetic peptide

<400> SEQUENCE: 243

Gln Val Gln Leu Val Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Phe Trp Asn Trp Ile Arg Gln Pro Ala Gly Lys Gly Leu Glu
        35                  40                  45

Trp Ile Gly Arg Ile Tyr Thr Ser Gly Thr Thr Asn Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Thr Ser Pro Tyr Tyr Tyr Asp Ser Ser His Tyr Tyr Asp Tyr
            100                 105                 110

Trp Gly Gln Gly Thr Leu Val Thr Val Ser Ser
        115                 120

<210> SEQ ID NO 244
<211> LENGTH: 107
<212> TYPE: PRT
<213> ORGANISM: Artificial sequence
<220> FEATURE:
<223> OTHER INFORMATION: Synthetic peptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Phe Asp Ala Ser Asn Leu Glu Lys Gly Val Pro Ser Arg Phe Ser Ala
    50                  55                  60

Thr Gly Ser Ala Thr Asp Phe Thr Phe Thr Ile Ser Ser Leu Gln Pro
65                  70                  75                  80

Glu Asp Thr Ala Thr Tyr Tyr Cys Gln Gln Ser Ala Asp Leu Pro Leu
                85                  90                  95

Thr Phe Gly Gln Gly Thr Arg Leu Asp Ile Lys
            100                 105

<210> SEQ ID NO 245
<211> LENGTH: 120
<212> TYPE: PRT
<213> ORGANISM: Artificial sequence
<220> FEATURE:
<223> OTHER INFORMATION: Synthetic peptide

<400> SEQUENCE: 245

Gln Val Gln Leu Val Gln Ser Gly Pro Gly Leu Val Lys Pro Ser Gln
1               5                   10                  15

Thr Leu Ser Leu Thr Cys Asn Val Ser Gly Gly Ser Ile Ser Asn Gly
            20                  25                  30

Gly Tyr His Trp Ser Trp Ile Arg Gln Val Pro Gly Lys Gly Leu Glu
        35                  40                  45

Trp Ile Gly His Ile Tyr Tyr Ser Gly Ser Thr Tyr Thr Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Ile Arg Gly Gly Pro Ile Asp Tyr Trp Gly Gln
            100                 105                 110

Gly Thr Leu Val Thr Val Ser Ser
        115                 120

<210> SEQ ID NO 246
<211> LENGTH: 107
<212> TYPE: PRT
<213> ORGANISM: Artificial sequence
<220> FEATURE:
<223> OTHER INFORMATION: Synthetic peptide

<400> SEQUENCE: 246

Asp Ile Gln Met Thr Gln Ser Pro Ser Ser Leu Ser Ala Ser Val Gly
1               5                   10                  15

Glu Arg Val Thr Ile Thr Cys Arg Ala Ser Gln Gly Ile Asp Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Leu Ala Pro Ser
                85                  90                  95

Ala Phe Gly Gln Gly Thr Lys Val Glu Ile Arg
            100                 105

<210> SEQ ID NO 247
<211> LENGTH: 125
<212> TYPE: PRT
<213> ORGANISM: Artificial sequence
<220> FEATURE:
<223> OTHER INFORMATION: Synthetic peptide

<400> SEQUENCE: 247

Gln Val Gln Leu Val Gln Ser Gly Ala Glu Met Arg Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Leu
        35                  40                  45

Gly Trp Ile Asn Pro Tyr Ser Gly Gly Thr Asn Tyr Ala Gln Lys Phe
    50                  55                  60

Gln Gly Arg Val Thr Met Thr Arg Asp Thr Ser Ile Ser Thr Ala His
65                  70                  75                  80

Met Glu Leu Ser Gly Leu Arg Ser Asp Asp Thr Ala Leu Tyr Phe Cys
                85                  90                  95

Ala Arg Leu Tyr Gly Ala Gly Ser His Tyr Asn His Tyr Asn Gly Met
            100                 105                 110

Asp Val Trp Gly Gln Gly Thr Leu Val Thr Val Ser Ser
        115                 120                 125

<210> SEQ ID NO 248
<211> LENGTH: 104
<212> TYPE: PRT
<213> ORGANISM: Artificial sequence
<220> FEATURE:
<223> OTHER INFORMATION: Synthetic peptide

<400> SEQUENCE: 248

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Val Ala Thr Tyr Tyr Cys Gln Gln Phe Asn Ser Tyr Phe Gly
                85                  90                  95

Gly Gly Thr Lys Val Glu Ile Lys
            100

<210> SEQ ID NO 249
<211> LENGTH: 99
<212> TYPE: PRT
<213> ORGANISM: Artificial sequence
<220> FEATURE:
<223> OTHER INFORMATION: Synthetic peptide

<400> SEQUENCE: 249

Gln Val Gln Leu Gln Gln Ser Gly Pro Gly Leu Val Arg Pro Ser Gln
1               5                   10                  15

Thr Leu Ser Leu Thr Cys Ser Val Ser Gly Gly Ser Val Ser Ser Gly
            20                  25                  30

Arg Tyr Phe Trp Asn Trp Ile Arg Gln Ser Ala Gly Lys Gly Leu Glu
        35                  40                  45

Trp Ile Gly Arg Ile His Ser Ser Gly Arg Thr Asn Ser Asn Pro Ser
    50                  55                  60

Leu Lys Ser Arg Val Thr Ile Ser Val Asp Thr Ser Lys Asn Gln Phe
65                  70                  75                  80

Ser Leu His Leu Gly Ser Val Thr Ala Ala Asp Thr Ala Val Tyr Tyr
                85                  90                  95

Cys Ala Arg

<210> SEQ ID NO 250
<211> LENGTH: 112
<212> TYPE: PRT
<213> ORGANISM: Artificial sequence

```
<220> FEATURE:
<223> OTHER INFORMATION: Synthetic peptide

<400> SEQUENCE: 250

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asn Gly Glu Thr Tyr Leu Phe Trp Tyr Leu Lys Pro Gly Gln Pro
        35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Val Leu Leu Pro Tyr Thr Phe Gly Gln Gly Thr Lys Leu Glu Ile Lys
            100                 105                 110

<210> SEQ ID NO 251
<211> LENGTH: 129
<212> TYPE: PRT
<213> ORGANISM: Artificial sequence
<220> FEATURE:
<223> OTHER INFORMATION: Synthetic peptide

<400> SEQUENCE: 251

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Arg Gly
            20                  25                  30

Leu Tyr Tyr Trp Ser Trp Ile Arg Gln Pro Ala Gly Lys Gly Leu Glu
        35                  40                  45

Trp Ile Gly Arg Ile Tyr Thr Ser Gly Ser Ile Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Ile Ala Thr Asp Thr Ala Val Tyr Tyr
                85                  90                  95

Cys Val Arg Asp Ala Pro Trp Gly Asp Phe Leu Thr Gly Tyr Phe Gly
            100                 105                 110

Phe Tyr Gly Met Asp Val Trp Gly Gln Gly Thr Leu Val Thr Val Ser
        115                 120                 125

Ser

<210> SEQ ID NO 252
<211> LENGTH: 107
<212> TYPE: PRT
<213> ORGANISM: Artificial sequence
<220> FEATURE:
<223> OTHER INFORMATION: Synthetic peptide

<400> SEQUENCE: 252

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Lys Phe Leu Ile
```

```
            35                  40                  45

Tyr Ala Ala Ser Ser Leu His Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Asp Asp Phe Ala Thr Tyr Tyr Cys Gln Gln Ser Phe Thr Thr Pro Tyr
                 85                  90                  95

Thr Phe Gly Gln Gly Thr Lys Leu Glu Ile Lys
            100                 105

<210> SEQ ID NO 253
<211> LENGTH: 131
<212> TYPE: PRT
<213> ORGANISM: Artificial sequence
<220> FEATURE:
<223> OTHER INFORMATION: Synthetic peptide

<400> SEQUENCE: 253

Gln Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Ser Phe
                 20                  25                  30

Glu Ile His Trp Val Arg Gln Gly Ser Gly Gln Gly Leu Glu Trp Met
             35                  40                  45

Gly Arg Met Asn Pro Lys Ser Gly Asp Thr Val Ser Ala Gln Lys Phe
 50                  55                  60

Gln Gly Arg Val Thr Leu Thr Arg Asp Thr Ser Ile Asn Ala Ala Tyr
 65                  70                  75                  80

Met Glu Leu Gly Ser Leu Ser Ser Glu Asp Thr Ala Val Tyr Tyr Cys
                 85                  90                  95

Ala Arg Gly Pro His Val Gly Glu Val Val Pro Gly Leu Met Ala Gly
            100                 105                 110

Thr Tyr Tyr Phe Pro Leu Asp Val Trp Gly Gln Gly Thr Leu Val Thr
            115                 120                 125

Val Ser Ser
    130

<210> SEQ ID NO 254
<211> LENGTH: 107
<212> TYPE: PRT
<213> ORGANISM: Artificial sequence
<220> FEATURE:
<223> OTHER INFORMATION: Synthetic peptide

<400> SEQUENCE: 254

Asp Ile Gln Met Thr Gln Ser Pro Ser Thr Leu Ser Ala Ser Ile Gly
  1               5                  10                  15

Asp Arg Val Thr Ile Thr Cys Arg Ala Ser Gln Ser Ile Ser Arg Trp
                 20                  25                  30

Leu Ala Trp Tyr Gln Gln Lys Pro Gly Lys Ala Pro Lys Leu Leu Ile
             35                  40                  45

Tyr Lys Val Ser Asp Leu Gln Ser Gly Val Pro Ser Arg Phe Ser Gly
 50                  55                  60

Ser Gly Tyr Gly Thr Glu Phe Thr Leu Thr Ile Gly Ser Leu Gln Pro
 65                  70                  75                  80

Asp Asp Leu Ala Thr Tyr Tyr Cys Gln Gln Tyr Asp Thr Tyr Pro Trp
                 85                  90                  95
```

Thr Phe Gly Gln Gly Thr Lys Leu Glu Ile Lys
            100                 105

<210> SEQ ID NO 255
<211> LENGTH: 120
<212> TYPE: PRT
<213> ORGANISM: Artificial sequence
<220> FEATURE:
<223> OTHER INFORMATION: Synthetic peptide

<400> SEQUENCE: 255

Gln Val Gln Leu Val Gln Ser Gly Ala Glu Val Lys Pro Gly Ser
1               5                   10                  15

Ser Val Lys Val Ser Cys Asn Ala Ser Gly Thr Phe Ser Asn Ser
            20                  25                  30

Ile Leu Asn Trp Val Arg Gln Ala Pro Gly Gln Gly Leu Glu Trp Met
            35                  40                  45

Gly Arg Ile Ile Pro Ile Val Gly Leu Val Asn Phe Ala Gln Lys Phe
50                  55                  60

Glu Gly Arg Val Thr Phe Thr Ala Asp Lys Phe Thr Asn Thr Ala Tyr
65                  70                  75                  80

Met Glu Leu Asn Ser Leu Arg Phe Glu Asp Thr Ala Val Tyr Tyr Cys
                85                  90                  95

Ala Ile Asn Gly Gly Lys Tyr Pro Gly Tyr Phe Asp Tyr Trp Gly Gln
            100                 105                 110

Gly Thr Leu Val Thr Val Ser Ser
            115                 120

<210> SEQ ID NO 256
<211> LENGTH: 108
<212> TYPE: PRT
<213> ORGANISM: Artificial sequence
<220> FEATURE:
<223> OTHER INFORMATION: Synthetic peptide

<400> SEQUENCE: 256

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln His Gln Pro Gly Gln Ala Pro Arg Leu Leu
            35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Ile Ile Ser Arg Leu Glu
65                  70                  75                  80

Pro Glu Asp Phe Ala Val Tyr Tyr Cys Gln Gln Tyr Gly Ser Ser Ala
                85                  90                  95

Ile Thr Phe Gly Gln Gly Thr Arg Leu Glu Ile Lys
            100                 105

<210> SEQ ID NO 257
<211> LENGTH: 127
<212> TYPE: PRT
<213> ORGANISM: Artificial sequence
<220> FEATURE:
<223> OTHER INFORMATION: Synthetic peptide

<400> SEQUENCE: 257

Gln Val Gln Leu Gln Glu Ser Gly Pro Gly Leu Val Lys Pro Ser Glu

```
                1               5                   10                  15
            Thr Leu Ser Leu Thr Cys Ala Val Ser Gly Gly Ser Ile Arg Ser Tyr
                        20                  25                  30

Phe Trp Ser Trp Ile Arg Gln Ala Pro Gly Lys Gly Leu Glu Trp Ile
                        35                  40                  45

Gly Asn Ile Tyr Tyr Ser Gly Arg Pro Asn Tyr Asn Pro Ser Leu Lys
                        50                  55                  60

Asn Arg Val Thr Ile Ser Ala Asp Thr Ser Asn Asn Glu Val Ser Leu
            65                  70                  75                  80

Glu Leu Ser Ala Val Thr Ala Ala Asp Thr Ala Val Tyr Phe Cys Ala
                        85                  90                  95

Arg Asp Glu Arg Leu Leu Val Glu Val Gly Thr Asp His Phe Tyr Tyr
                        100                 105                 110

Gly Leu Asp Val Trp Gly Gln Gly Thr Leu Val Thr Val Ser Ser
                        115                 120                 125

<210> SEQ ID NO 258
<211> LENGTH: 96
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (91)..(91)
<223> OTHER INFORMATION: Xaa can be any naturally occurring amino acid

<400> SEQUENCE: 258

Glu Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Xaa Tyr Cys Met Gln Ala
            85                  90                  95

<210> SEQ ID NO 259
<211> LENGTH: 125
<212> TYPE: PRT
<213> ORGANISM: Artificial sequence
<220> FEATURE:
<223> OTHER INFORMATION: Synthetic peptide

<400> SEQUENCE: 259

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Gly Ile Ser Trp Val Arg Gln Ala Pro Gly Gln Gly Leu Glu Trp Leu
        35                  40                  45

Gly Trp Ile Asn Thr Tyr Asn Gly Asp Thr Asn Tyr Ala Gln Lys Phe
    50                  55                  60

Gln Gly Arg Val Thr Met Thr Thr Asp Thr Ser Thr Ser Thr Gly Phe
65                  70                  75                  80
```

```
Met Glu Leu Arg Ser Leu Arg Ser Asp Asp Thr Ala Val Tyr Tyr Cys
                85                  90                  95

Ala Arg Asp Ser His Leu Ile Ser Ile Ala Val Ala Asn Thr Pro Asn
            100                 105                 110

Asp Phe Trp Gly Gln Gly Thr Leu Val Thr Val Ser Ser
        115                 120                 125

<210> SEQ ID NO 260
<211> LENGTH: 110
<212> TYPE: PRT
<213> ORGANISM: Artificial sequence
<220> FEATURE:
<223> OTHER INFORMATION: Synthetic peptide

<400> SEQUENCE: 260

Glu Ile Val Met Thr Gln Ser Pro Gly Thr Leu Ser Leu Ser Pro Gly
1               5                   10                  15

Asp Arg Val Thr Leu Ser Cys Arg Ala Ser Gln Ser Val Tyr Ser Tyr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Tyr Tyr Gly Asn Ser His
                85                  90                  95

Gln Gly Ala Ala Phe Gly Gln Gly Thr Lys Val Glu Val Lys
            100                 105                 110

<210> SEQ ID NO 261
<211> LENGTH: 130
<212> TYPE: PRT
<213> ORGANISM: Artificial sequence
<220> FEATURE:
<223> OTHER INFORMATION: Synthetic peptide

<400> SEQUENCE: 261

Gln Val Gln Leu Gln Glu Ser Gly Pro Gly Leu Val Lys Pro Ser Gln
1               5                   10                  15

Thr Leu Ser Leu Thr Cys Asn Val Ser Gly Gly Ser Ile Ser Ser Asp
            20                  25                  30

Asp Arg Tyr Trp Ser Trp Ile Arg Gln Pro Pro Gly Lys Gly Leu Glu
        35                  40                  45

Trp Leu Gly Phe Ile Tyr Tyr Ser Gly Ser Thr Asp Tyr Asn Pro Ser
    50                  55                  60

Leu Lys Ser Arg Val Thr Met Ser Leu Asp Thr Ser Lys Asn Gln Phe
65                  70                  75                  80

Ser Leu Lys Leu Asn Ser Val Thr Ala Ala Asp Thr Ala Met Tyr Tyr
                85                  90                  95

Cys Ala Thr Val Thr Ala Tyr Ser Pro Ala Thr Met Ile Val Val Gly
            100                 105                 110

Thr Glu His Gly Phe Asp Tyr Trp Gly Gln Gly Thr Leu Val Thr Val
        115                 120                 125

Ser Ser
    130
```

-continued

```
<210> SEQ ID NO 262
<211> LENGTH: 107
<212> TYPE: PRT
<213> ORGANISM: Artificial sequence
<220> FEATURE:
<223> OTHER INFORMATION: Synthetic peptide

<400> SEQUENCE: 262

Asp Ile Val Met Thr Gln Ser Pro Ser Ser Leu Ser Ala Ser Val Gly
1               5                   10                  15

Asp Arg Val Thr Ile Phe Cys Arg Ala Thr Gln Ser Ile Arg Ser Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 263
<211> LENGTH: 118
<212> TYPE: PRT
<213> ORGANISM: Artificial sequence
<220> FEATURE:
<223> OTHER INFORMATION: Synthetic peptide

<400> SEQUENCE: 263

Gln Val Gln Leu Val Glu Ser Gly Gly Val Val Gln Pro Gly Gly
1               5                   10                  15

Ser Leu Arg Leu Ser Cys Glu Val Ser Gly Leu Thr Phe Ser Asn Phe
            20                  25                  30

Gly Met Gln Trp Val Arg Gln Ala Pro Gly Lys Gly Leu Glu Trp Val
        35                  40                  45

Ala Phe Ile Arg Phe Asp Gly Ser Asn Lys Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Gly Ser Leu Arg Ala Glu Asp Thr Ala Val Tyr Phe Cys
                85                  90                  95

Gly Arg Val Leu Tyr Gly Ala Ala Ala Asp Phe Trp Gly Gln Gly Thr
            100                 105                 110

Leu Val Thr Val Ser Ser
        115

<210> SEQ ID NO 264
<211> LENGTH: 113
<212> TYPE: PRT
<213> ORGANISM: Artificial sequence
<220> FEATURE:
<223> OTHER INFORMATION: Synthetic peptide

<400> SEQUENCE: 264

Asp Ile Val Met Thr Gln Ser Pro Asp Ser Leu Ala Val Ser Leu Gly
1               5                   10                  15

Glu Arg Ala Thr Ile Asn Cys Thr Ser Ser His Ser Leu Leu Tyr Ser
            20                  25                  30
```

```
Ser Asp Asn Lys Asn Tyr Leu Thr Trp Tyr Gln Gln Lys Ala Gly Gln
         35                  40                  45

Pro Pro Lys Leu Leu Ile Tyr Trp Ala Ser Thr Arg Gln Ser Gly Val
     50                  55                  60

Pro Asp Arg Phe Ser Gly Ser Gly Ser Gly Thr Glu Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Lys Ser Phe Thr Phe Gly Gln Gly Thr Lys Val Glu Ile
             100                 105                 110

Lys

<210> SEQ ID NO 265
<211> LENGTH: 129
<212> TYPE: PRT
<213> ORGANISM: Artificial sequence
<220> FEATURE:
<223> OTHER INFORMATION: Synthetic peptide

<400> SEQUENCE: 265

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Asn Trp Val Arg Gln Ala Pro Gly Gln Gly Leu Glu Trp Met
         35                  40                  45

Gly Gly Ile Ile Pro Ile Phe Gly Lys Pro Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95

Ala Arg Gly Gln Gly Glu Ile Val Val Met Val Gly His Asp Asp Gly
             100                 105                 110

Gly Asp Tyr Leu Gly Tyr Trp Gly Gln Gly Thr Leu Val Thr Val Ser
         115                 120                 125

Ser

<210> SEQ ID NO 266
<211> LENGTH: 111
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (16)..(16)
<223> OTHER INFORMATION: Xaa can be any naturally occurring amino acid

<400> SEQUENCE: 266

Gln Ser Ala Leu Thr Gln Pro Arg Ser Val Ser Gly Ser Pro Gly Xaa
 1               5                  10                  15

Ser Val Thr Ile Ser Cys Thr Gly Thr Ser Ser Asn Val Gly Ala Tyr
             20                  25                  30

Asn Tyr Val Ser Trp Tyr Gln Gln His Pro Gly Lys Ala Pro Lys Leu
         35                  40                  45

Met Ile Phe Asp Val Thr Lys Arg Pro Ser Gly Val Pro Asp Arg Phe
     50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Tyr Ser Tyr Ala Gly Ser
                85                  90                  95

Tyr Thr Trp Ile Phe Gly Gly Gly Thr Lys Leu Thr Val Leu Gly
            100                 105                 110

<210> SEQ ID NO 267
<211> LENGTH: 129
<212> TYPE: PRT
<213> ORGANISM: Artificial sequence
<220> FEATURE:
<223> OTHER INFORMATION: Synthetic peptide

<400> SEQUENCE: 267

Gln Val Gln Leu Val Gln Ser Gly Pro Gly Leu Val Lys Pro Ser Glu
1               5                   10                  15

Thr Leu Ser Leu Thr Cys Ser Val Ser Gly Gly Ser Ile Ser Gly Ser
            20                  25                  30

Ile Trp Thr Trp Ile Arg Gln Ser Pro Gly Lys Gly Leu Glu Trp Ile
        35                  40                  45

Gly Tyr Ile Ser Leu Ser Gly Ser Thr Asn Phe Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Arg Lys Ser Ser Lys Met Val Arg Gly Ile Glu Val Phe Tyr
            100                 105                 110

Tyr Tyr Tyr Met Asp Val Trp Gly Lys Gly Thr Leu Val Thr Val Ser
        115                 120                 125

Ser

<210> SEQ ID NO 268
<211> LENGTH: 113
<212> TYPE: PRT
<213> ORGANISM: Artificial sequence
<220> FEATURE:
<223> OTHER INFORMATION: Synthetic peptide

<400> SEQUENCE: 268

Gln Ser Ala Leu Thr Gln Pro Ala Ser Val Ser Gly Ser Pro Gly Gln
1               5                   10                  15

Ser Ile Thr Ile Ser Cys Thr Gly Thr Ile Ser Asp Ile Gly Gly Tyr
            20                  25                  30

Asp Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ser Ser Tyr Thr Arg Thr
                85                  90                  95

Tyr Thr Pro His Val Val Phe Gly Gly Gly Thr Lys Leu Thr Val Leu
            100                 105                 110

Gly

<210> SEQ ID NO 269
<211> LENGTH: 125
<212> TYPE: PRT
<213> ORGANISM: Artificial sequence
<220> FEATURE:
<223> OTHER INFORMATION: Synthetic peptide

<400> SEQUENCE: 269

```
Gln Val Gln Leu Val Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Phe Tyr Trp Ser Trp Ile Arg Gln Pro Ala Gly Lys Gly Leu Glu
        35                  40                  45

Trp Ile Gly Arg Phe Tyr Thr Thr Gly Ser Thr His Tyr Asn Pro Ser
    50                  55                  60

Leu Lys Ser Arg Val Thr Ile Ser Ala Asp Thr Ser Lys Asn His Phe
65                  70                  75                  80

Ser Leu Asn Leu Thr Ser Leu Thr Ala Ala Asp Thr Ala Val Tyr Tyr
                85                  90                  95

Cys Ala Arg Gly Pro Val Ser Tyr Ser Gly Asn Leu Tyr Tyr Phe
            100                 105                 110

Asp Tyr Trp Gly Leu Gly Thr Leu Val Thr Val Ser Ser
        115                 120                 125
```

<210> SEQ ID NO 270
<211> LENGTH: 110
<212> TYPE: PRT
<213> ORGANISM: Artificial sequence
<220> FEATURE:
<223> OTHER INFORMATION: Synthetic peptide

<400> SEQUENCE: 270

```
Gln Ser Ala Leu Thr Gln Pro Ala Ser Val Ser Gly Ser Pro Gly Gln
1               5                   10                  15

Ser Ile Thr Ile Thr Cys Thr Gly Thr Ser Ser Asp Ile Gly Asn Asn
            20                  25                  30

Asn Tyr Val Ser Trp Tyr Gln Gln His Pro Gly Lys Ala Pro Lys Leu
        35                  40                  45

Ile Ile Phe Asp Val Asn Lys Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Asn
                85                  90                  95

Arg Thr Phe Ser Phe Gly Gly Gly Thr Lys Val Thr Val Leu
            100                 105                 110
```

<210> SEQ ID NO 271
<211> LENGTH: 126
<212> TYPE: PRT
<213> ORGANISM: Artificial sequence
<220> FEATURE:
<223> OTHER INFORMATION: Synthetic peptide

<400> SEQUENCE: 271

```
Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Phe
```

```
                    20                  25                  30
Gly Ile His Trp Val Arg Gln Ala Pro Gly Lys Gly Leu Glu Trp Val
            35                  40                  45

Ala Phe Ile Arg Tyr Asp Gly Ser Asp Lys Phe Tyr Leu Asp Ser Val
        50                  55                  60

Lys Gly Arg Phe Thr Ile Ser Arg Asp Asn Ser Lys Asn Thr Leu Phe
65                  70                  75                  80

Leu Gln Met Ser Ser Leu Arg Val Glu Asp Thr Ala Val Tyr Tyr Cys
                85                  90                  95

Ala Lys Arg Gly Gly His Asp Tyr Gly Tyr Tyr Asp Asn Asn Arg Tyr
            100                 105                 110

Ile Asp Leu Trp Gly Arg Gly Thr Leu Val Thr Val Ser Ser
        115                 120                 125

<210> SEQ ID NO 272
<211> LENGTH: 93
<212> TYPE: PRT
<213> ORGANISM: Artificial sequence
<220> FEATURE:
<223> OTHER INFORMATION: Synthetic peptide

<400> SEQUENCE: 272

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Arg Tyr Thr
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Glu Thr Gln Ala Ile
65                  70                  75                  80

Asp Glu Ala Asp Tyr Tyr Cys Gln Ala Trp Asp Thr Ser
                85                  90

<210> SEQ ID NO 273
<211> LENGTH: 107
<212> TYPE: PRT
<213> ORGANISM: Artificial sequence
<220> FEATURE:
<223> OTHER INFORMATION: Synthetic peptide

<400> SEQUENCE: 273

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Pro Gly Lys Ala Pro Asn Leu Leu Ile
        35                  40                  45

Tyr Lys Ala Ser Ser Leu Gln Ser Gly Val Pro Pro Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Tyr Trp Trp
                85                  90                  95

Thr Phe Gly Gln Gly Thr Lys Val Glu Ile Ile
            100                 105
```

```
<210> SEQ ID NO 274
<211> LENGTH: 130
<212> TYPE: PRT
<213> ORGANISM: Artificial sequence
<220> FEATURE:
<223> OTHER INFORMATION: Synthetic peptide

<400> SEQUENCE: 274

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Val Ser Trp Val Arg Gln Ala Pro Gly Gln Gly Leu Glu Trp Met
        35                  40                  45

Gly Gly Ile Ile Pro Lys Phe Ala Thr Ala Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly His Phe Pro Gln Arg Lys Pro Ile Thr Thr Ile Val Val Ile
            100                 105                 110

Thr Tyr Trp Ser Leu Asp Leu Trp Gly Arg Gly Thr Leu Val Thr Val
        115                 120                 125

Ser Ser
    130

<210> SEQ ID NO 275
<211> LENGTH: 125
<212> TYPE: PRT
<213> ORGANISM: Artificial sequence
<220> FEATURE:
<223> OTHER INFORMATION: Synthetic peptide

<400> SEQUENCE: 275

Gln Val Gln Leu Val Glu Ser Gly Ala Glu Gly Lys Lys Pro Gly Ser
1               5                   10                  15

Ser Val Lys Val Ser Cys Lys Ala Pro Gly Val Thr Phe Ser Arg Tyr
            20                  25                  30

Thr Ile Ser Trp Val Arg Gln Ala Pro Gly Gln Gly Leu Glu Trp Met
        35                  40                  45

Gly Arg Ile Ser Pro Ile Leu Gly Thr Ala Asn Tyr Ala Gln Lys Phe
    50                  55                  60

Gln Gly Arg Val Thr Ile Thr Ala Asp Lys Ser Ser Ser Thr Val Tyr
65                  70                  75                  80

Met Glu Leu Asn Arg Leu Lys Ser Asp Asp Thr Ala Val Tyr Tyr Cys
                85                  90                  95

Ala Arg Asp Ala Pro Ile Ile Leu Val Glu Gly Pro Glu Thr Gly Met
            100                 105                 110

Asp Val Trp Gly Gln Gly Thr Leu Val Thr Val Ser Ser
        115                 120                 125

<210> SEQ ID NO 276
<211> LENGTH: 111
<212> TYPE: PRT
<213> ORGANISM: Artificial sequence
<220> FEATURE:
<223> OTHER INFORMATION: Synthetic peptide
```

<400> SEQUENCE: 276

Gln Ser Ala Leu Thr Gln Pro Arg Ser Val Ser Ala Ser Pro Gly Gln
1               5                   10                  15

Ser Val Thr Ile Ser Cys Thr Gly Thr Asn Ser Asp Val Gly Gly Tyr
            20                  25                  30

Asp Tyr Val Ser Trp Tyr Gln Gln His Pro Gly Lys Ala Pro Lys Leu
        35                  40                  45

Met Ile Ser Asp Val Asn Met Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Cys Ser Tyr Ala Gly Ser
                85                  90                  95

Tyr Thr Phe Val Phe Gly Ser Gly Thr Lys Val Thr Val Leu Gly
            100                 105                 110

<210> SEQ ID NO 277
<211> LENGTH: 128
<212> TYPE: PRT
<213> ORGANISM: Artificial sequence
<220> FEATURE:
<223> OTHER INFORMATION: Synthetic peptide

<400> SEQUENCE: 277

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Asn Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Lys Lys Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Leu Tyr Gly Ser Gly Met Val Pro Asn Tyr Tyr Tyr
            100                 105                 110

Tyr Gly Leu Asp Val Trp Gly Gln Gly Thr Leu Val Thr Val Ser Ser
        115                 120                 125

<210> SEQ ID NO 278
<211> LENGTH: 121
<212> TYPE: PRT
<213> ORGANISM: Artificial sequence
<220> FEATURE:
<223> OTHER INFORMATION: Synthetic peptide

<400> SEQUENCE: 278

Gln Val Gln Leu Val Gln Ser Gly Gly Gly Leu Val Arg Pro Gly Gly
1               5                   10                  15

Ser Leu Arg Leu Ser Cys Thr Ala Ser Gly Phe Thr Leu Ser Thr Tyr
            20                  25                  30

Ser Met Thr Trp Val Arg Gln Ala Pro Gly Lys Gly Leu Glu Trp Val
        35                  40                  45

Ser Ser Ile Ser Ser Ser Ser Thr Tyr Lys Tyr Tyr Val Asp Ser Ile
    50                  55                  60

-continued

Lys Gly Arg Phe Thr Ile Ser Arg Asp Asn Ala Lys Asn Ser Leu Tyr
 65                  70                  75                  80

Leu Gln Met Glu Ser Leu Gly Val Glu Asp Thr Ala Val Tyr Tyr Cys
             85                  90                  95

Ser Arg Ala Asp Trp Asp Ser Gly Lys Gly Asp Leu Asp Ser Trp Gly
            100                 105                 110

Gln Gly Thr Leu Val Thr Val Ser Ser
            115                 120

<210> SEQ ID NO 279
<211> LENGTH: 112
<212> TYPE: PRT
<213> ORGANISM: Artificial sequence
<220> FEATURE:
<223> OTHER INFORMATION: Synthetic peptide

<400> SEQUENCE: 279

Gln Pro Val Val Thr Gln Ser Pro Ser Ala Ser Ala Ser Leu Gly Ala
 1               5                  10                  15

Ser Val Arg Leu Thr Cys Thr Leu Asn Ser Gly Arg Ser Lys Tyr Ala
             20                  25                  30

Ile Ala Trp His Gln Gln Pro Gly Lys Gly Pro Arg Tyr Leu Met
         35                  40                  45

Thr Leu Asn His Asp Gly Ser His Ser Lys Gly Asp Gly Ile Pro Phe
 50                  55                  60

Arg Phe Ser Gly Ser Ser Ser Gly Thr Glu Arg Tyr Leu Thr Ile Ser
 65                  70                  75                  80

Ser Leu Gln Ser Glu Asp Glu Ala Asp Tyr Tyr Cys Gln Thr Trp Gly
             85                  90                  95

Lys Gly Ile Val Val Phe Gly Gly Gly Thr Lys Leu Thr Val Leu Gly
            100                 105                 110

<210> SEQ ID NO 280
<211> LENGTH: 120
<212> TYPE: PRT
<213> ORGANISM: Artificial sequence
<220> FEATURE:
<223> OTHER INFORMATION: Synthetic peptide

<400> SEQUENCE: 280

Gln Val Gln Leu Val Gln Ser Gly Pro Arg Leu Val Lys Pro Ser Glu
 1               5                  10                  15

Thr Leu Ser Leu Thr Cys Thr Val Ser Gly Asp Ser Ser Gly Arg Tyr
             20                  25                  30

Tyr Trp Ser Trp Ile Arg Gln Thr Pro Gly Lys Gly Leu Glu Trp Ile
         35                  40                  45

Gly Tyr Ile Ser Tyr Thr Gly Ser Thr Asn Tyr Asn Pro Ser Leu Lys
 50                  55                  60

Ser Arg Val Thr Ile Ser Ser Asp Met Ser Lys Ser His Phe Ser Leu
 65                  70                  75                  80

Asn Leu Thr Ser Val Thr Ala Ala Asp Thr Ala Val Tyr Tyr Cys Ala
             85                  90                  95

Arg Gly Gly Trp Asn Leu Leu Val Ser Tyr Phe Asp Phe Trp Gly Leu
            100                 105                 110

Gly Thr Leu Val Thr Val Ser Ser
            115                 120

<210> SEQ ID NO 281

```
<211> LENGTH: 124
<212> TYPE: PRT
<213> ORGANISM: Artificial sequence
<220> FEATURE:
<223> OTHER INFORMATION: Synthetic peptide

<400> SEQUENCE: 281
```

Gln Val Gln Leu Val Gln Ser Gly Ala Glu Leu Lys Pro Gly Ala
1               5                   10                  15

Ser Val Lys Val Ser Cys Lys Pro Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Lys Ser Gly Glu Thr His Tyr Ala Gln Lys Phe
50                  55                  60

Arg Gly Trp Val Thr Leu Thr Arg Asp Thr Ser Ile Ser Thr Thr Tyr
65                  70                  75                  80

Met Asp Leu Thr Arg Leu Lys Ser Asp Asp Thr Ala Val Tyr Phe Cys
                85                  90                  95

Ala Arg Gly Asp Leu Glu Thr Thr Ile Phe Phe Tyr Asn Ala Val Asp
            100                 105                 110

Val Trp Gly Gln Gly Thr Leu Val Thr Val Ser Ser
        115                 120

```
<210> SEQ ID NO 282
<211> LENGTH: 107
<212> TYPE: PRT
<213> ORGANISM: Artificial sequence
<220> FEATURE:
<223> OTHER INFORMATION: Synthetic peptide

<400> SEQUENCE: 282
```

Asp Ile Gln Met Thr Gln Ser Pro Ser Ser Leu Ser Ala Ser Val Gly
1               5                   10                  15

Asp Arg Val Thr Ile Thr Cys Arg Ala Thr Glu Ser Ile Gly Ile Tyr
            20                  25                  30

Leu Asn Trp Tyr Gln Arg Lys Pro Gly Lys Ala Pro Asn Leu Leu Ile
        35                  40                  45

Phe Ala Thr Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Gly Phe Ser Ser Pro Phe
                85                  90                  95

Ser Phe Gly Gln Gly Thr Arg Leu Glu Ile Lys
            100                 105

```
<210> SEQ ID NO 283
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 283
```
gaggtgcagc tggtggagtc tggggaggc ttggtccagc ctggggggtc cctgagactc      60
tcctgtgcag cctctggatt cacctttagt agctattgga tgagctgggt ccggcaggct    120
ccagggaagg ggctggagtg ggtggccaac ataaagcaag atggaagtgc gaaatactat    180

```
gtggactctg tgaagggccg attcaccatc tccagagaca acgccaagaa ctcgctgtat    240
ctgcaaatga acagcctgag agccgaggac acggccgtct attactgtgc gagagatgga    300
ttactcggga tcagtgattt attataccc atatactact ttgactactg gggccaggga    360
accctggtca ccgtctcctc a                                              381

<210> SEQ ID NO 284
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 284
gacattgtga tgacccagtc tccatcctcc ctgtctgcat ctgtaggaga cagagtcacc     60
atcacttgcc gggcaagtca gaacattggg agctatttaa attggtatca gcagaaacca    120
gggaaagccc ctaacctcct gatgtatgct gcatccagtt tgcaaagtgg ggtcccatca    180
aggttcagtg gcagtggatc tgggacagat ttcactctca ccatcaccag tctgcaacct    240
gaagattttg caacttacta ctgtcaacag agttacagta ccctcgaac ttttggccag    300 gggacccagc tggagattaa a                                              321

<210> SEQ ID NO 285
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 285
caggttcagc tggtgcagtc tggagctgag gtgaagaggc ctggggcctc agtgaaggtc     60
tcctgcaagg cttctggtta ccctttacc agctacgcta tcagctgggt gcgacaggcc    120
cctggacaag gcttgagtg gatgggatgg atcagcggta acaatggtaa cacaaactat    180
gcacagaagc tccagggcag actcaccatg accacagaca catccacgag cacagcctac    240
atggagctga ggagcctgag atctgacgac acggccgttt attactgtgc gagagatgcc    300
gatattgtcg tggtggtagg tgctacgggg acctactact acggtatgga cgtctggggc    360
caagggaccc tggtcaccgt ctcctca                                        387

<210> SEQ ID NO 286
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 286
gacatcgtga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctatgat gcctccagtt tggaaagtgg ggtcccatca    180
aggttcagcg gcagtggatc tgggacagaa ttcactctca ccatcagcag cctgcagcct    240
gatgattttg caacttatta ctgccaacag tataaaagtt ctctgaggac gttcggccag    300
gggacccagc tggagattaa a                                              321

<210> SEQ ID NO 287
<211> LENGTH: 360
```

<212> TYPE: DNA
<213> ORGANISM: Artificial sequence
<220> FEATURE:
<223> OTHER INFORMATION: Synthetic oligonucleotide

<400> SEQUENCE: 287

```
caggtgcagc tggtgcagtc tgggggaggc ttggtccagc ctggggggtc cctgagactc      60
tcctgtgcag cctctggatt caccgtcagt aacaactaca tgagctgggt ccgccaggct     120
ccagggaagg ggctggagtg gtctcaatt ttttatagcg atggtaccac atacaacgca      180
gactccgtga agggcagatt caccatctcc agagacaatt ccaagaacac gctgtatctt     240
caaatgaaca gcctgagagc cgaggacacg gctgtgtatt actgtgcgag acaagcaagt     300
ggctacgacg cctactacat ggacgtctgg ggccagggaa ccctggtcac cgtctcctca     360
```

<210> SEQ ID NO 288
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 288

```
gacatygtga tgacccagtc tccttccacc ctgtctgcat ctgtaggaga cagagtcacc      60
atcacttgcc gggccagtca gagtattaat agctggttgg cctggtatca gcagaaacca     120
gggaaagccc ctaagctcct gatctatcag gcgtctactt tagaaagagg ggtcccatca     180
aggttcagcg gcagtggagc tgggacagaa ttcactctca ccattagcag cctgcagcct     240
gatgattttg caacttatta ctgccaacaa tatagtagtt cccgctcac tttcggcgga      300 gggaccaagg tggagctcaa a                                              321
```

<210> SEQ ID NO 289
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 289

```
caggtgcagc tggtgcagtc tggggctgaa gtgaagaagc ctgggtcctc ggtgaaggtc      60
tcctgcaagg cttctggagc caccttcggc agcgatactg tcacctgggt gcgacaggcc     120
cctggacaag ggcttgagtg gatgggaggg atcatccctt tttttggtga agcaaactac     180
gcacagaggt ttcagggcag agtcacgata accgcggaca gtccacgaa cacagcctac      240 atggaactga gcagcctgag atctgaggac acggccgtgt acttctgtgc gagacaaata     300
aacgagatgg ctacatttgg ggagatacat tattatacgt acatggatgt ctggggccaa     360
gggaccctgg tcaccgtctc ctca                                            384
```

<210> SEQ ID NO 290
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 290

```
gaaattgtga tgacccagtc tccaggcacc ctgtctttgt ctccagggga aagagccacc      60
ctctcctgca gggccagtca gagtattacc agcacctact agcctggta ccagcagaaa      120
```

-continued

| | |
|---|---|
| cctggccagg ctcccaggct cctcatctat ggtgcatcca acagggccac tggcatccca | 180 |
| gacaggttca gtggcagtgg gtctgggaca gacttcactc tcaccatcag cagactggag | 240 |
| cctgaagatt ttgcagtgta ttactgtcag cagtatcata gctcactttt cggcggaggg | 300 |
| accaaggtgg agatcaaa | 318 |

<210> SEQ ID NO 291
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 291

| | |
|---|---|
| caggtgcagc tggtgcagtc gggcccaggt ctggtgaagc cttcggagac cctgtccctc | 60 |
| acctgcactg tctctagtga ctccatcagg agttactcct ggagctggct ccggcagccc | 120 |
| ccagggaagg gcctggagtg gattgggttt atctattaca gtgggaacat caattacaac | 180 |
| ccgtccctca agagtcgagt caccatatca gtagacacgt ccaagaacca gttgtccctg | 240 |
| aacctgagct ctgtgaccgc tgcggacacg gccgtgtatt attgtgcgag agattggatt | 300 |
| acgattttgg gaggtactt cgatgtctgg ggccgtggca ccctggtcac cgtctcctca | 360 |

<210> SEQ ID NO 292
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 292

| | |
|---|---|
| gacatcgtga tgacccagtc tccagactcc ctggctgttt ctctgggcga gagggccacc | 60 |
| atcaactgca gtccagcca gaatctttta tacagctcca acaataagaa cttcttaact | 120 |
| tggtaccaac acaaaccagg acagcctcct aagctgctca tttcctgggc atctactcgg | 180 |
| gaatccgggg tccctgaccg attcagtggc agcgggtctg ggacagattt cactctcacc | 240 |
| atcagcagcc tgcaggctga agatgtggca ctttattact gtcagcaata ttatactatt | 300 |
| cctccaacgt tcggccaagg gaccaaggtg gaaatcaaa | 339 |

<210> SEQ ID NO 293
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 293

| | |
|---|---|
| caggtgcagc tggtgcagtc tgggggaggc ttcgtacagc cagggcggtc cctgagactg | 60 |
| tcctgtacag cctctggatt caactttggt gattatgtta tgagctgggt ccgccaggct | 120 |
| ccagggaagg ggctggagtg ggtaggtttc attagggca aaacttttgg tgcgacaaca | 180 |
| gagtacgccg cgtctgtgaa aggcagattt accatctcaa gggatgattc aaaaagcatc | 240 |
| gcctacctgc aaattaaatc cctgaaaacc gaggacacag ccgtctacta ttgtactaga | 300 |
| agggccacca gcacctggta cgaggactat tggggccagg gaaccctggt caccgtctcc | 360 |
| tca | 363 |

<210> SEQ ID NO 294
<211> LENGTH: 339

-continued

```
<212> TYPE: DNA
<213> ORGANISM: Artificial sequence
<220> FEATURE:
<223> OTHER INFORMATION: Synthetic oligonucleotide

<400> SEQUENCE: 294
gacatcgtga tgacccagtc tccggactcc ctggctgtgt ctctgggcga gagggccacc      60
atcaactgca agtccagcca gagtgtttta tacaccccca acaatcataa ttacttagct     120
tggtaccagc agaaaccagg acagcctcct aagctgctca tttactgggc atctgcccgg     180
gaacccgggg tccctgaccg attcagtggc agcgggtctg ggacagattt cactctcacc     240
ataagcagcc tgcaggctga ggatgtggca gtttattact gtcagcaata tcatattcct     300
ccgtacagtt ttggccaggg gaccaagctg gagatcaaa                            339

<210> SEQ ID NO 295
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 295
caggtgcagc tggtgcagtc gggcccagga ctggtgaagc cttcacagac cctgtccctc      60
acctgcactg tctctggtga ctccatcagc agtggtagtt actactggag ctggatccgg     120
cagcccgccg ggaagggact ggagtggatt gggcgtatct ataccagtgg gagcaccaac     180
tacaatccct ccctcaagag tcgagtcacc atttcagtag acacgtccaa gaaccagttc     240
tccctgaacc tgagctctgt gaccgccgca gacacggccg tgtattactg tgcgagagat     300
ccgattacga tttttggagg ggttattttc ggctggggaa tggacgtctg ggccaaggg     360 accctggtca ccgtctcctc a                                               381

<210> SEQ ID NO 296
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 296
gacattgtga tgacccagtc tccactctcc ctgcccgtca cccctggaga gccggcctcc      60
atctcctgca ggtctagtca gagcctcctg catagtaatg gatacaacta tttgtattgg     120
tacctgcaga agccagggca gtctccacag ctcctgatct atttgggttc taatcgggcc     180
tccggggtcc ctgacaggtt cagtggcagt ggatccggca cagatttac actgaaaatc     240 agcagagtgg aggctgagga tgttggggtt tattactgca tgcaagctct acaaactccc     300
gtcactttcg gccctgggac caaagtggat atcaaa                               336

<210> SEQ ID NO 297
<211> LENGTH: 420
<212> TYPE: DNA
<213> ORGANISM: Artificial sequence
<220> FEATURE:
<223> OTHER INFORMATION: Synthetic oligonucleotide

<400> SEQUENCE: 297
caggtccagc tggtgcagtc tggggctgaa gtgaagaagc ctgggtcctc agtgaaggtc      60
tcctgcaagg cttctggagg caccttcgac acctatgcta tcagctgggt gcgacaggcc     120
```

```
cctggacaag ggcttgagtg gatgggaggg attatccctg ttcttggtat agtagattat    180
gcacagaagt tccagggcag agtcacaatt actgcggcca aattcacgaa catagcctac    240
atggagctga gcagcctgag atctgaggac gcggccgtgt attactgtgc gagaggcctg    300
cggagccttt ctccccgggg acaagaggga cctactccag cgcccgggtg agaagggct     360 caataccact actactacat ggacgtctgg ggcacaggga ccctggtcac cgtctcctca    420
```

<210> SEQ ID NO 298
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 298

```
gaaattgtga tgacccagtc tccaggcacc ctgtctttgt ctccagggga aagagccacc     60
ctctcctgca gggccagtca gagtgttagt agcaactatt tagcctggta ccagcaaaaa    120
cctggccagg ctcccaggct cctcatctat ggtgcatccc gcagggccac tggcatccca    180
gacaggttca gtggcagtgg gtctgggcca gacttcactc tcaccatcag cagactggag    240
cctgaagatt ttgcagtgta ttattgtcag cagtatggta gttcacccgg cactttcggc    300
ggagggacca aggtggagat caaa                                           324
```

<210> SEQ ID NO 299
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 299

```
caggtgcagc tgcaggagtc gggcccagga ctggtgaggc cttcacagac cctgtccctc     60
acctgcactg tgtctggtgg ctccatcaac agtgatagtt actactggaa ctggatccgg    120
cagcccgccg ggaagggact ggagtggctt gggcgtgtct ataccagtgg gagcaccaac    180
tacaacccct ccctcaagag tcgagtcacc atatcagtag acacgtccaa gaaccaggtc    240
tccctgaggc tgaactccgt gaccgccgca gacacgggcg tatattactg tgcgagagtg    300
gtttggggga gttatcgttc ctaccactac tcctacggta tggacgtctg gggccaaggg    360
accctggtca ccgtctcctc a                                              381
```

<210> SEQ ID NO 300
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 300

```
gaaattgtga tgacccagtc tccaggcacc ctgtctttgt ctccagggga aagagccacc     60
ctctcctgca gggccagtca gagtgttggc agcagctact tagcctggta ccagcagaga    120
cctggccagg ctcccaggct cctcttctat ggtgcatcct acagggccac tggcatccca    180
gacaggttca gtgccagtgg gtctggaaca gacttcagtc tcaccatcaa cagactggag    240
cctgaagatt ttgcagtcta ttactgtcag cagtctggta gctcgccgga cttttggc     300 caggggacca agctggagat caaa                                           324
```

```
<210> SEQ ID NO 301
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 301
caggtgcagc tggtgcagtc tggagttgag gtgaagaagc ctggggcctc agtgaaggtc      60
tcctgcaagg cgtctggtta cgcctttacc acctatgcta tcagctgggt gcgacaggcc     120
cctggacaag ggcttgagtg gatgggttgg atcagcactt actatggtac cacatactat     180
gcacagaacc tccagggcag agtcaccatg accacagaca catccacgag cacatcctac     240
ttggaactga ggagcctaag atctgacgac acggccgtct attactgtgt gagagatcgg     300
tcgtggctgg ccacttcccg accatatgat gcttttgata tctggggcca agggaccctg     360
gtcaccgtct cctca                                                      375

<210> SEQ ID NO 302
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 302
gccatccaga tgacccagtc tccatcctcc ctgtctgcat ctgtaggaga cagagtcacc      60
atcacttgcc gggcaagtca ggacattagc agtactttag cctggtatca gcagaaaccg     120
ggaaaagctc ctaaactcct gatctatggt gcctccagtt tggaaagtgg ggtcccatcc     180
aggttcaacg gcagtggatc tgggacagat ttcactctca ccatcagcag cctgcagcct     240
gaagatttcg caacttatta ctgtcagcac ttttactatt ccccccgcac cttcggccaa     300
gggacacgac tggagattag a                                                321

<210> SEQ ID NO 303
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 303
caggtgcagc tggtgcagtc gggcccagga ctggtgaagc cttcacagac cctgtccctc      60
acctgcactg tctctggtgg ctccatcagc agtggtcgtt tctactggag ctgggtccgg     120
cagcccgccg ggaggggact ggagtggatt gggcgcatct ataccagtgg gagcaccaac     180
tacaacccct ccctcaagag tcgagtcagc atatcagtag acacgtccaa gaaccagttc     240
tccctgaagc tgagctctgt gaccgccgca gatacggccg tgtattactg tgcgactgaa     300
ctgtactact atggttcggg gagttatgac ccgctttggt cctggggcca gggaaccctg     360
gtcaccgtct cctca                                                      375

<210> SEQ ID NO 304
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 304
```

```
gacattgtga tgacccagtc tccatcctcc ctgtctgcat ctgtaggaga cagagtcacc      60
atcacttgcc aggcgagtca gggcattaac aacaatttaa attggcatca gcaaaaacca     120
ggtaaagccc ctaagctcct gatctacgat gcatccaatt tggaaagagg ggtcccatca     180
aggttcagtg gaagtggatc tgggacagat tttactttca ccatcagcag cctgcagcct     240
gaagatattg ctacatatta ctgtcaacag aatgccaatc tcccgcacac ttttggccag     300
gggaccaagc tggagatcaa a                                               321
```

<210> SEQ ID NO 305
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 305

```
caggtgcagc tggtgcagtc gggcccagga ctggtgaagc cttcacagac cctgtccctc      60
acctgcactg tctctggtgg ctccatcagc agtgggagtt acttctggaa ctggatccgg     120
cagcccgccg ggaagggact ggagtggatt gggcgtatct ataccagcgg gaccaccaac     180
tacaatccct ccctcaagag tcgcctcacc atttcagtag acacgtccaa gaaccaattc     240
tccctgaagc tgaactctgt gaccgccgca gacacggccg tgtattactg tgcgacaagc     300
ccgtattact atgatagttc tcattattac gactactggg gccagggaac cctggtcacc     360
gtctcctca                                                            369
```

<210> SEQ ID NO 306
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 306

```
gacatccaga tgacccagtc tccatcctcc ctgtctgcat ctgtaggaga cagagtcacc      60
atcacttgcc aggcgagtca ggacattacc aactatttaa attggtatca gcagaagcca     120
gggaaagccc ctaagctcct gatcttcgat gcttccaatt tggaaaaggg ggtcccatca     180
aggttcagtg gcactggatc tgcgacagat tttactttca ccatcagcag cctgcagcct     240
gaagatactg cgacatatta ctgtcaacag tctgctgatc tccccctcac cttcggccaa     300
gggacacgac tggacattaa a                                               321
```

<210> SEQ ID NO 307
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 307

```
caggtgcagc tggtgcagtc gggcccagga ctggtgaagc cttcacagac cctgtccctc      60
acctgcaatg tctctggtgg ctccatcagc aatggtggtt accactggag ttggatccgc     120
caggtcccag ggaagggcct ggagtggatt ggacacattt attacagtgg gagcacctcc     180
tacaccccgt ccctcaagag tcgacttacc atatcagtgg acacctctaa gaaccagttc     240
tccctgaagc tgagctctgt gactgccgcg acacggccg tatattactg tgcgagagat      300
aggatacggg gcgggcccat tgactactgg ggccagggaa ccctggtcac cgtctcctca     360
```

<210> SEQ ID NO 308
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 308

```
gacatccaga tgacccagtc tccatcctcc ctgtctgcat ctgttggaga aagagtcacc      60
atcacttgcc gggcgagtca gggcatcgac aattatttag cctggtatca acaaaaacca     120
gggaaagttc ctaaactcct gatctatgct gcatccactt tgcactcagg ggtcccatct     180
cggttcagtg gcagtggatc tgggacagat ttcactctca ccatcagcag cctgcagcct     240
gaagatgttg caacttatta ctgtcaaagg tataaccttg ccccgagcgc ttttggccag     300
gggaccaagg tggagatcag a                                               321
```

<210> SEQ ID NO 309
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 309

```
caggtgcagc tggtgcagtc tggggctgag atgaggaagc ctggggcctc agtgaaggtc      60
tcctgcaagg cttctggata caccttcagt gactactata tacactgggt gcgccaggcc     120
cctggacaag gcttgagtg gctgggatgg atcaacccctt atagtggagg cacaaattat     180
gcacagaagt tcagggcag ggtcaccatg accaggaca cgtccatcag cacagcccac      240
atggagctga gcgggctcag atctgacgac acggccctat atttctgtgc gagactatat     300
ggtgcgggga gtcattataa tcactacaac ggcatggacg tctggggtca agggaccctg     360
gtcaccgtct cctca                                                      375
```

<210> SEQ ID NO 310
<211> LENGTH: 312
<212> TYPE: DNA
<213> ORGANISM: Artificial sequence
<220> FEATURE:
<223> OTHER INFORMATION: Synthetic oligonucleotide

<400> SEQUENCE: 310

```
gacatccaga tgacccagtc tccttccacc ctgtctgcat ctgtaggaga cagagtcacc      60
atcacttgcc gggccagtca gagtattggt agtttattgg cctggtatca gcagaaaccg     120
gggaaagccc ctaagctcct gatctatagg gcgtctactt tacaaggtgg ggtcccatca     180
aggttcagcg gcagtggatc tgggacagaa ttcactctca ccatcagcag cctgcagcct     240
gatgatgttg ctacttatta ctgccaacaa tttaatagtt atttcggcgg agggaccaag     300
gtggagatca aa                                                         312
```

<210> SEQ ID NO 311
<211> LENGTH: 299
<212> TYPE: DNA
<213> ORGANISM: Artificial sequence
<220> FEATURE:
<223> OTHER INFORMATION: Synthetic oligonucleotide

<400> SEQUENCE: 311

```
caggtgcagc tgcagcagtc gggcccagga ctggtgaggc cgtcacagac cctgtccctc      60
acctgctctg tctctggtgg ctccgtcagt agtggtcgtt acttctggaa ctggatccgg     120
cagtccgccg ggaagggact ggagtggatt gggcgtatcc attccagtgg gagaaccaac     180
tccaacccct ccctcaagag tcgagtcacc atatcagtcg acacgtccaa gaaccagttc     240
tccctgcacc tgggctctgt gaccgccgca gacacggccg tctattactg tgcgagaga      299
```

<210> SEQ ID NO 312
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 312

```
gatattgtga tgacccagac tccactctct ctgtccgtca cccctggaca gccggcctcc      60
atctcctgca gtctagtca gagcctcctg catagtaatg gagagaccta tttattttgg     120
tacctgcaga agccaggcca gccgccacaa ctcctgatct atgaagtttc caaccggttc     180
tctggagtgc cagataggtt cagtggcagc gggtcaggga cagatttcac actgaagatc     240
agccgggtgg aggctgagga tgttggagtt tattactgca tgcaaagtgt actccttccg     300
tacacttttg gccaggggac caagctggag atcaag                                336
```

<210> SEQ ID NO 313
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 313

```
caggtgcagc tgcaggagtc gggcccagga ctggtgaagc cttcacagac cctgtccctc      60
acctgcactg tctctggtgc ctccatcagc agggtctttt actactggag ctggatccgg     120
cagcccgccg ggaagggact ggagtggatt gggcgcatct ataccagtgg gagcatcaac     180
tacaatcctt ccctcaagag tcgagtcacc atatcagtag acacgtccaa gaatcagttc     240
tccctgaggc tgagctctgt aatcgccaca gacacggccg tgtattattg tgtgagagat     300
gctccctggg gagattttt gactggttat tttggcttct acggtatgga cgtctggggc     360
caagggaccc tggtcaccgt ctcctca                                          387
```

<210> SEQ ID NO 314
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 314

```
gacattgtga tgacccagtc tccatcctcc ctgtctgcat ctgtaggaga cagagtcacc      60
atcacttgcc gggcaagtca gagcattaac acctatttaa attggtatca gcagaaacca     120
gggaaagccc ctaagttcct gatctatgct gcatccagtt tgcacagtgg ggtcccatca     180
aggttcagtg gtagtggatc tgggacagat ttcactctca ccatcaacag tctacaacct     240
gatgattttg caacttacta ctgtcaacag agtttcacta ccccgtacac ttttggccag     300
gggaccaagc tggagatcaa g                                                321
```

<210> SEQ ID NO 315
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 315

```
caggtgcagc tggtgcagtc tggggctgag gtgaagaagc ctggggcctc agtgaaggtc      60
tcctgtaaga cttctggata caccttcacc agctttgaaa tccactgggt gcgacagggc     120
agtggacaag gcttgagtg atgggacgt atgaatccta aaagtggtga cacagtctct       180
gcacagaagt tccagggcag agtcacccett accagggaca cgtccataaa tgcagcctac   240
atggagctgg gcagcctgag ttctgaggac acggccgtgt actactgtgc gagaggccca    300
cacgttggcg aagttgttcc aggtcttatg gcgggcacct actattttcc tttggacgtc    360
tggggccaag ggaccctggt caccgtctcc tca                                   393
```

<210> SEQ ID NO 316
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 316

```
gacatccaga tgacccagtc tcctccacc ctgtctgcat ctataggaga cagagtcacc       60
atcacttgcc gggccagtca gagcattagt cgctggttgg cctggtatca gcagaaacca    120
gggaaagccc ctaaactcct gatctataag gtgtctgatt tacaaagtgg ggtcccatca    180
aggttcagcg gcagtggata tgggacagaa ttcactctca ccatcggcag cctgcagcct   240
gatgatttgg caacttatta ttgccaacaa tatgatacat atccgtggac gttcggccag    300
gggaccaagc tggagatcaa g                                                321
```

<210> SEQ ID NO 317
<211> LENGTH: 359
<212> TYPE: DNA
<213> ORGANISM: Artificial sequence
<220> FEATURE:
<223> OTHER INFORMATION: Synthetic oligonucleotide

<400> SEQUENCE: 317

```
caggtccagc tggtgcaatc tggggctgag gtgaagaagc ctgggtcctc ggtgaaggtc      60
tcctgcaacg cttctggagg caccttcagc aactccattc ttaactgggt gcgacaggcc    120
cctggacaag gcttgagtg atgggaagg atcatcccta tcgttggtct agtaaacttc       180
gcacaaaagt tcgagggcag agtcacattt accgcggaca aattcacgaa cacagcctac     240
atggagctga acagtctgag atttgaggac acggccgtgt actactgtgc gataaatggg    300
gtaaatatcc cggatacttt gactactggg gccagggaac cctggtcacc gtctcctca     359
```

<210> SEQ ID NO 318
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 318

```
gacattgtga tgacccagtc tccaggcacc ctgtctttgt ctccagggga aagagccacc      60
```

```
ctctcctgca gggccagtca gagtgtgagc agcagctact tagcctggta ccagcaccaa    120
cctggccagg ctcccaggct cctcatctat gatgcatcca gcagggccac tggcatccca    180
gacaggttca gtggcagtgg gtctgggaca gacttcactc tcatcatcag cagactggag    240
cctgaagatt ttgcagtgta ttactgtcag cagtatggaa gctcagcgat caccttcggc    300
caagggacac gactggagat caag                                           324
```

<210> SEQ ID NO 319
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 319

```
caggtgcagc tgcaggagtc gggcccagga ctggtgaagc cttcggagac cctgtccctc    60
acctgcgctg tctctggtgg ctccatcagg agttatttct ggagctggat ccggcaggcc   120
ccagggaagg gactggaatg gattgggaat atctattaca gtgggcgccc caattacaac   180
ccctccctca gaatcgagt caccatatca gcagacacgt ccaacaatga ggtctcactg    240
gagctgagcg ctgtgaccgc tgcggacacg gccgtgtatt tctgtgcgag agatgagaga   300
ctactggtgg aggtcggaac cgaccacttc tactacggtt tggacgtctg ggccaaggg    360 accctggtca ccgtctcctc a                                              381
```

<210> SEQ ID NO 320
<211> LENGTH: 288
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (270)..(271)
<223> OTHER INFORMATION: n is a, c, g, or t

<400> SEQUENCE: 320

```
gaaattgtga tgacccagtc tccactctcc ctgtctgtca cccctggaga gccggcctcc    60
atctcctgca ggtctagtca gagcctccta catagtaatg gatacaactt tttggattgg   120
tatttgcaga agccagggca gtctccacag ctcctgattt atttgggttc taatcgggcc   180
tccggggtcc ctgacaggtt cagtggcagt ggatccggcg cagattttac actgaaaatc   240
agcagagtgg aggctgagga tgttggggtn nattactgca tgcaagct                 288
```

<210> SEQ ID NO 321
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 321

```
caggttcagc tggtgcagtc tggagctgag gtgaagaagc ctggggcctc agtgaaggtc    60
tcctgcaagg cctcgggcta cacctttacc agttttggta tcagctgggt gcgacaggcc   120
ccgggacaag gctagagtg ctgggatgg atcaacactt acaatggtga cacaaactat    180
gcacagaagt tccagggcag agtcaccatg acaacagata catccacgag tacaggcttc   240
atggagctga ggagcctgag atctgacgac acggccgtct attactgtgc gagagactcc   300
cacttaataa gtatagcagt ggctaatacg cccaatgact ctctggggcca gggaaccctg   360
```

```
gtcaccgtct cctca                                                   375

<210> SEQ ID NO 322
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 322
gaaattgtga tgacccagtc gccaggcacc ctgtctttgt ctccagggga cagagtcacc     60
ctctcctgca gggccagtca gagtgtttac agctactact tagcctggta ccagcagaaa    120
cctggccagg ctcccaggct cctcatgtat gatgcatcca tcagggccac tggcatccca    180
gacaggttca gtggcagtgg gtctgggaca gacttcactc tcaccatcag cagtctggag    240
cctgaagatt ttgcagtgta ctactgtcag tactatggta actcacacca gggggcggcg    300
ttcggccaag ggactaaggt ggaagtcaaa                                    330

<210> SEQ ID NO 323
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 323
caggtgcagc tgcaggagtc gggcccagga ctggtgaagc cttcacagac cctgtccctc     60
acctgcaatg tctctggtgg ctccatcagc agtgatgata gatactggag ctggatccgc    120
cagcccccag ggaagggcct ggagtggctt gggttcatct attacagtgg gagcaccgac    180
tacaacccgt ccctcaagag tcgagttacc atgtcactag acacctccaa gaaccagttc    240
tccctgaagc tgaactctgt gactgccgca gacacggcca tgtattactg tgccacagta    300
acagcttact ctcctgctac tatgatagta gtgggtaccg aacatgggtt tgactactgg    360
ggccagggaa ccctggtcac cgtctcctca                                    390

<210> SEQ ID NO 324
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 324
gacattgtga tgacccagtc tccatcctcc ctgtctgcat ctgtaggaga cagagtcacc     60
atcttttgcc gggcaactca gagcattcgc agcttttaa attggtatca gcagaaacca    120
gggaaagccc ctaacctcct gatctatgct gcatccagtt tgcaaagtgg ggtcccatcc    180
aggttcagtg gcagtggatc tgggacagat ttcactctca ccatcagcag tctacaacct    240
gaagattttg caacttacta ctgtcaacag agttacagta cccatggac gttcggccaa    300 gggaccaagg tggagatcaa g                                             321

<210> SEQ ID NO 325
<211> LENGTH: 353
<212> TYPE: DNA
<213> ORGANISM: Artificial sequence
<220> FEATURE:
<223> OTHER INFORMATION: Synthetic oligonucleotide
```

<400> SEQUENCE: 325

```
aggtgcagct ggtggagtct gggggaggcg tggtccagcc tggggggtcc ctgagactct      60
cctgtgaagt gtccggactc accttcagta actttggcat gcagtgggtc cgccaggctc     120
caggcaaggg tctggagtgg gtggccttta tacggtttga tggaagtaat aagtattatg     180
cagactccgt gaagggccga ttcaccatat ccagagacaa ctccaagaac acggtttatc     240
tccaaatggg cagcctgaga gccgaggaca cggcagtgta ttttgtggg  agagttctat     300
acggagccgc agctgacttt tggggccagg gaaccctggt caccgtctcc tca            353
```

<210> SEQ ID NO 326
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 326

```
gacatcgtga tgacccagtc tccagactcc ctggctgtgt ctctgggcga gagggccacc      60
atcaactgca cgtccagtca cagtctttta tacagctccg acaataagaa ctatttaact     120
tggtaccagc agaaagcagg acagcctcct aagctgctca tctactgggc ttctacccgg     180
caatccgggg tccctgaccg attcagtggc agcgggtctg gacagagtt  cactctcacc     240
atcagcagcc tgcaggctga agatgtggca gtctattact gtcagcagta ttatactaag     300
tctttcactt tcggccaagg gaccaaggtg gagatcaag                            339
```

<210> SEQ ID NO 327
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 327

```
caggtgcagc tggtgcagtc tggggctgag gtgaagaagc ctgggtcgtc ggtgaaggtc      60
tcctgcaagg cctctggagg caccttcagc agctatgcta tcaactgggt gcgacaggcc     120
cctggacaag gcttgagtg  gatgggaggg atcatccta  tctttggtaa accaaactac     180
gcacagaagt tccagggcag agtcacgatt accgcggaca atccacgag  cacagcctac     240
atggaactga aagcctgag  atctgaggac acggccgtat attactgtgc gcggggacag     300
ggagagattg tggtgatggt tggtcatgac gacgggggg  actaccttgg ctactggggc     360
cagggaaccc tggtcaccgt ctcctca                                         387
```

<210> SEQ ID NO 328
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 328

```
cagtctgccc tgactcagcc tcgctcgtg  tccgggtctc ctggacwgtc agtcaccatc      60
tcctgcactg gaaccagcag taatgttggt gcttataact atgtctcctg gtaccaacaa     120
cacccaggca aagcccccaa actcatgatt tttgatgtca ctaagcgcc  ctcaggggtc     180
cctgatcgct tctctggctc caagtctggc aacacggcct ccctgaccat ctctggactc     240
caggctgagg atgaggctga ttttactgc  tactcatatg caggcagcta cacttggatt     300
```

-continued ttcggcggag ggaccaagct gaccgtccta ggt    333

<210> SEQ ID NO 329
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 329
caggtgcagc tggtgcagtc gggcccagga ctggtgaagc cttcggagac cctgtccctc    60
acctgcagtg tctctggtgg ctccatcagt ggttccatct ggacctggat ccggcagtcc    120
ccagggaagg gactggagtg gattggatat atctctttaa gtgggagcac caacttcaac    180
ccctccctca agagtcgagt caccatttca gtagacacgt ccaagaacca gttctccctg    240
aagctgagct ctgtgaccgc cgcagacact gccgtgtatt actgtgcgag acatcggaaa    300
tcgtcgaaga tggttcgagg aattgaagtt ttctactact actacatgga cgtctggggc    360
aaagggaccc tggtcaccgt ctcctca    387

<210> SEQ ID NO 330
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 330
cagtctgccc tgactcagcc tgcctccgtg tctgggtctc ctggacagtc gatcaccatc    60
tcctgcactg gaaccatcag tgacattggt ggttatgact atgtctcctg gtaccaacaa    120
cacccaggca aagcccccaa actcatgatt tatgatgtca gtgatcggcc ctcaggggtt    180
tctaatcgct tctctggctc caagtctggc aacacggcct ccctgaccat ctctgggctc    240
cagtctgagg acgaggctga ttattactgc agttcatata caagaactta cactccccac    300
gtggtattcg gcggagggac caagctgacc gtcctaggt    339

<210> SEQ ID NO 331
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 331
caggtgcagc tggtgcagtc gggcccagga ctggtgaagc cttcacagac cctgtccctc    60
acctgcactg tctctggtgg ctccatcagc agtggaagtt tctactggag ctggatccgg    120
cagcccgccg ggaagggact ggagtggatt gggcgtttct ataccactgg aagcacccac    180
tacaatccct ccctcaagag tcgagtcacc atatcggcgg acacgtcgaa gaaccacttc    240
tccctgaacc tcacttcttt gaccgccgca gacacggccg tttattactg tgcgagaggg    300
ccggtctcct attatagtgg caacctctac tactttgact actggggcct gggaaccctg    360
gtcaccgtct cctca    375

<210> SEQ ID NO 332
<211> LENGTH: 330
<212> TYPE: DNA
<213> ORGANISM: Artificial sequence
<220> FEATURE:

<223> OTHER INFORMATION: Synthetic oligonucleotide

<400> SEQUENCE: 332

```
cagtctgccc tgactcagcc tgcctccgtg tctgggtctc ctggacagtc gatcaccatc    60
acctgcactg gaaccagcag tgacattggt aataataact atgtctcctg gtaccaacag   120
cacccaggca aggcccccaa actcatcatt tttgatgtca ataagcgacc ctcaggggtt   180
tctaaccgct tctctggctc caagtctgac aacacggcct ccctgaccat ctctgggctc   240
caggctgagg acgaggctga ttattactgc agctcatata caaacaacag gactttctcc   300
ttcggaggtg ggaccaaggt caccgtccta                                    330
```

<210> SEQ ID NO 333
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 333

```
caggtgcagc tggtgcagtc tgggggaggc gtggtccagc ctgggggtc cctgagactc      60
tcctgtgcag cgtctggatt caccttcagt agctttggca tccactgggt ccgccaggct   120
ccgggcaagg ggctggagtg ggtggcattt atacgatatg atggaagtga taagttctat   180
ttagactccg tgaagggccg attcaccatc tctagagaca attccaagaa tacgctgttt   240
ctgcaaatga gcagccttag agttgaagac acggctgtgt attactgtgc aagagaggg   300
gggcatgatt atggttacta cgacaacaat cgctacatcg atctctgggg ccgtggcacc   360
ctggtcaccg tctcctca                                                 378
```

<210> SEQ ID NO 334
<211> LENGTH: 280
<212> TYPE: DNA
<213> ORGANISM: Artificial sequence
<220> FEATURE:
<223> OTHER INFORMATION: Synthetic oligonucleotide

<400> SEQUENCE: 334

```
tcctatgtgc tgactcagcc accctcagtg tccgtgtccc cggacagac agccagcatc      60
acctgctctg gagataaaatt gggggataga tatacttgct ggtatcaaca gaagccaggc   120
cagtcccctg tattggtcat ctatcaagat actaagcggc cctcagggat ccctgagcga   180
ttctctggct ccaactctgg gaacacagcc actctgacca tcagcgagac ccaggctata   240
gatgaggctg actattactg tcaggcgtgg gacaccagca                          280
```

<210> SEQ ID NO 335
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 335

```
caggtgcagc tggtgcagtc tggggctgag gtgaagaagc ctgggtcctc ggtgaaggtc     60
tcctgcaagg cttctggagg caccttcagc agttatggtg ttagctgggt gcgacaggcc   120
cctggacaag gcttgagtg gatgggaggg atcatcccta agtttgctac agcaaaatac   180
gcacagaagt tccagggcag agtcacgatt accgcggacg aatccacgag cacagcctac   240
atggagctga gcagcctgag atctgaggac acggccgtgt attactgtgc gggacacttc   300
```

```
cccagagga aaccgattac tacgatagta gtgattactt actggtccct cgatctctgg      360
ggccgtggca ccctggtcac cgtctcctca                                      390

<210> SEQ ID NO 336
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 336
caggtgcagc tggtggagtc tgggctgag gggaagaagc ctgggtcctc ggtgaaggtc      60
tcctgcaagg ctccaggagt caccttcagc agatatacca tcagctgggt gcgacaggcc    120
cctggacagg ggcttgagtg gatgggaagg atcagcccaa tccttggcac agcaaactac    180
gcacagaagt tccagggcag agtcacgatt accgcggaca atcctcgag cacagtctac     240 atggaactga acagactgaa atctgacgac acggctgtat attactgtgc gagagatgca    300
ccgattattc tggttgaggg accggagacc ggtatggacg tctggggcca agggaccctg    360
gtcaccgtct cctca                                                     375

<210> SEQ ID NO 337
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 337
cagtctgccc tgactcagcc tcgctcagtg tccgcgtctc ctggacagtc agtcaccatc    60
tcctgcactg gcaccaacag tgatgttggt ggttatgact atgtctcctg gtaccagcaa    120
cacccaggca aagcccccaa actcatgatt tctgatgtca atatgcggcc ctcaggggtc    180
cctgatcgct tctctggctc caagtctggc aacacggcct ccctgaccat ctctgggctc    240
caatctgagg atgaggctga ttattactgc tgctcatatg caggcagcta cactttttgtc   300 ttcggaagtg ggaccaaggt caccgtccta ggt                                 333

<210> SEQ ID NO 338
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 338
caggtgcagc tggtgcagtc tggggaggc gtggtccagc ctgggaggtc cctgagactc      60
tcctgtgcag cgtctggatt caccttcaat agctatggca tgcactgggt ccgccaggct    120
ccaggcaagg gctggagtg gtggcagtt atatggtttg atggaagtaa aaatactat       180 gcagactccg tgaagggccg attcaccatc tccagagaca attccaagaa ctcactgtac    240
ttgcaaatga acagcctgag agccgaggac acggccgtgt attactgtgc gaaagaccctc   300 ctgtatggtt cggggatggt cccaaattac tactactacg gtttggacgt ctggggccaa    360
gggaccctgg tcaccgtctc ctca                                            384

<210> SEQ ID NO 339
<211> LENGTH: 363
<212> TYPE: DNA
```

<213> ORGANISM: Artificial sequence
<220> FEATURE:
<223> OTHER INFORMATION: Synthetic oligonucleotide

<400> SEQUENCE: 339

```
caggtgcagc tggtgcagtc tggggggaggc ctggtcaggc ctggggggtc cctgagactc    60
tcctgtacgg cctctggatt caccctcagt acttatagca tgacctgggt ccgccaggct   120
ccagggaagg gcctggagtg ggtctcatcc atcagtagtt cgtctaccta caagtactac   180
gtggactcga ttaagggccg attcaccatc tccagagaca acgccaagaa ctcactgtat   240
ctgcaaatgg agagcctggg agtcgaggac acggctgtgt attactgttc gagagcggac   300
tgggactccg ggaaaggaga ccttgactcc tggggccagg aaccctggt caccgtctcc   360
tca                                                                 363
```

<210> SEQ ID NO 340
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 340

```
cagcctgtgg tgactcagtc gccctctgcc tctgcctccc tgggagcctc ggtcagactc    60
acctgcactc tcaacagcgg cgcagtaaa tacgccatcg catggcacca gcaacagcca    120
gggaagggcc ctcgctactt gatgacactt aatcatgatg cagtcacag caaggagac    180
gggatccctt ttcgcttctc aggctccagc tctgggactg agcgctacct caccatctcc    240
agcctccagt ctgaggatga ggctgactat tactgtcaga cttggggcaa gggcatcgtg    300
gtattcggcg gagggaccaa gctgaccgtc ctaggt                              336
```

<210> SEQ ID NO 341
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 341

```
caggtgcagc tggtgcagtc gggcccacga ctggtgaagc cttcggagac cctgtccctc    60
acctgcactg tctctggtga ctccagcggt cgttactact ggagctggat ccggcagacc   120
ccagggaagg gactagaatg gattgggtat atctcttaca ctgggagcac caactacaac   180
ccctccctca agagtcgagt caccatatct tcagacatgt ccaagagcca cttctccctg   240
aacttgacct ctgtgaccgc tgcggacacg gccgtgtatt attgtgcgag aggggggatgg   300
aacctcctag taagctactt tgacttctgg ggcctgggaa ccctggtcac cgtctcctca   360
```

<210> SEQ ID NO 342
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 342

```
caggtgcagc tggtgcagtc tggggctgag ttgaagccgc ctggggcctc agtgaaggtc    60
tcctgcaagc cttctggata cacgttcacc gactactata cactgggt gcgacaggcc   120
cctggacaag ggcttgagtg gatgggatgg atcaaccta aaagtggaga aacacactat   180
```

```
gcacagaagt tcggggctg ggtcaccttg accagggaca cgtccatcag cacaacctac    240
atggacctga ccaggctgaa atctgacgac acggccgtgt atttctgtgc gagagggat    300 ctagagacta cgatcttctt ctacaacgct gtggacgtct ggggccaagg gaccctggtc   360
accgtctcct ca                                                      372
```

<210> SEQ ID NO 343
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 343

```
gacatccaga tgacccagtc tccatcttcc ctgtctgcat ctgtaggaga cagagtcacc    60
atcacttgcc gggcaactga gagtattggc atctatttaa attggtatca gcggaaacca   120
gggaaggccc ctaacctcct gatctttgct acatccagtt tgcagagtgg ggtcccgtca   180
aggttcagtg gcagtggatc tgggacagaa ttcactctca ccatcagcag tctgcaacct   240
gaagattttg caacttactt ttgtcaacag ggtttcagtt ctcctttcag ttttggccag   300
gggaccaggc tggagatcaa g                                             321
```

<210> SEQ ID NO 344
<211> LENGTH: 175
<212> TYPE: PRT
<213> ORGANISM: Artificial sequence
<220> FEATURE:
<223> OTHER INFORMATION: Synthetic peptide

<400> SEQUENCE: 344

Glu Ile Thr Leu Arg Thr Gln Ala Lys Cys Asn Pro Asn Leu His Tyr
1               5                   10                  15

Trp Thr Thr Gln Asp Glu Gly Ala Ala Ile Gly Leu Ala Trp Ile Pro
            20                  25                  30

Tyr Phe Gly Pro Ala Ala Glu Gly Ile Tyr Thr Glu Gly Ile Met His
        35                  40                  45

Asn Gln Asn Gly Leu Ile Cys Gly Leu Arg Gln Leu Ala Asn Glu Thr
    50                  55                  60

Thr Gln Ala Leu Gln Leu Phe Leu Arg Ala Thr Thr Glu Leu Arg Thr
65                  70                  75                  80

Phe Ser Ile Leu Asn Arg Lys Ala Ile Asp Phe Leu Leu Gln Arg Trp
                85                  90                  95

Gly Gly Thr Cys His Ile Leu Gly Pro Asp Cys Cys Ile Glu Pro His
            100                 105                 110

Asp Trp Thr Lys Asn Ile Thr Asp Lys Ile Asp Gln Ile Ile His Asp
        115                 120                 125

Phe Ile Asp Lys Pro Leu Pro Asp Gln Thr Asp Asn Asp Asn Trp Trp
    130                 135                 140

Thr Gly Trp Arg Gln Trp Val Pro Ala Gly Ile Gly Ile Thr Gly Val
145                 150                 155                 160

Ile Ile Ala Val Ile Ala Leu Leu Cys Ile Cys Lys Phe Leu Leu
                165                 170                 175

<210> SEQ ID NO 345
<211> LENGTH: 175
<212> TYPE: PRT
<213> ORGANISM: Artificial sequence
<220> FEATURE:
<223> OTHER INFORMATION: Synthetic peptide

<400> SEQUENCE: 345

Glu Ala Ile Val Asn Ala Gln Pro Lys Cys Asn Pro Asn Leu His Tyr
1               5                   10                  15

Trp Thr Thr Gln Asp Glu Gly Ala Ala Ile Gly Leu Ala Trp Ile Pro
                20                  25                  30

Tyr Phe Gly Pro Ala Ala Glu Gly Ile Tyr Ile Glu Gly Leu Met His
            35                  40                  45

Asn Gln Asp Gly Leu Ile Cys Gly Leu Arg Gln Leu Ala Asn Glu Thr
        50                  55                  60

Thr Gln Ala Leu Gln Leu Phe Leu Arg Ala Thr Thr Glu Leu Arg Thr
65                  70                  75                  80

Phe Ser Ile Leu Asn Arg Lys Ala Ile Asp Phe Leu Leu Gln Arg Trp
                85                  90                  95

Gly Gly Thr Cys His Ile Leu Gly Pro Asp Cys Cys Ile Glu Pro His
            100                 105                 110

Asp Trp Thr Lys Asn Ile Thr Asp Lys Ile Asp Gln Ile Ile His Asp
        115                 120                 125

Phe Val Asp Lys Thr Leu Pro Asp Gln Gly Asp Asn Asp Asn Trp Trp
130                 135                 140

Thr Gly Trp Arg Gln Trp Ile Pro Ala Gly Ile Gly Val Thr Gly Val
145                 150                 155                 160

Ile Ile Ala Val Ile Ala Leu Phe Cys Ile Cys Lys Phe Val Phe
                165                 170                 175

<210> SEQ ID NO 346
<211> LENGTH: 175
<212> TYPE: PRT
<213> ORGANISM: Artificial sequence
<220> FEATURE:
<223> OTHER INFORMATION: Synthetic peptide

<400> SEQUENCE: 346

Gln Thr Asn Thr Lys Ala Thr Gly Lys Cys Asn Pro Asn Leu His Tyr
1               5                   10                  15

Trp Thr Ala Gln Glu Gln His Asn Ala Ala Gly Ile Ala Trp Ile Pro
                20                  25                  30

Tyr Phe Gly Pro Gly Ala Glu Gly Ile Tyr Thr Glu Gly Leu Met His
            35                  40                  45

Asn Gln Asn Ala Leu Val Cys Gly Leu Arg Gln Leu Ala Asn Glu Thr
        50                  55                  60

Thr Gln Ala Leu Gln Leu Phe Leu Arg Ala Thr Thr Glu Leu Arg Thr
65                  70                  75                  80

Tyr Thr Ile Leu Asn Arg Lys Ala Ile Asp Phe Leu Leu Arg Arg Trp
                85                  90                  95

Gly Gly Thr Cys Arg Ile Leu Gly Pro Asp Cys Cys Ile Glu Pro His
            100                 105                 110

Asp Trp Thr Lys Asn Ile Thr Asp Lys Ile Asn Gln Ile Ile His Asp
        115                 120                 125

Phe Ile Asp Asn Pro Leu Pro Asn Gln Asp Asn Asp Asp Asn Trp Trp
130                 135                 140

Thr Gly Trp Arg Gln Trp Ile Pro Ala Gly Ile Gly Ile Thr Gly Ile
145                 150                 155                 160

Ile Ile Ala Ile Ile Ala Leu Leu Cys Val Cys Lys Leu Leu Cys

-continued

```
                165                 170                 175

<210> SEQ ID NO 347
<211> LENGTH: 6
<212> TYPE: PRT
<213> ORGANISM: Artificial sequence
<220> FEATURE:
<223> OTHER INFORMATION: Synthetic antibody

<400> SEQUENCE: 347

Ser Leu Arg Asn Tyr Tyr
1               5

<210> SEQ ID NO 348
<211> LENGTH: 3
<212> TYPE: PRT
<213> ORGANISM: Artificial sequence
<220> FEATURE:
<223> OTHER INFORMATION: Synthetic antibody

<400> SEQUENCE: 348

Gly Lys Asn
1

<210> SEQ ID NO 349
<211> LENGTH: 11
<212> TYPE: PRT
<213> ORGANISM: Artificial sequence
<220> FEATURE:
<223> OTHER INFORMATION: Synthetic antibody

<400> SEQUENCE: 349

Asn Ser Arg Asp Ser Ser Ser Asn His Leu Val
1               5                   10
```